(12) United States Patent
Pallas et al.

(10) Patent No.: US 7,135,437 B2
(45) Date of Patent: Nov. 14, 2006

(54) STABLE LIQUID PESTICIDE COMPOSITIONS

(75) Inventors: Norman R. Pallas, Florissant, MO (US); Jane L. Gillespie, St. Louis, MO (US); Lata Singh, Ellisville, MO (US); Xiaodong C. Xu, Valley Park, MO (US)

(73) Assignee: Monsanto Technology LLC, St. Louis, MO (US)

( * ) Notice: Subject to any disclaimer, the term of this patent is extended or adjusted under 35 U.S.C. 154(b) by 548 days.

(21) Appl. No.: 09/988,352

(22) Filed: Nov. 19, 2001

(65) Prior Publication Data

US 2003/0087764 A1    May 8, 2003

Related U.S. Application Data

(63) Continuation-in-part of application No. 09/926,521, filed as application No. PCT/US01/16550 on May 21, 2001.

(60) Provisional application No. 60/274,368, filed on Mar. 8, 2001, provisional application No. 60/273,234, filed on Mar. 2, 2001, provisional application No. 60/206,628, filed on May 24, 2000, provisional application No. 60/205,524, filed on May 19, 2000.

(51) Int. Cl.
 *A01N 25/30* (2006.01)
 *A01N 57/02* (2006.01)
 *A01P 13/00* (2006.01)

(52) U.S. Cl. ........................ 504/206; 504/364
(58) Field of Classification Search ............... 504/206, 504/364
 See application file for complete search history.

(56) References Cited

U.S. PATENT DOCUMENTS

| | | | |
|---|---|---|---|
| 2,764,602 A | 9/1956 | Ahlbrecht | |
| 2,764,603 A | 9/1956 | Ahlbrecht | |
| 3,147,064 A | 9/1964 | Brown et al. | |
| 3,799,758 A | 3/1974 | Franz | |
| 3,853,530 A | 12/1974 | Franz | |
| 3,977,860 A | 8/1976 | Franz | |
| 4,069,158 A | 1/1978 | Bertocchio et al. | |
| 4,140,513 A | 2/1979 | Prill | |
| 4,315,765 A | 2/1982 | Large | |
| 4,405,531 A | 9/1983 | Franz | |
| 4,440,562 A | 4/1984 | Prill | |
| 4,481,026 A | 11/1984 | Prisbylla | |
| 4,507,250 A | 3/1985 | Bakel | |
| 4,973,352 A | 11/1990 | Heinrich et al. | |
| 5,317,003 A | 5/1994 | Kassebaum et al. | |
| 5,389,598 A | 2/1995 | Berk et al. | |
| 5,464,807 A | 11/1995 | Claude et al. | |
| 5,563,111 A | 10/1996 | Hioki et al. | |
| 5,622,911 A | 4/1997 | Hasebe et al. | |
| 5,668,085 A | 9/1997 | Forbes et al. | |
| 5,703,015 A | 12/1997 | Berger et al. | |
| 5,750,468 A | 5/1998 | Wright et al. | |
| 5,849,663 A | 12/1998 | Hasebe et al. | |
| 5,863,863 A | 1/1999 | Hasebe et al. | |
| 5,863,909 A | 1/1999 | Kurita et al. | |
| 5,985,794 A | 11/1999 | Hasebe et al. | |
| 5,998,332 A | 12/1999 | Sato et al. | |
| 6,030,923 A | 2/2000 | Okano et al. | |
| 6,093,679 A | 7/2000 | Azuma et al. | |
| 6,117,820 A | 9/2000 | Cutler et al. | |
| 6,184,182 B1 | 2/2001 | Gillespie et al. | |
| 6,245,713 B1 | 6/2001 | Brinker et al. | |
| 6,369,001 B1 * | 4/2002 | Jimoh | 504/118 |
| 6,667,276 B1 * | 12/2003 | Maier et al. | 504/127 |

FOREIGN PATENT DOCUMENTS

| | | |
|---|---|---|
| DE | 4019362 A | 1/1991 |
| DE | 19752552 A | 6/1999 |
| EP | 0290416 A2 | 11/1988 |
| EP | 0 274 369 B1 | 9/1990 |
| EP | 0485207 A1 | 5/1992 |
| EP | 0 533 057 B1 | 9/1992 |
| EP | 0617894 A | 10/1994 |
| GB | 2233229 A | 1/1991 |
| GB | 2267825 A | 12/1993 |
| WO | WO 94/23578 | 10/1994 |
| WO | WO 95/33379 | 12/1995 |
| WO | WO 97/16969 | 5/1997 |
| WO | WO 97/32476 | 9/1997 |
| WO | WO 98/17109 | 4/1998 |
| WO | WO 99/27781 | 6/1999 |
| WO | WO 99/40785 A1 | 8/1999 |
| WO | WO 00/08927 | 2/2000 |
| WO | WO 00/15037 | 3/2000 |
| WO | WO 00/37166 | 6/2000 |
| WO | WO 00/59302 | 10/2000 |
| WO | WO 01/10210 A2 | 2/2001 |
| WO | WO 01/11957 A | 2/2001 |
| WO | WO 02/26036 A1 | 4/2002 |

OTHER PUBLICATIONS

Holmberg, K., When Oil and Water Mix and Mingle, http://www.responseonline.com/tech/emul.html, accessed Jan. 18, 2002, 4 pages, U.S.A.

(Continued)

*Primary Examiner*—S. Mark Clardy
(74) *Attorney, Agent, or Firm*—Senniger Powers; Joseph A. Schaper

(57) ABSTRACT

Aqueous pesticidial concentrate emulsions or microemulsions are described which are storage stable after exposure to temperatures ranging from 60° C. to −20° C.

40 Claims, No Drawings

OTHER PUBLICATIONS

Wyrill, III, J.B. and Burnside, O.C., Glyphosate Toxicity to Common Milkweed and Hemp Dogbane as Influenced by Surfactants, *Weed Science,* May 1977, pp. 275-287, vol. 25, Issue 3.

PCT International Search Report for counterpart application PCT/US01/16550 dated Mar. 5, 2003.

Annex to Form PCT/ISA/206, Communication Relating to the Results of the Partial International Search, relating International Application No. PCT/US 02/16032, dated May 6, 2003.

International Search Report for analogous application No. PCT/US 02/16032, dated Sep. 26, 2003.

* cited by examiner

STABLE LIQUID PESTICIDE COMPOSITIONS

REFERENCE TO RELATED APPLICATIONS

This application is a continuation-in-part of U.S. application Ser. No. 09/926,521, filed Apr. 26, 2002, which was the National Stage of International Application No. PCT/US01/16550, filed May 21, 2001, which claims the benefit of U.S. Provisional Application No. 60/206,628, filed May 24, 2000, U.S. Provisional Application No. 60/205,524, filed May 19, 2000, U.S. Provisional Application No. 60/273,234, filed Mar. 2, 2001, and U.S. Provisional Application No. 60/274,368, filed Mar. 8, 2001.

FIELD OF THE INVENTION

The present invention relates to stable pesticide emulsions and other liquid concentrates of water soluble pesticides such as N-phosphonomethylglycine (glyphosate). Herbicidal compositions of this invention comprise glyphosate or a salt or ester thereof, such as potassium glyphosate and a surfactant system including a cationic surfactant and optionally a nonionic surfactant. The invention also provides optically transparent, highly loaded glyphosate compositions containing cationic and nonionic surfactants having a cloud point of at least about 50° C. and a crystallization point not greater than about −20° C.

BACKGROUND OF THE INVENTION

Glyphosate is well known in the art as an effective post-emergent foliar-applied herbicide. In its acid form, glyphosate has a structure represented by formula (1):

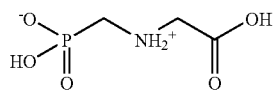

and is relatively insoluble in water (1.16% by weight at 25° C.). For this reason it is typically formulated as a water-soluble salt.

Monobasic, dibasic and tribasic salts of glyphosate can be made. However, it is generally preferred to formulate glyphosate and apply glyphosate to plants in the form of a monobasic salt. The most widely used salt of glyphosate is the mono(isopropylammonium), often abbreviated to IPA, salt. Commercial herbicides of Monsanto Company having the IPA salt of glyphosate as active ingredient include Roundup®, Roundup® Ultra, Roundup® UltraMax, Roundup® Xtra and Rodeo® herbicides. All of these are aqueous solution concentrate (SL) formulations and are generally diluted in water by the user prior to application to plant foliage. Another glyphosate salt which has been commercially formulated as SL formulations include the mono (trimethylsulfonium), often abbreviated to TMS salt, used for example in Touchdown® herbicide of Syngenta. Various salts of glyphosate, methods for preparing salts of glyphosate, formulations of glyphosate or its salts and methods of use of glyphosate or its salts for killing and controlling weeds and other plants are disclosed in U.S. Pat. No. 4,507,250 to Bakel, U.S. Pat. No. 4,481,026 to Prisbylla, U.S. Pat. No. 4,405,531 to Franz, U.S. Pat. No. 4,315,765 to Large, U.S. Pat. No. 4,140,513 to Prill, U.S. Pat. No. 3,977,860 to Franz, U.S. Pat. No. 3,853,530 to Franz, and U.S. Pat. No. 3,799,758 to Franz. The aforementioned patents are incorporated herein in their entirety by reference.

Among the water soluble salts of glyphosate known in the literature, but not known to be used commercially, is the potassium salt, having a structure represented by formula (2):

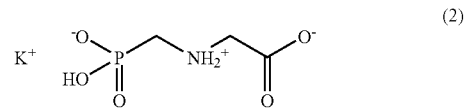

in the ionic form predominantly present in aqueous solution at a pH of about 4. This salt is disclosed, for example, by Franz in U.S. Pat. No. 4,405,531 cited above, as one of the "alkali metal" salts of glyphosate useful as herbicides, with potassium being specifically disclosed as one of the alkali metals, along with lithium, sodium, cesium and rubidium. Example C discloses the preparation of the monopotassium salt by reacting the specified amounts of glyphosate acid and potassium carbonate in an aqueous medium.

Very few herbicides have been commercialized as their potassium salts. The Pesticide Manual, 11th Edition, 1997, lists as potassium salts the auxin type herbicides 2,4-DB ((2,4-dichlorophenoxy)butanoic acid), dicamba (3,6-dichloro-2-methoxybenzoic acid), dichlorprop (2-(2,4-dichlorophenoxy)propanoic acid), MCPA ((4chloro-2-methylphenoxy)acetic acid), and picloram (4amino-3,5,6-trichloro-2-pyridinecarboxylic acid), the active ingredient of certain herbicide products sold by DowElanco under the trademark Tordon.

The solubility of glyphosate potassium salt in water is recorded in pending application Ser. No. 09/444,766, filed Nov. 22, 1999, the entire disclosure of which is incorporated herein by reference. As disclosed therein, glyphosate potassium salt has a solubility in pure water at 20° C. of about 54% by weight, that is, about 44% glyphosate acid equivalent (a.e.) by weight. This is very similar to the solubility of the IPA salt. Concentrations expressed as percent by weight herein relate to parts by weight of salt or acid equivalent per 100 parts by weight of solution. Thus a simple aqueous solution concentrate of glyphosate potassium salt can readily be provided at a concentration of, for example, 44% a.e. by weight, comparable to that commercially obtainable with glyphosate IPA salt, as in the aqueous solution concentrate available from Monsanto Company under the name D-Pak. Somewhat higher concentrations can be obtained by slight over neutralization, 5 to 10% for example, of an aqueous solution of glyphosate potassium salt with potassium hydroxide.

A major advantage of the IPA salt over many other salts of glyphosate has been its compatibility in aqueous solution concentrate formulations with a wide range of surfactants. As used herein, the term "surfactant" is intended to include a wide range of adjuvants that can be added to herbicidal glyphosate compositions to enhance the herbicidal efficacy thereof, as compared to the activity of the glyphosate salt in the absence of such adjuvant, stability, formulability or other beneficial solution property, irrespective of whether such adjuvant meets a more traditional definition of "surfactant."

Glyphosate salts generally require the presence of a suitable surfactant for best herbicidal performance. The surfactant can be provided in the concentrate formulation, or it can be added by the end user to the diluted spray composition. The choice of surfactant has a major bearing on herbicidal performance. For example, in an extensive study reported in Weed Science, 1977, volume 25, pages 275–287, Wyrill and Burnside found wide variation among surfactants in their ability to enhance the herbicidal efficacy of glyphosate, applied as the IPA salt.

Beyond some broad generalizations, the relative ability of different surfactants to enhance the herbicidal effectiveness of glyphosate is highly unpredictable.

Surfactants tending to give the most useful enhancement of glyphosate herbicidal effectiveness are generally but not exclusively cationic surfactants, including surfactants which form cations in aqueous solution or dispersion at pH levels of around 4–5 characteristic of SL formulations of monobasic salts of glyphosate. Examples are long-chain (typically $C_{12}$ to $C_{18}$) tertiary alkylamine surfactants and quaternary alkylammonium surfactants. An especially common tertiary alkylamine surfactant used in aqueous solution concentrate formulations of glyphosate IPA salt has been the very hydrophilic surfactant polyoxyethylene (15) tallowamine, i.e., tallowamine having in total about 15 moles of ethylene oxide in two polymerized ethylene oxide chains attached to the amine group as shown in formula (3):

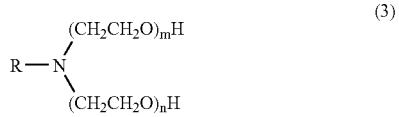

(3)

wherein R is a mixture of predominantly $C_{16}$ and $C_{18}$ alkyl and alkenyl chains derived from tallow and the total of m+n is an average number of about 15.

For certain applications, it has been found desirable to use a somewhat less hydrophilic alkylamine surfactant, such as one having less than about 10 moles of ethylene oxide, as suggested in U.S. Pat. No. 5,668,085 to Forbes et al., for example polyoxyethylene (2) cocoamine. That patent discloses illustrative aqueous compositions comprising such a surfactant together with the IPA, ammonium or potassium salts of glyphosate. The highest concentration of glyphosate in the potassium salt formulations shown in Table 3 of the '085 patent is 300 g glyphosate a.e./l, with a weight ratio of glyphosate a.e. to surfactant of 2:1.

A class of alkoxylated alkylamines is disclosed in WO 00/59302 for use in herbicidal spray compositions. Potassium glyphosate solutions including various Jeffamine™ EO/PO propylamines or propyldiamines are described therein.

A wide variety of quaternary ammonium surfactants have been disclosed as components of aqueous solution concentrate formulations of glyphosate IPA salt. Illustrative examples are N-methylpolyoxyethylene (2) cocoammonium chloride, disclosed in European Patent No. 0274369, N-methylpolyoxyethylene (15) cocoammonium chloride, disclosed in U.S. Pat. No. 5,317,003, and various quaternary ammonium compounds having formula (4):

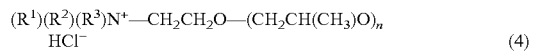

(4)

where $R^1$, $R^2$ and $R^3$ are each $C_{1-3}$ alkyl groups and n is an average number from 2 to 20, disclosed in U.S. Pat. No. 5,464,807.

PCT Publication No. WO 97/16969 discloses aqueous solution concentrate compositions of glyphosate, in the form of the IPA, methylammonium and diammonium salts, comprising a quaternary ammonium surfactant and an acid salt of a primary, secondary or tertiary alkylamine compound.

Other cationic surfactants which have been indicated as useful in aqueous solution concentrate compositions of glyphosate salts include those disclosed in PCT Publication No. WO 95/33379. It is further disclosed in PCT Publication No. WO 97/32476 that highly concentrated aqueous compositions of glyphosate salts can be made with certain of these same cationic surfactants, with the further addition of a defined component that enhances stability of the compositions. Glyphosate salts exemplified therein are the IPA salt and the mono- and diammonium salts.

A class of alkyletheramine, alkyletherammonium salt and alkyletheramine oxide surfactants has been disclosed in U.S. Pat. No. 5,750,468 to be suitable for preparation of aqueous solution concentrate formulations of various glyphosate salts, the potassium salt being included in the list of salts mentioned. It is disclosed therein that an advantage of the subject surfactants when used in an aqueous composition with glyphosate salts is that these surfactants permit the glyphosate concentration of the composition to be increased to very high levels.

Anionic surfactants, except in combination with cationic surfactants as disclosed in U.S. Pat. Nos. 5,389,598 and 5,703,015, are generally of little interest in SL formulations of glyphosate IPA salt. The '015 patent discloses a surfactant blend of a dialkoxylated alkylamine and an anionic eye irritancy reducing compound. The surfactant blend is disclosed as being suitable for preparation of aqueous solution concentrate formulations of various glyphosate salts, the potassium salt being included in the list of salts mentioned. Concentrates of the '015 patent contain from about 5 to about 50%, preferably about 35% to about 45% glyphosate a.i. and from about 5 to about 25% surfactant. Further, PCT Publication No. WO 00/08927 discloses the use of certain polyalkoxylated phosphate esters in combination with certain polyalkoxylated amidoamines in glyphosate containing formulations. Potassium is identified as one of several salts of glyphosate noted as being "suitable."

Nonionic surfactants are generally reported to be less compatible with glyphosate than cationic or amphoteric surfactants when used as the sole surfactant component of SL formulations of glyphosate; exceptions appear to include certain alkyl polyglucosides, as disclosed for example in Australian Patent No. 627503. Other nonionics that have been disclosed as useful with glyphosate include polyoxyethylene (10–100) $C_{16-22}$ alkylethers, as disclosed in PCT Publication No. WO 98/17109. Other nonionic surfactants are generally mixed with cationic surfactants to form a compatible surfactant system for use in liquid herbicidal concentrates. However, cationic/nonionic surfactant systems generally do not provide acceptable low temperature storage stability. Concentrates containing these surfactant systems can crystallize at temperatures at or below about 0° C., limiting the use of such concentrates in cold climates.

Glyphosate concentrates containing nonionic alkylether and cationic amine surfactants are described in U.S. Pat. No. 6,245,713. The surfactant mixture is said to enhance biological effectiveness of the glyphosate and provide enhanced rainfastness. Suitable glyphosates for use in the concentrates include sodium, potassium, ammonium, dimethylammonium, IPA, monoethanolammonium and TMS glyphosate salts. This patent is incorporated herein in its entirety by reference.

It is likely that serious consideration of glyphosate potassium salt as a herbicidal active ingredient has been inhibited by the relative difficulty in formulating this salt as a highly concentrated SL product together with preferred surfactant types. For example, a widely used surfactant in glyphosate IPA salt compositions, namely polyoxyethylene (15) tallowamine of formula (3) above, is highly incompatible in aqueous solution with glyphosate potassium salt. Further, PCT Publication No. WO 00/15037 notes the low compatibility of alkoxylated alkylamine surfactants in general with high-strength glyphosate concentrates. As disclosed therein, in order to "build in" an effective level of surfactant, an alkylglycoside surfactant is used in combination with an alkoxylated alkylamine surfactant to obtain high-strength concentrates containing the potassium salt of glyphosate.

The addition of such alkylglycosides resulted in higher viscosity formulations (as compared to formulations without alkylglycosides). Such an increase in the viscosity of these high-strength formulations is undesirable for various reasons. In addition to being more difficult to conveniently pour from the container or to wash residues therefrom, the deleterious effects resulting from higher viscosity formulations is more dramatically observed with respect to pumping requirements. Increasing volumes of liquid aqueous glyphosate products are being purchased by end-users in large refillable containers sometimes known as shuttles, which typically have an integral pump or connector for an external pump to permit transfer of liquid. Liquid aqueous glyphosate products are also shipped in bulk, in large tanks having a capacity of up to about 100,000 liters. The liquid is commonly transferred by pumping to a storage tank at a facility operated by a wholesaler, retailer or cooperative, from which it can be further transferred to shuttles or smaller containers for onward distribution. Because large quantities of glyphosate formulations are purchased and transported in early spring, the low temperature pumping characteristics of such formulations are extremely important.

When such alkylglycosides (e.g., Agrimul™ APG-2067 and 2-ethyl-hexyl glucoside) are added to a glyphosate concentrate, the concentrate is dark brown in color. It is desirable for a glyphosate concentrate to be lighter in color than the alkylglycoside-containing concentrates as disclosed in WO 00/15037, which have a color value of about 10 to 18 as measured by a Gardner colorimeter. When dye is added to a glyphosate concentrate having a Gardner color of 18, the concentrate remains dark brown in color. Concentrates having a Gardner color value of 10 are difficult to dye a wide variety of colors, for example blue, green, red or yellow, as is often desired to distinguish the glyphosate product from other herbicidal products.

It would be desirable to provide a storage-stable aqueous concentrate composition of the potassium salt of glyphosate having an agronomically useful surfactant content, or that is "fully loaded" with surfactant. These formulations exhibit a reduced viscosity such that they may be pumped with standard bulk pumping equipment at 0° C. at rates of at least 7.5 gallons per minute, usually more than 10 gallons per minute and preferably greater than 12.5 gallons per minute. An "agronomically useful surfactant content" means containing one or more surfactants of such a type or types and in such an amount that a benefit is realized by the user of the composition in terms of herbicidal effectiveness by comparison with an otherwise similar composition containing no surfactant. By "fully loaded" is meant having a sufficient concentration of a suitable surfactant to provide, upon conventional dilution in water and application to foliage, herbicidal effectiveness on one or more important weed species without the need for further surfactant to be added to the diluted composition.

By "storage-stable," in the context of an aqueous concentrate composition of glyphosate salt further containing a surfactant, is meant not exhibiting phase separation on exposure to temperatures up to about 50° C., and preferably not forming crystals of glyphosate or salt thereof on exposure to a temperature of about 0° C. for a period of up to about 7 days (i.e., the composition must have a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate SL formulation. Ideally the cloud point should be 60° C. or more, and the composition should withstand temperatures as low as about –10° C., preferably as low as about –20° C., for up to about 7 days without crystal growth, even in the presence of seed crystals of the glyphosate salt.

A surfactant that is described herein as "compatible" with a glyphosate salt at specified surfactant and glyphosate a.e. concentrations is one that provides a storage-stable aqueous concentrate as defined immediately above containing that surfactant and salt at the specified concentrations.

Users of liquid herbicidal products typically meter the dosage by volume rather than by weight, and such products are usually labeled with directions for suitable use rates expressed in volume per unit area, e.g., liters per hectare (l/ha) or fluid ounces per acre (oz/acre). Thus the concentration of herbicidal active ingredient that matters to the user is not percent by weight, but weight per unit volume, e.g., grams per liter (g/l) or pounds per gallon (lb/gal). In the case of glyphosate salts, concentration is often expressed as grams of acid equivalent per liter (g a.e./l).

Historically, surfactant-containing glyphosate IPA salt products such as Roundup® and Roundup® Ultra herbicides of Monsanto Company have most commonly been formulated at a glyphosate concentration of about 360 g a.e./l. The surfactant-containing glyphosate TMS salt product Touchdown® of Zeneca has been formulated at a glyphosate concentration of about 330 g a.e./l. Products at lower a.e. concentration, i.e., more dilute, are also sold in some markets, but carry a cost penalty per unit of glyphosate they contain, primarily reflecting packaging, shipping and warehousing costs.

Further benefits in cost savings and in convenience to the user are possible if a "fully loaded" aqueous concentrate composition, or at least one having an agronomically useful surfactant content, can be provided at a glyphosate concentration of at least about 320 g a.e./l, 340 g a.e./l, or significantly more than 360 g a.e./l, for example at least about 420 g a.e./l or more, or at least 440, 450, 460, 470, 480, 490, 500, 510, 520, 530, 540, 550, 560, 570, 580, 590, 660 g a.e./l or more.

At very high glyphosate a.e. concentrations such as these, a significant problem normally occurs. This is the difficulty in pouring and/or pumping of the aqueous concentrate arising from the high viscosity of the concentrate, especially as manifested at low temperatures. It would therefore be highly desirable to have a highly concentrated aqueous solution of glyphosate potassium salt fully loaded with an agronomically useful surfactant, such formulation preferably being less viscous than glyphosate potassium salt formulations containing alkylglycoside surfactants, such as those disclosed in PCT Publication No. WO 00/15037.

As will be clear from the disclosure that follows, these and other benefits are provided by the present invention.

SUMMARY OF THE INVENTION

Among the several features of the invention, therefore, may be noted the provision of a liquid concentrate pesticidal composition useful in agriculture wherein a water-soluble herbicide can be formulated with a surfactant system so as to withstand temperatures as low as about −10° C., preferably as low as about −20° C., for at least about 7 days without phase separation and without crystal growth, even in the presence of seed crystals of the herbicide; the provision of such a composition which is stable after storage at about 50° C. for at least 14 days, preferably at about 60° C. or more for at least 28 days; the provision of such a composition that allows for higher loading of herbicidal active ingredients and full loading of surfactants; and the provision of such a storage-stable composition having a broad weed control spectrum that is relatively easy to use.

Briefly, therefore, the present invention is directed to an aqueous pesticidal concentrate microemulsion composition comprising a water-soluble pesticide dissolved in an aqueous medium, a substantially water-immiscible organic solvent, and a surfactant component. The water-soluble pesticide is present in a concentration that is biologically effective when the composition is diluted in a suitable volume of water and applied to the foliage of a susceptible plant. The surfactant component comprises one or more surfactants present in a concentration sufficient to provide acceptable temperature stability of the microemulsion such that the microemulsion has a cloud point of at least about 50° C. and a crystallization point not greater than about −10° C. The concentrate composition is optically transparent.

The invention is also directed to a liquid herbicidal concentrate emulsion composition having a continuous aqueous phase and a discontinuous oil phase. The composition comprises glyphosate predominantly in the form of the potassium, monoammonium, diammonium, sodium, monoethanolamine, n-propylamine, ethylamine, ethylenediamine, hexamethylenediamine or trimethylsulfonium salt thereof, an oil phase comprising a substantially water-immiscible organic solvent, and a surfactant component. The glyphosate is in solution in the aqueous phase in a concentration that is biologically effective when the composition is diluted in a suitable volume of water to form an enhanced application mixture and applied to foliage of a susceptible plant. The surfactant component is in solution or stable suspension, emulsion, or dispersion in the aqueous phase, and comprises one or more surfactants present in a concentration sufficient to provide acceptable temperature stability of the emulsion such that the emulsion has a cloud point of at least about 50° C. and a crystallization point not greater than about −10° C.

Yet another embodiment of the present invention is directed to an aqueous pesticidal concentrate microemulsion composition comprising a water-soluble pesticide dissolved in an aqueous medium, a substantially water-immiscible organic solvent and a surfactant component. The water-soluble pesticide is present in a concentration that is biologically effective when the composition is diluted in a suitable volume of water and applied to the foliage of a susceptible plant. The surfactant component comprises at least one cationic surfactant and at least one nonionic surfactant, and is present in a concentration sufficient to provide acceptable temperature stability of the emulsion such that the emulsion has a cloud point of at least about 50° C. and a crystallization point not greater than about −10° C.

Another embodiment of the invention is directed to a liquid herbicidal concentrate emulsion composition having a continuous aqueous phase and a discontinuous oil phase. The emulsion comprises a water-soluble herbicide dissolved in the aqueous phase, an oil phase comprising a substantially water-immiscible organic solvent, and a surfactant component. The water-soluble herbicide is present in a concentration that is biologically effective when the composition is diluted in a suitable volume of water and applied to the foliage of a susceptible plant The surfactant component comprises at least one cationic surfactant, and the surfactant component is present in a concentration sufficient to provide acceptable temperature stability of the emulsion such that the emulsion has a cloud point of at least about 50° C. and a crystallization point not greater than about 0° C.

Still another embodiment of the invention is directed to an aqueous herbicidal concentrate composition comprising a water-soluble herbicide dissolved in an aqueous medium and a surfactant component. The water-soluble herbicide is present in a concentration that is biologically effective when the composition is diluted in a suitable volume of water and applied to the foliage of a susceptible plant. The surfactant component comprises at least one cationic surfactant; and one or more amine or quaternary ammonium salt compounds, each of which comprises an alkyl or aryl substituent having from about 4 to about 16 carbon atoms and not more than ten ethylene oxide linkages within the compound. The compounds are present in an amount which enhances the compatibility of the surfactant component with the herbicide. The surfactant component is present in a concentration sufficient to provide acceptable temperature stability of the composition such that the composition has a cloud point of at least about 50° C. and a crystallization point not greater than about 0° C.

Yet another embodiment of the invention is directed to an aqueous herbicidal concentrate composition comprising a water-soluble herbicide dissolved in an aqueous medium, and a surfactant component. The water-soluble herbicide is present in a concentration that is biologically effective when the composition is diluted in a suitable volume of water and applied to the foliage of a susceptible plant. The surfactant component comprises at least one cationic surfactant and at least one nonionic surfactant, and is present in a concentration sufficient to provide acceptable temperature stability of the composition such that the composition has a cloud point of at least about 50° C. and a crystallization point not greater than about 0° C.

DETAILED DESCRIPTION

Liquid pesticidal concentrates, especially those containing potassium glyphosate in combination with surfactants, are known to be difficult to stabilize against phase separation at elevated temperatures or crystallization at low temperatures. It has been discovered that the compatibility of a cationic surfactant, or a mixture of cationic and nonionic surfactants, with a water-soluble herbicide within a liquid herbicidal concentrate can be significantly improved by adding certain amine or quaternary ammonium salt compounds to the concentrate. These compounds are referred to herein as "stabilizers." Concentrates containing such surfactants in combination with the stabilizer also exhibit optical clarity and enhanced temperature stability, and provide improved weed control when diluted and applied to foliage.

Amine or quaternary ammonium salt compounds comprising an alkyl or aryl substituent having from about 4 to about 22 carbon atoms and not more than ten ethylene oxide linkages within the compound are effective in enhancing the compatibility of such surfactants, even in concentrates containing at least 400 g glyphosate a.e. per liter and with a glyphosate:surfactant weight ratio of between about 1:1 and 20:1. The compatibility is particularly enhanced for surfactants that are otherwise incompatible with the water-soluble herbicide. For example, potassium glyphosate concentrates comprising 5–15 wt % cationic surfactants, or mixtures of these cationic surfactants and nonionic surfactants, are storage stable when the stabilizer is added.

It has also been discovered that the low temperature storage stability of liquid herbicidal concentrates containing cationic and nonionic surfactants can be significantly improved by adding a substantially water-immiscible solvent to the concentrate to form an emulsion. Emulsions containing a solvent, such as Aromatic 150 or Isopar L, often exhibit a 10° C. improvement in low temperature storage stability as compared to similarly loaded herbicidal compositions which do not include the solvent. The emulsions can be formulated to remain optically clear during storage. Preferably, the concentrate is formulated as a microemulsion which remains optically transparent when stored for at least about 7, 14 or 28 days.

It has also been discovered that, when the surfactant component of the liquid herbicidal concentrate composition also includes an amine containing alkylene oxide linkages, lowering the degree of alkoxylation improves the low temperature storage stability of the composition. For example, a glyphosate composition containing an alkyl etheramine having not more than eight ethylene oxide linkages exhibit a crystallization point not greater than about –10° C., as compared to a similarly loaded glyphosate composition comprising an alkyl etheramine having ten ethylene oxide linkages which exhibits a crystallization point not greater than about 0° C.

In an embodiment of the invention, an aqueous herbicidal concentrate composition is provided which comprises a water-soluble herbicide dissolved in water. The water-soluble herbicide is present in a concentration that is biologically effective when the composition is diluted in a suitable volume of water and applied to the foliage of a susceptible plant. The composition also comprises a surfactant component in solution or stable suspension, microemulsion, or dispersion in the water. The surfactant component comprises one or more cationic surfactants, or a mixture of one or more cationic surfactants and one or more nonionic surfactants. The surfactant component is present in a concentration sufficient to provide acceptable temperature stability of the composition such that the composition has a cloud point of at least about 50° C. and a crystallization point not greater than about 0°C.

Preferably, the cationic surfactant comprises a stabilizer of the invention, that is, one or more amine or quaternary ammonium salt compounds, each of which comprises an alkyl or aryl substituent having from about 4 to about 16 carbon atoms and not more than ten ethylene oxide linkages within the compound. These compounds enhance the compatibility of the surfactant component with the herbicide, enhance the optical clarity and temperature stability of the composition, and provide improved weed growth control when the composition is diluted with water and applied to foliage.

In another embodiment of the invention, a substantially water-immiscible organic solvent is added to this composition to form a microemulsion. When the solvent is present in the concentrate composition, the storage stability of the composition is improved by decreasing the crystallization point by about 10° C. Such compositions exhibit a crystallization point not greater than about –10° C. or even about –20° C. if desired.

The liquid herbicidal concentrate aqueous and oil emulsion of the invention comprises a continuous aqueous phase containing a water-soluble herbicide dissolved therein. The water-soluble herbicide is present in a concentration that is biologically effective when the emulsion is diluted in a suitable volume of water and applied to the foliage of a susceptible plant. The oil phase of the emulsion comprises the substantially water-immiscible organic solvent. The emulsion also comprises a surfactant component in solution or stable suspension, emulsion, or dispersion in the water. The surfactant component comprises one or more surfactants present in a concentration sufficient to provide acceptable temperature stability of the emulsion such that the emulsion has a cloud point of at least about 50° C., preferably about 60° C. and a crystallization point not greater than about –10° C., preferably about –20° C. Such low temperature storage stability is desirable in colder climates to maintain a pourable and pumpable homogeneous composition.

In a preferred embodiment, a temperature stable microemulsion is formed. A microemulsion is an optically transparent composition which remains stable when stored within a given temperature range. Microemulsions are described by K. Holmberg in an article entitled "When oil and water mix and mingle" (visited Nov. 18, 2001) <http://www.responseonline.com/tech/emul.htm>. The term "optically transparent" or "clear" is defined as a complete lack of any visible nonuniformity when viewed in mass, in bottles or test tubes, by strong transmitted light for purposes of this invention.

Microemulsions of the invention are easily prepared by well known methods and using standard equipment in the art. A beaker or laboratory pot is adequate for low volume purposes, while larger volumes may be processed in standard industrial agitated tankage including reactors, dissolvers and bulk tanks. Agitation requirements are not critical and agitation need only be adequate to provide a homogeneous formulation. Medium speed agitation with stir bars, or agitators fitted with standard industrial props are preferred. Baffled tanks are preferred in industrial applications as a means to reduce vortexing and air entrainment, and to minimize the agitator prop speed required to achieve desired homogeneity. Heated or jacket vessels are preferred. High shear and high speed mixing are not preferred if excessive air entrapment in the formulation can occur. The composition constitutents may be added in any order into a suitable vessel. Preferably, the surfactant is first added followed by the stabilizer, water and the pesticide. Surfactants that are not flowable at the processing temperature may optionally be melted prior to formulation, or preferably melted in the processing equipment before the balance of the components are added.

Preferably, the surfactant system comprises a stabilizer of the invention, that is, one or more amine or quaternary ammonium salt compounds, each of which comprises an alkyl or aryl substituent having from about 4 to about 22 carbon atoms and not more than ten $C_2$–$C_5$ alkylene oxide linkages within the compound. These compounds enhance the compatibility of the surfactant component with the herbicide, enhance the optical clarity and temperature stability of the microemulsion, and provide improved weed growth control when the microemulsion is diluted with water and applied to foliage.

It is also preferred that the surfactant component comprises one or more cationic surfactants, or a mixture of one or more cationic surfactants and one or more nonionic surfactants.

The liquid concentrate compositions of the invention preferably comprise a water-soluble herbicide in a concentration between about 10 and about 60% by weight of the composition, a surfactant component in a concentration between about 0.5 and about 30% by weight of the composition and a stabilizer and/or a solvent component. The concentrations of the stabilizer and the solvent component are between 0 and about 30% and 0 and about 15% by weight of the composition, respectively.

In one embodiment of the invention the liquid concentrate composition preferably comprises glyphosate or a salt or ester thereof in a concentration between about 25 and about 50% by weight of the composition, a surfactant component in a concentration between about 1 and about 30% by weight of the composition, and a stabilizer in a concentration between about 0.01 and about 25% by weight of the composition. Even more preferably, the composition comprises glyphosate or a salt or ester thereof in a concentration between about 30 and about 47% by weight of the composition, a surfactant component in a concentration between about 2 and about 17% by weight of the composition, and a stabilizer in a concentration between about 0.05 and about 20% by weight of the composition. Most preferably, the composition comprises glyphosate or a salt or ester thereof in a concentration between about 32 and about 44% by weight of the composition, a surfactant component in a concentration between about 3 and about 15% by weight of the composition, and a stabilizer in a concentration between about 0.1 and about 15% by weight of the composition.

In another embodiment of the invention the liquid concentrate composition of the invention preferably comprises glyphosate or a salt or ester thereof in a concentration between about 25 and about 50% by weight of the composition, a surfactant component in a concentration between about 1 and about 30% by weight of the composition, and a solvent component in a concentration between about 0.01 and about 10% by weight of the composition. Even more preferably, the composition comprises glyphosate or a salt or ester thereof in a concentration between about 30 and about 47% by weight of the composition, a surfactant component in a concentration between about 2 and about 17% by weight of the composition, and a solvent component in a concentration between about 0.05 and about 7% by weight of the composition. Most preferably, the composition comprises glyphosate or a salt or ester thereof in a concentration between about 32 and about 44% by weight of the composition, a surfactant component in a concentration between about 3 and about 15% by weight of the composition, and a solvent component in a concentration between about 0.1 and about 5% by weight of the composition.

In yet another embodiment of the invention the liquid concentrate composition of the invention preferably comprises glyphosate or a salt or ester thereof in a concentration between about 25 and about 50% by weight of the composition, a surfactant component in a concentration between about 1 and about 30% by weight of the composition, a stabilizer in a concentration between about 0.01 and about 25% by weight of the composition, and a solvent component in a concentration between about 0.01 and about 10% by weight of the composition. Even more preferably, the composition comprises glyphosate or a salt or ester thereof in a concentration between about 30 and about 47% by weight of the composition, a surfactant component in a concentration between about 2 and about 17% by weight of the composition, a stabilizer in a concentration between about 0.05 and about 20% by weight of the composition, and a solvent component in a concentration between about 0.05 and about 7% by weight of the composition. Most preferably, the composition comprises glyphosate or a salt or ester thereof in a concentration between about 32 and about 44% by weight of the composition, a surfactant component in a concentration between about 3 and about 15% by weight of the composition, a stabilizer in a concentration between about 0.1 and about 15% by weight of the composition, and a solvent component in a concentration between about 0.1 and about 5% by weight of the composition.

Compositions of the invention have a viscosity of not greater than about 1000 cPs at 10° C., preferably not greater than about 900 cPs at 10° C., more preferably not greater than about 800, 700, 600, 500, 400 or 300 cPs at 10° C., and even more preferably not greater than about 200 cPs at 10° C., at 45/s shear rate.

The term "water-soluble" as used herein in relation to a herbicide or salt or ester thereof means having a solubility in deionized water at 20° C. of not less than about 50 g/l. Preferred water-soluble herbicides have a solubility in deionized water at 20° C. of not less than about 200 g/l. Particularly preferred water-soluble herbicides have a herbicidal active acid or anionic moiety and are most usefully present in a composition of the invention in the form of one or more water-soluble salts. The aqueous phase of the composition can optionally contain, in addition to the water-soluble herbicide, other salts contributing to the ionic strength of the aqueous phase.

A particularly preferred group of water-soluble herbicides are those that are normally applied post-emergence to the foliage of plants. While the invention is not limited to any particular class of foliar-applied water-soluble herbicide, it has been found to provide useful benefits for compounds that rely at least in part for their herbicidal effectiveness on systemic movement in plants. Systemic movement in plants can take place via apoplastic (non-living) pathways, including within xylem vessels and in intercellular spaces and cell walls, via symplastic (living) pathways, including within phloem elements and other tissues composed of cells connected symplastically by plasmodesmata, or via both apoplastic and symplastic pathways. For foliar-applied systemic herbicides, the most important pathway is the phloem, and the present invention is believed to provide the greatest benefits where the water-soluble herbicide is phloem-mobile. However, compositions of the invention can also be useful where the water-soluble herbicide is non-systemic, as in the case of paraquat.

Water-soluble herbicides suitable for use in compositions of the invention include acifluorfen, acrolein, amitrole, asulam, benazolin, bentazon, bialaphos, bromacil, bromoxynil, chloramben, chloroacetic acid, clopyralid, 2,4-D, 2,4-DB, dalapon, dicamba, dichlorprop, difenzoquat, diquat, endothall, fenac, fenoxaprop, flamprop, flumiclorac, fluoroglycofen, flupropanate, fomesafen, fosamine, glufosinate, glyphosate, imazameth, imazamethabenz, imazamox, imazapic, imazapyr, imazaquin, imazethapyr, ioxynil, MCPA, MCPB, mecoprop, methylarsonic acid, naptalam, nonanoic acid, paraquat, picloram, quinclorac, sulfamic acid, 2,3,6-TBA, TCA, triclopyr and water-soluble salts thereof.

Phloem-mobile herbicides that are preferred for use in compositions of the invention include but are not limited to aminotriazole, asulam, bialaphos, clopyralid, dicamba, glufosinate, glyphosate, imidazolinones such as imazameth, imazamethabenz, imazamox, imazapic, imazapyr, imazaquin and imazethapyr, phenoxies such as 2,4-D, 2,4-DB, dichlorprop, MCPA, MCPB and mecoprop, picloram and triclopyr. A particularly preferred group of water-soluble herbicides are salts of bialaphos, glufosinate and glyphosate. Another particularly preferred group of water-soluble herbicides are salts of imidazolinone herbicides.

Compositions of the invention can optionally contain more than one water-soluble herbicide in solution in the aqueous phase.

An especially preferred water-soluble herbicide useful in a composition of the present invention is glyphosate, the acid form of which is alternatively known as N-(phosphonomethyl)glycine. For example, glyphosate salts useful in compositions of the present invention are disclosed in U.S. Pat. Nos. 3,799,758 and 4,405,531. Glyphosate salts that can be used according to the present invention include but are not restricted to alkali metal, for example sodium and potassium, salts; ammonium salt; $C_{1-6}$ alkylammonium, for example dimethylammonium and isopropylammonium, salts; $C_{1-6}$ alkanolammonium, for example monoethanolammonium, salt; $C_{1-6}$ alkylsulfonium, for example trimethylsulfonium, salts; and mixtures thereof. The N-phosphonomethylglycine molecule has three acid sites having different pKa values; accordingly mono-, di- and tribasic salts, or any mixture thereof, or salts of any intermediate level of neutralization, can be used. Especially preferred glyphosate salts include the potassium salt, isopropylamine salt, ammonium salt, diammonium salt, monoethanolamine salt, and trimethylsulfonium salt. The potassium salt is most preferred.

The relative amount of potassium glyphosate loading in the microemulsion herbicidal composition of the present invention will vary depending upon many factors including the surfactant system and stabilizers employed, the rheological characteristics of the composition, and the temperature range at which the composition will be exposed. The potassium glyphosate loading in the herbicidal compositions of the invention is preferably at least 320 g a.e./L, and more preferably at least 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690 or 700 g a.e./L.

The stabilizers of the invention generally function by facilitating the dispersion of the composition surfactants within the water containing dissolved glyphosate. The stabilizers allow surfactants, in the presence of salts or electrolytes, to be added and subsequently dispersed into water at higher concentrations or at lower viscosities of the formulation than is otherwise achieved using only surfactant and water. Suitable stabilizers include primary, secondary or tertiary $C_4$ to $C_{16}$ alkyl or aryl amine compounds, or the corresponding quaternary ammonium compounds. Such stabilizers greatly enhance the compatibility of certain glyphosate salts (e.g., potassium or isopropylamine) with surfactants that otherwise exhibit low or marginal compatibility at a given glyphosate loading. Suitable alkyl or aryl amine compounds may also contain 0 to about 5 $C_2$–$C_4$ alkylene oxide groups, preferably ethylene oxide groups. Preferred alkylamine compounds include $C_6$ to $C_{12}$ alkylamines having 0 to 2 ethylene oxide groups. Similarly, etheramine compounds having 4 to 12 carbons and 0 to about 5 ethylene oxide groups, as well as the corresponding quaternary ammonium compounds, also enhance the compatibility of such formulations. In one embodiment, the compounds which enhance the compatibility of such surfactants include amines or quaternary ammonium salts having the formula:

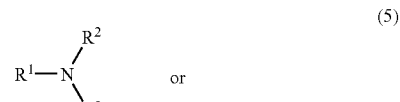

(5)

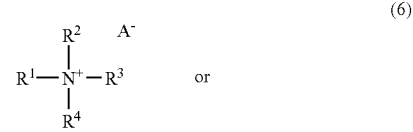

(6)

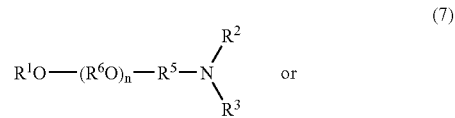

(7)

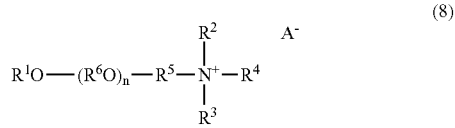

(8)

wherein $R^1$ is linear or branched alkyl or aryl having from about 4 to about 16 carbon atoms, $R^2$ is hydrogen, methyl, ethyl, or —$(CH_2CH_2O)_xH$, $R^3$ is hydrogen, methyl, ethyl, or —$(CH_2CH_2O)_yH$ wherein the sum of x and y is not more than about 5; $R^4$ is hydrogen or methyl; $R^6$ in each of the n ($R^6O$) groups is independently $C_2$–$C_4$ alkylene; $R^5$ is hydrocarbylene or substituted hydrocarbylene having from 2 to about 6 carbon atoms; and A- is an agriculturally acceptable anion. Non-limiting examples include, mixed $C_{8-16}$ alkyl amine (Armeen C), dimethylcocoamine (Arquad DMCD), cocoammonium chloride (Arquad C), PEG 2 cocoamine (Ethomeen C12), and PEG 5 cocoamine (Ethomeen C15), all of which are manufactured by Akzo Nobel, hexylamine, dimethylhexylamine, octylamine, dimethyloctylamine, dodecyltrimethyl amide and $C_{4-8}$ trialkyl amines. The most preferred stabilizer is octyamine.

In high load glyphosate formulations it is preferred to add the stabilizers in a weight ratio of surfactant:stabilizer between about 1:2 and about 100:1, and more preferably between about 1:1 and about 8:1. A particularly preferred range is between about 1.5:1 and about 6:1.

The substantially water-immiscible organic solvent of the invention is any solvent which has a solubility in water of less than about 10% w/w, and has a specific gravity between about 0.7 and about 1.2. The solvents aid in the formation of a microemulsion, and increase the dispersability of hydrophobic surfactants or surfactants with a hydrophobic moiety in the aqueous carrier phase. Preferred hydrophobic solvents have a solubility in water of less than about 7% w/w, more preferably less than about 5% w/w, and most preferably less than about 1% w/w. These solvents additionally have a specific gravity between about 0.7 and 1.2, more preferably between about 0.7 and 1.15, and most preferably between about 0.7 and 1.1. Non-limiting examples of preferred hydrophobic solvents include toluene, xylene, cyclohexane, dichloromethane, dichlorobenzene, perchloroethylene, petroleum naphthas, mineral oil, fuel oil, vegetable oil and kerosine. Preferred hydrophobic solvents include toluene, xylenes, petroleum naphthas and oils. Commercially available preferred solvents include Aromatic 150 (from Exxon)

and Isopar L (from Exxon). Preferred solvents include aliphatic hydrocarbons, halogenated alkyls, aryl hydrocarbons, or mixtures thereof. Examples of commercially available organic solvents include Aromatic 150 (from Exxon) and Isopar L (from Exxon).

Compositions of the invention can optionally contain one or more water-insoluble herbicides in solution in the solvent or in suspension in a concentration that is biologically effective when the composition is diluted in a suitable volume of water and applied to the foliage of a susceptible plant. Preferred water-insoluble herbicide is selected from the group consisting of acetochlor, aclonifen, alachlor, ametryn, amidosulfuron, anilofos, atrazine, azafenidin, azimsulfuron, benfluralin, benfuresate, bensulfuron-methyl, bensulide, benzfendizone, benzofenap, bromobutide, bromofenoxim, butachlor, butafenacil, butamifos, butralin, butroxydim, butylate, cafenstrole, carfentrazone-ethyl, carbetamide, chlorbromuron, chloridazon, chlorimuron-ethyl, chlorotoluron, chlornitrofen, chlorotoluron, chlorpropham, chlorsulfuron, chlorthal-dimethyl, chlorthiamid, cinidon-ethyl, cinmethylin, cinosulfuron, clethodim, clodinafop-propargyl, clomazone, clomeprop, cloransulam-methyl, cyanazine, cycloate, cyclosulfamuron, cycloxydim, cyhalofop-butyl, daimuron, desmedipham, desmetryn, dichlobenil, diclofop-methyl, diflufenican, dimefuron, dimepiperate, dimethachlor, dimethametryn, dimethenamid, dinitramine, dinoterb, diphenamid, dithiopyr, diuron, EPTC, esprocarb, ethalfluralin, ethametsulfuron-methyl, ethofumesate, ethoxysulfuron, etobenzanid, fenoxaprop-ethyl, fenuron, flamprop-methyl, flazasulfuron, fluazifop-butyl, fluazifop-P-butyl, fluazoate, fluchloralin, flumetsulam, flumiclorac-pentyl, flumioxazin, fluometuron, fluorochloridone, flupoxam, flurenol, fluridone, fluroxypyr-1-methylheptyl, flurtamone, fluthiacet-methyl, graminicides, halosulfuron, haloxyfop, hexazinone, imazosulfuron, indanofan, isoproturon, isouron, isoxaben, isoxaflutole, isoxapyrifop, lenacil, linuron, mefenacet, metamitron, metazachlor, methabenzthiazuron, methyldymron, metobenzuron, metobromuron, metolachlor, S-metolachlor, metosulam, metoxuron, metribuzin, metsulfuron, molinate, monolinuron, naproanilide, napropamide, neburon, nicosulfuron, norflurazon, orbencarb, oryzalin, oxadiargyl, oxadiazon, oxasulfuron, pebulate, pendimethalin, pentanochlor, pentoxazone, phenmedipham, piperophos, pretilachlor, primisulfuron, prodiamine, profluazol, prometon, prometryn, propachlor, propanil, propaquizafop, propazine, propham, propisochlor, propyzamide, prosulfocarb, prosulfuron, pyraflufen-ethyl, pyrazogyl, pyrazolynate, pyrazosulfuron-ethyl, pyrazoxyfen, pyributicarb, pyridate, pyriminobac-methyl, quinclorac, quinmerac, quizalofop, quizalofop-P, rimsulfuron, sethoxydim, siduron, simazine, simetryn, sulcotrione, sulfentrazone, sulfometuron, sulfosulfuron, tebutam, tebuthiuron, tepraloxydim, terbacil, terbumeton, terbuthylazine, terbutryn, thenylchlor, thiazopyr, thidiazimin, thifensulfuron, thiobencarb, tiocarbazil, tralkoxydim, triallate, triasulfuron, tribenuron, trietazine, trifluralin, triflusulfuron and vernolate.

Preferred cationic and nonionic surfactants effective in formulating herbicidal compositions and concentrates of the invention, particularly in formulating compositions and concentrates containing potassium, ammonium or diammonium glyphosate, are listed below.

Cationic surfactants effective in forming herbicide formulations include:

(a) aminated alkoxylated alcohol having the formula:

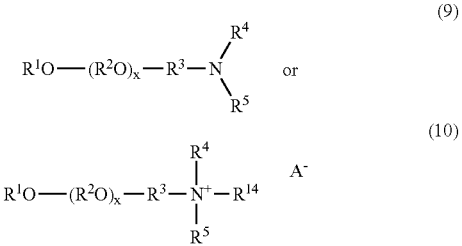

wherein $R^1$ is hydrogen or hydrocarbyl or substituted hydrocarbyl having from 1 to about 30 carbon atoms; $R^2$ in each of the x $(R^2O)$ and y $(R^2O)$ groups is independently $C_2$–$C_4$ alkylene; $R^3$ and $R^6$ are each independently hydrocarbylene or substituted hydrocarbylene having from 1 to about 6 carbon atoms; $R^4$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-(R^6)_n-C(O)OR^7$, $-C(=S)NR^{12}R^{13}$ or together with $R^5$ and the nitrogen atom to which they are attached, form a cyclic or heterocyclic ring; $R^5$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-(R^6)_n-C(O)OR^7$, $-C(=S)NR^{12}R^{13}$, or together with $R^4$ and the nitrogen atom to which they are attached, form a cyclic or heterocyclic ring; $R^7$ is hydrogen or a linear or branched alkyl group having 1 to about 4 carbon atoms; $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, or $-C(=S)NR^{12}R^{13}$, n is 0 or 1, x and y are independently an average number from 1 to about 60, and A- is an agriculturally acceptable anion. In this context, preferred $R^1$, $R^3$, $R^4$, $R^5$, $R^6$, $R^{11}$, $R^{12}$ and $R^{13}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment, $R^3$ is linear alkylene, preferably ethylene, and $R^1$, $R^2$, $R^4$ and $R^5$ are as previously defined. In another embodiment, $R^4$ is H, alkyl, or $-R^2OR^7$ and $R^1$, $R^2$, $R^3$, $R^5$ and $R^7$ are as previously defined. In yet another embodiment, $R^1$ is a linear or branched alkyl or linear or branched alkenyl group having from about 8 to about 25 carbon atoms, $R^2$ in each of the x $(R^2O)$ groups is independently $C_2$–$C_4$ alkylene, $R^3$ is a linear or branched alkylene group having from 1 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x $(R^2O)$ groups is independently ethylene or propylene, $R^3$ is a linear or branched alkylene group having from 1 to about 4 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2O$) groups is independently ethylene or propylene, $R^3$ is an ethylene or a 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the x ($R^2O$) groups is independently ethylene or propylene, $R^3$ is an ethylene or a 2-hydroxypropylene group, $R^4$ and $R^5$ are methyl, and x is an average number from about 4 to about 20. Compounds of formula (2) have the preferred groups as described above and $R^{14}$ is preferably hydrogen or a linear or branched alkyl or alkenyl group, more preferably alkyl, and most preferably methyl. Preferred monoalkoxylated amines include PEG 13 or 18 $C_{14-15}$ ether propylamines and PEG 7, 10, 15 or 20 $C_{16-18}$ ether propylamines (from Tomah) and PEG 13 or 18 $C_{14-15}$ ether dimethyl propylamines and PEG 10, 15 or 20 or 25 $C_{16-18}$ ether dimethyl propylamines (from Tomah).

(b) hydroxylated amides having the formula:

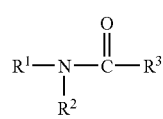

(11)

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and $R^3$ is hydroxyalkyl, polyhydroxyalkyl, or poly(hydroxyalkyl)alkyl. In this context, preferred $R^1$ and $R^2$ hydrocarbyl groups are linear or branched alkyl, linear or branched alkenyl, linear or branched alkynyl, aryl, or aralkyl groups. Preferably, the hydroxylated amides have the formula:

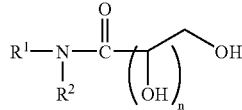

(12)

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and n is 1 to about 8. In this context, preferred $R^1$ and $R^2$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ is hydrogen, a linear or branched alkyl or linear or branched alkenyl group having from 1 to about 30 carbon atoms, and n is about 4 to about 8; or $R^1$ and $R^2$ are independently linear or branched alkyl or linear or branched alkenyl groups having from about 4 to about 30 carbon atoms and n is about 4 to about 8. More preferably, $R^1$ is a linear or branched alkyl or linear or branched alkenyl group having from about 8 to about 22 carbon atoms, $R^2$ is hydrogen or a linear or branched alkyl or linear or branched alkenyl group having from 1 to about 6 carbon atoms, and n is about 4 to about 8; or $R^1$ and $R^2$ are independently linear or branched alkyl or linear or branched alkenyl groups having from about 4 to about 8 carbon atoms, and n is about 4 to about 8.

(c) diamines having the formula:

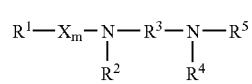

(13)

wherein $R^1$, $R^2$ and $R^5$ are independently hydrogen or hydrocarbyl or substituted hydrocarbyl having from 1 to about 30 carbon atoms or $-R^8(OR^9)_nOR^{10}$, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, and X is $-C(O)-$ or $-SO_2-$. In this context, preferred $R^1$, $R^2$, $R^3$, $R^4$, $R^5$ and $R^{10}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$ and $R^5$ are independently hydrogen, a linear or branched alkyl or alkenyl group having from 1 to about 6 carbon atoms, and $R^3$ is a linear or branched alkylene having from 2 to about 6 carbon atoms. More preferably, $R^1$, $R^2$, $R^4$ and $R^5$ are independently hydrogen, or a linear or branched alkyl group having from 1 to about 6 carbon atoms, and $R^3$ is a linear or branched alkylene having from 2 to about 6 carbon atoms. Most preferably, $R^1$, $R^2$, $R^4$, and $R^5$ are independently hydrogen or methyl, and $R^3$ is ethylene or propylene.

(d) mono- or di-ammonium salts having the formula:

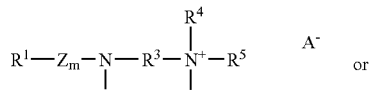

(14)

or

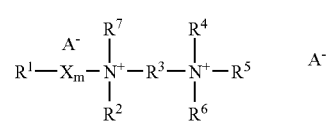

(15)

wherein $R^1$, $R^2$, $R^4$, $R^5$ and $R^7$ are independently hydrogen or hydrocarbyl or substituted hydrocarbyl having from 1 to about 30 carbon atoms or $-R^8(OR^9)_nOR^{10}$, $R^6$ is hydrocarbyl or substituted hydrocarbyl having from 1 to about 30 carbon atoms, $R^3$ is hydrocarbylene or substituted hydrocarbylene having from 2 to about 30 carbon atoms, $R^8$ and $R^9$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is $-C(O)-$ or $-SO_2-$, Z is $-C(O)-$, and $A^-$ is an agriculturally acceptable anion. In this context, preferred $R^1-R^{10}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^2$, $R^4$, $R^5$ and $R^7$ are independently hydrogen, or a linear or branched alkyl or alkenyl group having from 1 to about 6 carbon atoms, $R^6$ is a linear or branched alkyl or alkenyl group having from about 8 to about 30 carbon atoms, m is 0 or 1, and $R^3$ is a linear or branched alkylene having from 2 to about 22 carbon atoms. More preferably, $R^1$, $R^2$, $R^4$, $R^5$ and $R^7$ are independently hydrogen, or a linear or branched alkyl group having from 1 to about 6 carbon atoms, $R^6$ is a linear or branched alkyl group having from about 8 to about 22 carbon atoms, m is 0 or 1, and $R^3$ is a linear or branched alkylene having from 2 to about 20 carbon atoms. Most preferably, $R^1$, $R^2$, $R^4$, $R^5$ and $R^7$ are independently hydrogen or methyl, $R^6$ is a linear or branched alkyl group having from about 8 to about 18 carbon atoms, m is 0 or 1, and $R^3$ is ethylene or propylene.

(e) poly(hydroxyalkyl)amines having the formula:

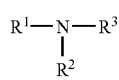

(16)

wherein $R^1$ is hydrocarbyl or substituted hydrocarbyl having from about 4 to about 30 carbon atoms or —$R^4OR^5$, $R^2$ is hydrogen or hydrocarbyl or substituted hydrocarbyl having from 1 to about 30 carbon atoms, $R^3$ is hydroxyalkyl, polyhydroxyalkyl, or poly(hydroxyalkyl)alkyl, $R^4$ is hydrocarbylene or substituted hydrocarbylene having from 2 to about 18 carbon atoms, and $R^5$ is hydrogen or hydrocarbyl or substituted hydrocarbyl having from 1 to about 30 carbon atoms. Preferably, the poly(hydroxyalkyl)amines have the formula:

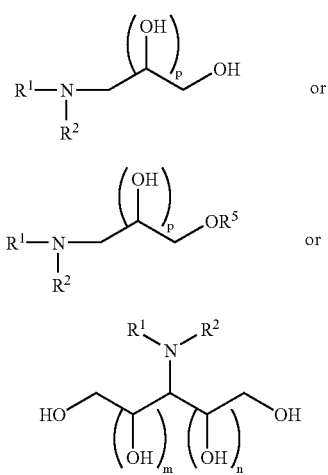

wherein $R^1$ is hydrocarbyl or substituted hydrocarbyl having from about 4 to about 30 carbon atoms or —$R^3$ $OR^4$; $R^2$ is hydrogen or hydrocarbyl or substituted hydrocarbyl having from 1 to about 30 carbon atoms, $R^3$ is hydrocarbylene or substituted hydrocarbylene having from 2 to about 18 carbon atoms, $R^4$ is hydrogen or hydrocarbyl or substituted hydrocarbyl having from 1 to about 30 carbon atoms, $R^5$ is —$(R^6O)_yR^7$; $R^6$ in each of the y($R^6O$) groups is independently $C_2$–$C_4$ alkylene; $R^7$ is hydrogen or a linear or branched alkyl group having 1 to about 4 carbon atoms; y is an average number from 0 to about 30, m and n are independently integers from 0 to about 7, the sum of m and n is not greater than about 7, and p is an integer from 1 to about 8. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 30 carbon atoms or —$R^3OR^4$, $R^2$ is hydrogen, a linear or branched alkyl or linear or branched alkenyl group having from 1 to about 30 carbon atoms, $R^3$ is a linear or branched alkylene or alkenylene group having from 2 to about 6 carbon atoms, $R^4$ is a linear or branched alkyl or alkenyl group having from about 8 to about 22 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 30 carbon atoms, m and n are independently integers from 0 to about 7, the sum of m and n is from about 3 to 7, and p is an integer from about 4 to about 8. More preferably, $R^1$ is a linear or branched alkyl or linear or branched alkenyl group having from about 8 to about 22 carbon atoms or —$R^3OR^4$, $R^2$ is hydrogen or a linear or branched alkyl or linear or branched alkenyl group having from 1 to about 6 carbon atoms, $R^3$ is a linear or branched alkylene or alkenylene group having from 2 to about 6 carbon atoms, $R^4$ is a linear or branched alkyl or alkenyl group having from about 8 to about 18 carbon atoms, m and n are independently integers from 0 to about 7, the sum of m and n is from about 3 to 7, and p is an integer from about 4 to about 8; or $R^1$ and $R^2$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms or —$R^3OR^4$, $R^2$ is hydrogen or methyl, m and n are independently integers from 0 to about 4, $R^3$ is a linear or branched alkylene group having from 2 to about 6 carbon atoms, $R^4$ is a linear or branched alkyl group having from about 8 to about 18 carbon atoms, the sum of m and n is about 4, and p is an integer of about 4. Most preferably, $R^1$ is a linear or branched alkyl group having from about 8 to about 18 carbon atoms or —$R^3OR^4$, $R^2$ is methyl, $R^3$ is ethylene, propylene, hydroxyethylene or 2-hydroxypropylene, $R^4$ is a linear or branched alkyl group having from about 8 to about 18 carbon atoms, m and n are independently integers from 0 to about 4, the sum of m and n is about 4, and p is an integer of about 4. Such compounds are commercially available from Aldrich and Clariant.

(f) alkoxylated poly(hydroxyalkyl)amines having the formula:

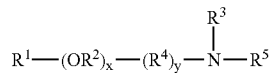

(19)

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2$–$C_4$ alkylene; $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1. In this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferred alkoxylated poly(hydroxyalkyl)amines have the formula:

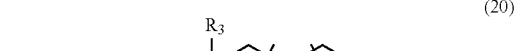

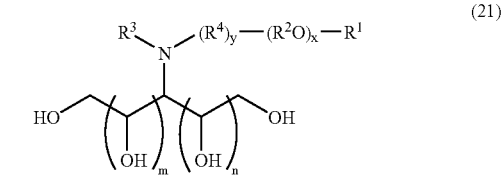

wherein $R^1$ and $R^3$ are independently hydrogen, hydrocarbyl or substituted hydrocarbyl having from 1 to about 30 carbon atoms, $R^2$ in each of the x ($R^2O$) groups is independently $C_2-C_4$ alkylene; $R^4$ is hydrocarbylene or substituted hydrocarbylene having from 1 to about 30 carbon atoms, m and n are independently integers from 0 to about 7, the sum of m and n is not greater than about 7, p is an integer from 1 to about 8, x is an average number from 0 to about 30, and y is 0 or 1. in this context, preferred $R^1$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) group. Preferably, $R^1$ is a linear or branched alkyl or linear or branched alkenyl group having from about 8 to about 30 carbon atoms; $R^2$ in each of the x ($R^2O$) groups is independently $C_2-C_4$ alkylene; $R^3$ is hydrogen, a linear or branched alkyl or linear or branched alkenyl group having from 1 to about 30 carbon atoms; $R^4$ is a linear or branched alkylene having from 1 to about 30 carbon atoms, m and n are independently integers from 0 to about 7, the sum of m and n is from about 3 to 7, p is an integer from 1 to about 8, x is an average number from 0 to about 30, and y is 0 or 1. More preferably, $R^1$ is a linear or branched alkyl group having from about 8 to about 22 carbon atoms; $R^2$ in each of the x ($R^2O$) groups is independently ethylene or propylene; $R^3$ is hydrogen, or a linear or branched alkyl group having from 1 to about 6 carbon atoms; $R^4$ is a linear or branched alkylene having from 1 to about 6 carbon atoms, m and n are independently integers from 0 to about 7, the sum of m and n is from about 3 to 7, p is an integer from 1 to about 8, x is an average number from 0 to about 30, and y is 0 or 1. Most preferably, $R^1$ is a linear or branched alkyl group having from about 8 to about 18 carbon atoms; $R^2$ in each of the x ($R^2O$) groups is independently ethylene or propylene; $R^3$ is hydrogen or methyl; m and n are independently integers from 0 to about 7, the sum of m and n is from about 3 to 7, p is an integer from 1 to about 8, x is an average number from 0 to about 30, and y is 0.

(g) di-poly(hydroxyalkyl)amine having the formula:

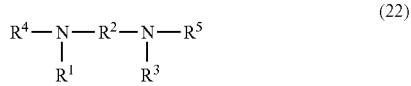

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and $R^4$ and $R^5$ are independently hydroxyalkyl, polyhydroxyalkyl, or poly(hydroxyalkyl)alkyl. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, the di-poly(hydroxyalkyl)amine has the formula:

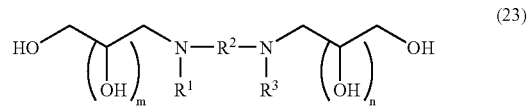

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and m and n are independently integers from 1 to about 8. In this context, preferred $R^1$, $R^2$, and $R^3$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^3$ are independently hydrogen or a linear or branched alkyl group having from 1 to about 18 carbon atoms, $R^2$ is a linear or branched alkylene or linear or branched alkenylene group having from 2 to about 18 carbon atoms, and m and n are independently integers from 1 to about 8. More preferably, $R^1$ and $R^3$ are independently hydrogen or a linear or branched alkyl group having from 6 to about 12 carbon atoms, $R^2$ is a linear or branched alkylene group having from 2 to about 6 carbon atoms, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 16 carbon atoms, and m and n are independently integers from about 4 to about 8. Most preferably, $R^1$ and $R^3$ are independently hydrogen or a linear or branched alkyl group having from 6 to about 12 carbon atoms, $R^2$ is ethylene or propylene, and m and n are independently integers from about 4 to about 8; or $R^1$ and $R^3$ are independently hydrogen or a linear or branched alkyl group having from 1 to about 4 carbon atoms, $R^2$ is a linear or branched alkylene group having from 2 to about 12 carbon atoms, and m and n are independently integers from about 4 to about 8.

(h) quaternary poly(hydroxyalkyl)amine salts having the formula:

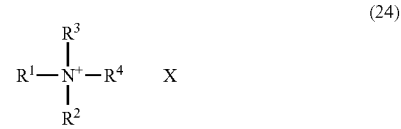

wherein $R^1$ is hydrocarbyl or substituted hydrocarbyl having from about 4 to about 30 carbon atoms or $-X_m-(R^4O)_yR^5$, $R^2$ and $R^3$ are independently hydrogen or hydrocarbyl or substituted hydrocarbyl having from 1 to about 30 carbon atoms, $R^4$ is hydroxyalkyl, polyhydroxyalkyl, or poly(hydroxyalkyl)alkyl, X- is an agriculturally acceptable anion; $R^4$ in each of the y($R^4O$) groups is independently $C_2-C_4$ alkylene; $R^5$ is hydrogen or a linear or branched alkyl group having 1 to about 4 carbon atoms; X is hydrocarbylene or substituted hydrocarbylene having from 2 to about 18 carbon toms; m is 0 or 1; and y is an average number from 0 to about 30. In this context, preferred $R^1$, $R^2$, and $R^3$ hydrocarbyl groups are linear or branched alkyl, linear or branched alkenyl, linear or branched alkynyl, aryl, or aralkyl groups. Preferably, the quaternary poly(hydroxyalkyl) amine salts have the formula:

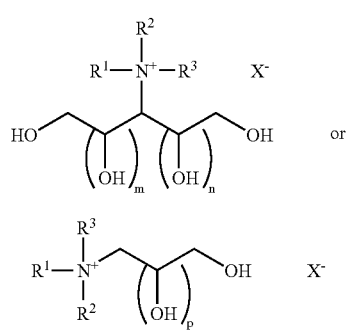

(25)

(26)

wherein $R^1$ is hydrocarbyl or substituted hydrocarbyl having from about 4 to about 30 carbon atoms, $R^2$ and $R^3$ are independently hydrogen or hydrocarbyl or substituted hydrocarbyl having from 1 to about 30 carbon atoms, m and n are independently integers from 0 to about 7, the sum of m and n is not greater than about 7, p is an integer from 1 to about 8, and X- is an agriculturally acceptable anion. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ and $R^3$ are independently hydrogen or a linear or branched alkyl or linear or branched alkenyl group having from 1 to about 30 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 30 carbon atoms, m and n are independently integers from 0 to about 7, the sum of m and n is not greater than about 7, and p is an integer from about 4 to about 8. More preferably, $R^1$ is a linear or branched alkyl or linear or branched alkenyl group having from about 8 to about 22 carbon atoms, $R^2$ and $R^3$ are independently hydrogen or a linear or branched alkyl or linear or branched alkenyl group having from 1 to about 6 carbon atoms, m and n are independently integers from 0 to about 7, the sum of m and n is from about 3 to 7, and p is an integer from about 4 to about 8; or $R^1$, $R^2$ and $R^3$ are independently linear or branched alkyl or linear or branched alkenyl groups having from about 4 to about 8 carbon atoms, m and n are independently integers from 0 to about 7, the sum of m and n is from about 3 to 7, and p is an integer from about 4 to about 8. Even more preferably, $R^1$ is a linear or branched alkyl group having from about 8 to about 18 carbon atoms, $R^2$ and $R^3$ are independently hydrogen or methyl, m and n are independently integers from 0 to about 4, the sum of m and n is about 4, and p is an integer of about 4. Most preferably, $R^1$ is a linear or branched alkyl group having from about 8 to about 18 carbon atoms, $R^2$ and $R^3$ are methyl, m and n are independently integers from 0 to about 4, the sum of m and n is about 4, and p is an integer of about 4.

(i) triamines having the formula:

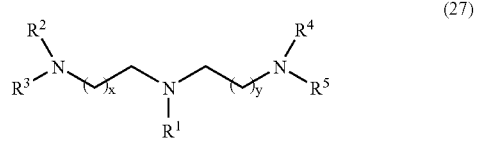

(27)

wherein $R^1$ is hydrocarbyl or substituted hydrocarbyl having from 1 to about 30 carbon atoms; $R^2$, $R^3$, $R^4$ and $R^5$ are independently hydrogen, hydrocarbyl or substituted hydrocarbyl having from 1 to about 30 carbon atoms, or —$(R^8)_s$ $(R^7O)_nR^6$; $R^6$ is hydrogen or a linear or branched alkyl group having from 1 to about 4 carbon atoms, $R^7$ in each of the n $(R^7O)$ groups is independently $C_2$–$C_4$ alkylene; $R^8$ is hydrocarbylene or substituted hydrocarbylene having from 1 to about 6 carbon atoms, n is an average number from 1 to about 10, s is 0 or 1, and x and y are independently an integer from 1 to about 4. In this context, preferred $R^1$, $R^2$, $R^3$, $R^4$, $R^5$, and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl groups having from about 8 to about 30 carbon atoms, $R^2$, $R^3$, $R^4$ and $R^5$ are independently hydrogen, a linear or branched alkyl or linear or branched alkenyl group having from 1 to about 30 carbon atoms, or —$(R^7O)_nR^6$, $R^6$ is hydrogen, methyl or ethyl; $R^7$ in each of the n $(R^7O)$ groups is independently $C_2$–$C_4$ alkylene, n is an average number from 1 to about 10, and x and y are independently an integer from 1 to about 4. More preferably, $R^1$ is a linear or branched alkyl group having from about 8 to about 18 carbon atoms, $R^2$, $R^3$, $R^4$ and $R^5$ are independently hydrogen, a linear or branched alkyl group having from 1 to about 6 carbon atoms, or —$(R^7O)_nR^6$, $R^6$ is hydrogen or methyl, $R^7$ in each of the n $(R^7O)$ groups is independently ethylene or propylene, n is an average number from 1 to about 5, and x and y are independently an integer from 1 to about 4. Most preferably, $R^1$ is a linear or branched alkyl group having from about 8 to about 18 carbon atoms, $R^2$, $R^3$, $R^4$ and $R^5$ are independently hydrogen, or —$(R^7O)_nR^6$, $R^6$ is hydrogen, $R^7$ in each of the n $(R^7O)$ groups is independently ethylene or propylene, n is an average number from 1 to about 5, and x and y are independently an integer from 1 to about 4. Commercially available triamines include Acros and Clariant Genamin 3119.

(j) diamines having the formula:

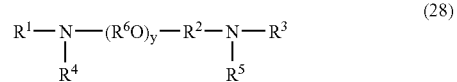

(28)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $C(=NR^{11})NR^{12}R^{13}$—, —$C(=O)$ $NR^{12}R^{13}$—, —$C(=S)NR^{12}R^{13}$—, —$C(=NR^{12})$—, —C(S)—, or —C(O)—, $R^6$ in each of the x ($R^6O$) and y ($R^6O$) groups is independently $C_2$–$C_4$ alkylene, $R^7$ is hydrogen, or a linear or branched alkyl group having from 1 to about 30 carbon atoms, $R^{11}$ $R^{12}$ and $R^{13}$ are hydrogen, hydrocarbyl or substituted hydrocarbyl having from 1 to about 30 carbon atoms, x is an average number from 1 to about 50, and y is an average number from 0 to about 60. In this context, preferred $R^1$, $R^2$, $R^3$, $R^4$, and $R^5$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$ and $R^5$ are independently hydrogen or a linear or branched alkyl or linear or branched alkenyl group having from 1 to about 22 carbon atoms or —$(R^6O)_xR^7$, $R^2$ is a linear or branched alkylene or linear or branched alkenylene group having from 1 to about 6 carbon atoms, $R^6$ in each of the x($R^6O$) and y ($R^6O$) groups is independently $C_2$–$C_4$ alkylene, $R^7$ is hydrogen, or a linear or branched alkyl group having from 1 to about 4 carbon atoms, x is an average number from 1 to about 30, and y is an average number from 0 to about 60. More preferably, $R^1$, $R^3$, $R^4$ and $R^5$ are independently hydrogen or a linear or branched alkyl group having from about 1 to about 18 carbon atoms or —$(R^6O)_xR^7$, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 15, and y is an average number from 0 to about 60. Most preferably, $R^1$ and $R^3$ are independently linear or branched alkyl groups having from about 8 to about 18 carbon atoms and $R^4$ and $R^5$ are independently hydrogen, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 0 to about 50.

(k) mono- or di-quaternary ammonium salts having the formula:

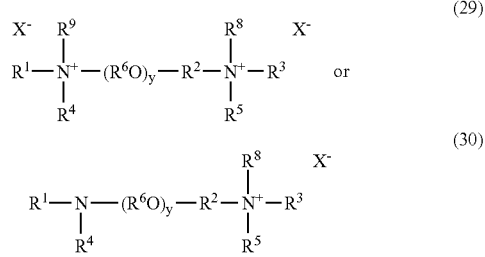

wherein $R^1$, $R^3$, $R^4$, $R^5$, $R^8$ and $R^9$ are independently hydrogen, polyhydroxyalkyl, hydrocarbyl or substituted hydrocarbyl having from 1 to about 30 carbon atoms, or —$(R^6O)_xR^7$, $R^2$ is hydrocarbylene or substituted hydrocarbylene having from 2 to about 30 carbon atoms, $R^6$ in each of the x ($R^6O$) and y ($R^6O$) groups is independently $C_2$–$C_4$ alkylene, $R^7$ is hydrogen, or a linear or branched alkyl group having from 1 to about 4 carbon atoms, x is an average number from 1 to about 30, y is an average number from about 3 to about 60, and $X^-$ is an agriculturally acceptable anion. In this context, preferred $R^1$, $R^2$, $R^3$, $R^4$, $R^5$, $R^8$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^3$, $R^4$, $R^5$, $R^8$ and $R^9$ are independently hydrogen or a linear or branched alkyl or alkenyl group having from about 1 to about 22 carbon atoms or —$(R^6O)_xR^7$, $R^2$ is a linear or branched alkylene or alkenylene group having from about 1 to about 6 carbon atoms, $R^6$ in each of the x($R^6O$) and y ($R^6O$) groups is independently $C_2$–$C_4$ alkylene, $R^7$ is hydrogen, or a linear or branched alkyl group having from 1 to about 4 carbon atoms, x is an average number from 1 to about 30, and y is an average number from 1 to about 60. More preferably, $R^1$, $R^3$, $R^4$, $R^5$, $R^8$ and $R^9$ are independently hydrogen or a linear or branched alkyl group having from about 1 to about 18 carbon atoms or —$(R^6O)_xR^7$, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 1 to about 60. Most preferably, $R^1$ and $R^3$ are independently linear or branched alkyl groups having from about 8 to about 18 carbon atoms and $R^4$, $R^5$, $R^8$ and $R^9$ are independently hydrogen or methyl, $R^2$ is a linear or branched alkylene group having from about 1 to about 6 carbon atoms, $R^6$ in each of the x ($R^6O$) and y ($R^6O$) groups is independently ethylene or propylene, $R^7$ is hydrogen, or a linear or branched alkyl group having from 1 to about 4 carbon atoms, x is an average number from 1 to about 10, and y is an average number from 10 to about 50.

(l) a secondary or tertiary amine having the formula:

$$R^1-N\genfrac{}{}{0pt}{}{R^2}{R^3} \qquad (31)$$

wherein $R^1$ and $R^2$ are hydrocarbyl having from 1 to about 30 carbon atoms, and $R^3$ is hydrogen or hydrocarbyl having from 1 to about 30 carbon atoms. In this context, preferred $R^1$, $R^2$, and $R^3$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$ and $R^3$ are independently hydrogen or a linear or branched alkyl or linear or branched alkenyl group having from 1 to about 6 carbon atoms. More preferably, $R^1$ is a linear or branched alkyl group having from about 12 to about 22 carbon atoms, and $R^2$ and $R^3$ are independently hydrogen, methyl or ethyl. In one embodiment of the amine of formula (27), $R^1$ is a linear or branched alkyl group having from about 12 to about 22 carbon atoms, and $R^2$ and $R^3$ are independently linear or branched hydroxyalkyl groups having from 1 to about 6 carbon atoms.

In one embodiment, the surfactant has the formula (31) wherein $R^1$ is hydrocarbyl or substituted hydrocarbyl having from about 8 to about 30 carbon atoms, $R^2$ is a hydroxyalkyl, polyhydroxyalkyl or poly(hydroxyalkyl)alkyl group, and $R^3$ is hydrogen, hydroxyalkyl, polyhydroxyalkyl or poly(hydroxyalkyl)alkyl. In this context, preferred $R^1$ hydrocarbyl groups are linear or branched alkyl, linear or branched alkenyl, linear or branched alkynyl, aryl, or aralkyl groups. In one embodiment, $R^1$ is a linear or branched alkyl, linear or branched alkenyl, linear or branched alkynyl, aryl, or aralkyl group having from about 8 to about 30 carbon atoms, $R^2$ is a linear or branched hydroxyalkyl group having from 1 to about 6 carbon atoms, and $R^3$ is hydrogen or a linear or branched hydroxyalkyl group having from 1 to about 6 carbon atoms. Preferably, $R^1$ is a linear or branched alkyl, linear or branched alkenyl, linear or branched alkynyl, aryl, or aralkyl group having from about 8 to about 22 carbon atoms, $R^2$ is a linear or branched hydroxyalkyl group having from 1 to about 4 carbon atoms, and $R^3$ is hydrogen or a linear or branched hydroxyalkyl group having from 1 to about 4 carbon atoms. More preferably, $R^1$ is a linear or branched alkyl, linear or branched alkenyl, linear or branched alkynyl, aryl, or aralkyl group having from about 8 to about 18 carbon atoms, $R^2$ is hydroxymethyl or hydroxyethyl, and $R^3$ is hydrogen, hydroxymethyl or hydroxyethyl.

(m) monoalkylated amines having the formula:

(32)

wherein $R^1$ and $R^4$ are independently hydrocarbyl or substituted hydrocarbyl groups having from 1 to about 30 carbon atoms or —$R^5SR^6$, $R^2$ in each of the x ($R^2O$) groups is independently $C_2$–$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60. In this context, preferred $R^1$, $R^4$, and $R^6$ hydrocarbyl groups are linear or branched alkyl, linear or branched alkenyl, linear or branched alkynyl, aryl, or aralkyl groups. In one embodiment, $R^1$ includes from about 7 to about 30 carbon atoms, preferably from about 8 to about 22 carbon atoms, and the remaining groups are as described above. Preferably, $R^1$ and $R^4$ are independently a linear or branched alkyl or linear or branched alkenyl group having from 1 to about 25 carbon atoms, $R^2$ in each of the x ($R^2O$) groups is independently $C_2$–$C_4$ alkylene, $R^3$ is hydrogen, methyl or ethyl, and x is an average number from 1 to about 40. More preferably, $R^1$ and $R^4$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) groups is independently ethylene or propylene, $R^3$ is hydrogen or methyl, and x is an average number from about 1 to about 10. Most preferably, $R^1$ is a linear or branched alkyl group having from about 16 to about 22 carbon atoms and $R^4$ is methyl, $R^2$ in each of the x ($R^2O$) groups is ethylene, $R^3$ is hydrogen, and x is an average number from about 1 to about 5, or $R^1$ is a linear or branched alkyl group having from about 8 to about 15 carbon atoms and $R^4$ is methyl, $R^2$ in each of the x ($R^2O$) groups is ethylene, $R^3$ is hydrogen, and x is an average number from about 5 to about 10.

(n) dialkoxylated quaternary ammonium salts having the formula:

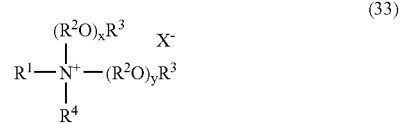

(33)

wherein $R^1$ is hydrocarbyl or substituted hydrocarbyl having from 1 to about 30 carbon atoms, $R^2$ in each of the x ($R^2O$) and y ($R^2O$) groups is independently $C_2$–$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X- is an agriculturally acceptable anion. In this context, preferred $R^1$ and $R^4$ hydrocarbyl groups are linear or branched alkyl, linear or branched alkenyl, linear or branched alkynyl, aryl, or aralkyl groups. Preferably, $R^1$ and $R^4$ are independently a linear or branched alkyl or linear or branched alkenyl group having from 1 to about 25 carbon atoms, $R^2$ in each of the x ($R^2O$) and y ($R^2O$) groups is independently $C_2$–$C_4$ alkylene, $R^3$ is hydrogen, methyl or ethyl, and the sum of x and y is an average number from about 2 to about 30. More preferably, $R^1$ and $R^4$ are independently a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x any y is an average number from about 2 to about 20. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) and y ($R^2O$) groups is independently ethylene or propylene, $R^3$ is hydrogen or methyl, and x is an average number from about 2 to about 20. Most preferably, $R^1$ is a linear or branched alkyl group having from about 8 to about 22 carbon atoms and $R^4$ is a linear or branched alkyl group having from 1 to about 6 carbon atoms, $R^2$ in each of the x ($R^2O$) and y ($R^2O$) groups is independently ethylene or propylene, $R^3$ is hydrogen or methyl, and x is an average number from about 2 to about 15, or $R^1$ and $R^4$ are independently a linear or branched alkyl group having from about 8 to about 22 carbon atoms, $R^2$ in each of the x ($R^2O$) and y ($R^2O$) groups is independently ethylene or propylene, $R^3$ is hydrogen or methyl, and x is an average number from about 5 to about 15. Preferred dialkoxylated quaternary ammonium surfactants include Ethoquad™ C12 (a PEG 2 coco methyl ammonium chloride from Akzo Nobel), Ethoquad™ C15 (a PEG 5 tallow ammonium chloride from Akzo Nobel), Ethoquad™ T25 (a PEG 15 tallow methyl ammonium chloride from Akzo Nobel), PEG 5 coco methyl ammonium chloride, PEG 5 tallow methyl ammonium chloride, PEG 5 ditallow ammonium bromide, PEG 10 ditallow ammonium bromide, di-dodecyl diEO 10 ammonium bromide, di-coco di EO (15) ammonium chloride, di-dodecyl di EO (15) ammonium chloride, di-dodecyl di EO (10) ammonium bromide, dialkyl (tallow and stearyl) di EO (19.6) ammonium bromide, polypropylene glycol-40 diethyl ammonium chloride (Emcol CC-42 from CK Witco), polypropylene glycol-55 diethyl ammonium chloride (Emcol CC-55 from CK Witco) and tallow methyl EO (8) ammonium chloride.

(o) monoalkoxylated quaternary ammonium salts having the formula:

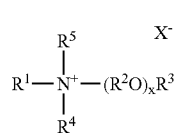

(34)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2O$) groups is independently $C_2$–$C_4$ alkylene, $R^3$ is hydrogen, or a linear or branched alkyl group having from 1 to about 30 carbon atoms, x is an average number from 1 to about 60, and X- is an agriculturally acceptable anion. In this context, preferred $R^1$, $R^4$, and $R^5$ hydrocarbyl groups are linear or branched alkyl, linear or branched alkenyl, linear or branched alkynyl, aryl, or aralkyl groups. Preferably, $R^1$, $R^4$ and $R^5$ are independently a linear or branched alkyl or linear or branched alkenyl group having from 1 to about 25 carbon atoms, $R^2$ in each of the x ($R^2O$) groups is independently $C_2$–$C_4$ alkylene, $R^3$ is hydrogen, methyl or ethyl, and x is an average number from 1 to about 40. More preferably, $R^1$, $R^4$ and $R^5$ are independently a linear or branched alkyl group having from 1 to about 22 carbon atoms, $R^2$ in each of the x ($R^2O$) groups is independently ethylene or propylene, $R^3$ is hydrogen or methyl, and x is an average number from 1 to about 30. Even more preferably, $R^1$ is a linear or branched alkyl group having from about 8 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 22 carbon atoms, and x is an average number from 1 to about 30. Even more preferably, $R^1$ is a linear or branched alkyl group having from about 8 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 6 carbon atoms, and x is an average number from about 5 to about 25. Most preferably, $R^1$ is a linear or branched alkyl group having from about 16 to about 22 carbon atoms, $R^2$ in each of the x ($R^2O$) groups is independently ethylene or propylene, $R^3$ is hydrogen or methyl, $R^4$ and $R^5$ are independently a linear or branched alkyl group having from 1 to about 3 carbon atoms, and x is an average number from about 5 to about 25. Preferred monoalkoxylated quaternary ammonium surfactants include PEG 7 $C_{18}$ dimethyl ammonium chloride and PEG 22 $C_{18}$ dimethyl ammonium chloride.

(p) quaternary ammonium salts having the formula:

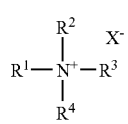

(35)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X- is an agriculturally acceptable anion. In this context, preferred $R^1$, $R^2$, $R^3$, and $R^4$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, and $R^2$, $R^3$ and $R^4$ are independently a linear or branched alkyl or linear or branched alkenyl group having from 1 to about 30 carbon atoms. More preferably, $R^1$ is a linear or branched alkyl or linear or branched alkenyl group having from about 8 to about 22 carbon atoms, and $R^2$, $R^3$ and $R^4$ are independently a linear or branched alkyl or linear or branched alkenyl group having from 1 to about 6 carbon atoms. Even more preferably, $R^1$ is a linear or branched alkyl group having from about 8 to about 16 carbon atoms, and $R^2$, $R^3$ and $R^4$ are independently a linear or branched alkyl group having from 1 to about 6 carbon atoms. Most preferably, $R^1$ is a linear or branched alkyl group having from about 8 to about 14 carbon atoms, and $R^2$, $R^3$ and $R^4$ are methyl. Preferred commercially available quaternary ammonium surfactants include Arquad™ C-50 (a dodecyl trimethyl ammonium chloride from Akzo Nobel) and Arquad™ T-50 (a tallow trimethyl ammonium chloride from Akzo Nobel).

(q) etheramines having the formula:

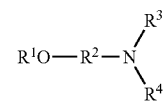

(36)

wherein $R^1$ is hydrocarbyl or substituted hydrocarbyl having from 1 to about 30 carbon atoms; $R^2$ is hydrocarbylene or substituted hydrocarbylene having from 2 to about 30 carbon atoms; $R^3$ and $R^4$ are independently hydrogen, hydrocarbyl or substituted hydrocarbyl having from 1 to about 30 carbon atoms, or —($R^5O$)$_x$$R^6$, $R^5$ in each of the x($R^5$—O) groups is independently $C_2$–$C_4$ alkylene, $R^6$ is hydrogen, or a linear or branched alkyl group having from 1 to about 4 carbon atoms, and x is an average number from 1 to about 50. In this context, preferred $R^1$, $R^2$, $R^3$, and $R^4$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl, linear or branched alkenyl, linear or branched alkynyl, aryl, or aralkyl group having from 8 to about 25 carbon atoms, $R^2$ is a linear or branched alkylene or alkenylene group having from 2 to about 30 carbon atoms, $R^3$ and $R^4$ are independently hydrogen, a linear or branched alkyl, linear or branched alkenyl, linear or branched alkynyl, aryl, or aralkyl group having from 1 to about 30 carbon atoms, or —($R^5O$)$_x$ $R^6$, $R^5$ in each of the x ($R^5O$) groups is independently $C_2$–$C_4$ alkylene, $R^6$ is hydrogen, methyl or ethyl, and x is an average number from 1 to about 30. More preferably, $R^1$ is a linear or branched alkyl or alkenyl group having from 8 to about 22 carbon atoms, $R^2$ is a linear or branched alkylene or alkenylene group having from 2 to about 6 carbon atoms, $R^3$ and $R^4$ are independently hydrogen, a linear or branched alkyl or alkenyl group having from 1 to about 6 carbon atoms, or —($R^5O$)$_x$$R^6$, $R^5$ in each of the x ($R^5O$) groups is independently ethylene or propylene, $R^6$ is hydrogen or methyl, and x is an average number from 1 to about 15. Most preferably, $R^1$ is a linear or branched alkyl or alkenyl group having from 8 to about 18 carbon atoms, $R^2$ is ethylene or propylene, $R^3$ and $R^4$ are independently hydrogen, methyl, or $—(R^5O)_xR^6$, $R^5$ in each of the x ($R^5O$) groups is independently ethylene or propylene, $R^6$ is hydrogen, and x is an average number from 1 to about 5.

(r) diamines having the formula:

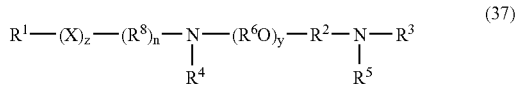

(37)

wherein $R^1$, $R^3$, $R^4$ and $R^5$ are independently hydrogen, hydrocarbyl or substituted hydrocarbyl having from 1 to about 30 carbon atoms, or $—(R^6O)_xR^7$; $R^2$ and $R^8$ are independently hydrocarbylene or substituted hydrocarbylene having from 2 to about 30 carbon atoms, $R^6$ in each of the x ($R^6O$) and y ($R^6O$) groups is independently $C_2$–$C_4$ alkylene, $R^7$ is hydrogen, or a linear or branched alkyl group having from 1 to about 30 carbon atoms, x is an average number from 1 to about 30, X is $—O—$, $—N(R^6)—$, $—C(O)—$, $—C(O)O—$, $—OC(O)—$, $—N(R^9)C(O)—$, $—C(O)N(R^9)—$, $—S—$, $—SO—$, or $—SO_2—$, y is 0 or an average number from 1 to about 30, n and z are independently 0 or 1, and $R^9$ is hydrogen or hydrocarbyl or substituted hydrocarbyl. In this context, preferred $R^1$, $R^2$, $R^3$, $R^4$, $R^5$ and $R^9$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^4$ are independently a linear or branched alkyl or linear or branched alkenyl group having from about 1 to about 22 carbon atoms, $R^2$ and $R^8$ are independently linear or branched alkylene groups having from about 2 to about 25 carbon atoms, $R^3$ and $R^5$ are each independently hydrogen or a linear or branched alkyl group having from 1 to about 6 carbon atoms and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 8 to about 25 carbon atoms, and n, y and z are 0; or $R^1$, $R^2$, $R^3$ and $R^4$ are independently hydrogen or a linear or branched alkyl or alkenyl group having from about 1 to about 6 carbon atoms, $R^2$ is a linear or branched alkylene or alkenylene group having from about 1 to about 6 carbon atoms, $R^6$ in each of the y ($R^6O$) groups is independently $C_2$–$C_4$ alkylene, y is an average number from 1 to about 20 and n and z are 0; or $R^1$ and $R^3$ are independently a linear or branched alkyl or linear or branched alkenyl group having from about 8 to about 22 carbon atoms, $R^2$ is a linear or branched alkylene group having from about 2 to about 25 carbon atoms; and $R^4$ and $R^5$ are each independently hydrogen, a linear or branched alkyl or alkenyl group having from 1 to about 6 carbon atoms, or $—(R^6O)_xR^7$, $R^6$ in each of the x ($R^6O$) groups is independently $C_2$–$C_4$ alkylene, $R^7$ is hydrogen, or a linear or branched alkyl group having from 1 to about 4 carbon atoms, x is an average number from 1 to about 30, and n, y and z are 0; or $R^1$ is a linear or branched alkyl or linear or branched alkenyl group having from about 1 to about 22 carbon atoms, $R^2$ is a linear or branched alkylene group having from about 2 to about 25 carbon atoms, $R^3$, $R^4$ and $R^5$ are each independently hydrogen or a linear or branched alkyl group having from 1 to about 6 carbon atoms, X is $—C(O)—$ or $—SO_2—$, n and y are 0 and z is 1. More preferably, $R^1$ and $R^4$ are independently a linear alkyl or linear or branched alkenyl group having from about 4 to about 18 carbon atoms, $R^2$ is a linear or branched alkylene group having from about 2 to about 6 carbon atoms, $R^3$ and $R^5$ are each independently hydrogen or a linear or branched alkyl group having from 1 to about 6 carbon atoms, and n, y and z are 0; or $R^1$, $R^2$, $R^3$ and $R^4$ are independently hydrogen or a linear or branched alkyl group having from about 1 to about 6 carbon atoms, $R^2$ is a linear or branched alkylene group having from about 8 to about 25 carbon atoms, and y is 0; or $R^1$, $R^2$, $R^3$ and $R^4$ are independently hydrogen or a linear or branched alkyl group having from about 1 to about 6 carbon atoms, $R^2$ is a linear or branched alkylene group having from about 1 to about 6 carbon atoms, $R^6$ in each of the y ($R^6O$) groups is independently ethylene or propylene, y is an average number from 1 to about 10 and n and z is 0; or $R^1$ and $R^3$ are independently a linear or branched alkyl group having from about 8 to about 22 carbon atoms, $R^2$ is a linear or branched alkylene group having from about 2 to about 6 carbon atoms, and $R^4$ and $R^5$ are each independently hydrogen, a linear or branched alkyl group having from 1 to about 6 carbon atoms, or $—(R^6O)_xR^7$, $R^6$ in each of the x ($R^6O$) groups is independently ethylene or propylene, $R^7$ is hydrogen or methyl, x is an average number from 1 to about 15, and n, y and z are 0; or $R^1$ is a linear or branched alkyl group having from about 1 to about 22 carbon atoms, $R^2$ is a linear or branched alkylene group having from about 2 to about 6 carbon atoms, $R^3$, $R^4$ and $R^5$ are each independently hydrogen, X is $—C(O)—$ or $—SO_2—$, n and y are 0 and z is 1. Preferred diamines include Gemini 14-2-14, Gemini 14-3-14, Gemini 10-2-10, Gemini 10-3-10, Gemini 10-4-10, and Gemini 16-2-16 ($C_{10}$, $C_{14}$ or $C_{16}$ ethylene, propylene or butylene N-methyl diamines from Monsanto), Ethoduomeens™, and Jeffamine™ EDR-148.

(s) amine oxides having the formula:

(38)

wherein $R^1$, $R^2$ and $R^3$ are independently hydrogen, hydrocarbyl or substituted hydrocarbyl having from 1 to about 30 carbon atoms, $—(R^4O)_xR^5$, or $—R^6(OR^4)_xOR^5$; $R^4$ in each of the x ($R^4O$) groups is independently $C_2$–$C_4$ alkylene, $R^5$ is hydrogen, or a hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8. In this context, preferred $R^1$, $R^2$, $R^3$, $R^5$ and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ and $R^2$ are independently hydrogen, a linear or branched alkyl or linear or branched alkenyl group having from 1 to about 30 carbon atoms, or $—(R^4O)_xR^5$; $R^3$ is a linear or branched alkyl or linear or branched alkenyl group having from about 8 to about 30 carbon atoms, $R^4$ in each of the x ($R^4O$) groups is independently $C_2$–$C_4$ alkylene; $R^5$ is hydrogen or a linear or branched alkyl or linear or branched alkenyl group having from 1 to about 30 carbon atoms, and x is an average number from 1 to about 30. More preferably, $R^1$ and $R^2$ are independently hydrogen, or a linear or branched alkyl group having from 1 to about 6 carbon atoms, and $R^3$ is a linear or branched alkyl group having from about 8 to about 22 carbon atoms; or $R^1$ and $R^2$ are independently —$(R^4O)_xR^5$, $R^3$ is a linear or branched alkyl group having from about 8 to about 22 carbon atoms, $R^4$ in each of the x $(R^4O)$ groups is ethylene or propylene, $R^5$ is hydrogen or a linear or branched alkyl or linear or branched alkenyl group having from 1 to about 30 carbon atoms, and x is an average number from 1 to about 10. Most preferably, $R^1$ and $R^2$ are independently methyl, and $R^3$ is a linear or branched alkyl group having from about 8 to about 18 carbon atoms; or $R^1$ and $R^2$ are independently —$(R^4O)_xR^5$, $R^3$ is a linear or branched alkyl group having from about 8 to about 18 carbon atoms, $R^4$ in each of the x $(R^4O)$ groups is ethylene or propylene, $R^5$ is hydrogen or an alkyl group having from about 8 to about 18 carbon atoms, and x is an average number from 1 to about 5. Commercially available amine oxide surfactants include Chemoxide L70.

(t) alkoxylated amine oxides having the formula:

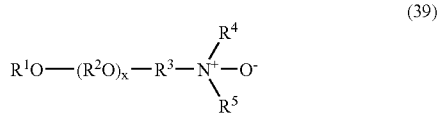

(39)

wherein $R^1$ is hydrogen or hydrocarbyl or substituted hydrocarbyl having from 1 to about 30 carbon atoms; $R^2$ in each of the x $(R^2O)$ and y $(R^2O)$ groups is independently $C_2$–$C_4$ alkylene; $R^3$ is a hydrocarbylene or substituted hydrocarbylene having from 2 to about 6 carbon atoms; $R^4$ and $R^5$ are each independently hydrogen, hydrocarbyl or substituted hydrocarbyl having from 1 to about 30 carbon atoms, —$(R^6)_n$—$(R^2O)_yR^7$; $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60. In this context, preferred $R^1$, $R^4$, $R^5$ and $R^6$ hydrocarbyl (hydrocarbylene) groups include linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x $(R^2O)$ groups is independently $C_2$–$C_4$ alkylene, $R^3$ is a linear or branched alkylene or alkenylene group having from 2 to about 6 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x $(R^2O)$ groups is independently ethylene or propylene, $R^3$ is a linear or branched alkylene or alkenylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x $(R^2O)$ groups is independently ethylene or propylene, $R^3$ is an ethylene, propylene or 2-hydroxypropylene group, $R^4$ and $R^5$ are each independently hydrogen or methyl, and x is an average number from about 4 to about 20. Most preferably, $R^1$ is a linear or branched alkyl group having from about 12 to about 18 carbon atoms, $R^2$ in each of the x $(R^2O)$ groups is independently ethylene or propylene, $R^3$ is an ethylene, propylene, or 2-hydroxypropylene group, $R^4$ and $R^5$ are methyl, and x is an average number from about 4 to about 20.

(u) dialkoxylated amines having the formula:

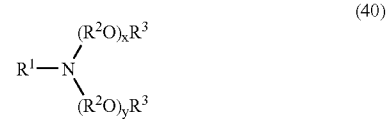

(40)

wherein $R^1$ is hydrogen or hydrocarbyl or substituted hydrocarbyl having from 1 to about 30 carbon atoms, —$R^4SR^5$, or —$(R^2O)_zR^3$, $R^2$ in each of the x $(R^2O)$, y $(R^2O)$ and z $(R^2O)$ groups is independently $C_2$–$C_4$ alkylene, $R^3$ is hydrogen, or a linear or branched alkyl group having from 1 to about 22 carbon atoms, $R^4$ is a linear or branched alkyl group having from about 6 to about 30 carbon atoms, $R^5$ is a linear or branched alkyl group having from about 4 to about 15 carbon atoms, and x, y and z are independently an average number from 1 to about 40. In this context, preferred $R^1$ hydrocarbyl groups are hydrogen, linear or branched alkyl, linear or branched alkenyl, linear or branched alkynyl, aryl, or aralkyl groups. Preferably, $R^1$ is hydrogen, a linear or branched alkynyl, aryl, or aralkyl group having from about 1 to about 30 carbon atoms, $R^2$ in each of the x $(R^2O)$, y $(R^2O)$ and z $(R^2O)$ groups is independently $C_2$–$C_4$ alkylene, $R^3$ is hydrogen, methyl or ethyl, and x and y are independently an average number from 1 to about 20. More preferably, $R^1$ is hydrogen or a linear or branched alkynyl, aryl, or aralkyl group having from about 8 to about 25 carbon atoms, $R^2$ in each of the x $(R^2O)$, y $(R^2O)$ and z $(R^2O)$ groups is independently ethylene or propylene, $R^3$ is hydrogen or methyl, and x and y are independently an average number from 1 to about 30. Even more preferably, $R^1$ is hydrogen or a linear or branched alkynyl, aryl, or aralkyl group having from about 8 to about 22 carbon atoms, $R^2$ in each of the x $(R^2O)$, y $(R^2O)$ and z $(R^2O)$ groups is independently ethylene or propylene, $R^3$ is hydrogen or methyl, and x and y are independently an average number from 1 to about 5. Preferred commercially available dialkoxylated amines include Trymeen™ 6617 (from Cognis), TAM 45, 60, 80 and 105 (from Witco), and Ethomeen™ C/12, C/15, C/20, C/25, T/12, T/15, T/20 and T/25 (from Akzo Nobel).

and (v) aminated alkoxylated alcohols having the following chemical structure:

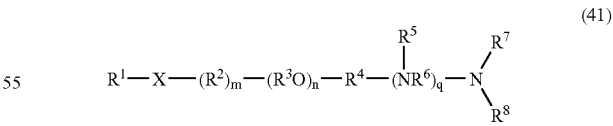

(41)

wherein $R^1$, $R^7$, $R^8$, and $R^9$ are each independently hydrogen, hydrocarbyl or substituted hydrocarbyl having from 1 to about 30 carbon atoms, or —$(R^{11})_s(R^3O)_vR^{10}$; X is —O—, —OC(O)—, —C(O)O—, —N($R^{12}$)C(O)—, —C(O)N($R^{12}$)—, —S—, —SO—, —$SO_2$— or —N($R^9$)—; $R^3$ in each of the n $(R^3O)$ groups and the v $(R^3O)$ groups is independently $C_2$–$C_4$ alkylene; $R^{10}$ is hydrogen, or a linear or branched alkyl group having from 1 to about 30 carbon atoms; n is an average number from 1 to about 60; v is an average number from 1 to about 50; $R^2$ and $R^{11}$ are each independently hydrocarbylene or substituted hydrocarbylene having from 1 to about 6 carbon atoms; $R^4$ is hydrocarbylene or substituted hydrocarbylene having from 2 to about 6 carbon atoms; $R^{12}$ is hydrogen or hydrocarbyl or substituted hydrocarbyl having from 1 to about 30 carbon atoms; m and s are each independently 0 or 1; $R^6$ is hydrocarbylene or substituted hydrocarbylene having from 2 to about 30 carbon atoms, —C(=NR$^{12}$)—, —C(S)—, or —C(O)—; q is an integer from 0 to 5; and $R^5$ is hydrogen or hydrocarbyl or substituted hydrocarbyl having from 1 to about 30 carbon atoms. In this context, preferred $R^1$, $R^2$, $R^4$, $R^5$, $R^6$, $R^7$, $R^8$, $R^9$, $R^{11}$ and $R^{12}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

In one embodiment, any of the amine or quaternary ammonium surfactants as described in sections (a)–(v) above are included in liquid glyphosate concentrates other than IPA glyphosate, such as glyphosate concentrates containing potassium, di-ammonium, ammonium, sodium, monoethanolamine, n-propylamine, methylamine, ethylamine, hexamethylenediamine, dimethylamine, or trimethylsulfonium glyphosate and mixtures thereof, which contain a stabilizer and at least about 30 wt. % glyphosate a.e., more preferably at least about 35%, 40%, 45% or more wt. % a.e., or at least about 360 g a.e. glyphosate per liter, more preferably at least 370, 380, 390, 400, 410, 420, 430, 440 or 450 g a.e./l or more.

A subclass of such cationic surfactants described above includes a monoalkoxylated amine having the formula:

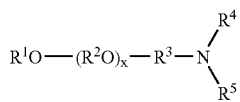
(42)

wherein $R^1$ is hydrogen or hydrocarbyl or substituted hydrocarbyl having from 1 to about 30 carbon atoms; $R^2$ in each of the x ($R^2$O) and y ($R^2$O) groups is independently $C_2$–$C_4$ alkylene; $R^3$ is hydrocarbylene or substituted hydrocarbylene having from 2 to about 30 carbon atoms; $R^4$ and $R^5$ are each independently hydrogen, hydrocarbyl or substituted hydrocarbyl having from 1 to about 30 carbon atoms, —($R^6$)$_n$—($R^2$O)$_y$$R^7$, or $R^4$ and $R^5$, together with the nitrogen atom to which they are attached, form a cyclic or heterocyclic ring; $R^6$ is hydrocarbylene or substituted hydrocarbylene having from 1 to about 30 carbon atoms; $R^7$ is hydrogen or a linear or branched alkyl group having 1 to about 4 carbon atoms, n is 0 or 1, x and y are independently an average number from 1 to about 60. In this context, preferred $R^1$, $R^3$, $R^4$, $R^5$, and $R^6$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$ is a linear or branched alkyl or linear or branched alkenyl group having from about 8 to about 25 carbon atoms, $R^2$ in each of the x ($R^2$O) groups is independently $C_2$–$C_4$ alkylene, $R^3$ is a linear or branched alkylene group having from 2 to about 20 carbon atoms, $R^4$ and $R^5$ are each independently hydrogen or a linear or branched alkyl group having from 1 to about 6 carbon atoms, and x is an average number from 1 to about 30. More preferably, $R^1$ is a linear or branched alkyl group having from about 12 to about 22 carbon atoms, $R^2$ in each of the x ($R^2$O) groups is independently ethylene or propylene, $R^3$ is a linear or branched alkylene group having from 2 to about 6 carbon atoms, $R^4$ and $R^5$ are each independently hydrogen, methyl, or tris(hydroxymethyl)methyl, and x is an average number from about 2 to about 30. Even more preferably, $R^1$ is a linear or branched alkyl group having from about 12 to about 18 carbon atoms, $R^2$ in each of the x ($R^2$O) groups is independently ethylene or propylene, $R^3$ is ethylene or propylene, $R^4$ and $R^1$ are each independently hydrogen, methyl or tris(hydroxymethyl)methyl, and x is an average number from about 4 to about 20. Most preferably, $R^1$ is a linear or branched alkyl group having from about 12 to about 18 carbon atoms, $R^2$ in each of the x ($R^2$O) groups is independently ethylene or propylene, $R^3$ is ethylene, $R^4$ and $R^5$ are methyl, and x is an average number from about 4 to about 20. Preferred monoalkoxylated amines include PEG 13 or 18 $C_{14-15}$ ether propylamines and PEG 7, 10, 15 or 20 $C_{15-16}$ ether propylamines (from Tomah) and PEG 13 or 18 $C_{14-15}$ ether dimethyl propylamines and PEG 10, 15 or 20 or 25 $C_{16-18}$ ether dimethyl propylamines (from Tomah) and Surfonic™ AGM-550 from Huntsman.

Quaternary ammonium, sulfonium and sulfoxonium salts are also effective cationic surfactants in forming potassium glyphosate concentrates and have a chemical structure:

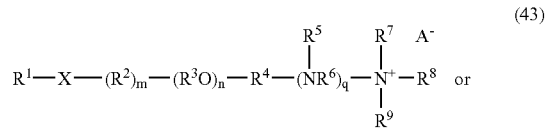
(43)

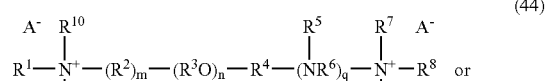
(44)

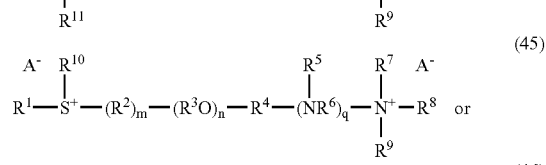
(45)

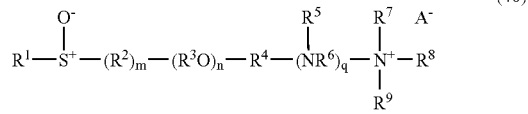
(46)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or —($R^{13}$)$_s$($R^3$O)$_v$$R^{12}$; X is —O—, —OC(O)—, —N($R^{14}$)C(O)—, —C(O)N($R^{14}$)—, —C(O)O—, or —S—; $R^3$ in each of the n ($R^3$O) groups and v ($R^3$O) groups is independently $C_2$–$C_4$ alkylene; $R^{12}$ is hydrogen, or a linear or branched alkyl group having from 1 to about 30 carbon atoms; n is an average number from 1 to about 60; v is an average number from 1 to about 50; $R^2$ and $R^{13}$ are each independently hydrocarbylene or substituted hydrocarbylene having from 1 to about 6 carbon atoms; m and s are each independently 0 or 1; $R^4$ is hydrocarbylene or substituted hydrocarbylene having from 2 to about 6 carbon atoms; $R^6$ is hydrocarbylene or substituted hydrocarbylene having from 2 to about 30 carbon atoms, —C(=NR$^{12}$)—, —C(S)—, or C(O)—; $R^{14}$ is hydrogen or hydrocarbyl or substituted hydrocarbyl having from 1 to about 30 carbon atoms, q is an integer from 0 to 5; $R^5$ is hydrogen or hydrocarbyl or substituted hydrocarbyl having from 1 to about 30 carbon atoms; and each A is an agriculturally acceptable anion. In this context, preferred $R^1$, $R^2$, $R^4$, $R^5$, $R^6$, $R^7$, $R^8$, $R^9$, $R^{10}$, $R^{11}$, $R^{13}$, and $R^{14}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups.

Another cationic surfactant effective in the formulations of the invention is a diamine or diammonium salt having the formula:

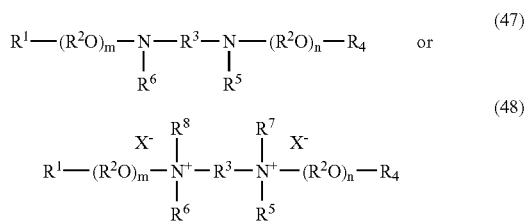

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m $(R^2O)$ and n $(R^2O)$ groups and $R^9$ are independently $C_2$–$C_4$ alkylene, $R^3$ is hydrocarbylene or substituted hydrocarbylene having from about 2 to about 6 carbon atoms or $-(R^2O)_p R_9-$, m and n are individually an average number from 0 to about 50, and p is an average number from 0 to about 60. In this context, preferred $R^1$, $R^3$, $R^4$, $R^5$, $R$, $R^7$ and $R^8$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. In one embodiment of formula (44), $R^3$ is hydrocarbylene having from about 2 to about 6 carbon atoms, and the remaining groups are as defined above.

Some preferred cationic surfactants include alkylamine ethoxylates (including etheramines and diamines) such as tallowamine ethoxylate, cocoa mine ethoxylate, etheramine ethoxylate, tallow ethylenediamine ethoxylate and amidoamine ethoxylates; alkylamine quaternary amines such as alkoxylated quaternary amines (e.g., ethoxylated quaternary amines or propoxylated quaternary amines); alkylamine acetates such as tallowamine acetate or octylamine acetate; and amine oxides such as ethoxylated amine oxides (e.g., N,N-bis(2-hydroxyethyl) cocoamine-oxide), nonethoxylated amine oxides (e.g., cethyldimethylamine-oxide) and amidoamine oxides.

Preferred cationic surfactants include amines and quaternary amines substituted with alkoxy groups containing between about 2 and 15 ethoxy and/or propoxy units, and $C_{12-18}$ alkyl groups. More preferred are $C_{12-18}$ dialkoxylated amines and quaternary amines. Still more preferred are diethoxylated tallow amines containing between about 4 and about 15 units of ethoxylation, and PEG 2 to 20 tallow ammonium chlorides optionally including a methyl group. Most preferred commercially available dialkoxylated amines include Trymeen™ 6617 (from Cognis), TAM 45, 60, 80 and 105 (from Witco), and Ethomeen™ C/12, C/15, C/20, C/25, T/12, T/15, T/20 and T/25 (from Akzo Nobel). Most preferred dialkoxylated quaternary ammonium surfactants include Ethoquad™ C12, C15, T25 (from Akzo Nobel), and Emcol CC42 and CC-55 (from CK Witco). Other suitable cationic surfactants may be determined by those skilled in the art by routine experimentation.

The compositions of the invention are stable at glyphosate a.e.:cationic surfactant loadings, on a weight percent basis, of about 1:2 to about 200:1. High glyphosate:cationic surfactant loadings are generally limited by herbicidal efficacy considerations rather than composition stability because sufficient surfactant must be present for adequate glyphosate activation. High surfactant loading generally requires the inclusion of a stabilizer at a preferred ratio of cationic surfactant:stabilizer between about 1:100 and about 100:1.

Nonionic surfactants suitable for use in formulating the herbicidal compositions and concentrates of the invention include:

(a) alkoxylated alcohols having the formula:

wherein $R^1$ is hydrocarbyl or substituted hydrocarbyl having from 1 to about 30 carbon atoms, $R^2$ in each of the x $(R^2O)$ groups is independently $C_2$–$C_4$ alkylene, $R^3$ is hydrogen, or a linear or branched alkyl group having from 1 to about 4 carbon atoms, and x is an average number from 1 to about 60. In this context, preferred $R^1$ hydrocarbyl groups are linear or branched alkyl, linear or branched alkenyl, linear or branched alkynyl, aryl, or aralkyl groups. Preferably, $R^1$ is a linear or branched alkyl or linear or branched alkenyl group having from about 8 to about 30 carbon atoms, $R^2$ in each of the x $(R^2O)$ groups is independently $C_2$–$C_4$ alkylene, $R^3$ is hydrogen, methyl or ethyl, and x is an average number from about 5 to about 50. More preferably, $R^1$ is a linear or branched alkyl group having from about 8 to about 25 carbon atoms, $R^2$ in each of the x $(R^2O)$ groups is independently ethylene or propylene, $R^3$ is hydrogen or methyl, and x is an average number from about 8 to about 40. Even more preferably, $R^1$ is a linear or branched alkyl group having from about 12 to about 22 carbon atoms, R in each of the x $(R^2O)$ groups is independently ethylene or propylene, $R^3$ is hydrogen or methyl, and x is an average number from about 8 to about 30. Preferred commercially available alkoxylated alcohols include: Emulgin™, L, Procol™ LA-15 (from Protameen); Brij™ 35, Brij™ 56, Brij™ 76, Brij™ 78, Brij™ 97, Brij™ 98 and Tergitol™ XD (from Sigma Chemical Co.); Neodol™ 25-12 and Neodol™ 45-13 (from Shell); hetoxol™ CA-10, hetoxol™ CA-20, hetoxol™ CS-9, hetoxol™ CS-15, hetoxol™ CS-20, hetoxol™ CS-25, hetoxol™ CS-30, Plurafac™ A38 and Plurafac™ LF700 (from BASF); ST-8303 (from Cognis); Arosurf™ 66 E10 and Arosurf™ 66 E20 (from Witco/Crompton); ethoxylated (9.4 EO) tallow, propoxylated (4.4 EO) tallow and alkoxylated (5–16 EO and 2–5 PO) tallow (from Witco/Crompton).

(b) dialkoxylated alcohols having the formula:

wherein $R^1$ is independently hydrogen, or a linear or branched alkyl group having from 1 to about 4 carbon atoms, $R^2$ in each of the x $(R^2O)$ and the y $(R^2O)$ groups is independently $C_2$–$C_4$ alkylene, $R^3$ is hydrocarbylene or substituted hydrocarbylene having from 2 to about 30 carbon atoms, and x and y are independently an average number from 1 to about 60. In this context, preferred $R^3$ hydrocarbylene groups are linear or branched alkylene, linear or branched alkenylene, linear or branched alkynylene, arylene, or aralkylene groups. Preferably, $R^1$ is hydrogen, methyl or ethyl, $R^2$ in each of the x $(R^2O)$ and the y $(R^2O)$ groups is independently $C_2$–$C_4$ alkylene, $R^3$ is a linear or branched alkylene or linear or branched alkenylene group having from about 8 to about 25 carbon atoms, and x and y are independently an average number from about 1 to about 20. More preferably, $R^1$ is hydrogen or methyl, $R^2$ in each of the x ($R^2O$) and the y ($R^2O$) groups is independently ethylene or propylene, $R^3$ is a linear or branched alkylene or linear or branched alkenylene group having from about 8 to about 18 carbon atoms, and x and y are independently an average number from 1 to about 10. Even more preferably, $R^1$ is hydrogen, $R^2$ in each of the x ($R^2O$) and the y ($R^2O$) groups is independently ethylene or propylene, $R^3$ is a linear or branched alkylene group having from about 8 to about 18 carbon atoms, and x and y are independently an average number from 1 to about 5.

(c) alkoxylated dialkylphenols having the formula:

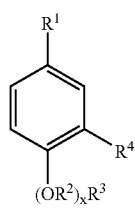

(51)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x ($R^2O$) groups is independently $C_2$–$C_4$ alkylene, $R^3$ is hydrogen, or a linear or branched alkyl group having from 1 to about 4 carbon atoms, and x is an average number from 1 to about 60. Preferably, $R^1$ and $R^4$ are independently linear or branched alkyl groups having from 8 to about 30 carbon atoms, $R^2$ in each of the x ($R^2O$) groups is independently $C_2$–$C_4$ alkylene, $R^3$ is hydrogen, methyl or ethyl, and x is an average number from about 5 to about 50. More preferably, $R^1$ and $R^4$ are independently linear or branched alkyl groups having from about 8 to about 22 carbon atoms, $R^2$ in each of the x ($R^2O$) groups is independently ethylene or propylene, $R^3$ is hydrogen or methyl, and x is an average number from about 8 to about 40. Even more preferably, $R^1$ and $R^4$ are independently linear or branched alkyl groups having from about 8 to about 16 carbon atoms, $R^2$ in each of the x ($R^2O$) groups is independently ethylene or propylene, $R^3$ is hydrogen or methyl, and x is an average number from about 10 to about 30. Preferred commercially available alkoxylated dialkylphenols include ethoxylated dinonyl phenols such as Surfonic™ DNP 100, Surfonic™ DNP 140, and Surfonic™ DNP 240 (from Huntsman).

Other suitable nonionic surfactants include alkylpolyglucosides; glycerol esters such as glyceryl monolaurate, and ethyoxylated glyceryl monococoate; ethoxylated castor oil; ethoxylated reduced sugar esters such as polyoxyethylene sorbitol monolaurate; esters of other polyhydric alcohols such as sorbitan monolaurate and sucrose monostearate; ethoxylated amides such as polyoxyethylene cocoamide; ethoxylated esters such as monolaurate of polyethylene glycol 1000 and dilaurate of polyethylene glycol 6000; ethoxylated alkyl or arylphenols such as nonylphenol ethoxylate, octylphenol ethoxylates, dodecylphenol ethoxylates, dinonylphenol ethoxylates and tristyrylphenol ethoxylates; alcohol ethoxylates such as fatty alcohol ethoxylates (e.g., oleyl alcohol ethoxylate), tridecylalcohol ethoxylates and other alcohol ethoxylates such as Neodols and oxoalcohol ethoxylates; and ethylene oxide/propylene oxide copolymers such as Pluronic type, Tetronic type, or Tergitol XH type.

Additional nonionic surfactants for inclusion in surfactant compositions that may be used in the invention are polyoxyethylene (5–30) $C_{8-22}$ alkylethers and polyoxyethylene (5–30) $C_{8-12}$ alkylphenylethers, wherein "(5–30)" means that the average number of ethylene oxide units in the polyoxyethylene chains of these surfactants is from about 5 to about 30. Examples of such nonionic surfactants include polyoxyethylene nonylphenols, octanols, decanols and trimethylnonanols. Particular nonionic surfactants that have proved useful include NEODOL™ 91-6 of Shell (a polyoxyethylene (6) $C_{9-11}$ linear primary alcohol), NEODOL™ 1-7 of Shell (a polyoxyethylene (7) $C_{11}$, linear primary alcohol), TERGITO™ 15-S-9 of Union Carbide (a polyoxyethylene (9) $C_{12-15}$ secondary alcohol) and SURFONIC™ NP95 of Huntsman (a polyoxyethylene (9.5) nonylphenol).

Preferred nonionic surfactants include alkoxylated alcohols comprising about 5 to about 25 ethoxy and propoxy groups and a $C_{12-18}$ alkyl group. More preferred are about 10 to about 20 alkoxylated $C_{16-18}$ alcohols. Non-exclusive examples include the commercially available products Emulgin-L, Arosurf 66 and Plurafac P700. Other suitable nonionic surfactants may be determined by those skilled in the art by routine experimentation.

Other surfactants for use in herbicidal compositions and concentrates of the invention include compounds of the formula:

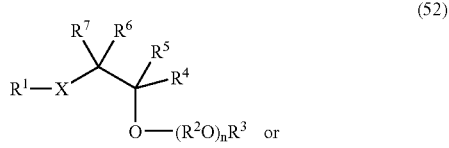

(52)

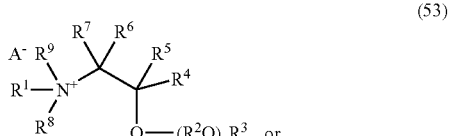

(53)

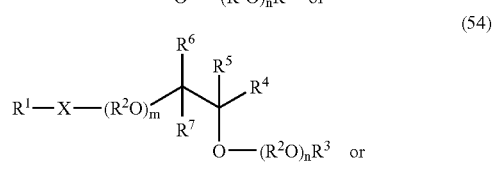

(54)

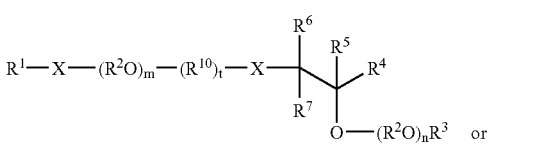

(55)

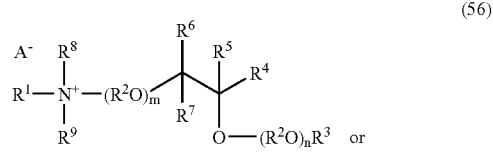

(56)

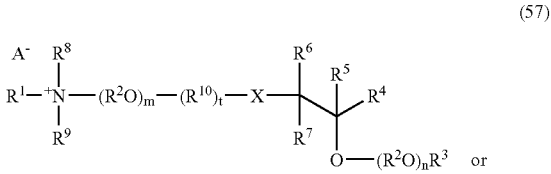

(57)

-continued

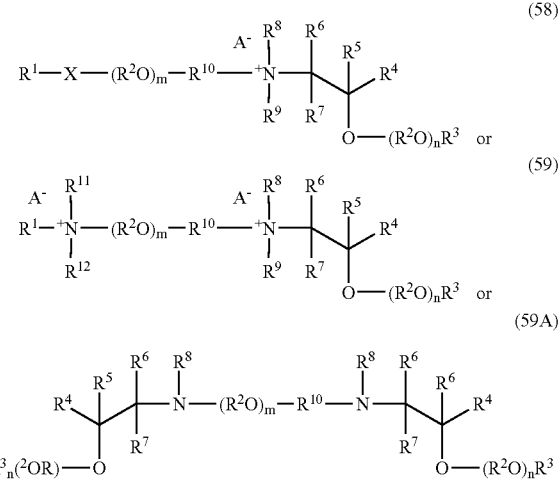

wherein $R^1$, $R^9$, and $R^{12}$ are independently hydrocarbyl or substituted hydrocarbyl having from 1 to about 30 carbon atoms, or $-(R^2O)_pR^{13}$; $R^2$ in each of the m ($R^2O$), n ($R^2O$), p ($R^2O$) and q ($R^2O$) groups is independently $C_2$–$C_4$ alkylene; $R^3$, $R^8$, $R^{11}$, $R^{13}$ and $R^{15}$ are independently hydrogen, or a hydrocarbyl or substituted hydrocarbyl having from 1 to about 30 carbon atoms; $R^4$ is $-(CH_2)_yOR^{13}$ or $-(CH_2)_yO(R^2O)_qR^3$; $R^5$, $R^6$ and $R^7$ are independently hydrogen, hydrocarbyl or substituted hydrocarbyl having from 1 to about 30 carbon atoms, or $R^4$; $R^{10}$ is hydrocarbylene or substituted hydrocarbylene having from 2 to about 30 carbon atoms; $R^{14}$ is hydrogen, hydrocarbyl or substituted hydrocarbyl having from 1 to about 30 carbon atoms, or $-(CH_2)_zO(R^2O)_xR^3$; m, n, p and q are independently an average number from 1 to about 50; X is independently $-O-$, $-N(R^{14})-$, $-C(O)-$, $-C(O)O-$, $-OC(O)-$, $-N(R^{15})C(O)-$, $-C(O)N(R^{15})-$, $-S-$, $-SO-$, or $-SO_2-$; t is 0 or 1; A- is an agriculturally acceptable anion; and y and z are independently an integer from 0 to about 30. In this context, preferred $R^1$, $R^3$, and $R^5$–$R^{15}$ hydrocarbyl (hydrocarbylene) groups are linear or branched alkyl (alkylene), linear or branched alkenyl (alkenylene), linear or branched alkynyl (alkynylene), aryl (arylene), or aralkyl (aralkylene) groups. Preferably, $R^1$, $R^9$, and $R^{12}$ are independently linear or branched alkyl or alkenyl groups having from 1 to about 22 carbon atoms, or $-(R^2O)_pR^{13}$; $R^2$ in each of the m ($R^2O$), n ($R^2O$), p ($R^2O$) and q ($R^2O$) groups is independently $C_2$–$C_4$ alkylene; $R^3$ is hydrogen, methyl or ethyl; $R^4$ is $-(CH_2)_yOR^{13}$ or $-(CH_2)_yO(R^2)_qR^3$; $R^5$, $R^6$ and $R^7$ are independently hydrogen, linear or branched alkyl or alkenyl groups having from 1 to about 22 carbon atoms, or $R^4$; $R^8$, $R^{11}$, $R^{13}$ and $R^{15}$ are independently hydrogen, or linear or branched alkyl or alkenyl groups having from 1 to about 22 carbon atoms; $R^{10}$ is a linear or branched alkylene or alkenylene group having from 2 to about 18 carbon atoms; $R^{14}$ is a linear or branched alkyl or alkenyl group having from 1 to about 22 carbon atoms, or $-(CH_2)_zO(R^2O)_pR^3$; m, n, p and q are independently an average number from 1 to about 30; X is independently $-O-$, $-N(R^{14})-$, $-C(O)-$, $-C(O)O-$, $-OC(O)-$, $-N(R^{15})C(O)-$, $-C(O)N(R^{15})-$, $-S-$, $-SO-$, or $-SO_2-$, t is 0 or 1; A- is an agriculturally acceptable anion; and y and z are independently an integer from 0 to about 30. More preferably, $R^1$ is a linear or branched alkyl or alkenyl groups having from about 8 to about 18 carbon atoms, or $-(R^2O)_pR^{13}$; $R^9$ and $R^{12}$ are independently linear or branched alkyl or alkenyl groups having from 1 to about 22 carbon atoms, or $-(R^2O)_pR^{13}$; $R^2$ in each of the m ($R^2O$), n ($R^2O$), p ($R^2O$) and q ($R^2O$) groups is independently ethylene or propylene; $R^3$ is hydrogen or methyl; $R^4$ is $-(CH^2)_yOR^{13}$ or $-(CH_2)_yO(R^2O)_qR^3$; $R^8$, $R^{11}$, $R^{15}$ are independently hydrogen, or linear or branched alkyl or alkenyl groups having from 1 to about 22 carbon atoms; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or $-(CH_2)_zO(R^2O)_pR^3$; m, n, p and q are independently an average number from 1 to about 20; X is independently $-O-$, $-N(R^{14})-$, $-C(O)-$, $-C(O)O-$, $-OC(O)-$, $-N(R^{15})C(O)-$, $-C(O)N(R^{15})-$, $-S-$, $-SO-$, or $-SO_2-$, t is 0 or 1; A- is an agriculturally acceptable anion; and y and z are independently an integer from 0 to about 10. Most preferably, $R^1$ is a linear or branched alkyl or alkenyl groups having from about 12 to about 18 carbon atoms, or $-(R^2O)_pR^{13}$; $R^9$ and $R^{12}$ are independently linear or branched alkyl or alkenyl groups having from 1 to about 6 carbon atoms, or $-(R^2O)_pR^{13}$; $R^2$ in each of the m ($R^2O$), n ($R^2O$), p ($R^2O$) and q ($R^2O$) groups is independently ethylene or propylene; $R^3$ is hydrogen; $R^4$ is $-(CH_2)_yOR^{13}$ or $-(CH_2)_yO(R^2O)_qR^3$; $R^8$, $R^{11}$, $R^{15}$ are independently hydrogen, or linear or branched alkyl or alkenyl groups having from 1 to about 6 carbon atoms; $R^5$, $R^6$ and $R^7$ are independently hydrogen, linear or branched alkyl or alkenyl groups having from 1 to about 22 carbon atoms, or $R^4$; $R^{10}$ is a linear or branched alkylene or alkenylene group having from 2 to about 6 carbon atoms; $R^{13}$ is hydrogen, or linear or branched alkyl or alkenyl groups having from about 6 to about 22 carbon atoms; $R^{14}$ is a linear or branched alkyl or alkenyl group having from 1 to about 22 carbon atoms, or $-(CH_2)_zO(R^2)_pR^3$; m, n, p and q are independently an average number from 1 to about 5; X is independently $-O-$ or $-N(R^{14})-$, t is 0 or 1; A- is an agriculturally acceptable anion; and y and z are independently an integer from 1 to about 3.

Fluoro-organic wetting agents useful in this invention are organic molecules represented by the formula:

wherein $R_f$ is a fluoroaliphatic radical and G is a group which contains at least one hydrophilic group such as cationic or nonionic groups. $R_f$ is a fluorinated, monovalent, aliphatic organic radical containing at least four carbon atoms. Preferably, it is a saturated perfluoroaliphatic monovalent organic radical. However, hydrogen or chlorine atoms can be present as substituents on the skeletal chain. Although radicals containing a large number of carbon atoms can function adequately, compounds containing not more than about 20 carbon atoms are preferred because large radicals usually represent a less efficient utilization of fluorine than is possible with shorter skeletal chains. Preferably, $R_f$ contains about 5 to 14 carbon atoms. The cationic groups which are usable in the fluoro-organic wetting agents employed in this invention can include an amine or a quaternary ammonium cationic group. Such amine and quaternary ammonium cationic hydrophilic groups can have formulas such as $NH_2$, $NHR^2$, $-N(R^2)_2$, $-(NH_3)X$, $-(NH_2R^2)X$, $-(NH(R^2)_2X)$, or $-(N(R^2)_3)X$, where X is an anionic counterion such as halide, hydroxide, sulfate, bisulfate, acetate or carboxylate, and each $R^2$ is independently a $C_{1-28}$ alkyl group. Preferably, X is halide, hydroxide, or bisulfate. Preferably, the cationic fluoro-organic wetting agents used in this invention contain hydrophilic groups which are quaternary ammonium cationic groups. The nonionic groups which are usable in the fluoro-organic wetting agents employed in this invention include groups which are hydrophilic but which under pH conditions of normal agronomic use are not ionized. The nonionic groups can have formulas such as —O(CH2CH2)XH wherein x is greater than zero, preferably 1–30, —$SO_2NH_2$, $SO_2NHCH_2CH_2OH$, $SO_2N(CH_2CH_2OH)_2$, —$CONH_2$, —$CONHCH_2CH_2OH$, or —$ON(CH_2CH_2OH)_2$. Several fluoro-organic wetting agents suitable for use in the invention are available from 3M under the Fluorad trademark. They include nonionic agents Fluorad FC-170C, Fluorad FC-171 and Fluorad FC-430.

Additional cationic surfactants suitable for use in the herbicidal compositions of the invention are those described in U.S. Pat. Nos. 5,703,015, 5,750,468, 5,389,598, 5,563,111, 5,622,911, 5,849,663, 5,863,909, 5,985,794, 6,030,923 and 6,093,679, which are incorporated herein by reference. Cationic fluoro-organic surfactants useful herein include Fluorad FC-750 and other surfactants as described, for example, in U.S. Pat. Nos. 2,764,602, 2,764,603, 3,147,064, and 4,069,158.

Alkylpolyglycosides are also suitable for use in the compositions and concentrates of the invention, and are described, for example, in U.S. Pat. No. 6,117,820. As used herein the term "alkylglycoside" includes mono- and poly-alkylglycosides. Glycosides are represented by the formula:

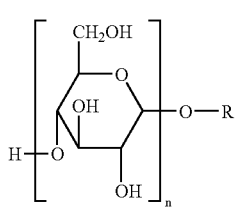

(61)

wherein n is the degree of polymerization, or number of glycose groups, and R is a branched or straight chain alkyl group preferably having from 4 to 18 carbon atoms, or a mixture of alkyl groups having an average value within the given range. The number of glycose groups per alkyl group may vary and alkyl mono- or di-, or polyglucose or saccharide derivatives are possible. Commercial alkylpolyglycosides usually contain a mixture of derivatives with n expressed as an average. Preferably n is between 1 and about 5, and more preferably between 1 and about 3. Typical of alkylglycosides is the product commercially available under the trade names AL2042 (Imperial Chemical Industries PLC) wherein n is an average of 1.7 and R is a mixture of octyl (45%) and decyl (55%), the product commercially available under the trade name AGRIMUL PG2069 (Henkel Corp) wherein n is an average of 1.6 and R is a mixture of nonyl (20%), decyl (40%) and undecyl (40%), and the product commercially available under the trade name BEROL AG6202 (Akzo Nobel) which is 2-ethyl-1-hexylglycoside.

In one embodiment of the invention, the herbicidal compositions include at least one nonionic surfactant and at least one cationic surfactant such as those described herein. Such surfactant combinations are described in U.S. Pat. Nos. 6,245,713 and 5,998,332, which are incorporated herein by reference.

Preferably the weight ratio of cationic:nonionic surfactants is between about 20:1 and about 1:1, and more preferably between about 10:1 and about 1:1. In high load glyphosate formulations, stable microemulsions may be achieved at glyphosate a.e.:total surfactant loading, on a weight basis, of about 1:3 to about 100:1. As with embodiments containing only cationic surfactants, high glyphosate:surfactant ratios are generally limited by herbicidal efficacy considerations rather than composition stability because sufficient surfactant must be present to enable adequate glyphosate herbicidal effect. High surfactant loading generally requires the inclusion of a stabilizer at a preferred weight ratio of total surfactant:stabilizer between about 1:50 and about 50:1.

The surfactant component of the invention comprises any combination of the surfactants and stabilizers as described above. The surfactant composition is particularly preferred for use in formulating compositions or concentrates containing potassium, di-ammonium, ammonium, sodium, monoethanolamine, n-propylamine, methylamine, ethylamine, hexamethylenediamine, dimethylamine and/or trimethylsulfonium glyphosate. The surfactant composition can be incorporated into a composition or concentrate comprising any combination of these glyphosate salts.

The density of any glyphosate-containing formulation of the invention is preferably at least 1.3 grams/liter, more preferably at least about 1.305, 1.310, 1.315, 1.320, 1.325, 1.330, 1.335, 1.340, 1.345, 1.350, 1.355, 1.360, 1.365, 1.370, 1.375, 1.380, 1.385, 1.390, 1.395, 1.400, 1.405, 1.410, 1.415, 1.420, 1.425, 1.430, 1.435, 1.440, 1.445, or 1.450 grams/liter.

The surfactant component of the compositions of the present invention may optionally contain a glycol or glycol ether of formula:

$$HO—(R^4O)_x—R^5 \qquad (62)$$

wherein $R^4$ in each of the x ($R^4O$) groups is independently a linear or branched $C_{2-6}$ alkylene group, x is 1 to about 4, and $R^5$ is hydrogen or a $C_1$–$C_4$ hydrocarbyl group. Contemplated glycols and glycol ethers include but are not limited to monoethylene glycol, diethylene glycol, propylene glycol or the methyl, ethyl, n-propyl, butyl or t-butyl ethers thereof, dipropylene glycol or the methyl, ethyl, n-propyl, -butyl or t-butyl ethers thereof, tripropylene glycol, or the methyl, ethyl, n-propyl, -butyl or t-butyl ethers thereof, 1,3-butanediol, 1,4-butanediol, 2-methyl-1,3-propanediol, 2,2-dimethyl-1,3-propanediol, 2-methyl-1,3-pentanediol and 2-methyl-2,4-pentanediol. Preferred are glycols having 4 or more carbon atoms. Of these, 2-methyl -1,3-propanediol and 1,4-butanediol are more preferred glycols.

In the invention, a microemulsion is defined as a liquid system in which a surfactant component is dispersed within a continuous aqueous liquid phase containing a dissolved salt of glyphosate. In order to form, and maintain, the microemulsion, the substantially water-immiscible organic solvent of the invention is employed to attain appropriate stability of the microemulsion. The microemulsions of the invention are physically stable liquid systems which are also storage stable. They are optically transparent at room temperature and are isotropic. They are formed by the gentle admixture of the ingredients and do not require shearing or other addition of energy. The order of additional of ingredients is not a critical aspect of the invention.

Other components such as solvents and organic acids may be added to the microemulsions of the invention to enhance microemulsion stability. These additives generally function to increase solubility or dispersability of the surfactants in the aqueous carrier phase thus enabling the formulation of robust microemulsions exhibiting enhanced thermal and pH stability, reduced viscosity, and high glyphosate loading.

Solvents may be added to the compositions to increase the solubility or dispersibility of the surfactants in the aqueous carrier phase and thereby attain appropriate stability of the microemulsion. Water soluble solvents may be added to increase the solubility of surfactants with a hydrophilic moiety in the aqueous carrier phase. Non-limiting examples of water soluble solvents include acetates, $C_{1-6}$ alkanols, $C_{1-6}$ diols, $C_{1-6}$ alkyl ethers of alkylene glycols and polyalkylene glycols, and mixtures thereof. The alkanol can be selected from methanol, ethanol, n-propanol, isopropanol, the various positional isomers of butanol, pentanol, and hexanol, and mixtures thereof. It may also be possible to utilize in addition to, or in place of, said alkanols, the diols such as methylene, ethylene, propylene and butylene glycols, and mixtures thereof, and including polyalkylene glycols. Mixtures of hydrophobic and hydrophilic solvents may also be used.

It is preferred to limit the total amount of solvent to preferably no more than about 25%, and more preferably, no more than about 15%, of the composition. A particularly preferred range is about 0–15%. If any of these organic solvents has a solubility of less than 25% in water (at room temperature, 21° C.), then the amount of such limited water solubility solvents should not exceed about 5%, with the amount of water soluble solvents (such as ethyl alcohol) then raised to an amount sufficient to maintain the microemulsion. These amounts of solvents are generally referred to as dispersion-effective or solubilizing effective amounts.

Organic acids may be added to the compositions to enhance the stability of the microemulsion. It is believed, without being bound to any particular theory, that organic acids, or their respective salts, stabilize the high load microemulsions by a couple different mechanisms. First, the hydrophilic and hydrophobic portions of the acids function as coupling agents between the aqueous carrier phase and the nonionic moieties of the surfactants. Second, the acids act as buffers thus stabilizing the composition pH. Suitable organic acids include, among others, acetic, dichloroacetic, citric, malic, oxalic, salicylic and tartaric. Effective concentrations of organic acids are generally between about 0.1 wt % and 5 wt %.

Other additives including inorganic acids and oxidizing agents may be added to the compositions of the invention to enhance microemulsion stability. Non-limiting examples include boric acid, perchloric acid, phosphoric acid, sulfuric acid, hydrogen peroxide, lithium perchlorate, sodium phosphate, sodium chlorate and sodium iodide.

The present invention also includes a method for killing or controlling weeds or unwanted vegetation comprising the steps of diluting a liquid concentrate in a convenient amount of water to form a tank mix and applying a herbicidally effective amount of the tank mix to the foliage of the weeds or unwanted vegetation. Similarly included in the invention is the method of killing or controlling weeds or unwanted vegetation comprising the steps of diluting a solid particulate concentrate in a convenient amount of water to form a tank mix and applying a herbicidally effective amount of the tank mix to the foliage of the weeds or unwanted vegetation.

In a herbicidal method of using a composition of the invention, the composition is diluted in a suitable volume of water to provide an application solution which is then applied to foliage of a plant or plants at an application rate sufficient to give a desired herbicidal effect. This application rate is usually expressed as amount of glyphosate per unit area treated, e.g., grams acid equivalent per hectare (g a.e./ha). What constitutes a "desired herbicidal effect" is, typically and illustratively, at least 85% control of a plant species as measured by growth reduction or mortality after a period of time during which the glyphosate exerts its full herbicidal or phytotoxic effects in treated plants. Depending on plant species and growing conditions, that period of time can be as short as a week, but normally a period of at least two weeks is needed for glyphosate to exert its full effect.

The selection of application rates that are herbicidally effective for a composition of the invention is within the skill of the ordinary agricultural scientist. Those of skill in the art will likewise recognize that individual plant conditions, weather and growing conditions, as well as the specific active ingredients and their weight ratio in the composition, will influence the degree of herbicidal effectiveness achieved in practicing this invention. With respect to the use of glyphosate compositions, much information is known about appropriate application rates. Over two decades of glyphosate use and published studies relating to such use have provided abundant information from which a weed control practitioner can select glyphosate application rates that are herbicidally effective on particular species at particular growth stages in particular environmental conditions.

The method of the present invention where the water-soluble herbicide is glyphosate, more particularly a water-soluble glyphosate salt, is applicable to any and all plant species on which glyphosate is biologically effective as a herbicide. This encompasses a very wide variety of plant species worldwide. Likewise, compositions of the invention containing a glyphosate salt can be applied to any and all plant species on which glyphosate is biologically effective. Therefore, for example, compositions of the invention containing glyphosate as an herbicidal active ingredient can be applied to a plant in a herbicidally effective amount, and can effectively control one or more plant species of one or more of the following genera without restriction: *Abutilon, Amaranthus, Artemisia, Asclepias, Avena, Axonopus, Borreria, Brachiaria, Brassica, Bromus, Chenopodium, Cirsium, Commelina, Convolvulus, Cynodon, Cyperus, Digitaria, Echinochloa, Eleusine, Elymus, Equisetum, Erodium, Helianthus, Imperata, Ipomoea, Kochia, Lolium, Malva, Oryza, Ottochloa, Panicum, Paspalum, Phalaris, Phragmites, Polygonum, Poitulaca, Pteridium, Pueraria, Rubus, Saesola, Setaria, Sida, Sinapis, Sorghum, Triticum, Typha, Ulex, Xanthium* and *Zea.*

Particularly important annual broadleaf species for which glyphosate compositions are used are exemplified without limitation by the following: velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), russian thistle (*Salsola* spp.), sida (*Sida* spp.), wild mustard (*Sinapis aevensis*) and cocklebur (*Xanthium* spp.)

Particularly important annual narrowleaf species for which glyphosate compositions are used are exemplified without limitation by the following: wild oat (*Avena fatua*), carpetgrass (*Axonopus* spp.), downy brome (*Bromus tectorum*), crabgrass (*Digitaria* spp.), Japanese millet (*Echi-* nochloa crus-galli), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial broadleaf species for which glyphosate compositions are used are exemplified without limitation by the following mugwort (*Artemisia* spp.), milkweed (*Asc/epias* spp.), canada thistle (*Cirsium arvense*), field bindweed (*Convolvulus arvensis*) and kudzu (*Pueraria* spp.).

Particularly important perennial narrowleaf species for which glyphosate compositions are used are exemplified without limitation by the following: brachiaria (*Brachiaria* spp.), bermudagrass (*Cynodon dactylon*), yellow nutsedge (*Cyperus esculentus*), purple nutsedge (*C. rotundus*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial species for which glyphosate compositions are used are exemplified without limitation by the following: horsetail (*Equisetum* spp.), bracken (*Pteridium aquilinum*), blackberry (*Rubus* spp.) and gorse (*Ulex europaeus*).

Thus, for example, the glyphosate compositions of the present invention, and a process for treating plants with such compositions, can be useful on any of the above species. In a particular contemplated process, a plant treatment composition is formed by diluting a composition of the invention in a suitable volume of water for application to a field. Preferably, a plant treatment composition comprising glyphosate is formed by diluting a composition of the present invention in water and the plant treatment composition is applied to weeds or undesired plants.

Application of plant treatment compositions to foliage of plants is preferably accomplished by spraying, using any conventional means for spraying liquids, such as spray nozzles or spinning-disk atomizers. Compositions of the present invention can be used in precision farming techniques, in which apparatus is employed to vary the amount of exogenous chemical substance applied to different parts of a field, depending on variables such as the particular plant species present, plant growth stage, soil moisture status, etc. In one embodiment of such techniques, a global positioning system operated with the spraying apparatus can be used to apply the desired amount of the composition to different parts of a field.

A plant treatment composition is preferably dilute enough to be readily sprayed using standard agricultural spray equipment. Suitable application rates for the present invention vary depending upon such factors as the type and concentration of active ingredient and the plant species involved. Useful rates for applying an aqueous composition to a field of foliage can range from about 25 to about 1,000 liters per hectare (l/ha), preferably about 50 to about 300 l/ha, by spray application.

Definitions

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "hydrocarbylene" as used herein describes radicals joined at two ends thereof to other radicals in an organic compound, and which consist exclusively of the elements carbon and hydrogen. These moieties include alkylene, alkenylene, alkynylene, and arylene moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The "substituted hydrocarbyl" moieties described herein are hydrocarbyl moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The "substituted hydrocarbylene" moieties described herein are hydrocarbylene moieties which are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

Unless otherwise indicated, the alkyl groups described herein are preferably lower alkyl containing from one to 18 carbon atoms in the principal chain and up to 30 carbon atoms. They may be straight or branched chain or cyclic and include methyl, ethyl, propyl, isopropyl, n-butyl, isobutyl, hexyl, 2-ethylhexyl, and the like.

Unless otherwise indicated, the alkenyl groups described herein are preferably lower alkenyl containing from two to 18 carbon atoms in the principal chain and up to 30 carbon atoms. They may be straight or branched chain or cyclic and include ethenyl, propenyl, isopropenyl, butenyl, isobutenyl, hexenyl, and the like.

Unless otherwise indicated, the alkynyl groups described herein are preferably lower alkynyl containing from two to 18 carbon atoms in the principal chain and up to 30 carbon atoms. They may be straight or branched chain and include ethynyl, propynyl, butynyl, isobutynyl, hexynyl, and the like.

The terms "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

As used herein, the alkyl, alkenyl, alkynyl, aryl and aralkyl groups can be substituted with at least one atom other than carbon, including moieties in which a carbon chain atom is substituted with a hetero atom such as nitrogen, oxygen, silicon, phosphorous, boron, sulfur, or a halogen atom. These substituents include hydroxy, nitro, amino, amido, nitro, cyano, sulfoxide, thiol, thioester, thioether, ester and ether, or any other substituent which can increase the compatibility of the surfactant and/or its efficacy enhancement in the potassium glyphosate formulation without adversely affecting the storage stability of the formulation.

The terms "halogen" or "halo" as used herein alone or as part of another group refer to chlorine, bromine, fluorine, and iodine. Fluorine substituents are often preferred in surfactant compounds.

Unless otherwise indicated, the term "hydroxyalkyl" includes alkyl groups substituted with at least one hydroxy group, and includes bis(hydroxyalkyl)alkyl, tris(hydroxyalkyl)alkyl and poly(hydroxyalkyl)alkyl groups. Preferred hydroxyalkyl groups include hydroxymethyl (—$CH_2OH$), and hydroxyethyl (—$C_2H_4OH$), bis(hydroxymethyl)methyl (—$CH(CH_2OH)_2$), and tris(hydroxymethyl)methyl (—$C(CH_2OH)_3$).

The term "cyclic" as used herein alone or as part of another group denotes a group having at least one closed ring, and includes alicyclic, aromatic (arene) and heterocyclic groups.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heterocyclo include heteroaromatics such as furyl, thienyl, pyridyl, oxazolyl, pyrrolyl, indolyl, quinolinyl, or isoquinolinyl and the like, and non-aromatic heterocyclics such as tetrahydrofuryl, tetrahydrothienyl, piperidinyl, pyrrolidino, etc. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioester, thioether, ketal, acetal, ester and ether.

The term "heteroaromatic" as used herein alone or as part of another group denote optionally substituted aromatic groups having at least one heteroatom in at least one ring, and preferably 5 or 6 atoms in each ring. The heteroaromatic group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary heteroaromatics include furyl, thienyl, pyridyl, oxazolyl, pyrrolyl, indolyl, quinolinyl, or isoquinolinyl and the like. Exemplary substituents include one or more of the following groups: hydrocarbyl, substituted hydrocarbyl, keto, hydroxy, protected hydroxy, acyl, acyloxy, alkoxy, alkenoxy, alkynoxy, aryloxy, halogen, amido, amino, nitro, cyano, thiol, thioether, thioester, ketal, acetal, ester and ether.

The term "acyl," as used herein alone or as part of another group, denotes the moiety formed by removal of the hydroxyl group from the group —COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo and $R^2$ is hydrogen, hydrocarbyl or substituted hydrocarbyl.

The term "acyloxy," as used herein alone or as part of another group, denotes an acyl group as described above bonded through an oxygen linkage (—O—), e.g., RC(O)O— wherein R is as defined in connection with the term "acyl."

When a maximum or minimum "average number" is recited herein with reference to a structural feature such as oxyethylene units or glucoside units, it will be understood by those skilled in the art that the integer number of such units in individual molecules in a surfactant preparation typically varies over a range that can include integer numbers greater than the maximum or smaller than the minimum "average number." The presence in a composition of individual surfactant molecules having an integer number of such units outside the stated range in "average number" does not remove the composition from the scope of the present invention, so long as the "average number" is within the stated range and other requirements are met.

The term "pesticides" includes chemicals and microbial agents used as active ingredients of products for control of crop and lawn pests and diseases, animal ectoparasites, and other pests in public health. The term also includes plant growth regulators, pest repellants, synergists, herbicide safeners (which reduce the phytotoxicity of herbicides to crop plants) and preservatives, the delivery of which to the target may expose dermal and especially ocular tissue to the pesticide.

EXAMPLES

The following Examples are provided for illustrative purposes only and are not intended to limit the scope of the present invention. The Examples will permit better understanding of the invention and perception of its advantages and certain variations of execution.

Spray compositions of the Examples contained an exogenous chemical, such as glyphosate potassium salt, in addition to the excipient ingredients listed. The amount of exogenous chemical was selected to provide the desired rate in grams per hectare (g/ha) when applied in a spray volume of 93 l/ha. Several exogenous chemical rates were applied for each composition. Thus, except where otherwise indicated, when spray compositions were tested, the concentration of exogenous chemical varied in direct proportion to exogenous chemical rate, but the concentration of excipient ingredients was held constant across different exogenous chemical rates.

Concentrate compositions were tested by dilution, dissolution or dispersion in water to form spray compositions. In these spray compositions prepared from concentrates, the concentration of excipient ingredients varied with that of exogenous chemical.

In the following Examples illustrative of the invention, greenhouse and field tests were conducted to evaluate the relative herbicidal effectiveness of glyphosate compositions. Compositions included for comparative purposes may be identified as follows:

| Composition | Formulation |
| --- | --- |
| Composition 570I | 570 g/l of glyphosate IPA salt in aqueous solution with no added surfactant |
| Composition 41I | 41% by weight of glyphosate IPA salt in aqueous solution, together with phosphate ester and tallow amine surfactants. This formulation is sold by Monsanto Company under the Roundup Ultra ® trademark. |
| Composition 725K | 725 g/l potassium glyphosate salt in aqueous solution with no surfactant |

-continued

| Composition | Formulation |
|---|---|
| Composition 304I | 30.4 wt. % glyphosate a.e. as IPA salt, 3.3 wt. % 2,4-D a.e. as IPA salt, and 9.76% of ethoxylated tallowamines and dipropylene glycol |
| Composition IPA | Glyphosate |
| Roundup ® UltraMax | 50% by weight (445 g a.e./l) of glyphosate IPA salt in aqueous solution, together with surfactant. This formulation is sold by onsanto Company under the Roundup ® UltraMax trademark. |

Various excipients were used in compositions of the Examples. They may be identified as follows:

| | | |
|---|---|---|
| C1 | 2'ethylhexylamine | |
| C2 | 5'methyl glutamate | |
| C3 | EXP-81 | experimental cationic surfactant di-$C_{12}$ di-EO 10 ammonium chloride |
| C5 | EXP-86-B | experimental nonionic $C_{16-18}$ PO (3.1) EO (10.4) |
| C6 | Acetic Acid (diCl) | di chloro acetic acid |
| C7 | Acetic Acid | |
| C8 | Adma 8 | Octyldimethyl amine |
| C9 | Adma WC | $C_{8-20}$ alkyldimethylamine blend |
| C10 | ADMOX | myristyl dimethyl amine oxide |
| C11 | Arosurf 66-E10 | PEG-20 isostearyl ether |
| C13 | Alkamide DC-212 | Cocoamine DEA |
| C14 | Armeen C | Mixed $C_{8-16}$ alkyl primary amine |
| C15 | Aromatic 150 | Toluene |
| C16 | EXP-01A | experimental nonionic $C_{16-18}$ EO (9.4) |
| C17 | EXP-01B | experimental nonionic $C_{16-18}$ EO (9.4) PO (2.2) |
| C18 | EXP-01C | experimental nonionic $C_{16-18}$ EO (9.4) PO (4.2) |
| C20 | EXP-01E | experimental nonionic $C_{16-18}$ EO (9.4) PO (5.3) |
| C21 | EXP-01F | experimental nonionic $C_{16-18}$ EO (9.6) PO (4.4) |
| C22 | EXP-01G | experimental nonionic $C_{16-18}$ PO (4.4) |
| C23 | EXP-01H | experimental nonionic $C_{16-18}$ EO (15.6) PO (4.4) |
| C24 | BG 510 | Rhodafac BG 510 ethoxylated alkyl phosphoric acid ester |
| C25 | bis(2'ethylhexylamine) | |
| C26 | Boric Acid | |
| C27 | Brij 56 | polyoxyethylene (10 EO) cetyl ether |
| C28 | Brij 78 | PEG 20 $C_{18}$ alcohol |
| C29 | BTC 818 | Dialkyl dimethyl ammonium chloride |
| C30 | Cetac 30 | Cetrimonium chloride (hexadecyltrimethylammonium chloride) |
| C32 | citric acid | |
| C33 | Colloid 111D | Rhodia polyacrylate |
| C34 | dithioerythriol | |
| C36 | Dodecyl trimethyl ammonium bromide | |
| C37 | Dodecyl trimethyl ammonium chloride | |
| C38 | dodecyl trimethyl amide | |
| C39 | diethylene glycol | |
| C40 | Emcol CC-42 | Polypropylene glycol-40 diethyl ammonium chloride |
| C41 | Emcol CC-55 | |
| C42 | Ethoquad C15 | PEG 5 tallow ammonium chloride |
| C43 | Ethoquad T25 | PEG 15 tallow methyl ammonium chloride |
| C44 | Ethyl Alcohol | |
| C45 | Ethylene Glycol | |
| C46 | Emulgin-L | Ceterath 2 propoxylate 9 ethoxylate |
| C47 | Ethomeen C12 | PEG 2 cocoamine |
| C48 | EXP-BI | experimental nonionic $C_{16-18}$ EO (5) PO (3.1) |
| C49 | Ethoquad C12 | PEG 2 coco methyl ammonium chloride |

-continued

| | | |
|---|---|---|
| C60 | EXP-19 | di-coco di EO (15) quaternary ammonium chloride |
| C61 | EXP-195 | di-$C_{12}$ di EO (15) (not derived from coco) |
| C62 | EXP-197 | dialkyl (tallow and stearyl) di EO (19.6) quaternary ammonium bromide |
| C63 | EXP-113 | di-C12 di EO (10) ammonium bromide |
| C70 | Exxate 700 | Oxo-heptyl acetate |
| C71 | F88 FL | |
| C72 | Geropan SDS | Sodium dioctyl sulfosuccinate |
| C73 | $H_2O_2$ | |
| C74 | Hexylamine | |
| C75 | Hexanol | |
| C76 | HTMA Br | |
| C77 | Isopar-L | Petroleum naphtha |
| C78 | Isopropylamine | |
| C79 | Plurafac LF 7000 | alkoxylated $C_{16}$–$C_{18}$ alkyl |
| C80 | Lithium Perchlorate | |
| C81 | Makon NF-12 | Polyalkoxylated aliphatic base |
| C82 | Malic Acid | |
| C83 | Mirataine | Sodium lauriminodipropionate |
| C84 | MSPO II | mono sodium di hydrogen phosphate |
| C85 | N-propylamine | |
| C86 | Neodol N45-13 | $C_{14-15}$ PEG (13) |
| C87 | $NaClO_3$ | |
| C88 | N,N-dimethylhexylamine | |
| C89 | N,N-dimethyloctylamine | |
| C90 | Octadecylamine | |
| C91 | Octylamine | |
| C92 | OTMACI | Octyl trimethyl ammonium chloride |
| C93 | Oxalic Acid | |
| C94 | Perchloric Acid | |
| C95 | Phenyl trimethyl ammonium bromide | |
| C96 | Phosphoric Acid | |
| C97 | Polyethylene Glycol 400 | |
| C98 | Propylene Glycol bis(2APE) | |
| C99 | Propylene Glycol 2000 | |
| C100 | Rhodapex CD 128 | $C_{8-10}$ ethoxylated ammonium sulfate |
| C101 | Rhodapex PA 603 | Ammonium Laureth (3 EO) sulfate |
| C102 | Rhodonat LMO | sucro-glyceride derivative |
| C103 | Sodium Salicylate | |
| C104 | Sodium Iodide | |
| C105 | Sulfuric Acid | |
| C106 | TAM MeCl | methyl chloride quaternary form of Witcamine Ethoxylated tallow amine 8 EO (TAM 80) |
| C107 | TAM 45 | Ethoxylated tallow amine 4.5 EO |
| C108 | TAM 60 | Ethoxylated tallow amine 6 EO |
| C109 | TAM 80 | Ethoxylated tallow amine 8 EO |
| C110 | TAM 105 | Ethoxylated tallow amine 10.5 EO |
| C111 | tartaric acid | |
| C112 | Tergitol XD | CH3(CH2)3—O—(CH2CH2O)$_{18}$H |
| C113 | tert octyl amine | |
| C114 | THF-OH | |
| C115 | tributylamine | |
| C116 | triethanolamine | |
| C117 | triethylhexylamm Br | |
| C118 | triisooctylamine | |
| C119 | triphenylamine | |
| C120 | Trisodium Citrate | |
| C121 | Varonic-210 | cocoamine EO (10) |
| C122 | | xylenes |
| C123 | Surfonic AGM-510 | tallowamine ethoxylate (6EO) |
| C124 | Surfonic AGM-550 | CAS # 176022-82-5 |
| C125 | Armeen DMCD | Dimethylcocoamine |
| C127 | Sigma DPG | Dipropylene Glycol |
| C128 | n-decylamine | |
| C129 | | 55% TAM 105 + 45% Ethomeen C12 |
| C130 | Crompton C-6202 | 54% TAM 45 + 23% TAM 105 + 23% dipropylene glycol |
| C131 | C-6228 | 77% TAM 60 + dipropylene glycol |
| C132 | hetoxol CA10 | POE 10 Cetyl Ether |
| C133 | hetoxol STA10 | POE 10 Stearyl Ether |
| C134 | Tergitol 15-S-9 | |
| C135 | Tergitol 15-S-12 | |
| C136 | Witco | Ethoxylated (15) tallow ammonium chloride |

| | | |
|---|---|---|
| C137 | Ethoquad T20 | PEG 10 Tallow methyl ammonium chloride |
| C138 | | Polypropylene glycol |
| C139 | Aromatic 100 | trimethylbenzene/xylene/cumene mixture |
| C140 | NMP | N-methyl pyrrolidone |
| C141 | Witcamine 405 | Witco |
| C142 | PF 8000 | Witco |
| C143 | Hetoxol CS15 | $C_{16-18}$ alcohol 15 EO |
| C144 | Hetoxol CS20 | $C_{16-18}$ alcohol 20 EO |
| C145 | Ethomeen T25 | Ethoxylated 15 tallow amine |
| C146 | | tetrabutylammonium hydroxide |
| C147 | Mackine 101 | cocoamidopropyl dimethylamine |

Example 1

The stability of a 477 g a.e./L potassium glyphosate solution was evaluated. 36.5% a.e. potassium glyphosate, 12% Witcamine TAM 80 (C109), 5% octylamine (C91) and water to 100% were combined at room temperature followed by mixing with a magnetic stir bar at about 50° C. until a homogeneous sample was produced. A single phase, clear solution was obtained at 50° C. and at room temperature. Stability was maintained during 3 days of cycling, over a 12 hour period, between −10 and 10° C.

Example 2

The stability of a 523 g a.e./L potassium glyphosate solution was evaluated. 39.3% a.e. potassium glyphosate, 12% Witcamine TAM 80 (C109), 6% octylamine (C91) and water to 100% were combined at room temperature followed by mixing with a magnetic stir bar at about 50° C. until a homogeneous sample was produced. A single phase, clear solution was obtained at 50° C. and at room temperature. Stability was maintained during 3 days of cycling, over a 12 hour period, between −10 and 10° C.

Example 3

The stability of a 477 g a.e./L potassium glyphosate solution was evaluated. 36.5% a.e. potassium glyphosate, 12% Witcamine TAM 105 (C110), 5% octylamine (C91) and water to 100% were combined at room temperature followed by mixing with a magnetic stir bar at about 50° C. until a homogeneous sample was produced. A single phase, clear solution was obtained at 50° C. and at room temperature.

Examples 4–6

In examples 4–6 the stability of high load potassium glyphosate formulations were evaluated for formulations with varying surfactant and octylamine concentrations. The formulation components were combined at room temperature followed by mixing with a magnetic stir bar at about 50° C. until a homogeneous sample was produced. Unless otherwise indicated, the formulations were evaluated at 50° C. and room temperature. A "clear" result indicates a transparent single phase solution was obtained. A "cloudy" result indicates a cloudy single phase solution was obtained. A "fail" result indicates phase separation occurred.

Example 4

Stabilizer compatibility evaluation of composition trial 526 comprising 37.4% a.e. (about 490 g a.e./L) potassium glyphosate, 6.0% EMCOL CC-40 (Surf), 0–6.0% Octylamine (Stab) and water to 100%.

| Run | A7Y | B3C | C2I | D0L | E8M |
|---|---|---|---|---|---|
| Surf. | C40 | C40 | C40 | C40 | C40 |
| wt % | 12.0 | 12.0 | 12.0 | 12.0 | 12.0 |
| Stab. | C91 | C91 | C91 | C91 | C91 |
| wt % | 2.0 | 3.0 | 5.0 | 5.0 | 6.0 |
| 50° C. | Cloudy | Cloudy | Cloudy | Cloudy | Cloudy |
| RT | Fail | Fail | Fail | Fail | Cloudy |

Example 5

Stabilizer compatibility evaluation of composition trial 527 comprising 37.4% a.e. (about 490 g a.e./L) potassium glyphosate and the listed surfactant (Surf.) and octylamine stabilizer (Stab.) components.

| Run | A0P | B4H | C3S | D7U | E3X | F0L | G7Y | H3B |
|---|---|---|---|---|---|---|---|---|
| Surf. 1 | C110 | C109 | C110 | C109 | C110 | C109 | C110 | C109 |
| wt % | 6.0 | 6.0 | 6.0 | 6.0 | 6.0 | 6.0 | 6.0 | 6.0 |
| Surf. 2 | C27 | C27 | C46 | C46 | C5 | C5 | C5 | C5 |
| wt % | 4.0 | 4.0 | 4.0 | 4.0 | 4.0 | 4.0 | 4.0 | 4.0 |
| Stab. | C91 | C91 | C91 | C91 | C91 | C91 | C91 | C91 |
| wt % | 5.0 | 5.0 | 5.0 | 5.0 | 5.0 | 5.0 | 6.0 | 6.0 |
| 50° C. | Cloudy | Cloudy | Cloudy | Cloudy | Cloudy | Cloudy | Cloudy | Cloudy |
| RT | Fail | Fail | Clear | Clear | Cloudy | Cloudy | Clear | Clear |

Example 6

Stabilizer compatibility evaluation of composition trial 528 comprising 37.4% a.e. (about 490 9 a.e./L) potassium glyphosate and the listed surfactant (Surf.) and octylamine stabilizer (Stab.) components.

| Run | A2Z | B5V | C0B | D6M | E4G | F9L | G3C |
|---|---|---|---|---|---|---|---|
| Surf. 1 | C110 | C109 | C110 | C110 | C109 | C40 | C40 |
| wt % | 7.2 | 7.2 | 7.2 | 7.2 | 7.2 | 7.2 | 7.2 |
| Surf. 2 | C46 | C46 | C5 | C5 | C5 | C46 | C5 |
| wt % | 4.8 | 4.8 | 4.8 | 4.8 | 4.8 | 4.8 | 4.8 |
| Stab. | C91 | C91 | C91 | C91 | C91 | C91 | C91 |
| wt % | 5.0 | 5.0 | 5.0 | 7.0 | 7.0 | 6.0 | 6.0 |
| 50° C. | Cloudy | Cloudy | Cloudy | Cloudy | Cloudy | Cloudy | Cloudy |
| RT | Cloudy | Cloudy | Clear | Clear | Clear | — | — |

Examples 7–14

In examples 7–14 the stability of high load potassium glyphosate formulations were evaluated for formulations with varying compatibilization and short chain length alkyl amine concentrations. The formulation components were combined at room temperature followed by mixing with a magnetic stir bar at about 50° C. until a homogeneous sample was produced. Unless otherwise indicated, the formulations were evaluated overnight at high temperature (about 50° C.), room temperature, 10 ° C., 0° C. and −10° C. Additionally, a −10°C. sample was evaluated after one week. A "clear" result indicates a transparent single phase solution was obtained. A "cloudy" result indicates a cloudy single phase solution was obtained. A "fail" result indicates phase separation occurred.

Example 7

480 g a.e./l potassium glyphosate, 4.92% TAM 80, 7.38% Emulgin L, 0–3.0% Isopar L compatibilizer (Stab.), 0–6.0% Hexylamine (Amine), and Water to 100%

| Run | Stab. | Amine | HT | RT | 10° C. | 0° C. | −10° C. | −10° C. (1 wk) |
|---|---|---|---|---|---|---|---|---|
| 908W1L | 0% | 3.0% | Clear | Clear | Clear | Clear | Fail | Fail |
| 908Z3D | 3.0% | 2.0% | Cloudy | Fail | Fail | Fail | Fail | Fail |
| 908O9F | 1.0% | 4.0% | Clear | Clear | Clear | Clear | Fail | Fail |
| 908J6B | 0% | 6.0% | Clear | Clear | Clear | Cloudy | Cloudy | Cloudy |
| 908E4K | 0% | 4.0% | Clear | Clear | Clear | Cloudy | Cloudy | Fail |
| 908K9R | 2.25% | 1.5% | Cloudy | Fail | Fail | Fail | Fail | Fail |
| 908E2D | 1.5% | 0% | Fail | Fail | Fail | Fail | Fail | Fail |
| 908F6X | 0% | 0% | Fail | Fail | Fail | Fail | Fail | Fail |
| 908G5T | 2.25% | 4.5% | Cloudy | Cloudy | Cloudy | Cloudy | Fail | Fail |
| 908H0A | 3.0% | 6.0% | Cloudy | Cloudy | Cloudy | Cloudy | Fail | Fail |
| 908I8J | 3.0% | 0% | Fail | Fail | Fail | Fail | Fail | Fail |
| 908J2M | 1.5% | 6.0% | Clear | Cloudy | Cloudy | Fail | Fail | Fail |
| 908K7G | 0.75% | 1.5% | Fail | Fail | Fail | Fail | Fail | Fail |
| 908L9L | 3.0% | 3.0% | Cloudy | Fail | Fail | Fail | Fail | Fail |
| 908M6S | 1.7% | 2.7% | Clear | Cloudy | Cloudy | Fail | Fail | Fail |

Example 8

480 g a.e./l potassium glyphosate, 4.92% TAM 80, 7.38% Emulgin-L, 0–3.0% Isopar L stabilizer (Stab.), 0–6.0% Octylamine (Amine), and Water to 100%

| Run | Stab. | Amine | HT | RT | 10° C. | 0° C. | −10° C. | −10° C. (1 wk) |
|---|---|---|---|---|---|---|---|---|
| 909A4V | 0% | 3.0% | Clear | Clear | Clear | Clear | Fail | Fail |
| 909B5H | 3.0% | 2.0% | Cloudy | Fail | Fail | Fail | Fail | Fail |
| 909C6B | 1.0% | 4.0% | Clear | Clear | Clear | Clear | Cloudy | Cloudy |
| 909D2I | 0% | 6.0% | Clear | Clear | Clear | Clear | Cloudy | Cloudy |
| 909E3C | 0% | 4.0% | Clear | Clear | Clear | Clear | Cloudy | Cloudy |
| 909F3P | 2.25% | 1.5% | Cloudy | Fail | Fail | Fail | Fail | Fail |
| 909G1T | 1.5% | 0% | Fail | Fail | Fail | Fail | Fail | Fail |
| 909H9M | 0% | 0% | Fail | Fail | Fail | Fail | Fail | Fail |
| 909I4B | 2.25% | 4.5% | Clear | Clear | Clear | Clear | Cloudy | Fail |
| 909J8O | 3.0% | 6.0% | Clear | Clear | Clear | Clear | Fail | Fail |
| 909K6J | 3.0% | 0% | Fail | Fail | Fail | Fail | Fail | Fail |
| 909L6S | 1.5% | 6.0% | Clear | Clear | Clear | Clear | Cloudy | Cloudy |
| 909M2K | 0.75% | 1.5% | Fail | Fail | Fail | Fail | Fail | Fail |
| 909N0K | 3.0% | 3.0% | Cloudy | Cloudy | Fail | Cloudy | Fail | Fail |
| 909O7E | 1.7% | 2.7% | Clear | Clear | Clear | Clear | Fail | Fail |

Example 9

480 g a.e./l potassium glyphosate, 4.92% TAM 80, 7.38% Emulgin-L, 0–3.0% Isopar L stabilizer (Stab.), 0–6.0% Decylamine (Amine), and Water to 100%

| Run | Stab. | Amine | HT | RT | 10° C. | 0° C. | −10° C. | −10° C.(1 wk) |
|---|---|---|---|---|---|---|---|---|
| 910A2C | 0% | 3.0% | Fail | Fail | Fail | Fail | Fail | Fail |
| 910B6T | 3.0% | 2.0% | Fail | Fail | Fail | Fail | Fail | Fail |
| 910C7B | 1.0% | 4.0% | Fail | Fail | Fail | Fail | Fail | Fail |
| 910D1U | 0% | 6.0% | Fail | Fail | Fail | Fail | Fail | Fail |
| 910E0P | 0% | 4.0% | Fail | Fail | Fail | Fail | Fail | Fail |
| 910F6A | 2.25% | 1.5% | Fail | Fail | Fail | Fail | Fail | Fail |
| 910G9K | 1.5% | 0% | Fail | Fail | Fail | Fail | Fail | Fail |
| 910H6Z | 0% | 0% | Fail | Fail | Fail | Fail | Fail | Fail |
| 910I7W | 2.25% | 4.5% | Fail | Fail | Fail | Fail | Fail | Fail |
| 910J1W | 3.0% | 6.0% | Clear | Clear | Clear | Clear | Cloudy | Cloudy |
| 910K8B | 3.0% | 0% | Fail | Fail | Fail | Fail | Fail | Fail |
| 910L2Y | 1.5% | 6.0% | Cloudy | Clear | Clear | Clear | Cloudy | Cloudy |
| 910M8L | 0.75% | 1.5% | Fail | Fail | Fail | Fail | Fail | Fail |
| 910N0E | 3.0% | 3.0% | Fail | Fail | Fail | Fail | Fail | Fail |
| 910O3G | 1.7% | 2.7% | Fail | Fail | Fail | Fail | Fail | Fail |

Example 10

480 g a.e./l potassium glyphosate, 4.92% TAM 80, 7.38% Emulgin-L, 0–3.0% Isopar L stabilizer (Stab), 0–6.0% Dodecylamine (Amine), and Water to 100%

| Run | Stab. | Amine | HT | RT | 10° C. | 0° C. | −10° C. | −10° C.(1 wk) |
|---|---|---|---|---|---|---|---|---|
| 911A3K | 0% | 3.0% | Fail | Fail | Fail | Fail | Fail | Fail |
| 911B6H | 3.0% | 2.0% | Fail | Fail | Fail | Fail | Fail | Fail |
| 911C3K | 1.0% | 4.0% | Fail | Fail | Fail | Fail | Fail | Fail |
| 911D4F | 0% | 6.0% | Fail | Fail | Fail | Fail | Fail | Fail |
| 911E0I | 0% | 4.0% | Fail | Fail | Fail | Fail | Fail | Fail |
| 911F9H | 2.25% | 1.5% | Fail | Fail | Fail | Fail | Fail | Fail |
| 911G5V | 1.5% | 0% | Fail | Fail | Fail | Fail | Fail | Fail |
| 911H7J | 0% | 0% | Fail | Fail | Fail | Fail | Fail | Fail |
| 911I8S | 2.25% | 4.5% | Fail | Fail | Fail | Fail | Fail | Fail |
| 911J4K | 3.0% | 6.0% | Fail | Fail | Fail | Fail | Fail | Fail |
| 911K2P | 3.0% | 0% | Fail | Fail | Fail | Fail | Fail | Fail |
| 911L6G | 1.5% | 6.0% | Fail | Fail | Fail | Fail | Fail | Fail |
| 911M1P | 0.75% | 1.5% | Fail | Fail | Fail | Fail | Fail | Fail |
| 911N5Q | 3.0% | 3.0% | Fail | Fail | Fail | Fail | Fail | Fail |
| 911O8Z | 1.7% | 2.7% | Fail | Fail | Fail | Fail | Fail | Fail |

Example 11

480 g a.e./l potassium glyphosate, 4.92% TAM 80, 7.38% Emulgin-L, 0–3.0% Aromatic 150 stabilizer (Stab.), 0–6.0% Octylamine (Amine), and Water to 100%

| Run | Stab. | Amine | HT | RT | 0° C. | −10° C. | −10° C.(1 wk) | −20° C.(5 wks) |
|---|---|---|---|---|---|---|---|---|
| 912A6J | 0% | 3.0% | Clear | Clear | Clear | Fail | Fail | Fail |
| 912B8V | 3.0% | 2.0% | Fail | Fail | Fail | Fail | Fail | Fail |
| 912C3D | 1.0% | 4.0% | Clear | Clear | Clear | Cloudy | Cloudy | Fail |
| 912D5J | 0% | 6.0% | Clear | Clear | Clear | Cloudy | Cloudy | Fail |
| 912E0Q | 0% | 4.0% | Clear | Clear | Clear | Cloudy | Cloudy | Fail |
| 912F7H | 2.25% | 1.5% | Fail | Fail | Fail | Fail | Fail | Fail |
| 912G4D | 1.5% | 0% | Fail | Fail | Fail | Fail | Fail | Fail |
| 912H8K | 0% | 0% | Fail | Fail | Fail | Fail | Fail | Fail |
| 912I3W | 2.25% | 4.5% | Clear | Clear | Clear | Cloudy | Cloudy | Cloudy |

-continued

| Run | Stab. | Amine | HT | RT | 0° C. | −10° C. | −10° C.(1 wk) | −20° C.(5 wks) |
|---|---|---|---|---|---|---|---|---|
| 912J9K | 3.0% | 6.0% | Clear | Clear | Clear | Clear | Clear | Cloudy |
| 912K2Z | 3.0% | 0% | Fail | Fail | Fail | Fail | Fail | Fail |
| 912L6Q | 1.5% | 6.0% | Clear | Clear | Clear | Cloudy | Cloudy | Fail |
| 912M2A | 0.75% | 1.5% | Fail | Fail | Fail | Fail | Fail | Fail |
| 912N7T | 3.0% | 3.0% | Clear | Clear | Clear | Clear | Clear | Cloudy |
| 912O4B | 1.7% | 2.7% | Clear | Clear | Clear | Clear | Cloudy | Fail |

Example 12

480 g a.e./l potassium glyphosate, 4.92% TAM 45, 7.38% Emulgin-L, 0–3.0% Isopar L stabilizer (Stab.), 0–6.0% Octylamine (amine), and Water to 100%

| Run | Stab. | Amine | HT | RT | 10° C. | 0° C. | −10° C. | −10° C.(1 wk) |
|---|---|---|---|---|---|---|---|---|
| 913A7R | 0% | 3.0% | Clear | Clear | Clear | Clear | Fail | Fail |
| 913B3E | 3.0% | 2.0% | Clear | Clear | Clear | Clear | Cloudy | Cloudy |
| 913C4P | 1.0% | 4.0% | Clear | Clear | Clear | Clear | Cloudy | Cloudy |
| 913D8R | 0% | 6.0% | Clear | Clear | Clear | Clear | Cloudy | Cloudy |
| 913E4B | 0% | 4.0% | Clear | Clear | Clear | Clear | Cloudy | Fail |
| 913F0S | 2.25% | 1.5% | Clear | Clear | Clear | Clear | Fail | Fail |
| 913G1A | 1.5% | 0% | Fail | Fail | Fail | Fail | Fail | Fail |
| 913H3M | 0% | 0% | Fail | Fail | Fail | Fail | Fail | Fail |
| 913I5V | 2.25% | 4.5% | Clear | Clear | Clear | Clear | Cloudy | Cloudy |
| 913E2I | 3.0% | 6.0% | Clear | Clear | Clear | Clear | Cloudy | Cloudy |
| 913I8M | 3.0% | 0% | Fail | Fail | Fail | Fail | Fail | Fail |
| 913T6V | 1.5% | 6.0% | Clear | Clear | Clear | Clear | Cloudy | Cloudy |
| 913J7N | 0.75% | 1.5% | Clear | Clear | Clear | Clear | Fail | Fail |
| 913P2Z | 3.0% | 3.0% | Clear | Clear | Clear | Clear | Clear | Fail |
| 913U5V | 1.7% | 2.7% | Clear | Clear | Clear | Clear | Cloudy | Fail |

Example 13

480 g a.e./l potassium glyphosate, 4.92% TAM 45, 7.38% Emulgin-L, 0–3.0% Aromatic 150 stabilizer (Stab.), 0–6.0% Octylamine (Amine), and Water to 100%

| Run | Stab. | Amine | HT | RT | 10° C. | 0° C. | −10° C. | −10° C.(1 wk) |
|---|---|---|---|---|---|---|---|---|
| 914A2C | 0% | 3.0% | Clear | Clear | Clear | Clear | Fail | Fail |
| 914B7H | 3.0% | 2.0% | Clear | Clear | Clear | Clear | Cloudy | Cloudy |
| 914C3S | 1.0% | 4.0% | Clear | Clear | Clear | Clear | Cloudy | Fail |
| 914D7N | 0% | 6.0% | Clear | Clear | Clear | Clear | Cloudy | Cloudy |
| 914E4H | 0% | 4.0% | Clear | Clear | Clear | Clear | Cloudy | Fail |
| 914F8F | 2.25% | 1.5% | Fail | Fail | Clear | Clear | Cloudy | Cloudy |
| 914G3O | 1.5% | 0% | Fail | Fail | Fail | Fail | Fail | Fail |
| 914H1P | 0% | 0% | Fail | Fail | Fail | Fail | Fail | Fail |
| 914I2W | 2.25% | 4.5% | Clear | Clear | Clear | Clear | Clear | Cloudy |
| 914J6C | 3.0% | 6.0% | Clear | Clear | Clear | Clear | Clear | Cloudy |
| 914K9A | 3.0% | 0% | Fail | Fail | Fail | Fail | Fail | Fail |
| 914L2T | 1.5% | 6.0% | Clear | Clear | Clear | Clear | Cloudy | Cloudy |
| 914M4D | 0.75% | 1.5% | Clear | Clear | Clear | Clear | Fail | Fail |
| 914N9L | 3.0% | 3.0% | Clear | Clear | Clear | Clear | Clear | Cloudy |
| 914O3X | 1.7% | 2.7% | Clear | Clear | Clear | Clear | Cloudy | Cloudy |

Example 14

37% (about 480 g a.e./L) potassium glyphosate, Emulgen-L (Surf. 1), TAM 60 (Surf. 2) or TAM 80 (Surf. 2-Run 915A3W), octylamine (Stab. 1), Aromatic 150 (Stab. 2), and Water to 100%.

| Run | Surf. 1 | Surf. 2 | Stab. 1 | Stab. 2 | −10° C. (1 wk) | −20° C. (6 wks) |
|---|---|---|---|---|---|---|
| 915A3W | 2.46% | 3.69% | 1.5% | 1.54% | Clear | Fail |
| 915B8J | 2.44% | 3.69% | 1.51% | 1.51% | Clear | Fail |
| 915C6Z | — | 4.61% | 1.01% | — | Clear | Clear |
| 915D0L | — | 5.29% | 0.99% | — | Clear | Clear |
| 915E5T | — | 6.13% | 1.02% | — | Clear | Clear |
| 915F9K | — | 4.66% | 2% | — | Clear | Clear |
| 915G6N | — | 5.25% | 2% | — | Clear | Clear |
| 915H3U | — | 7.35% | 1.02% | — | Clear | Fail |
| 915I8D | — | 9% | 1.1% | — | Clear | Fail |
| 915J6W | — | 4.63% | — | — | Clear | Fail |
| 915K9B | — | 8.19% | 1% | — | Clear | Clear |

Examples 15–151

In examples 15–151 the stability of high load glyphosate formulations were evaluated for formulations with varying compatibilization and short chain length alkyl amine concentrations. Unless otherwise indicated the potassium salt of glyphosate was evaluated. The formulation components were combined at room temperature followed by mixing with a magnetic stir bar at about 60° C. until a homogeneous sample was produced. Unless otherwise noted, the formulations were evaluated at high temperature (about 60° C.) and overnight at the indicated temperatures. A sample that failed was not further tested at lower temperatures. A "clear" result indicates a transparent single phase solution was obtained. A "cloudy" result indicates a cloudy single phase solution was obtained. A "fail" result indicates phase separation or solidification occurred.

Example 15

Stabilizer compatibility evaluation of composition trial 101 comprising 36.9% a.e. (about 480 g a.e./L) potassium glyphosate and the listed surfactant (Surf.) and stabilizer (Stab.) components.

| Run | A3D | B7Y | C4R | D9W | E2F | F1M | G6K | H6Y |
|---|---|---|---|---|---|---|---|---|
| Surf. 1 | C46 | C46 | C46 | C27 | C27 | C46 | C46 | C46 |
| wt % | 4.8 | 4.8 | 4.8 | 4.8 | 4.8 | 4.9 | 4.9 | 4.9 |
| Surf. 2 | C40 | C40 | C40 | C109 | C109 | C40 | C40 | C40 |
| wt % | 7.2 | 7.2 | 7.2 | 7.2 | 7.2 | 7.4 | 7.4 | 7.4 |
| Stab. | C74 | C92 | C92 | C74 | C74 | C74 | C74 | C74 |
| wt % | 6 | 6 | 6 | 5 | 5 | 3 | 5 | 7 |
| 60° C. | Clear | Clear | Fail | Fail | Fail | Fail | Fail | Fail |
| RT | Clear | Fail | No test | No test | No test | No test | No test | No test |
| 10° C. | Clear | No test | No test | No test | No test | No test | No test | No test |

Example 16

Stabilizer compatibility evaluation of composition trial 104 comprising 31% a.e. (about 370 g a.e./L) potassium glyphosate and the listed surfactant (Surf.) and octylamine stabilizer (Stab.) components.

| Run | A6Y | B2W | C6H | D0M | E1S | F5F | G8K | H5B |
|---|---|---|---|---|---|---|---|---|
| Surf. 1 | C16 | C17 | C18 | C18 | C20 | C21 | C22 | C23 |
| wt % | 4 | 4 | 4 | 4 | 4 | 4 | 4 | 4 |
| Surf. 2 | C109 | C109 | C109 | C109 | C109 | C109 | C109 | C109 |
| wt % | 6 | 6 | 6 | 6 | 6 | 6 | 6 | 6 |
| Stab. | C91 | C91 | C91 | C91 | C91 | C91 | C91 | C91 |
| wt % | 6 | 6 | 6 | 6 | 6 | 6 | 6 | 6 |
| 60° C. | Clear | Clear | Clear | Clear | Clear | Clear | Clear | Clear |
| RT | Clear | Fail | Fail | Fail | Fail | Fail | Fail | Fail |
| 10° C. | Fail | No test | No test | No test | No test | No test | No test | No test |
| 0° C. | No test | No test | No test | No test | No test | No test | No test | No test |

Example 17

Stabilizer compatibility evaluation of composition trial 106 comprising 31% a.e. (about 370 g a.e./L) isopropylamine glyphosate and the listed surfactant (Surf.) and stabilizer (Stab.) components.

| Run | A3E | B9L | C3C | D3W | E8K |
|---|---|---|---|---|---|
| Surf. 1 | C27 | C27 | C27 | C27 | C27 |
| wt % | 4.8 | 4.8 | 4.8 | 4.8 | 4.8 |
| Surf. 2 | C43 | C43 | C43 | C43 | C43 |
| wt % | 7.2 | 7.2 | 7.2 | 7.2 | 7.2 |
| Stab. 1 | C15 | C15 | C15 | C15 | C15 |
| wt % | 3.3 | 5.2 | 1.7 | 5.2 | 1 |
| Stab. 2 | C30 | C30 | C30 | C30 | C30 |
| wt % | 8.3 | 5.5 | 2.1 | 10.6 | 6.8 |
| 60° C. | Clear | Clear | Clear | Clear | Clear |
| RT | Clear | Fail | Clear | Clear | Clear |
| 10° C. | Fail | Fail | Fail | Fail | Fail |
| 0° C. | No test | No test | No test | No test | No test |

Example 18

Stabilizer compatibility evaluation of composition trial 108 comprising 36.9% a.e. (about 480 g a.e./L) potassium glyphosate and the listed surfactant (Surf.) and octylamine stabilizer (Stab.) components.

| Run | A4J | B5T | C2W | D9O | E7G | F9K | G5N | H6R |
|---|---|---|---|---|---|---|---|---|
| Surf. 1 | C46 | C46 | C46 | C46 | C46 | C46 | C110 | C11 |
| wt % | 3.6 | 4.8 | 6 | 7.2 | 8.4 | 12 | 12 | 4.8 |
| Surf. 2 | C110 | C110 | C110 | C110 | C110 | — | — | — |
| wt % | 8.4 | 7.2 | 6 | 4.8 | 3.6 | — | — | — |
| Stab. | C91 | C91 | C91 | C91 | C91 | C91 | C91 | C91 |
| wt % | 5 | 5 | 5 | 5 | 5 | 5 | 5 | 5 |
| 60° C. | Clear | Clear | Clear | Clear | Clear | Clear | Clear | Clear |
| RT | Fail | Fail | Fail | Fail | Fail | Fail | Fail | Clear |
| 10° C. | No test | No test | No test | No test | No test | No test | No test | Clear |
| 0° C. | No test | No test | No test | No test | No test | No test | No test | Cloudy |
| 0° C.* | No test | No test | No test | No test | No test | No test | No test | Cloudy |

*@ 1 week

Example 19

Stabilizer compatibility evaluation of composition trial 110 comprising 36.9% a.e. (about 480 g a.e./L) potassium glyphosate and the listed surfactant (Surf.) and stabilizer (Stab.) components.

| Run | A3C | B6K | C4F | D9L |
|---|---|---|---|---|
| Surf. 1 | C46 | C46 | C46 | C11 |
| wt % | 4.8 | 4.8 | 4.8 | 4.8 |
| Surf. 2 | C110 | C110 | C110 | C110 |
| wt % | 7.2 | 7.2 | 7.2 | 7.2 |
| Stab. | C91 | C74 | C85 | C91 |
| wt % | 6 | 4 | 4 | 5 |
| 60° C. | Clear | Clear | Clear | Clear |
| RT | Clear | Clear | Fail | Clear |
| 10° C. | Fail | Fail | Fail | Fail |
| 0° C. | No test | No test | No test | No test |

Example 20

Stabilizer compatibility evaluation of composition trial 112 comprising 36.9% a.e. (about 480 g a.e./L) potassium glyphosate and the listed surfactant (Surf.) and stabilizer (Stab.) components.

| Run | A3S | B9F | C6G | D5K | E0P | F7H | G1C |
|---|---|---|---|---|---|---|---|
| Surf. 1 | C46 | C46 | C46 | C46 | C46 | C46 | C120 |
| wt % | 3.6 | 4.8 | 6 | 7.2 | 8.4 | 12 | 12 |
| Surf. 2 | C121 | C121 | C121 | C121 | C121 | — | — |
| wt % | 8.4 | 7.2 | 6 | 4.8 | 3.6 | — | — |
| Stab. | C91 | C91 | C91 | C91 | C91 | C91 | C91 |
| wt % | 5 | 5 | 5 | 5 | 5 | 5 | 5 |
| 60° C. | Fail | Fail | Fail | Fail | Fail | Fail | Fail |
| RT | No test | No test | No test | No test | No test | No test | No test |
| 10° C. | No test | No test | No test | No test | No test | No test | No test |
| 0° C. | No test | No test | No test | No test | No test | No test | No test |

Example 21

Stabilizer compatibility evaluation of composition trial 114 comprising 36.9% a.e. (about 480 g a.e./L) potassium glyphosate and the listed surfactant (Surf.) and stabilizer (Stab.) components.

| Run | A4V | B8K | C5F | D9L | E2B | F3S | G0B |
|---|---|---|---|---|---|---|---|
| Surf. 1 | C5 | C5 | C5 | C5 | C5 | C5 | C110 |
| wt % | 3.6 | 4.8 | 6 | 7.2 | 8.4 | 12 | 12 |
| Surf. 2 | C110 | C110 | C110 | C110 | C110 | — | — |
| wt % | 8.4 | 7.2 | 6 | 4.8 | 3.6 | — | — |
| Stab. | C91 | C91 | C91 | C91 | C91 | C91 | C91 |
| wt % | 5 | 5 | 5 | 5 | 5 | 5 | 5 |
| 60° C. | Clear | Clear | Clear | Clear | Clear | Clear | Clear |
| RT | Fail | Fail | Fail | Fail | Fail | Fail | Fail |
| 10° C. | No test | No test | No test | No test | No test | No test | No test |
| 0° C. | No test | No test | No test | No test | No test | No test | No test |

Example 22

Stabilizer compatibility evaluation of composition trial 116 comprising 36.9% a.e. (about 480 g a.e./L) potassium glyphosate and the listed surfactant (Surf.) and stabilizer (Stab.) components.

| Run | A5T | B9J | C3S | D1W | E8H | F5X | G9Z |
|---|---|---|---|---|---|---|---|
| Surf. 1 | C46 | C46 | C46 | C46 | C46 | C46 | C40 |
| wt % | 3.6 | 4.8 | 6 | 7.2 | 8.4 | 12 | 12 |
| Surf. 2 | C40 | C40 | C40 | C40 | C40 | — | — |
| wt % | 8.4 | 7.2 | 6 | 4.8 | 3.6 | — | — |
| Stab. | C91 | C91 | C91 | C91 | C91 | C91 | C91 |
| wt % | 5 | 5 | 5 | 5 | 5 | 5 | 5 |
| 60° C. | Clear | Clear | Clear | Clear | Clear | Clear | Clear |
| RT | Fail | Fail | Fail | Fail | Fail | Fail | Fail |
| 10° C. | No test | No test | No test | No test | No test | No test | No test |
| 0° C. | No test | No test | No test | No test | No test | No test | No test |

Example 23

Stabilizer compatibility evaluation of composition trial 117 comprising 36.9% a.e. (about 480 g a.e./L) potassium glyphosate and the listed surfactant (Surf.) and stabilizer (Stab.) components.

| Run | A6B | B4K | C5T | D9I | E2X | F6V | G5Q | H8N | I5X | J9P |
|---|---|---|---|---|---|---|---|---|---|---|
| Surf. 1 | C27 | C27 | C27 | C27 | C27 | C27 | C27 | C27 | C27 | C27 |
| wt % | 4.9 | 4.9 | 4.9 | 4.9 | 4.9 | 4.9 | 4.9 | 4.9 | 4.9 | 4.9 |
| Surf. 2 | C43 | C43 | C43 | C43 | C43 | C43 | C43 | C43 | C43 | C43 |
| wt % | 7.4 | 7.4 | 7.4 | 7.4 | 7.4 | 7.4 | 7.4 | 7.4 | 7.4 | 7.4 |
| Stab. | C90 | C38 | C113 | C85 | C74 | C78 | C92 | C117 | C95 | C36 |
| wt % | 6 | 6 | 6 | 6 | 6 | 6 | 6 | 6 | 6 | 6 |
| 60° C. | Clear | Clear | Clear | Clear | Clear | Clear | Clear | Clear | Clear | Clear |
| RT | Clear | Fail | Fail | Fail | Clear | Fail | Clear | Fail | Fail | Fail |
| 10° C. | Clear | No test | No test | No test | Clear | No test | Fail | No test | No test | No test |
| 0° C. | Cloudy | No test | No test | No test | Cloudy | No test | No test | No test | No test | No test |

Example 24

Stabilizer compatibility evaluation of composition trial 118 comprising 36.9% a.e. (about 480 g a.e./L) potassium glyphosate and the listed surfactant (Surf.) and stabilizer (Stab.) components.

| Run | A4V | B6K | C3J | D0W | E6B | F2X | G7I | H9Q | I4T |
|---|---|---|---|---|---|---|---|---|---|
| Surf. 1 | C27 | C27 | C27 | C27 | C27 | C27 | C27 | C27 | C27 |
| wt % | 4.9 | 4.9 | 4.9 | 4.9 | 4.9 | 4.9 | 4.9 | 4.9 | 4.9 |
| Surf. 2 | C43 | C43 | C43 | C43 | C43 | C43 | C43 | C43 | C43 |
| wt % | 7.4 | 7.4 | 7.4 | 7.4 | 7.4 | 7.4 | 7.4 | 7.4 | 7.4 |
| Stab. | C1 | C25 | C116 | C118 | C115 | C113 | C119 | C89 | C88 |
| wt % | 6 | 6 | 6 | 6 | 6 | 6 | 6 | 6 | 6 |
| 60° C. | Clear | Clear | Clear | Clear | Clear | Clear | Clear | Clear | Clear |
| RT | Fail | Fail | Fail | Fail | Fail | Fail | Fail | Fail | Clear |
| 10° C. | No Test | No test | No test | No test | No test | No Test | No test | No test | No test |
| 0° C. | No Test | No test | No test | No test | No test | No Test | No test | No test | No test |

Example 25

Stabilizer compatibility evaluation of composition trial 119 comprising 31% a.e. (about 370 g a.e./L) isopropylamine glyphosate and the listed surfactant (Surf.) and stabilizer (Stab.) components.

| Run | A4V | B6K | C3J | D0W | E6B | F2X | G7I | H9Q | I4T |
|---|---|---|---|---|---|---|---|---|---|
| Surf. 1 | C27 | C27 | C27 | C27 | C27 | C27 | C27 | C27 | C27 |
| wt % | 4.9 | 4.9 | 4.9 | 4.9 | 4.9 | 4.9 | 4.9 | 4.9 | 4.9 |
| Surf. 2 | C43 | C43 | C43 | C43 | C43 | C43 | C43 | C43 | C43 |
| wt % | 7.4 | 7.4 | 7.4 | 7.4 | 7.4 | 7.4 | 7.4 | 7.4 | 7.4 |
| Stab. | C74 | C92 | C36 | C91 | C92 | C89 | C78 | C85 | C74 |
| wt % | 4 | 4 | 4 | 4 | 7 | 7 | 7 | 7 | 5.5 |
| 60° C. | Clear | Clear | Clear | Clear | Clear | Clear | Clear | Clear | Clear |
| RT | Clear | Clear | Clear | Fail | Fail | Fail | Fail | Fail | Clear |
| 10° C. | Fail | Fail | Fail | No test | No test | No test | No test | No test | Cloudy |
| 0° C. | No Test | No test | No test | No test | No test | No test | No test | No test | Fail |

Example 26

Stabilizer compatibility evaluation of composition trial 120 comprising 36.9% (about 480 g a.e./L) potassium glyphosate (Run A5R), 31% a.e. (about 370 g a.e./L) isopropylamine glyphosate (all other runs) and the listed surfactant (Surf.) and stabilizer (Stab.) components.

| Run | A5R | B2W | C7V | D5T | E9P |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C110 | C110 | C110 | C110 | C110 |
| wt % | 7.4 | 7.4 | 7.4 | 7.4 | 7.4 |
| Stab. 1 | C74 | C74 | C92 | C92 | C92 |
| wt % | 5.5 | 5.5 | 6 | 6 | 5 |
| Stab. 2 | C25 | C25 | C25 | — | — |
| wt % | 0.3 | 0.3 | 0.3 | — | — |
| 60° C. | Clear | Clear | Clear | Clear | Clear |
| RT | Clear | Clear | Clear | Clear | Clear |
| 10° C. | Fail | Fail | Clear | Clear | Clear |
| 0° C. | No test | No test | Fail | Fail | Clear |

Example 27

Stabilizer compatibility evaluation of composition trial 122 comprising 36.9% a.e. (about 480 g a.e./L) potassium glyphosate and the listed surfactant (Surf.) and stabilizer (Stab.) components.

| Run | A8N | B6K | C4L | D2M | E3A | F7C | G6Y |
|---|---|---|---|---|---|---|---|
| Surf. 1 | C5 | C5 | C5 | C5 | C5 | C5 | C40 |
| wt % | 3.6 | 4.8 | 6 | 7.2 | 8.4 | 12 | 12 |
| Surf. 2 | C40 | C40 | C40 | C40 | C40 | — | — |
| wt % | 8.4 | 7.2 | 6 | 4.8 | 3.6 | — | — |
| Stab. | C91 | C91 | C91 | C91 | C91 | C91 | C91 |
| wt % | 5 | 5 | 5 | 5 | 5 | 5 | 5 |
| 60° C. | Fail | Fail | Fail | Fail | Fail | Fail | Clear |
| RT | No test | No test | No test | No test | No test | No test | Fail |
| 10° C. | No test | No test | No test | No test | No test | No test | No test |
| 0° C. | No test | No test | No test | No test | No test | No test | No test |

Example 28

Stabilizer compatibility evaluation of composition trial 124 comprising 36.9% a.e. (about 480 g a.e./L) potassium glyphosate and the listed surfactant (Surf.) and stabilizer (Stab.) components.

| Run | A5N | B7U | C0P | D5J | E4W | F9K | G5V |
|---|---|---|---|---|---|---|---|
| Surf. 1 | C11 | C11 | C11 | C11 | C11 | C11 | C110 |
| wt % | 3.6 | 4.8 | 6 | 7.2 | 8.4 | 12 | 12 |
| Surf. 2 | C110 | C110 | C110 | C110 | C110 | — | — |
| wt % | 8.4 | 7.2 | 6 | 4.8 | 3.6 | | |
| Stab. | C91 | C91 | C91 | C91 | C91 | C91 | C91 |
| wt % | 5 | 5 | 5 | 5 | 5 | 5 | 5 |
| 60° C. | Clear | Clear | Fail | Fail | Fail | Fail | Fail |
| RT | Clear | Clear | No test | No test | No test | No test | No test |
| 10° C. | Clear | Clear | No test | No test | No test | No test | No test |
| 0° C. | Fail | Fail | No test | No test | No test | No test | No test |

Example 29

Stabilizer compatibility evaluation of composition trial 125 comprising 31% a.e. (about 370 g a.e./L) isopropylamine glyphosate and the listed surfactant (Surf.) and stabilizer (Stab.) components.

| Run | A9B | B6I | C4D | D2L | E2A |
|---|---|---|---|---|---|
| Surf. 1 | C27 | C27 | C27 | C27 | C27 |
| wt % | 4.8 | 4.8 | 4.8 | 4.8 | 4.8 |
| Surf. 2 | C43 | C43 | C43 | C43 | C43 |
| wt % | 7.2 | 7.2 | 7.2 | 7.2 | 7.2 |
| Stab. | C74 | C92 | C92 | C92 | C92 |
| wt % | 5.5 | 6 | 5 | 7 | 6 |
| Other Add. | C32 | — | — | — | C15 |
| wt % | 0.3 | | | | 0.3 |
| 60° C. | Clear | Clear | Clear | Clear | Clear |
| RT | Clear | Clear | Clear | Clear | Clear |
| 10° C. | Fail | Fail | Fail | Fail | Fail |
| 0° C. | No test | No test | No test | No test | No test |

Example 30

Stabilizer compatibility evaluation of composition trial 126 comprising 31% a.e. (about 370 g a.e./L) isopropylamine glyphosate and the listed surfactant (Surf.) and stabilizer (Stab.) components.

| Run | A9L | B5Y | C3S | D8U | E1R |
|---|---|---|---|---|---|
| Surf. 1 | C27 | C27 | C27 | C46 | C46 |
| wt % | 7.2 | 4.8 | 4.8 | 4.8 | 4.8 |
| Surf. 2 | C43 | C43 | C110 | C43 | C43 |
| wt % | 7.2 | 7.2 | 7.2 | 7.2 | 7.2 |
| Stab. | C36 | C74 | C92 | C92 | C74 |
| wt % | 2.3 | 6 | 6 | 6 | 6 |
| Other Add. | C15 | C32 | C32 | — | C32 |
| wt % | 3.3 | 0.3 | 0.3 | — | 0.3 |
| 60° C. | Clear | Clear | Clear | Clear | Clear |
| RT | Clear | Clear | Clear | Clear | Clear |
| 10° C. | Fail | Fail | Fail | Fail | Fail |
| 0° C. | No test | No test | No test | No test | No test |

Example 31

Stabilizer compatibility evaluation of composition trial 127 comprising 31% a.e. (about 370 g a.e./L) isopropylamine glyphosate and the listed surfactant (Surf.) and stabilizer (Stab.) components.

| Run | A5G | B9K | C4M | D2X | E8O | F2W |
|---|---|---|---|---|---|---|
| Surf. 1 | C27 | C27 | C27 | C27 | C27 | C27 |
| wt % | 4 | 4 | 4 | 4 | 4 | 4 |
| Surf. 2 | C110 | C110 | C110 | C110 | C110 | C110 |
| wt % | 6 | 6 | 6 | 6 | 6 | 6 |
| Stab. | C74 | C74 | C74 | C74 | C91 | C38 |
| wt % | 3 | 4 | 5 | 6 | 5 | 5 |
| 60° C. | Fail | Fail | Fail | Fail | Fail | Fail |
| RT | Fail | Fail | Fail | Fail | Fail | Fail |
| 10° C. | No test | No test | No test | No test | No test | No test |
| 0° C. | No test | No test | No test | No test | No test | No test |

Example 32

Stabilizer compatibility evaluation of composition trial 128 comprising 31% a.e. (about 370 g a.e./L) isopropylamine glyphosate and the listed surfactant (Surf.) and stabilizer (Stab.) components.

| Run | A4P | B3D | C5G | D4H | E8J | F1V | G4X |
|---|---|---|---|---|---|---|---|
| Surf. 1 | C5 | C5 | C27 | C46 | C46 | C46 | C46 |
| wt % | 4 | 4 | 4.8 | 4.9 | 4.9 | 4.9 | 4.9 |
| Surf. 2 | C109 | C109 | C42 | C110 | C110 | C110 | C110 |
| wt % | 6 | 6 | 7.2 | 7.4 | 7.4 | 7.4 | 7.4 |
| Stab. | C74 | C92 | C74 | C92 | C92 | C74 | C74 |
| wt % | 6 | 6 | 6 | 3 | 4 | 3 | 6 |
| 60° C. | Clear | Clear | Clear | Fail | Clear | Clear | Clear |
| RT | Clear | Clear | Clear | No test | Clear | Clear | Clear |
| 10° C. | Cloudy | Fail | Fail | No test | Clear | Clear | Clear |
| 0° C. | Cloudy | No test | No test | No test | Fail | Cloudy | Cloudy |

Example 33

Stabilizer compatibility evaluation of composition trial 129 comprising 31% a.e. (about 370 g a.e./L) isopropylamine glyphosate and the listed surfactant (Surf.) and stabilizer (Stab.) components.

| Run | A6H | B4F | C9K | D3M | E1S | F0L | G5N | H3Z | I6F | J2U |
|---|---|---|---|---|---|---|---|---|---|---|
| Surf. 1 | C46 | C46 | C46 | C46 | C46 | C46 | C46 | C46 | C46 | C46 |
| wt % | 4.9 | 4.9 | 4.9 | 4.9 | 4.9 | 4.9 | 4.9 | 4.9 | 4.9 | 4.9 |

-continued

| Run | A6H | B4F | C9K | D3M | E1S | F0L | G5N | H3Z | I6F | J2U |
|---|---|---|---|---|---|---|---|---|---|---|
| Surf. 2 | C110 | C110 | C110 | C110 | C110 | C110 | C110 | C110 | C110 | C110 |
| wt % | 7.4 | 7.4 | 7.4 | 7.4 | 7.4 | 7.4 | 7.4 | 7.4 | 7.4 | 7.4 |
| Stab. | C74 | C74 | C92 | C92 | C91 | C91 | C91 | C91 | C91 | — |
| wt % | 2 | 1 | 2 | 1 | 1 | 2 | 3 | 4 | 5 | — |
| 60° C. | Clear | Clear | Clear | Clear | Clear | Clear | Clear | Clear | Clear | Fail |
| RT | Clear | Clear | Clear | Clear | Clear | Clear | Clear | Clear | Clear | No test |
| 10° C. | Clear | Clear | Clear | Clear | Clear | Clear | Clear | Clear | Clear | No test |
| 0° C. | Fail | Fail | Fail | Fail | Fail | Clear | Clear | Clear | Clear | No test |

Example 34

Stabilizer compatibility evaluation of composition trial 130 comprising 36.9% a.e. (about 480 g a.e./L) potassium glyphosate and the listed surfactant (Surf.) and stabilizer (Stab.) components.

| Run | A8M | B6H | C0S | D1J | E3X | F5G | G4K | H7V |
|---|---|---|---|---|---|---|---|---|
| Surf. 1 | C27 | C27 | C46 | C46 | C46 | C46 | C46 | C46 |
| wt % | 4 | 4 | 4.8 | 4.8 | 4.8 | 4.8 | 4.8 | 4.8 |
| Surf. 2 | C43 | C43 | C121 | C121 | C110 | C110 | C40 | C40 |
| wt % | 6 | 6 | 7.2 | 7.2 | 7.2 | 7.2 | 7.2 | 7.2 |
| Stab. | C91 | C74 | C91 | C74 | C91 | C91 | C91 | C92 |
| wt % | 6 | 6 | 6 | 6 | 5 | 4 | 6 | 6 |
| 60° C. | Fail | Fail | Fail | Clear | Fail | Fail | Clear | Fail |
| RT | No test | No test | No test | Clear | No test | No test | Clear | No test |
| 10° C. | No test | No test | No test | Clear | No test | No test | Clear | No test |
| 0° C. | No test | No test | No test | Cloudy | No test | No test | Fail | No test |

Example 35

Stabilizer compatibility evaluation of composition trial 131 comprising 36.9% a.e. (about 480 g a.e./L) potassium glyphosate and the listed surfactant (Surf.) and stabilizer (Stab.) components.

| Run | A4F | B7J | C7L | D1A | E7N | F5O |
|---|---|---|---|---|---|---|
| Surf. 1 | C11 | C11 | C5 | C5 | C5 | C5 |
| wt % | 4.8 | 4.8 | 4.8 | 4.8 | 4.8 | 4.8 |
| Surf. 2 | C110 | C110 | C110 | C110 | C40 | C40 |
| wt % | 7.2 | 7.2 | 7.2 | 7.2 | 7.2 | 7.2 |
| Stab. | C91 | C92 | C92 | C91 | C91 | C92 |
| wt % | 6 | 6 | 6 | 6 | 6 | 6 |
| 60° C. | Fail | Fail | Fail | Fail | Clear | Fail |
| RT | No test | No test | No test | No test | Clear | No test |
| 10° C. | No test | No test | No test | No test | Cloudy | No test |
| 0° C. | No test | No test | No test | No test | Cloudy | No test |

Example 36

Stabilizer compatibility evaluation of composition trial 133 comprising 31% a.e. (about 370 g a.e./L) isopropylamine glyphosate and the listed surfactant (Surf.) and stabilizer (Stab.) components.

| Run | A0B | B5K | C2P | D6G | E1Z | F7U | G9A | H4D |
|---|---|---|---|---|---|---|---|---|
| Surf. 1 | C27 | C27 | C46 | C46 | C46 | C46 | C27 | C46 |
| wt % | 4.8 | 4.8 | 4.8 | 4.9 | 4.9 | 4.8 | 4.9 | 4.8 |
| Surf. 2 | C43 | C43 | C43 | C110 | C110 | C110 | C43 | C40 |
| wt % | 7.2 | 7.2 | 7.2 | 7.4 | 7.4 | 7.2 | 7.4 | 7.2 |
| Stab. | C92 | C74 | C92 | C92 | C92 | C91 | C91 | C74 |
| wt % | 7 | 5.5 | 6 | 6 | 1 | 6 | 6 | 6 |
| 60° C. | Fail | Fail | Fail | Fail | Clear | Clear | Clear | Clear |
| RT | No test | No test | No test | No test | Fail | Clear | Clear | Fail |
| 10° C. | No test | No test | No test | No test | No test | Fail | Fail | No test |
| 0° C. | No test | No test | No test | No test | No test | No test | No test | No test |

Example 37

Stabilizer compatibility evaluation of composition trial 134 comprising 36.9% a.e. (about 480 g a.e./L) potassium glyphosate and the listed surfactant (Surf.) and stabilizer (Stab.) components.

| Run | A6V | B7U | C0S | D3N | E9L | F1X | G6J | H8M |
|---|---|---|---|---|---|---|---|---|
| Surf. 1 | C27 | C27 | C27 | C27 | C46 | C46 | C46 | C46 |
| wt % | 4.8 | 4.8 | 4.8 | 4.8 | 4.8 | 4.8 | 4.8 | 4.8 |
| Surf. 2 | C110 | C110 | C110 | C110 | C110 | C110 | C110 | C110 |
| wt % | 7.2 | 7.2 | 7.2 | 7.2 | 7.2 | 7.2 | 7.2 | 7.2 |
| Stab. | C74 | C91 | C91 | C74 | C74 | C74 | C74 | C91 |
| wt % | 6.5 | 6.5 | 4 | 4 | 3 | 5 | 7 | 3 |
| 60° C. | Clear | Clear | Clear | Clear | Clear | Fail | Clear | Fail |
| RT | Fail | Fail | Fail | Fail | Fail | No test | Clear | No test |
| 10° C. | No test | No test | No test | No test | No test | No test | Fail | No test |
| 0° C. | No test | No test | No test | No test | No test | No test | Fail | No test |

Example 38

Stabilizer compatibility evaluation of composition trial 135 comprising 36.9% a.e. (about 480 g a.e./L) potassium glyphosate and the listed surfactant (Surf.) and stabilizer (Stab.) components.

| Run | A3C | B9H | C4R | D0Z | E5M | F2W | G6B | H7U |
|---|---|---|---|---|---|---|---|---|
| Surf. 1 | C27 | C27 | C46 | C46 | C27 | C27 | C27 | C27 |
| wt % | 4.9 | 4.9 | 4.9 | 4.9 | 4.8 | 4.9 | 4.9 | 4.9 |
| Surf. 2 | C43 | C43 | C110 | C110 | C43 | C43 | C110 | C110 |
| wt % | 7.4 | 7.4 | 7.4 | 7.4 | 7.2 | 7.4 | 7.4 | 7.4 |
| Other | — | — | — | — | C114 | C114 | C114 | C114 |
| wt % | — | — | — | — | 1 | 1 | 1 | 1 |
| Stab. | C91 | C91 | C91 | C91 | C91 | C91 | C91 | C91 |
| wt % | 6.5 | 6.5 | 6.5 | 6.5 | 6.5 | 6.5 | 6.5 | 6.5 |
| 60° C. | Clear | Clear | Clear | Clear | Clear | Clear | Clear | Clear |
| RT | Fail | Fail | Clear | Clear | Fail | Fail | Fail | Fail |
| 10° C. | No test | No test | Fail | Fail | No test | No test | No test | No test |
| 0° C. | No test | No test | No test | No test | No test | No test | No test | No test |

Example 39

Stabilizer compatibility evaluation of composition trial 136 comprising 36.9% a.e. (about 480 g a.e./L) potassium glyphosate and the listed surfactant (Surf.) and stabilizer (Stab.) components.

| Run | A8I | B4R | C3N | D9J | E1S | F0L | G4X | H3C |
|---|---|---|---|---|---|---|---|---|
| Surf. 1 | C27 | C27 | C27 | C27 | C27 | C27 | C27 | C27 |
| wt % | 4.9 | 4.9 | 4.8 | 4.8 | 4.8 | 4.8 | 4.8 | 4.8 |
| Surf. 2 | C43 | C43 | C110 | C110 | C43 | C43 | C43 | C43 |
| wt % | 7.4 | 7.4 | 7.2 | 7.2 | 7.2 | 7.2 | 7.2 | 7.2 |
| Other | — | — | C114 | C114 | C114 | C114 | — | — |
| wt % | — | — | 3 | 1.5 | 1.5 | 3 | — | — |
| Stab. | C91 | C91 | C91 | C91 | C91 | C91 | C91 | C91 |
| wt % | 6 | 6 | 5 | 5 | 5 | 5 | 10 | 12 |
| 60° C. | Clear | Clear | Clear | Clear | Clear | Clear | Clear | Clear |
| RT | Fail | Fail | Fail | Fail | Fail | Fail | Fail | Fail |
| 10° C. | No test | No test | No test | No test | No test | No test | No test | No test |
| 0° C. | No test | No test | No test | No test | No test | No test | No test | No test |

Example 40

Stabilizer compatibility evaluation of composition trial 137 comprising 36.9% a.e. (about 480 g a.e./L) potassium glyphosate and the listed surfactant (Surf.) and stabilizer (Stab.) components.

| Run | A7H | B5T | C8K | D1L |
|---|---|---|---|---|
| Surf. 1 | C27 | C27 | C27 | C27 |
| wt % | 4.8 | 4.8 | 4.8 | 4.8 |
| Surf. 2 | C110 | C110 | C110 | C110 |
| wt % | 7.2 | 7.2 | 7.2 | 7.2 |
| Other | C114 | C114 | C77 | C77 |
| wt % | 0.25 | 0.5 | 0.25 | 0.5 |
| Stab. | C91 | C91 | C91 | C91 |
| wt % | 3 | 3 | 3 | 3 |
| 60° C. | Clear | Clear | Clear | Clear |
| RT | Fail | Fail | Fail | Fail |
| 10° C. | No test | No test | No test | No test |
| 0° C. | No test | No test | No test | No test |

Example 41

Stabilizer compatibility evaluation of composition trial 138 comprising 36.5% a.e. (about 480 g a.e./L) (Run HOV@ 38% —about 513 g a.e./L) potassium glyphosate and the listed surfactant (Surf.) and stabilizer (Stab.) components.

| Run | A9J | B5D | C5K | D3X | E7U | F1P | G4B | H0V | I8P |
|---|---|---|---|---|---|---|---|---|---|
| Surf. 1 | C46 | C46 | C46 | C46 | C46 | C46 | C46 | C46 | C46 |
| wt % | 5.8 | 5.8 | 5.8 | 5.8 | 5.8 | 5.8 | 5.8 | 5.8 | 5.8 |
| Surf. 2 | C110 | C110 | C110 | C110 | C110 | C110 | C110 | C110 | C110 |
| wt % | 8.8 | 8.8 | 8.8 | 8.8 | 8.8 | 8.8 | 8.8 | 8.8 | 8.8 |
| Stab. | C91 | C74 | C91 | C91 | C91 | C91 | C91 | C91 | C91 |
| wt % | 7 | 7 | 8.5 | 6.5 | 7 | 7.5 | 8.5 | 9 | 9 |
| 60° C. | Fail | Fail | Fail | Fail | Fail | Fail | Fail | Fail | Fail |
| RT | No test | No test | No test | No test | No test | No test | No test | No test | No test |
| 10° C. | No test | No test | No test | No test | No test | No test | No test | No test | No test |
| 0° C. | No test | No test | No test | No test | No test | No test | No test | No test | No test |

Example 42

Stabilizer compatibility evaluation of composition trial 139 comprising 31% a.e. (about 370 g a.e./L) isopropylamine glyphosate and the listed surfactant (Surf.) and stabilizer (Stab.) components.

| Run | A5L | B2S | C7H |
|---|---|---|---|
| Surf. 1 | C46 | C46 | C46 |
| wt % | 4.9 | 4.9 | 4.9 |
| Surf. 2 | C110 | C110 | C110 |
| wt % | 7.4 | 7.4 | 7.4 |
| Stab. | C91 | C91 | C91 |
| wt % | 5 | 5 | 5 |
| 60° C. | Fail | Fail | Fail |
| RT | No test | No test | No test |
| 10° C. | No test | No test | No test |
| 0° C. | No test | No test | No test |

Example 43

Stabilizer compatibility evaluation of composition trial 140 comprising 31% a.e. (about 370 g a.e./L) isopropylamine glyphosate and the listed surfactant (Surf.) and stabilizer (Stab.) components.

| Run | A0P | B6F | C4Z | D2W | E7K |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C110 | C110 | C110 | C110 | C110 |
| wt % | 7.4 | 7.4 | 7.4 | 7.4 | 7.4 |
| Stab. 1 | C38 | C38 | C38 | C38 | C91 |
| wt % | 0.5 | 1 | 0.5 | 1 | 0.5 |
| Stab. 2 | — | — | C91 | C91 | — |
| wt % | — | — | 1 | 1 | — |
| 60° C. | Fail | Fail | Clear | Fail | Clear |
| RT | No test | No test | Clear | No test | Clear |
| 10° C. | No test | No test | Clear | No test | Clear |
| 0° C. | No test | No test | Fail | No test | Fail |

| Run | F6G | G9B | H2V | I5S |
|---|---|---|---|---|
| Surf. 1 | C46 | C46 | C46 | C46 |
| wt % | 4.9 | 4.9 | 4.9 | 4.9 |
| Surf. 2 | C110 | C110 | C110 | C110 |
| wt % | 7.4 | 7.4 | 7.4 | 7.4 |
| Stab. 1. | C91 | C91 | C91 | C30 |
| wt % | 1 | 1 | 1 | 0.5 |
| Stab. 2 | — | C30 | C30 | — |
| wt % | — | 0.5 | 1 | — |
| 60° C. | Clear | Clear | Clear | Clear |
| RT | Clear | Fail | Clear | Clear |
| 10° C. | Clear | No test | Fail | Fail |
| 0° C. | Fail | No test | No test | No test |

Example 44

Stabilizer compatibility evaluation of composition trial 141 comprising 31% a.e. (about 370 g a.e./L) isopropylamine glyphosate and the listed surfactant (Surf.) and stabilizer (Stab.) components.

| Run | A7J | B6G | C4L | D0S | E7N | F4B | G6W | H9L | I1V |
|---|---|---|---|---|---|---|---|---|---|
| Surf. 1 | C27 | C27 | C27 | C27 | C27 | C27 | C27 | C27 | C27 |
| wt % | 4.9 | 4.9 | 4.9 | 4.9 | 4.9 | 4.9 | 4.9 | 4.9 | 4.9 |
| Surf. 2 | C110 | C110 | C110 | C110 | C110 | C110 | C110 | C110 | C110 |
| wt % | 7.4 | 7.4 | 7.4 | 7.4 | 7.4 | 7.4 | 7.4 | 7.4 | 7.4 |
| Stab. | C91 | C91 | C91 | C91 | C91 | C91 | C91 | C91 | C91 |
| wt% | 5 | 6 | 7 | 8 | 9 | 10 | 4 | 3 | 2 |
| 60° C. | Clear | Clear | Clear | Clear | Clear | Clear | Clear | Clear | Clear |
| RT | Clear | Clear | Clear | Clear | Clear | Clear | Clear | Clear | Clear |
| 10° C. | Fail | Fail | Fail | Fail | Fail | Fail | Fail | Fail | Fail |
| 0° C. | No test | No test | No test | No test | No test | No test | No test | No test | No test |

Example 45

Stabilizer compatibility evaluation of composition trial 143 comprising 36.7% a.e. (about 480 g a.e./L) potassium glyphosate and the listed surfactant (Surf.) and stabilizer (Stab.) components.

| Run | A3W | B3P | C7Y | D5J | E0C |
|---|---|---|---|---|---|
| Surf. 1 | C27 | C27 | C27 | C27 | C27 |
| wt % | 4.9 | 4.9 | 4.9 | 4.9 | 4.9 |
| Surf. 2 | C110 | C110 | C110 | C110 | C110 |
| wt % | 7.4 | 7.4 | 7.4 | 7.4 | 7.4 |
| Stab. | C91 | C91 | C91 | C91 | C91 |
| wt % | 2 | 4 | 6 | 8 | 10 |
| 60° C. | Clear | Cloudy | Cloudy | Clear | Clear |
| RT | Clear | Fail | Fail | Clear | Clear |
| 10° C. | Fail | No test | No test | Cloudy | Cloudy |
| 0° C. | No test | No test | No test | Fail | Fail |

Example 46

Stabilizer compatibility evaluation of composition trial 144 comprising 36.7% a.e. (about 480 g a.e./L) potassium glyphosate and the listed surfactant (Surf.) and stabilizer (Stab.) components.

| Run | A6U | B1X | C6Y | D2P | E8H |
|---|---|---|---|---|---|
| Surf. 1 | C27 | C27 | C27 | C27 | C27 |
| wt % | 4.9 | 4.9 | 4.9 | 4.9 | 4.9 |
| Surf. 2 | C40 | C40 | C40 | C40 | C40 |
| wt % | 7.4 | 7.4 | 7.4 | 7.4 | 7.4 |
| Stab. | C91 | C91 | C91 | C91 | C91 |
| wt % | 2 | 4 | 6 | 8 | 10 |
| 60° C. | Fail | Clear | Clear | Clear | Clear |
| RT | No test | Fail | Fail | Fail | Fail |
| 10° C. | No test | No test | No test | No test | No test |
| 0° C. | No test | No test | No test | No test | No test |

Example 47

Stabilizer compatibility evaluation of composition trial 145 comprising 36.7% a.e. (about 480 g a.e./L) potassium glyphosate and the listed surfactant (Surf.) and stabilizer (Stab.) components.

| Run | A3E | B0K | C4V | D1Q | E3T |
|---|---|---|---|---|---|
| Surf. 1 | C11 | C11 | C11 | C11 | C11 |
| wt % | 4.9 | 4.9 | 4.9 | 4.9 | 4.9 |
| Surf. 2 | C40 | C40 | C40 | C40 | C40 |
| wt % | 7.4 | 7.4 | 7.4 | 7.4 | 7.4 |
| Stab. | C91 | C91 | C91 | C91 | C91 |
| wt % | 2 | 4 | 6 | 8 | 10 |
| 60° C. | Clear | Clear | Clear | Clear | Clear |
| RT | Fail | Fail | Fail | Fail | Fail |
| 10° C. | No test | No test | No test | No test | No test |
| 0° C. | No test | No test | No test | No test | No test |

Example 48

Stabilizer compatibility evaluation of composition trial 146 comprising 36.7% a.e. (about 480 g a.e./L) potassium glyphosate and the listed surfactant (Surf.) and stabilizer (Stab.) components.

| Run | A3E | B0K | C4V | D1Q | E3T |
|---|---|---|---|---|---|
| Surf. 1 | C11 | C11 | C11 | C11 | C11 |
| wt % | 4.9 | 4.9 | 4.9 | 4.9 | 4.9 |
| Surf. 2 | C110 | C110 | C110 | C110 | C110 |
| wt % | 7.4 | 7.4 | 7.4 | 7.4 | 7.4 |
| Stab. | C91 | C91 | C91 | C91 | C91 |
| wt % | 2 | 4 | 6 | 8 | 10 |
| 60° C. | Cloudy | Fail | Clear | Clear | Clear |
| RT | Fail | No test | Clear | Clear | Clear |
| 10° C. | No test | No test | Fail | Fail | Fail |
| 0° C. | No test | No test | No test | No test | No test |

Example 49

Stabilizer compatibility evaluation of composition trial 147 comprising 36.7% a.e. (about 480 g a.e./L) potassium glyphosate and the listed surfactant (Surf.) and stabilizer (Stab.) components.

| Run | A5F | B9I | C2S | D6G | E8V |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C40 | C40 | C40 | C40 | C40 |
| wt % | 7.4 | 7.4 | 7.4 | 7.4 | 7.4 |
| Stab. | C91 | C91 | C91 | C91 | C91 |
| wt % | 2 | 4 | 6 | 8 | 10 |
| 60° C. | Clear | Cloudy | Cloudy | Clear | Clear |
| RT | Cloudy | Fail | Clear | Clear | Clear |
| 10° C. | Fail | No test | Fail | Fail | Fail |
| 0° C. | No test | No test | No test | No test | No test |

Example 50

Stabilizer compatibility evaluation of composition trial 148 comprising 36.7% a.e. (about 480 g a.e./L) potassium glyphosate and the listed surfactant (Surf.) and stabilizer (Stab.) components.

| Run | A6H | B2Z | C7J | D0R | E3D |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C41 | C41 | C41 | C41 | C41 |
| wt % | 7.4 | 7.4 | 7.4 | 7.4 | 7.4 |
| Stab. | C91 | C91 | C91 | C91 | C91 |
| wt % | 2 | 4 | 6 | 8 | 10 |
| 60° C. | Clear | Fail | Fail | Clear | Clear |
| RT | Clear | Fail | Fail | Clear | Clear |
| 10° C. | Fail | Cloudy | Cloudy | Fail | Fail |
| 0° C. | No test | Fail | Fail | No test | Fail |

Example 51

Stabilizer compatibility evaluation of composition trial 149 comprising 36.7% a.e. (about 480 g a.e./L) potassium glyphosate and the listed surfactant (Surf.) and stabilizer (Stab.) components.

| Run | A2D | B0O | C4V | D2B | E7Q |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C110 | C110 | C110 | C110 | C110 |
| wt % | 7.4 | 7.4 | 7.4 | 7.4 | 7.4 |
| Stab. | C91 | C91 | C91 | C91 | C91 |
| wt % | 2 | 4 | 6 | 8 | 10 |
| 60° C. | Clear | Clear | Clear | Clear | Clear |
| RT | Clear | Clear | Clear | Clear | Clear |
| 10° C. | Clear | Clear | Clear | Clear | Clear |
| 0° C. | Fail | Fail | Fail | Fail | Fail |

Example 52

Stabilizer compatibility evaluation of composition trial 150 comprising 36.7% a.e. (about 480 g a.e./L) potassium glyphosate and the listed surfactant (Surf.) and stabilizer (Stab.) components.

| Run | A4R | B9K | C2A |
|---|---|---|---|
| Surf. 1 | C46 | C46 | C46 |
| wt % | 4.9 | 4.9 | 4.9 |
| Surf. 2 | C110 | C110 | C110 |
| wt % | 7.4 | 7.4 | 7.4 |
| Stab. | C30 | C30 | C30 |
| wt % | 1 | 2 | 3 |
| 60° C. | Clear | Clear | Clear |
| RT | Fail | Fail | Fail |
| 10° C. | No test | No test | No test |
| 0° C. | No test | No test | No test |

Example 53

Stabilizer compatibility evaluation of composition trial 151 comprising 31% a.e. (about 370 g a.e./L) isopropylamine glyphosate and the listed surfactant (Surf.) and stabilizer (Stab.) components.

| Run | A1T | B5S | C3G | D9L | E8E | F5H | G3K | H7R | I5B | J0Z | K5Q |
|---|---|---|---|---|---|---|---|---|---|---|---|
| Surf. 1 | C46 | C46 | C46 | C46 | C46 | C46 | C46 | C46 | C46 | C46 | C46 |
| wt % | 4.8 | 4.8 | 4.8 | 4.8 | 4.8 | 4.8 | 4.8 | 4.8 | 4.8 | 4.8 | 4.8 |
| Surf. 2 | C110 | C110 | C110 | C110 | C110 | C110 | C110 | C110 | C110 | C110 | C110 |
| wt % | 7.2 | 7.2 | 7.2 | 7.2 | 7.2 | 7.2 | 7.2 | 7.2 | 7.2 | 7.2 | 7.2 |
| Stab. 1 | C91 | C91 | C91 | C91 | C91 | C91 | C91 | C91 | C91 | C91 | C91 |
| wt % | 1 | 2 | 3 | 4 | 5 | 6 | 7 | 8 | 1 | 1 | 1 |
| Stab. 2 | — | — | — | — | — | — | — | — | C30 | C30 | C30 |
| wt % | — | — | — | — | — | — | — | — | 1 | 2 | 3 |
| 60° C. | Clear | Clear | Clear | Clear | Clear | Clear | Clear | Clear | Fail | Fail | Fail |
| RT | Clear | Clear | Clear | Clear | Clear | Clear | Clear | Clear | No test | No test | No test |
| 10° C. | Fail | Fail | Fail | Fail | Fail | Fail | Fail | Fail | No test | No test | No test |
| 0° C. | No test | No test | No test | No test | No test | No test | No test | No test | No test | No test | No test |

Example 54

Stabilizer compatibility evaluation of composition trial 152 comprising 31% a.e. (about 370 g a.e./L) isopropylamine glyphosate and the listed surfactant (Surf.) and stabilizer (Stab.) components.

| Run | A5N | B5L | C2U | D9Y | E6H | F0S |
|---|---|---|---|---|---|---|
| Surf. 1 | C27 | C27 | C27 | C27 | C27 | C27 |
| wt % | 4 | 4 | 4 | 4 | 4 | 4 |
| Surf. 2 | C110 | C110 | C110 | C110 | C110 | C110 |
| wt % | 6 | 6 | 6 | 6 | 6 | 6 |
| Stab. | C91 | C91 | C91 | C91 | C91 | C91 |
| wt % | 1 | 2 | 3 | 4 | 5 | 6 |
| 60° C. | Clear | Clear | Clear | Clear | Clear | Clear |
| RT | Clear | Clear | Clear | Clear | Clear | Clear |
| 10° C. | Cloudy | Cloudy | Cloudy | Cloudy | Cloudy | Cloudy |
| 0° C. | Fail | Fail | Fail | Fail | Fail | Fail |

Example 55

Stabilizer compatibility evaluation of composition trial 153 comprising 31% a.e. (about 370 g a.e./L) isopropylamine glyphosate and the listed surfactant (Surf.) and stabilizer (Stab.) components.

| Run | A7Y | B2D | C2C | D7J | E9O | F7Y |
|---|---|---|---|---|---|---|
| Surf. 1 | C46 | C46 | C46 | C46 | C46 | C46 |
| wt % | 4.8 | 4.8 | 4.8 | 4.8 | 4.8 | 4.8 |
| Surf. 2 | C110 | C110 | C110 | C110 | C110 | C110 |
| wt % | 7.2 | 7.2 | 7.2 | 7.2 | 7.2 | 7.2 |
| Stab. | C92 | C92 | C92 | C92 | C92 | C92 |
| wt % | 1 | 2 | 3 | 4 | 5 | 6 |
| 60° C. | Cloudy | Cloudy | Cloudy | Cloudy | Cloudy | Cloudy |
| RT | Fail | Fail | Fail | Fail | Fail | Fail |
| 10° C. | No test | No test | No test | No test | No test | No test |
| 0° C. | No test | No test | No test | No test | No test | No test |

Example 56

Stabilizer compatibility evaluation of composition trial 154 comprising 31% a.e. (about 370 g a.e./L) isopropylamine glyphosate and the listed surfactant (Surf.) and stabilizer (Stab.) components.

| Run | A2T | B1Q | C9K | D5L | E7W | F7K |
|---|---|---|---|---|---|---|
| Surf. 1 | C46 | C46 | C46 | C46 | C46 | C46 |
| wt % | 4.8 | 4.8 | 4.8 | 4.8 | 4.8 | 4.8 |
| Surf. 2 | C110 | C110 | C110 | C110 | C110 | C110 |
| wt % | 7.2 | 7.2 | 7.2 | 7.2 | 7.2 | 7.2 |
| Stab. | C76 | C76 | C76 | C76 | C76 | C76 |
| wt % | 1 | 2 | 3 | 4 | 5 | 6 |
| 60° C. | Fail | Fail | Fail | Fail | Fail | Fail |
| RT | No test | No test | No test | No test | No test | No test |
| 10° C. | No test | No test | No test | No test | No test | No test |
| 0° C. | No test | No test | No test | No test | No test | No test |

Example 57

Stabilizer compatibility evaluation of composition trial 155 comprising 36.7% a.e. (about 480 g a.e./L) potassium glyphosate and the listed surfactant (Surf.) and stabilizer (Stab.) components.

| Run | A6T | B2U | C3V |
|---|---|---|---|
| Surf. 1 | C46 | C46 | C46 |
| wt % | 4.9 | 4.9 | 4.9 |
| Surf. 2 | C110 | C110 | C110 |
| wt % | 7.4 | 7.4 | 7.4 |
| Stab. 1 | C91 | C91 | C91 |
| wt % | 6.5 | 6.5 | 6.5 |
| Stab. 2 | C114 | C44 | C75 |
| wt % | 6.8 | 6.82 | 6.8 |
| 60° C. | Clear | Clear | Clear |
| RT | Fail | Fail | Fail |
| 10° C. | No test | No test | No test |
| 0° C. | No test | No test | No test |

Example 58

Stabilizer compatibility evaluation of composition trial 156 comprising 36.7% a.e. (about 480 g a.e./L) potassium glyphosate and the listed surfactant (Surf.) and stabilizer (Stab.) components.

| Run | A3P | B2X | C9Y | D5N | E7B | F1Z | G8M | H5C | I9K | J4F |
|---|---|---|---|---|---|---|---|---|---|---|
| Surf. 1 | C46 | C46 | C46 | C46 | C46 | C46 | C46 | C46 | C46 | C46 |
| wt % | 4.9 | 4.9 | 4.9 | 4.9 | 4.9 | 4.9 | 4.9 | 4.9 | 4.9 | 4.9 |
| Surf. 2 | C110 | C110 | C110 | C110 | C110 | C110 | C110 | C110 | C110 | C110 |
| wt % | 7.4 | 7.4 | 7.4 | 7.4 | 7.4 | 7.4 | 7.4 | 7.4 | 7.4 | 7.4 |
| Stab. | C91 | C91 | C91 | C91 | C91 | C91 | C91 | C91 | C91 | C91 |
| wt % | 1 | 2 | 3 | 4 | 5 | 6 | 7 | 8 | 9 | 10 |
| 60° C. | Fail | Fail | Fail | Fail | Fail | Clear | Fail | Fail | Fail | Fail |
| RT | No test | No test | No test | No test | No test | Fail | No test | No test | No test | No test |
| 10° C. | No test | No test | No test | No test | No test | No test | No test | No test | No test | No test |
| 0° C. | No test | No test | No test | No test | No test | No test | No test | No test | No test | No test |

Example 59

Stabilizer compatibility evaluation of composition trial 157 comprising 36.7% a.e. (about 480 g a.e./L) potassium glyphosate and the listed surfactant (Surf.) and stabilizer (Stab.) components.

| Run | A7U | B2S | C8J | D4F | E0A |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C110 | C110 | C110 | C110 | C110 |
| wt % | 7.4 | 7.4 | 7.4 | 7.4 | 7.4 |
| Stab. | C92 | C92 | C92 | C92 | C92 |
| wt % | 2 | 4 | 6 | 8 | 10 |
| 60° C. | Clear | Clear | Clear | Clear | Clear |
| RT | Fail | Clear | Clear | Clear | Clear |
| 10° C. | No test | Fail | Fail | Fail | Fail |
| 0° C. | No test | No test | No test | No test | No test |

Example 60

Stabilizer compatibility evaluation of composition trial 158 comprising 36.7% a.e. (about 480 g a.e./L) potassium glyphosate and the listed surfactant (Surf.) and stabilizer (Stab.) components.

| Run | A7U | B2S | C8J | D4F | E0A |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C110 | C110 | C110 | C110 | C110 |
| wt % | 7.4 | 7.4 | 7.4 | 7.4 | 7.4 |
| Stab. | C76 | C76 | C76 | C76 | C76 |
| wt % | 2 | 4 | 6 | 8 | 10 |
| 60° C. | Clear | Clear | Clear | Clear | Clear |
| RT | Fail | Fail | Fail | Fail | Fail |
| 10° C. | No test | No test | No test | No test | No test |
| 0° C. | No test | No test | No test | No test | No test |

Example 61

Stabilizer compatibility evaluation of composition trial 159 comprising 36.7% a.e. (about 480 g a.e./L) potassium glyphosate and the listed surfactant (Surf.) and stabilizer (Stab.) components.

| Run | A7U | B2S | C8J | D4F | E0A |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C110 | C110 | C110 | C110 | C110 |
| wt % | 7.4 | 7.4 | 7.4 | 7.4 | 7.4 |
| Stab. | C74 | C74 | C74 | C74 | C74 |
| wt % | 2 | 4 | 6 | 8 | 10 |
| 60° C. | Clear | Clear | Clear | Clear | Clear |
| RT | Fail | Clear | Clear | Fail | Fail |
| 10° C. | No test | Fail | Fail | No test | No test |
| 0° C. | No test | No test | No test | No test | No test |

Example 62

Stabilizer compatibility evaluation of composition trial 160 comprising 36.9% a.e. (about 480 g a.e./L) potassium glyphosate and the listed surfactant (Surf.) and stabilizer (Stab.) components.

| Run | A5V | B9K | C2A | D5X | E0L | F6Y | G2R | H7P |
|---|---|---|---|---|---|---|---|---|
| Surf. 1 | C46 | C46 | C27 | C46 | C46 | C46 | C46 | C46 |
| wt % | 4.9 | 4.9 | 4.8 | 4.9 | 4.9 | 4.9 | 4.9 | 4.9 |
| Surf. 2 | C110 | C110 | C110 | C110 | C110 | C110 | C110 | C110 |
| wt % | 7.4 | 7.4 | 7.2 | 7.4 | 7.4 | 7.4 | 7.4 | 7.4 |
| Stab. | C85 | C85 | C85 | C85 | C85 | C85 | C85 | — |
| wt % | 0.25 | 0.5 | 1 | 2 | 3 | 4 | 5 | — |
| 60° C. | Clear | Clear | Clear | Clear | Cloudy | Cloudy | Clear | Clear |
| RT | Fail | Fail | Fail | Fail | Fail | Fail | Fail | Fail |
| 10° C. | No test | No test | No test | No test | No test | No test | No test | No test |
| 0° C. | No test | No test | No test | No test | No test | No test | No test | No test |

Example 63

Stabilizer compatibility evaluation of composition trial 161 comprising 36.9% a.e. (about 480 g a.e./L) potassium glyphosate and the listed surfactant (Surf.) and stabilizer (Stab.) components.

| Run | A5F | B2H | C5W | D9N | E8A | F7E | G4G |
|---|---|---|---|---|---|---|---|
| Surf. 1 | C46 | C46 | C27 | C46 | C46 | C46 | C46 |
| wt % | 4.9 | 4.9 | 4.8 | 4.9 | 4.9 | 4.9 | 4.9 |
| Surf. 2 | C110 | C110 | C110 | C110 | C110 | C110 | C110 |
| wt % | 7.4 | 7.4 | 7.2 | 7.4 | 7.4 | 7.4 | 7.4 |
| Stab. 1 | C91 | C91 | C91 | C91 | C91 | C91 | C91 |
| wt % | 1 | 1 | 1 | 1 | 2 | 3 | 4 |
| Stab. 2 | C74 | C74 | C74 | C74 | C74 | C74 | C74 |
| wt % | 1 | 2 | 3 | 4 | 1 | 1 | 1 |
| 60° C. | Clear | Clear | Clear | Clear | Clear | Clear | Clear |
| RT | Fail | Fail | Clear | Clear | Fail | Fail | Clear |
| 10° C. | No test | No test | Fail | Fail | No test | No test | Fail |
| 0° C. | No test | No test | Fail | Fail | No test | No test | No test |

Example 64

Stabilizer compatibility evaluation of composition trial 163 comprising 36.7% a.e. (about 480 g a.e./L) potassium glyphosate and stabilizer (Stab.) components with no added surfactant.

| Run | A2Z | B4U | C0N | D8D | E2D | F1B | G8S | H1P | I5R | J8D | K5V | L3R |
|---|---|---|---|---|---|---|---|---|---|---|---|---|
| Stab. | C87 | C73 | C93 | C96 | C26 | C80 | C7 | C32 | C120 | C80 | C103 | C104 |
| wt % | 2 | 3 | 3 | 3 | 3 | 3 | 3 | 3 | 3 | 3 | 3 | 3 |
| 60° C. | Fail | Fail | Fail | Fail | Fail | Fail | Fail | Fail | Fail | Fail | Fail | Fail |
| RT | No test | No test | No test | No test | No test | No test | No test | No test | No test | No test | No test | No test |
| 10° C. | No test | No test | No test | No test | No test | No test | No test | No test | No test | No test | No test | No test |
| 0° C. | No test | No test | No test | No test | No test | No test | No test | No test | No test | No test | No test | No test |

Example 65

Stabilizer compatibility evaluation of composition trial 164 comprising 36.7% a.e. (about 480 g a.e./L) potassium glyphosate and the listed surfactant (Surf.) and stabilizer (Stab.) components.

| Run | A6T | B2U | C3V | D7U |
|---|---|---|---|---|
| Surf. 1 | C46 | C46 | C46 | C46 |
| wt % | 4.9 | 4.9 | 4.9 | 4.9 |
| Surf. 2 | C110 | C110 | C110 | C109 |
| wt % | 7.4 | 7.4 | 7.4 | 7.4 |
| Stab. 1 | C74 | C74 | C74 | C74 |
| wt % | 3 | 5 | 7 | 6.5 |
| 60° C. | Clear | Clear | Clear | Clear |
| RT | Clear | Clear | Clear | Clear |
| 10° C. | Fail | Fail | Fail | Fail |
| 0° C. | No test | No test | No test | No test |

Example 66

Stabilizer compatibility evaluation of composition trial 165 comprising 31% a.e. (about 370 g a.e./L) isopropylamine glyphosate and the listed surfactant (Surf.) and stabilizer (Stab.) components.

| Run | A3S | B6G | C1K | D7P | E4R | F0B |
|---|---|---|---|---|---|---|
| Surf. 1 | C46 | C16 | C17 | C18 | C21 | C5 |
| wt % | 4.9 | 4.9 | 4.9 | 4.9 | 4.9 | 4.9 |
| Surf. 2 | C109 | C109 | C109 | C109 | C109 | C109 |
| wt % | 7.4 | 7.4 | 7.4 | 7.4 | 7.4 | 7.4 |
| Stab. | C74 | C74 | C74 | C74 | C74 | C74 |
| wt % | 6.5 | 6.5 | 6.5 | 6.5 | 6.5 | 6.5 |
| 60° C. | Clear | Clear | Clear | Clear | Clear | Clear |
| RT | Fail | Fail | Fail | Fail | Fail | Fail |
| 10° C. | No test | No test | No test | No test | No test | No test |
| 0° C. | No test | No test | No test | No test | No test | No test |

Example 67

Stabilizer compatibility evaluation of composition trial 167 comprising 5% a.e. (about 480 g a.e./L) potassium glyphosate and stabilizer (Stab.) components with no added surfactant.

| Run | A6G | B2Q | C9K | D7N | E3T | F0J | G3X | H7R | I2Y | J0L | K1E | L5V |
|---|---|---|---|---|---|---|---|---|---|---|---|---|
| Stab. | C87 | C73 | C93 | C96 | C26 | C80 | C7 | C32 | C120 | C80 | C103 | C104 |
| wt % | 2 | 2 | 2 | 2 | 2 | 2 | 2 | 2 | 2 | 2 | 2 | 2 |
| 60° C. | Fail | Fail | Fail | Fail | Fail | Fail | Fail | Fail | Fail | Fail | Fail | Fail |
| RT | No test | No test | No test | No test | No test | No test | No test | No test | No test | No test | No test | No test |
| 10° C. | No test | No test | No test | No test | No test | No test | No test | No test | No test | No test | No test | No test |
| 0° C. | No test | No test | No test | No test | No test | No test | No test | No test | No test | No test | No test | No test |

Example 68

Stabilizer compatibility evaluation of composition trial 175 comprising 5% a.e. (about 480 g a.e./L) potassium glyphosate and stabilizer (Stab.) components with no added surfactant.

| Run | A3F | B8J | C0S | D2M | E8W | F8R |
|---|---|---|---|---|---|---|
| Stab. | C93 | C82 | C2 | C111 | C34 | C34 |
| wt % | 0.3 | 0.3 | 0.3 | 0.3 | 0.3 | 0.3 |
| 60° C. | Fail | Fail | Fail | Fail | Fail | Fail |
| RT | No test | No test | No test | No test | No test | No test |
| 10° C. | No test | No test | No test | No test | No test | No test |
| 0° C. | No test | No test | No test | No test | No test | No test |

Example 69

Stabilizer compatibility evaluation of composition trials 176 (A3D) and 178 comprising 36.9% a.e. potassium glyphosate (about 480 g a.e./L) and the listed surfactant (Surf.) and stabilizer (Stab.) components.

| Run | A3D | A2P | B4X | C9K | D1B | E7R | F3B | G5V |
|---|---|---|---|---|---|---|---|---|
| Surf. 1 | C46 | C79 | C79 | C79 | C79 | C79 | C79 | C110 |
| wt % | 4.9 | 3 | 4 | 5 | 6 | 7 | 10 | 10 |
| Surf. 2 | C110 | C110 | C110 | C110 | C110 | C110 | — | — |
| wt % | 7.4 | 7 | 6 | 5 | 4 | 3 | — | — |
| Stab. | C91 | C91 | C91 | C91 | C91 | C91 | C91 | C91 |
| wt % | 6.5 | 6.5 | 6.5 | 6.5 | 6.5 | 6.5 | 6.5 | 6.5 |
| 60° C. | Fail | Fail | Fail | Fail | Fail | Fail | Fail | Fail |
| RT | No test | No test | No test | No test | No test | No test | No test | No test |
| 10° C. | No test | No test | No test | No test | No test | No test | No test | No test |
| 0° C. | No test | No test | No test | No test | No test | No test | No test | No test |

Example 70

Stabilizer compatibility evaluation of composition trial 180 comprising 36.9% a.e. (about 480 g a.e./L) potassium glyphosate and the listed surfactant (Surf.) and stabilizer (Stab.) components.

| Run | A7H | B2L | C3Q | D9K | E6N | F7K |
|---|---|---|---|---|---|---|
| Surf. 1 | C79 | C79 | C79 | C79 | C5 | C5 |
| wt % | 4 | 5 | 4 | 5 | 4 | 4 |
| Surf. 2 | C110 | C110 | C48 | C48 | C110 | C48 |
| wt % | 6 | 5 | 6 | 5 | 6 | 6 |
| Stab. | C91 | C91 | C91 | C91 | C91 | C91 |
| wt % | 6.5 | 6.5 | 6.5 | 6.5 | 6.5 | 6.5 |
| 60° C. | Fail | Fail | Fail | Fail | Fail | Fail |
| RT | No test | No test | No test | No test | No test | No test |
| 10° C. | No test | No test | No test | No test | No test | No test |
| 0° C. | No test | No test | No test | No test | No test | No test |

Example 71

Stabilizer compatibility evaluation of composition trial 182 comprising 36.9% a.e. (about 480 g a.e./L) potassium glyphosate and the listed surfactant (Surf.) and stabilizer (Stab.) components.

| Run | A5T | B3U | C2W | D9C | E1A | F6X |
|---|---|---|---|---|---|---|
| Surf. 1 | C79 | C5 | C27 | C79 | C5 | C27 |
| wt % | 4.9 | 4.9 | 4.9 | 4.9 | 4.9 | 4.9 |
| Surf. 2 | C110 | C110 | C110 | C48 | C48 | C48 |
| wt % | 7.4 | 7.4 | 7.4 | 7.4 | 7.4 | 7.4 |
| Stab. | C91 | C91 | C91 | C91 | C91 | C91 |
| wt % | 6.5 | 6.5 | 6.5 | 6.5 | 6.5 | 6.5 |
| 60° C. | Fail | Fail | Fail | Fail | Fail | Fail |
| RT | No test | No test | No test | No test | No test | No test |
| 10° C. | No test | No test | No test | No test | No test | No test |
| 0° C. | No test | No test | No test | No test | No test | No test |

Example 72

Stabilizer compatibility evaluation of composition trial 184 comprising 36.9% a.e. (about 480 g a.e./L) potassium glyphosate and the listed surfactant (Surf.) and stabilizer (Stab.) components.

| Run | A9I | B5V | C5K | D0P | E3Z | F5N | G4L |
|---|---|---|---|---|---|---|---|
| Surf. 1 | C27 | C27 | C46 | C5 | C79 | C48 | C3 |
| wt % | 4.9 | 4.9 | 4.9 | 4.9 | 4.9 | 4.9 | 12.3 |

-continued

| Run | A9I | B5V | C5K | D0P | E3Z | F5N | G4L |
|---|---|---|---|---|---|---|---|
| Surf. 2 | C3 | C3 | C3 | C3 | C3 | C3 | — |
| wt % | 7.4 | 7.4 | 7.4 | 7.4 | 7.4 | 7.4 | — |
| Stab. | C91 | C91 | C91 | C91 | C91 | C91 | C91 |
| wt % | 6.5 | 6.5 | 6.5 | 6.5 | 6.5 | 6.5 | 6.5 |
| 60° C. | Fail | Fail | Fail | Fail | Fail | Fail | Fail |
| RT | No test | No test | No test | No test | No test | No test | No test |
| 10° C. | No test | No test | No test | No test | No test | No test | No test |
| 0° C. | No test | No test | No test | No test | No test | No test | No test |

Example 73

Stabilizer compatibility evaluation of composition trial 185 comprising 36.7% a.e. (about 480 g a.e./L) potassium glyphosate and the listed surfactant (Surf.) and stabilizer (Stab.) components.

| Run | A2H | B6G | C1A | D9P | E5T | F7N | G3D | H8K | I8J |
|---|---|---|---|---|---|---|---|---|---|
| Surf. 1 | C46 | C46 | C46 | C46 | C46 | C46 | C46 | C46 | C46 |
| wt % | 4.9 | 4.9 | 4.9 | 4.9 | 4.9 | 4.9 | 4.9 | 4.9 | 4.9 |
| Surf. 2 | C110 | C110 | C110 | C110 | C110 | C110 | C110 | C110 | C110 |
| wt % | 7.4 | 7.4 | 7.4 | 7.4 | 7.4 | 7.4 | 7.4 | 7.4 | 7.4 |
| Stab. 1 | C91 | C91 | C91 | C91 | — | C91 | C91 | C91 | C91 |
| wt % | 4 | 3 | 2 | 3 | — | 3 | 4 | 5 | 6 |
| Stab. 2 | — | C47 | C47 | C47 | C47 | C47 | C47 | C47 | — |
| wt % | — | 1 | 2 | 1 | 4 | 3 | 2 | 1 | — |
| 60° C. | Fail | Fail | Fail | Fail | Fail | Fail | Fail | Fail | Fail |
| RT | No test | No test | No test | No test | No test | No test | No test | No test | No test |
| 10° C. | No test | No test | No test | No test | No test | No test | No test | No test | No test |
| 0° C. | No test | No test | No test | No test | No test | No test | No test | No test | No test |

Example 74

Stabilizer compatibility evaluation of composition trial 186 comprising 36.9% a.e. (about 480 g a.e./L) potassium glyphosate and the listed surfactant (Surf.) and stabilizer (Stab.) components.

| Run | A3R | B1W | C1N | D8G | E3S | F9T |
|---|---|---|---|---|---|---|
| Surf. 1 | C5 | C5 | C5 | C5 | C5 | C5 |
| wt % | 4.9 | 4.9 | 4.9 | 4.9 | 4.9 | 4.9 |
| Surf. 2 | C110 | C110 | C110 | C110 | C110 | C110 |
| wt % | 7.4 | 7.4 | 7.4 | 7.4 | 7.4 | 7.4 |
| Stab. | C91 | C91 | C91 | C91 | C91 | C91 |
| wt % | 0 | 2 | 4 | 6 | 8 | 5 |
| 60° C. | Fail | Fail | Fail | Fail | Fail | Fail |
| RT | No test | No test | No test | No test | No test | No test |
| 10° C. | No test | No test | No test | No test | No test | No test |
| 0° C. | No test | No test | No test | No test | No test | No test |

Example 75

Stabilizer compatibility evaluation of composition trial 187 comprising 36.9% a.e. (about 480 g a.e./L) potassium glyphosate and the listed surfactant (Surf.) and stabilizer (Stab.) components.

| Run | A8H | B9P | C6F | D0S | E2A | F5D |
|---|---|---|---|---|---|---|
| Surf. 1 | C46 | C46 | C46 | C46 | C46 | C46 |
| wt % | 4.9 | 4.9 | 4.9 | 4.9 | 4.9 | 4.9 |
| Surf. 2 | C110 | C110 | C110 | C110 | C110 | C110 |
| wt % | 7.4 | 7.4 | 7.4 | 7.4 | 7.4 | 7.4 |
| Stab. 1 | C45 | C91 | C91 | C91 | C91 | C91 |
| wt % | 6 | 1 | 2 | 3 | 4 | 5 |
| Stab. 2 | — | C45 | C45 | C45 | C45 | C45 |
| wt % | — | 5 | 4 | 3 | 2 | 1 |
| 60° C. | Fail | Fail | Fail | Fail | Fail | Fail |
| RT | No test | No test | No test | No test | No test | No test |
| 10° C. | No test | No test | No test | No test | No test | No test |
| 0° C. | No test | No test | No test | No test | No test | No test |

Example 76

Stabilizer compatibility evaluation of composition trial 188 comprising 36.9% a.e. (about 480 g a.e./L) potassium glyphosate and the listed surfactant (Surf.) and stabilizer (Stab.) components.

| Run | A7U | B2S | C8N | D4G | E1W | F2V |
|---|---|---|---|---|---|---|
| Surf. 1 | C46 | C46 | C46 | C46 | C46 | C46 |
| wt % | 4.9 | 4.9 | 4.9 | 4.9 | 4.9 | 4.9 |
| Surf. 2 | C110 | C110 | C110 | C110 | C110 | C110 |
| wt % | 7.4 | 7.4 | 7.4 | 7.4 | 7.4 | 7.4 |
| Stab. 1 | C98 | C91 | C91 | C97 | C91 | C91 |
| wt % | 6 | 2 | 4 | 6 | 2 | 4 |
| Stab. 2 | — | C98 | C98 | — | C97 | C97 |
| wt % | — | 4 | 2 | — | 4 | 2 |
| 60° C. | Fail | Fail | Fail | Fail | Fail | Fail |
| RT | No test | No test | No test | No test | No test | No test |
| 10° C. | No test | No test | No test | No test | No test | No test |
| 0° C. | No test | No test | No test | No test | No test | No test |

Example 77

Stabilizer compatibility evaluation of composition trial 189 comprising 36.7% a.e. (about 480 g a.e./L) potassium glyphosate and the listed surfactant (Surf.) and stabilizer (Stab.) components.

| Run | A7K | B1P | C3Z | D0R | E3K | F2C | G7J | H4F | I5N |
|---|---|---|---|---|---|---|---|---|---|
| Surf. 1 | C46 | C46 | C46 | C46 | C46 | C46 | C46 | C46 | C46 |
| wt % | 4.9 | 4.9 | 4.9 | 4.9 | 4.9 | 4.9 | 4.9 | 4.9 | 4.9 |
| Surf. 2 | C110 | C110 | C110 | C110 | C110 | C110 | C110 | C110 | C110 |
| wt % | 7.4 | 7.4 | 7.4 | 7.4 | 7.4 | 7.4 | 7.4 | 7.4 | 7.4 |
| Stab. 1 | C99 | C91 | C91 | C100 | C91 | C91 | C101 | C91 | C91 |
| wt % | 6 | 2 | 4 | 6 | 2 | 4 | 6 | 2 | 4 |
| Stab. 2 | — | C99 | C99 | — | C100 | C100 | — | C101 | C101 |
| wt % | — | 4 | 2 | — | 4 | 2 | — | 4 | 2 |
| 60° C. | Fail | Fail | Fail | Fail | Fail | Fail | Fail | Fail | Fail |
| RT | No test | No test | No test | No test | No test | No test | No test | No test | No test |
| 10° C. | No test | No test | No test | No test | No test | No test | No test | No test | No test |
| 0° C. | No test | No test | No test | No test | No test | No test | No test | No test | No test |

Example 78

Stabilizer compatibility evaluation of composition trial 190 comprising 36.7% a.e. (about 480 g a.e./L) potassium glyphosate and the listed surfactant (Surf.) and stabilizer (Stab.) components.

| Run | A2S | B6B | C9K | D5L | E2Z | F0F | G5B | H3K | I1Z |
|---|---|---|---|---|---|---|---|---|---|
| Surf. 1 | C46 | C46 | C46 | C46 | C46 | C46 | C46 | C46 | C46 |
| wt % | 4.9 | 4.9 | 4.9 | 4.9 | 4.9 | 4.9 | 4.9 | 4.9 | 4.9 |
| Surf. 2 | C110 | C110 | C110 | C110 | C110 | C110 | C110 | C110 | C110 |
| wt % | 7.4 | 7.4 | 7.4 | 7.4 | 7.4 | 7.4 | 7.4 | 7.4 | 7.4 |
| Stab. 1 | C83 | C91 | C91 | C24 | C91 | C91 | C13 | C91 | C91 |
| wt % | 6 | 2 | 4 | 6 | 2 | 4 | 6 | 2 | 4 |
| Stab. 2 | — | C83 | C83 | — | C24 | C24 | — | C13 | C13 |
| wt % | — | 4 | 2 | — | 4 | 2 | — | 4 | 2 |
| 60° C. | Fail | Fail | Fail | Fail | Fail | Fail | Fail | Fail | Fail |
| RT | No test | No test | No test | No test | No test | No test | No test | No test | No test |
| 10° C. | No test | No test | No test | No test | No test | No test | No test | No test | No test |
| 0° C. | No test | No test | No test | No test | No test | No test | No test | No test | No test |

Example 79

Stabilizer compatibility evaluation of composition trial 191 comprising 36.7% a.e. (about 480 g a.e./L) potassium glyphosate and the listed surfactant (Surf.) and stabilizer (Stab.) components.

| Run | A7H | B9W | C5N | D3M | E1J | F8V | G3K | H2A | I0E |
|---|---|---|---|---|---|---|---|---|---|
| Surf. 1 | C46 | C46 | C46 | C46 | C46 | C46 | C46 | C46 | C46 |
| wt % | 4.9 | 4.9 | 4.9 | 4.9 | 4.9 | 4.9 | 4.9 | 4.9 | 4.9 |
| Surf. 2 | C110 | C110 | C110 | C110 | C110 | C110 | C110 | C110 | C110 |
| wt % | 7.4 | 7.4 | 7.4 | 7.4 | 7.4 | 7.4 | 7.4 | 7.4 | 7.4 |
| Stab. 1 | C72 | C91 | C91 | C102 | C91 | C91 | C84 | C91 | C91 |
| wt % | 6 | 2 | 4 | 6 | 2 | 4 | 6 | 2 | 4 |
| Stab. 2 | — | C72 | C72 | — | 102 | C102 | — | C84 | C84 |
| wt % | — | 4 | 2 | — | 4 | 2 | — | 4 | 2 |
| 60° C. | Fail | Fail | Fail | Fail | Fail | Clear | Fail | Fail | Fail |
| RT | No test | No test | No test | No test | No test | Clear | No test | No test | No test |
| 10° C. | No test | No test | No test | No test | No test | No test | No test | No test | No test |
| 0° C. | No test | No test | No test | No test | No test | No test | No test | No test | No test |

Example 80

Stabilizer compatibility evaluation of composition trial 721 comprising 36.9% a.e. (about 480 g a.e./L) potassium glyphosate and the listed surfactant (Surf.) and stabilizer (Stab.) components.

| Run | A9K | B3C | C5M | D2Z | E0L | F1A |
|---|---|---|---|---|---|---|
| Surf. 1 | C46 | C46 | C46 | C46 | C46 | C46 |
| wt % | 2.5 | 3.7 | 6.2 | 7.4 | 8.6 | 9.8 |
| Surf. 2 | C109 | C109 | C109 | C109 | C109 | C109 |
| wt % | 9.8 | 8.6 | 6.2 | 4.9 | 3.7 | 2.5 |
| Stab. | C91 | C91 | C91 | C91 | C91 | C91 |
| wt % | 4 | 4 | 4 | 4 | 4 | 4 |
| 60° C. | Clear | Clear | Fail | Fail | Fail | Cloudy |
| RT | Clear | Clear | Fail | Fail | Fail | Cloudy |
| −10° C. | Cloudy | Fail | Fail | Fail | Fail | Cloudy |

Example 81

Stabilizer compatibility evaluation of composition trial 722 comprising 36.9% a.e. (about 480 g a.e./L) potassium glyphosate and the listed surfactant (Surf.) and stabilizer (Stab.) components.

| Run | A6B | B2U | C9L | D1Z | E3K | F0R |
|---|---|---|---|---|---|---|
| Surf. | C109 | C109 | C109 | C109 | C109 | C109 |
| wt % | 9.2 | 10.6 | 12.3 | 9.2 | 10.6 | 12.3 |
| Stab. | C91 | C91 | C91 | C91 | C91 | C91 |
| wt % | 4 | 4 | 4 | 6 | 6 | 6 |
| 60° C. | Clear | Clear | Clear | Clear | Clear | Clear |
| RT | Clear | Clear | Clear | Clear | Clear | Clear |
| −10° C. | Clear | Clear | Clear | Clear | Clear | Clear |
| −10° C.* | Clear | Clear | Clear | Clear | Clear | Clear |

*@ 4 Weeks

Example 82

Stabilizer compatibility evaluation of composition trial 723 comprising 36.9% a.e. (about 480 g a.e./L) potassium glyphosate and the listed surfactant (Surf.) and stabilizer (Stab.) components.

| Run | A7J | B4P | C2B | D8M | E3I | F0V |
|---|---|---|---|---|---|---|
| Surf. | C110 | C110 | C110 | C110 | C110 | C110 |
| wt % | 9.2 | 10.6 | 12.3 | 9.2 | 10.6 | 12.3 |
| Stab. | C91 | C91 | C91 | C91 | C91 | C91 |
| wt % | 4 | 4 | 4 | 6 | 6 | 6 |
| 60° C. | Clear | Fail | Fail | Clear | Clear | Clear |
| RT | Clear | No test | No test | Clear | Clear | Clear |
| −10° C. | Clear | No test | No test | Clear | Clear | Clear |
| −10° C.* | Clear | No test | No test | Clear | Clear | Fail |

@ 4 Weeks

Example 83

Stabilizer compatibility evaluation of composition trial 724 comprising 36.9% a.e. (about 480 g a.e./L) potassium glyphosate and the listed surfactant (Surf.) and stabilizer (Stab.) components.

| Run | A7J | B4P | C2B | D8M | E3I | F0V |
|---|---|---|---|---|---|---|
| Surf. | C43 | C43 | C43 | C43 | C43 | C43 |
| wt % | 9.2 | 10.6 | 12.3 | 9.2 | 10.6 | 12.3 |
| Stab. | C91 | C91 | C91 | C91 | C91 | C91 |
| wt % | 4 | 4 | 4 | 6 | 6 | 6 |
| 60° C. | Fail | Fail | Fail | Clear | Fail | Fail |
| RT | No test | No test | No test | Clear | No test | No test |
| −10° C. | No test | No test | No test | Fail | No test | No test |

Example 84

Stabilizer compatibility evaluation of composition trial 725 comprising 36.9% a.e. (about 480 g a.e./L) potassium glyphosate and the listed surfactant (Surf.) and stabilizer (Stab.) components.

| Run | A2S | B9K | C5N | D3C | E6H | F4A |
|---|---|---|---|---|---|---|
| Surf. | C106 | C106 | C106 | C106 | C106 | C106 |
| wt % | 9.2 | 10.6 | 12.3 | 9.2 | 10.6 | 12.3 |
| Stab. | C91 | C91 | C91 | C91 | C91 | C91 |
| wt % | 4 | 4 | 4 | 6 | 6 | 6 |
| 60° C. | Clear | Fail | Fail | Clear | Clear | Fail |
| RT | Clear | No test | No test | Clear | Clear | No test |
| −10° C. | Clear | No test | No test | Clear | Clear | No test |
| −10° C.* | Clear | No test | No test | Clear | Clear | No test |

*4 weeks

Example 85

Stabilizer compatibility evaluation of composition trial 726 comprising 36.9% a.e. (about 480 g a.e./L) potassium glyphosate and the listed surfactant (Surf.) and stabilizer (Stab.) components.

| Run | A8N | B3C | C1L | D0Q | E6G |
|---|---|---|---|---|---|
| Surf. 1 | C46 | C46 | C46 | C46 | C46 |
| wt % | 4.9 | 4.9 | 4.9 | 4.9 | 4.9 |
| Surf. 2 | C109 | C109 | C109 | C109 | C109 |
| wt % | 7.4 | 7.4 | 7.4 | 7.4 | 7.4 |
| Stab. | C91 | C91 | C91 | C91 | — |
| wt % | 4 | 3 | 2 | 1 | |
| 60° C. | Clear | Fail | Fail | Fail | Fail |
| RT | Clear | No test | No test | No test | No test |
| −10° C. | Clear | No test | No test | No test | No test |

Example 86

Stabilizer compatibility evaluation of composition trial 727 comprising 36.9% a.e. (about 480 g a.e./L) potassium glyphosate and the listed surfactant (Surf.) and stabilizer (Stab.) components.

| Run | A7Y | B3L | C2Z | D9B |
|---|---|---|---|---|
| Surf.1 | C109 | C109 | C109 | C109 |
| wt % | 12.3 | 12.3 | 12.3 | 12.3 |
| Stab. | C91 | C91 | C91 | — |
| wt % | 3 | 2 | 1 | — |
| 60° C. | Clear | Fail | Fail | Fail |
| RT | Clear | No test | No test | No test |
| −10° C. | Clear | No test | No test | No test |
| −10° C.* | Clear | No test | No test | No test |

*@ 4 Weeks

Example 87

Stabilizer compatibility evaluation of composition trial 728 comprising 36.9% a.e. (about 480 g a.e./L) potassium glyphosate and the listed surfactant (Surf.) and stabilizer (Stab.) components.

| Run | A2E | B3A | C5C | D0L | E2N | F8T | G4N | H6B |
|---|---|---|---|---|---|---|---|---|
| Surf. 1 | C46 | C46 | C46 | C46 | C46 | C46 | C46 | C46 |
| wt % | 1.2 | 2.5 | 3.7 | 4.9 | 1.2 | 2.5 | 3.7 | 4.9 |
| Surf. 2 | C109 | C109 | C109 | C109 | C110 | C110 | C110 | C110 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 3 | 3 | 3 | 3 | 4 | 4 | 4 | 4 |
| 60° C. | Fail | Fail | Fail | Fail | Fail | Fail | Fail | Fail |
| RT | No test | No test | No test | No test | No test | No test | No test | No test |
| −10° C. | No test | No test | No test | No test | No test | No test | No test | No test |

Example 88

Stabilizer compatibility evaluation of composition trial 729 comprising 36.9% a.e. (about 480 g a.e./L) potassium glyphosate and the listed surfactant (Surf.) and stabilizer (Stab.) components.

| Run | A4C | B9O | C3F | D6B | E7L | F2S | G7B | H0W |
|---|---|---|---|---|---|---|---|---|
| Surf. 1 | C46 | C46 | C46 | C46 | C46 | C46 | C46 | C46 |
| wt % | 1.2 | 2.5 | 3.7 | 4.9 | 1.2 | 2.5 | 3.7 | 4.9 |
| Surf. 2 | C110 | C110 | C110 | C110 | C43 | C43 | C43 | C43 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 5 | 5 | 5 | 5 | 6 | 6 | 6 | 6 |
| 60° C. | Fail | Fail | Fail | Fail | Fail | Fail | Fail | Fail |
| RT | No test | No test | No test | No test | No test | No test | No test | No test |
| −10° C. | No test | No test | No test | No test | No test | No test | No test | No test |

Example 89

Stabilizer compatibility evaluation of composition trial 730 comprising 36.9% a.e. (about 480 g a.e./L) potassium glyphosate and the listed surfactant (Surf.) and stabilizer (Stab.) components.

| Run | A7T | B3F | C2P | D9L | E5N | F0B | G7R | H4E |
|---|---|---|---|---|---|---|---|---|
| Surf. 1 | C46 | C46 | C46 | C46 | C46 | C46 | C46 | C46 |
| wt % | 1.2 | 2.5 | 3.7 | 4.9 | 1.2 | 2.5 | 3.7 | 4.9 |
| Surf. 2 | C106 | C106 | C106 | C106 | C109 | C109 | C109 | C109 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 5 | 5 | 5 | 5 | 5 | 5 | 5 | 5 |
| 60° C. | Fail | Fail | Fail | Fail | Clear | Clear | Clear | Clear |
| RT | No test | No test | No test | No test | Clear | Clear | Clear | Clear |
| −10° C. | No test | No test | No test | No test | Clear | Cloudy | Cloudy | Cloudy |

Example 90

Stabilizer compatibility evaluation of composition trial 731 comprising 36.9% a.e. (about 480 g a.e./L) potassium glyphosate and the listed surfactant (Surf.) and stabilizer (Stab.) components.

| Run | A7T | B3F | C2P | D9L | E5N | F0B | G7R | H4E |
|---|---|---|---|---|---|---|---|---|
| Surf. 1 | C5 | C5 | C5 | C5 | C5 | C5 | C5 | C5 |
| wt % | 1.2 | 2.5 | 3.7 | 4.9 | 1.2 | 2.5 | 3.7 | 4.9 |
| Surf. 2 | C109 | C109 | C109 | C109 | C110 | C110 | C110 | C110 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 5 | 5 | 5 | 5 | 5 | 5 | 5 | 5 |
| 60° C. | Clear | Cloudy | Cloudy | Cloudy | Clear | Fail | Fail | Fail |
| RT | Clear | Fail | Fail | Fail | Clear | No test | No test | No test |
| −10° C. | Cloudy | No test | No test | No test | Cloudy | No test | No test | No test |

Example 91

Stabilizer compatibility evaluation of composition trial 732 comprising 36.9% a.e. (about 480 g a.e./L) potassium glyphosate and the listed surfactant (Surf.) and stabilizer (Stab.) components.

| Run | A4R | B6T | C0S | D0M | E2X | F4K | G1A | H3Y |
|---|---|---|---|---|---|---|---|---|
| Surf. 1 | C79 | C79 | C79 | C79 | C5 | C5 | C5 | C5 |
| wt % | 1.2 | 2.5 | 3.7 | 4.9 | 1.2 | 2.5 | 3.7 | 4.9 |
| Surf. 2 | C109 | C109 | C109 | C109 | C110 | C110 | C110 | C110 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 5 | 5 | 5 | 5 | 5 | 5 | 5 | 5 |
| 60° C. | Clear | Fail | Fail | Fail | Clear | Fail | Fail | Fail |
| RT | Clear | No test | No test | No test | Clear | No test | No test | No test |
| −10° C. | Cloudy | No test | No test | No test | Cloudy | No test | No test | No test |

Example 92

Stabilizer compatibility evaluation of composition trial 733 comprising 36.9% a.e. (about 480 g a.e./L) potassium glyphosate and the listed surfactant (Surf.) and stabilizer (Stab.) components.

| Run | A9G | B3M | C7K | D2W | E1J | F9T | G0S | H7J |
|---|---|---|---|---|---|---|---|---|
| Surf. 1 | C5 | C5 | C5 | C5 | C79 | C79 | C79 | C79 |
| wt % | 1.2 | 2.5 | 3.7 | 4.9 | 1.2 | 2.5 | 3.7 | 4.9 |
| Surf. 2 | C109 | C109 | C109 | C109 | C109 | C109 | C109 | C109 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 3 | 3 | 3 | 3 | 3 | 3 | 3 | 3 |
| 60° C. | Clear | Cloudy | Fail | Fail | Cloudy | Fail | Fail | Fail |
| RT | Clear | Fail | No test | No test | Fail | No test | No test | No test |
| −10° C. | Cloudy | No test | No test | No test | No test | No test | No test | No test |

Example 93

Stabilizer compatibility evaluation of composition trial 734 comprising 36.9% a.e. (about 480 g a.e./L) potassium glyphosate and the listed surfactant (Surf.) and stabilizer (Stab.) components.

| Run | A5R | B8V | C0A | D7F | E4H | F3Y | G9X | H5U |
|---|---|---|---|---|---|---|---|---|
| Surf. 1 | C5 | C5 | C5 | C5 | C11 | C11 | C11 | C11 |
| wt % | 1.2 | 2.5 | 3.7 | 4.9 | 1.2 | 2.5 | 3.7 | 4.9 |
| Surf. 2 | C109 | C109 | C109 | C109 | C109 | C109 | C109 | C109 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 1 | 1 | 1 | 1 | 3 | 3 | 3 | 3 |
| 60° C. | Fail | Fail | Fail | Fail | Clear | Clear | Cloudy | Cloudy |
| RT | No test | No test | No test | No test | Clear | Clear | Fail | Fail |
| −10° C. | No test | No test | No test | No test | Clear | Clear | No test | No test |

Example 94

Stabilizer compatibility evaluation of composition trial 735 comprising 36.9% a.e. (about 480 g a.e./L) potassium glyphosate and the listed surfactant (Surf.) and stabilizer (Stab.) components.

| Run | A9K | B2J | C8X | D7Q | E8L | F2V |
|---|---|---|---|---|---|---|
| Surf. 1 | C42 | C42 | C42 | C42 | C42 | C42 |
| wt % | 9.2 | 10.6 | 12.3 | 9.2 | 10.6 | 12.3 |
| Stab. | C91 | C91 | C91 | C91 | C91 | C91 |
| wt % | 6 | 6 | 6 | 4 | 4 | 4 |
| 60° C. | Clear | Clear | Clear | Clear | Clear | Clear |
| RT | Clear | Clear | Clear | Clear | Clear | Clear |
| −10° C. | Clear | Clear | Clear | Clear | Clear | Clear |
| −10° C.* | Clear | Clear | Clear | Clear | Clear | Clear |

*@ 4 Weeks

Example 95

Stabilizer compatibility evaluation of composition trial 736 comprising 36.9% a.e. (about 480 g a.e./L) potassium glyphosate and the listed surfactant (Surf.) and stabilizer (Stab.) components.

| Run | A4F | B7M | C1A | D5K | E0R | F8E | G5H | H3B |
|---|---|---|---|---|---|---|---|---|
| Surf. 1 | C5 | C5 | C5 | C5 | C11 | C11 | C11 | C11 |
| wt % | 1.2 | 2.5 | 3.7 | 4.9 | 1.2 | 2.5 | 3.7 | 4.9 |
| Surf. 2 | C109 | C109 | C109 | C109 | C109 | C109 | C109 | C109 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 2 | 2 | 2 | 2 | 2 | 2 | 2 | 2 |
| 60° C. | Fail | Fail | Fail | Fail | Fail | Fail | Fail | Fail |
| RT | No test | No test | No test | No test | No test | No test | No test | No test |
| −10° C. | No test | No test | No test | No test | No test | No test | No test | No test |

Example 96

Stabilizer compatibility evaluation of composition trial 737 comprising 36.9% a.e. (about 480 g a.e./L) potassium glyphosate and the listed surfactant (Surf.) and stabilizer (Stab.) components.

| Run | A4F | B7M | C1A | D5K | E0R | F8E | G5H | H3B |
|---|---|---|---|---|---|---|---|---|
| Surf. 1 | C11 | C11 | C11 | C11 | C11 | C11 | C11 | C11 |
| wt % | 1.2 | 2.5 | 3.7 | 4.9 | 1.2 | 2.5 | 3.7 | 4.9 |
| Surf. 2 | C109 | C109 | C109 | C109 | C110 | C110 | C110 | C110 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 4 | 4 | 4 | 4 | 4 | 4 | 4 | 4 |
| 60° C. | Clear | Clear | Clear | Cloudy | Fail | Fail | Fail | Fail |
| RT | Clear | Clear | Clear | Fail | No test | No test | No test | No test |
| −10° C. | Cloudy | Fail | Fail | No test | No test | No test | No test | No test |

Example 97

Stabilizer compatibility evaluation of composition trial 738 comprising 36.9% a.e. (about 480 g a.e./L) potassium glyphosate and the listed surfactant (Surf.) and stabilizer (Stab.) components.

| Run | A8M | B3E | C9K | D1S | E5Z | F8J |
|---|---|---|---|---|---|---|
| Surf. 1 | C109 | C109 | C109 | C42 | C42 | C42 |
| wt % | 9.2 | 10.6 | 12.3 | 9.2 | 10.6 | 12.3 |
| Stab. | C91 | C91 | C91 | C91 | C91 | C91 |
| wt % | 2 | 2 | 2 | 2 | 2 | 2 |
| 60° C. | Clear | Clear | Fail | Clear | Clear | Clear |
| RT | Clear | Clear | Fail | Clear | Clear | Clear |
| −10° C. | Clear | Clear | Fail | Clear | Clear | Fail |
| −10° C.* | Fail | Fail | No test | Clear | Fail | No test |

*@ 4 Weeks

Example 98

Stabilizer compatibility evaluation of composition trial 739 comprising 36.9% a.e. (about 480 g a.e./L) potassium glyphosate and the listed surfactant (Surf.) and stabilizer (Stab.) components.

| Run | A4F | B7M | C1A | D5K | E0R | F8E | G5H | H3B |
|---|---|---|---|---|---|---|---|---|
| Surf. 1 | C11 | C11 | C11 | C11 | C11 | C11 | C11 | C11 |
| wt % | 1.2 | 2.5 | 3.7 | 4.9 | 1.2 | 2.5 | 3.7 | 4.9 |
| Surf. 2 | C43 | C43 | C43 | C43 | C42 | C42 | C42 | C42 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 4 | 4 | 4 | 4 | 4 | 4 | 4 | 4 |
| 60° C. | Fail | Fail | Fail | Fail | Clear | Clear | Clear | Fail |
| RT | No test | No test | No test | No test | Clear | Clear | Clear | No test |
| −10° C. | No test | No test | No test | No test | Clear | Clear | Clear | No test |

Example 99

Stabilizer compatibility evaluation of composition trial 740 comprising 36.9% a.e. (about 480 g a.e./L) potassium glyphosate and the listed surfactant (Surf.) and stabilizer (Stab.) components.

| Run | A8J | B1X | C5T | D4V | E9K | F4G | G2W | H0C |
|---|---|---|---|---|---|---|---|---|
| Surf. 1 | C46 | C46 | C46 | C46 | C11 | C11 | C11 | C11 |
| wt % | 1.2 | 2.5 | 3.7 | 4.9 | 1.2 | 2.5 | 3.7 | 4.9 |
| Surf. 2 | C42 | C42 | C42 | C42 | C43 | C43 | C43 | C43 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 4 | 4 | 4 | 4 | 4 | 4 | 4 | 4 |
| 60° C. | Clear | Clear | Cloudy | Cloudy | Fail | Fail | Fail | Fail |
| RT | Clear | Clear | Fail | Fail | No test | No test | No test | No test |
| −10° C. | Clear | Clear | No test | No test | No test | No test | No test | No test |
| −10° C.* | Clear | Fail | No test | No test | No test | No test | No test | No test |

*@ 4 Weeks

Example 100

Stabilizer compatibility evaluation of composition trial 741 comprising 36.9% a.e. (about 480 g a.e./L) potassium glyphosate and the listed surfactant (Surf.) and stabilizer (Stab.) components.

| Run | A2V | B8J | C3D | D9K | E2Y | F0I |
|---|---|---|---|---|---|---|
| Surf. 1 | C46 | C46 | C46 | C46 | C46 | C46 |
| wt % | 4.9 | 4.9 | 4.9 | 4.9 | 4.9 | 4.9 |
| Surf. 2 | C109 | C109 | C109 | C109 | C109 | C109 |
| wt % | 7.4 | 7.4 | 7.4 | 7.4 | 7.4 | 7.4 |
| Surf. 3 | C112 | C112 | C33 | C33 | C71 | C71 |
| wt % | 0.1 | 1 | 0.1 | 1 | 0.1 | 1 |
| Stab. | C91 | C91 | C91 | C91 | C91 | C91 |
| wt % | 2 | 2 | 2 | 2 | 2 | 2 |
| 60° C. | Fail | Fail | Fail | Fail | Fail | Fail |
| RT | No test | No test | No test | No test | No test | No test |
| −10° C. | No test | No test | No test | No test | No test | No test |

Example 101

Stabilizer compatibility evaluation of composition trial 742 comprising 36.9% a.e. (about 480 g a.e./L) potassium glyphosate and the listed surfactant (Surf.) and stabilizer (Stab.) components.

| Run | A0W | B6G | C2X | D7N | E7Z | F0L | G4J | H3C |
|---|---|---|---|---|---|---|---|---|
| Surf. 1 | C11 | C11 | C11 | C11 | C11 | C11 | C11 | C11 |
| wt % | 1.2 | 2.5 | 3.7 | 4.9 | 1.2 | 2.5 | 3.7 | 4.9 |
| Surf. 2 | C109 | C109 | C109 | C109 | C42 | C42 | C42 | C42 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 5 | 5 | 5 | 5 | 5 | 5 | 5 | 5 |
| 60° C. | Clear | Clear | Clear | Cloudy | Clear | Clear | Clear | Cloudy |
| RT | Fail | Fail | Fail | Fail | Fail | Fail | Fail | Fail |
| −10° C. | No test | No test | No test | No test | No test | No test | No test | No test |

Example 102

Stabilizer compatibility evaluation of composition trial 743 comprising 36.9% a.e. (about 480 g a.e./L) potassium glyphosate and the listed surfactant (Surf.) and stabilizer (Stab.) components.

| Run | A0W | B6G | C2X | D7N | E7Z | F0L | G4J | H3C |
|---|---|---|---|---|---|---|---|---|
| Surf. 1 | C22 | C22 | C22 | C22 | C22 | C22 | C22 | C22 |
| wt % | 1.2 | 2.5 | 3.7 | 4.9 | 1.2 | 2.5 | 3.7 | 4.9 |
| Surf. 2 | C109 | C109 | C109 | C109 | C42 | C42 | C42 | C42 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 5 | 5 | 5 | 5 | 5 | 5 | 5 | 5 |
| 60° C. | Fail | Fail | Fail | Fail | Fail | Fail | Fail | Fail |
| RT | No test | No test | No test | No test | No test | No test | No test | No test |
| −10° C. | No test | No test | No test | No test | No test | No test | No test | No test |

Example 103

Stabilizer compatibility evaluation of composition trial 744 comprising 36.9% a.e. (about 480 g a.e./L) potassium glyphosate and the listed surfactant (Surf.) and stabilizer (Stab.) components.

| Run | A6B | B3G | C1P | D7Y | E4N | F8J | G3U | H2V |
|---|---|---|---|---|---|---|---|---|
| Surf. 1 | C21 | C21 | C21 | C21 | C21 | C21 | C21 | C21 |
| wt % | 1.2 | 2.5 | 3.7 | 4.9 | 1.2 | 2.5 | 3.7 | 4.9 |
| Surf. 2 | C109 | C109 | C109 | C109 | C42 | C42 | C42 | C42 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 5 | 5 | 5 | 5 | 5 | 5 | 5 | 5 |
| 60° C. | Fail | Fail | Fail | Fail | Fail | Fail | Fail | Fail |
| RT | No test | No test | No test | No test | No test | No test | No test | No test |
| −10° C. | No test | No test | No test | No test | No test | No test | No test | No test |

Example 104

Stabilizer compatibility evaluation of composition trial 745 comprising 36.9% a.e. (about 480 g a.e./L) potassium glyphosate and the listed surfactant (Surf.) and stabilizer (Stab.) components.

| Run | A1W | B5G | C8K | D0L | E8H | F5R | G3Z | H1A |
|---|---|---|---|---|---|---|---|---|
| Surf. 1 | C17 | C17 | C17 | C17 | C17 | C17 | C17 | C17 |
| wt % | 1.2 | 2.5 | 3.7 | 4.9 | 1.2 | 2.5 | 3.7 | 4.9 |
| Surf. 2 | C109 | C109 | C109 | C109 | C42 | C42 | C42 | C42 |
| wt % | 11.1 | 9.8 | 8.6 | 7.4 | 11.1 | 9.8 | 8.6 | 7.4 |
| Stab. | C91 | C91 | C91 | C91 | C91 | C91 | C91 | C91 |
| wt % | 5 | 5 | 5 | 5 | 5 | 5 | 5 | 5 |
| 60° C. | Fail | Fail | Fail | Fail | Fail | Fail | Fail | Fail |
| RT | No test | No test | No test | No test | No test | No test | No test | No test |
| −10° C. | No test | No test | No test | No test | No test | No test | No test | No test |

Example 105

Stabilizer compatibility evaluation of composition trial 747 comprising 36.9% a.e. (about 480 g a.e./L) potassium glyphosate and the listed surfactant (Surf.) and stabilizer (Stab.) components.

| Run | A3C | B7H | C9S | D4L | E0K | F3G |
|---|---|---|---|---|---|---|
| Surf. 1 | C46 | C46 | C46 | C63 | C62 | C60 |
| wt % | 4.9 | 4.9 | 4.9 | 12.3 | 12.3 | 12.3 |
| Surf. 2 | C63 | C62 | C60 | — | — | — |
| wt % | 7.4 | 7.4 | 7.4 | — | — | — |
| Stab. | C91 | C91 | C91 | C91 | C91 | C91 |
| wt % | 6.5 | 6.5 | 6.5 | 6.5 | 6.5 | 6.5 |
| 60° C. | Fail | Fail | Fail | Fail | Fail | Fail |
| RT | No test | No test | No test | No test | No test | No test |
| −10° C. | No test | No test | No test | No test | No test | No test |

Example 106

Stabilizer compatibility evaluation of composition trial 749 comprising 5% a.e. (about 480 g a.e./L) potassium glyphosate and the listed stabilizer components.

| Run | A7U | B3C | C4F | D7H | E3M | F9K | G8F |
|---|---|---|---|---|---|---|---|
| Surf. | C93 | C96 | C26 | C7 | C6 | C94 | C82 |
| wt % | 2 | 2 | 2 | 2 | 2 | 2 | 2 |
| 60° C. | Fail | Fail | Fail | Fail | Fail | Fail | Fail |
| RT | No test | No test | No test | No test | No test | No test | No test |
| −10° C. | No test | No test | No test | No test | No test | No test | No test |

Example 107

Stabilizer compatibility evaluation of composition trial 751 comprising 36.9% a.e. (about 480 g a.e./L) potassium glyphosate and the listed surfactant (Surf.) and stabilizer (Stab.) components.

| Run | A7B | B2N | C2Z | D9R | E7P | F3M | G2W |
|---|---|---|---|---|---|---|---|
| Surf. | C27 | C28 | C46 | C86 | C86 | C27 | C28 |
| wt % | 4.9 | 4.9 | 4.9 | 4.9 | 4.9 | 12.3 | 12.3 |
| Stab. | C30 | C30 | C30 | C110 | C30 | — | — |
| wt % | 7.4 | 7.4 | 7.4 | 7.4 | 7.4 | — | — |
| 60° C. | Fail | Fail | Fail | Fail | Fail | Fail | Fail |
| RT | No test | No test | No test | No test | No test | No test | No test |
| −10° C. | No test | No test | No test | No test | No test | No test | No test |

Example 108

Stabilizer compatibility evaluation of composition trial 753 comprising 36.9% a.e. (about 480 g a.e./L) potassium glyphosate and the listed surfactant (Surf.) and stabilizer (Stab.) components.

| Run | A8H | B2O | C8L | D4E | E9S | F3V | G5Q | H6B |
|---|---|---|---|---|---|---|---|---|
| Surf. | C27 | C27 | C27 | C27 | C27 | C5 | C5 | C5 |
| wt % | 4.9 | 4.9 | 4.9 | 4.9 | 4.9 | 4.9 | 4.9 | 4.9 |
| Stab. | C30 | C90 | C37 | C38 | C9 | C30 | C90 | C37 |
| wt % | 7.4 | 7.4 | 7.4 | 7.4 | 7.4 | 7.4 | 7.4 | 7.4 |
| 60° C. | Fail | Fail | Fail | Fail | Fail | Fail | Fail | Fail |
| RT | No test | No test | No test | No test | No test | No test | No test | No test |
| −10° C. | No test | No test | No test | No test | No test | No test | No test | No test |

Example 109

Compatibility evaluation of composition trial 755 comprising 36.9% a.e. (about 480 g a.e./L) potassium glyphosate and the listed surfactant (Surf.) and stabilizer (Stab.) components.

| Run | A5G | B1M | C9S | D9W | E4R | F2D | G0V |
|---|---|---|---|---|---|---|---|
| Surf 1 | C27 | C46 | C86 | C86 | C86 | C81 | C81 |
| wt % | 4.9 | 4.9 | 4.9 | 4.9 | 4.9 | 4.9 | 4.9 |
| Surf. 2 | — | C109 | C110 | C109 | — | C109 | C110 |
| wt % | — | 7.4 | 7.4 | 7.4 | — | 7.4 | 7.4 |
| Stab. | C30 | — | — | — | C30 | — | — |
| wt % | 7.4 | — | — | — | 7.4 | — | — |
| 60° C. | Fail | Fail | Fail | Fail | Fail | Fail | Fail |
| RT | No test | No test | No test | No test | No test | No test | No test |
| −10° C. | No test | No test | No test | No test | No test | No test | No test |

Example 110

Compatibility evaluation of composition trial 757 comprising 36.9% a.e. (about 480 g a.e./L) potassium glyphosate and the listed surfactant (Surf.) and stabilizer (Stab.) components.

| Run | A5G | B1M | C95 | D9W | E4R |
|---|---|---|---|---|---|
| Surf. 1 | C27 | C46 | C86 | C81 | C5 |
| wt % | 4.9 | 4.9 | 4.9 | 4.9 | 4.9 |
| Surf. 2 | C109 | C109 | C109 | C109 | — |
| wt % | 7.4 | 7.4 | 7.4 | 7.4 | — |
| Stab. | — | — | — | — | C30 |
| wt % | — | — | — | — | 7.4 |
| 60° C. | Fail | Fail | Fail | Fail | Fail |
| RT | No test | No test | No test | No test | No test |
| −10° C. | No test | No test | No test | No test | No test |

Example 111

Stabilizer compatibility evaluation of composition trial 759 comprising 31% a.e. (about 370 g a.e./L) glyphosate salt as indicated, and the listed surfactant (Surf.) and stabilizer (Stab.) components.

| Run | A7U | B3N | BX4F | C7P | D3B | E0T | F8M |
|---|---|---|---|---|---|---|---|
| Gly Salt | IPA | MA | MA | MEA | NH₄ | TMS | NPA |
| Surf. 1 | C46 | C46 | C46 | C46 | C46 | C46 | C46 |
| wt % | 4 | 4 | 4 | 4 | 4 | 4 | 4 |
| Surf. 2 | C110 | C110 | C109 | C110 | C110 | C110 | C110 |
| wt % | 6 | 6 | 6 | 6 | 6 | 6 | 6 |
| Stab. | C91 | C91 | C91 | C91 | C91 | C91 | C91 |
| wt % | 6.5 | 6.5 | 6.5 | 6.5 | 6.5 | 6.5 | 6.5 |
| 60° C. | Fail | Fail | Fail | Fail | Fail | Fail | Fail |
| RT | No test | No test | No test | No test | No test | No test | No test |
| −10° C. | No test | No test | No test | No test | No test | No test | No test |

Example 112

Stabilizer compatibility evaluation of composition trial 761 comprising 36.9% a.e. (about 480 g a.e./L) potassium glyphosate and the listed surfactant (Surf.) and stabilizer (Stab.) components.

| Run | A8F | B4O |
|---|---|---|
| Surf. 1 | C21 | C27 |
| wt % | 4.9 | 4.9 |
| Surf. 2 | C109 | C63 |
| wt % | 7.4 | 7.4 |
| Stab. | C74 | C74 |
| wt % | 6.5 | 6.5 |
| 60° C. | Fail | Fail |
| RT | No test | No test |
| −10° C. | No test | No test |

Example 113

Stabilizer compatibility evaluation of composition trial 762 comprising 36.9% a.e. (about 480 g a.e./L) potassium glyphosate and the listed surfactant (Surf.) and stabilizer (Stab.) components.

| Run | A9A | B7H | C4Y | D9Q | E3C |
|---|---|---|---|---|---|
| Surf. 1 | C27 | C27 | C27 | C27 | C27 |
| wt % | 4.9 | 3.7 | 4.9 | 4.9 | 4.9 |
| Surf. 2 | C109 | C109 | — | — | — |
| wt % | 7.4 | 7.4 | — | — | — |
| Stab. | C9 | C9 | C9 | C91 | C8 |
| wt % | 7 | 7 | 7.4 | 7.4 | 7.4 |
| 60° C. | Fail | Fail | Fail | Fail | Fail |
| RT | No test | No test | No test | No test | No test |
| −10° C. | No test | No test | No test | No test | No test |

Example 114

Stabilizer compatibility evaluation of composition trial 763 comprising 36.9% a.e. (about 480 g a.e./L) potassium glyphosate, and the listed surfactant (Surf.) and stabilizer (Stab.) components.

| Run | A5T | B1I | C3Z | D2S | E8N | F6W |
|---|---|---|---|---|---|---|
| Surf. | C27 | C27 | C27 | C27 | C27 | C27 |
| wt % | 9.2 | 7.4 | 6.2 | 4.6 | 10.6 | 12.3 |
| Stab. | C9 | C9 | C9 | C9 | C9 | C9 |
| wt % | 6 | 6 | 6 | 6 | 6 | 6 |
| 60° C. | Fail | Fail | Fail | Fail | Fail | Fail |
| RT | No test | No test | No test | No test | No test | No test |
| −10° C. | No test | No test | No test | No test | No test | No test |

Example 115

Stabilizer compatibility evaluation of composition trial 764 comprising 36.9% a.e. (about 480 g a.e./L) potassium glyphosate, and the listed surfactant (Surf.) and stabilizer (Stab.) components.

| Run | A4E | B2L | C7Y | D0Q | E4V | F1R |
|---|---|---|---|---|---|---|
| Surf. 1 | C46 | C27 | C46 | C46 | C27 | C46 |
| wt % | 4.9 | 4.9 | 4.9 | 4 | 4 | 4 |
| Surf. 2 | C109 | C43 | C110 | C109 | C43 | C110 |
| wt % | 7.4 | 7.4 | 7.4 | 6 | 6 | 6 |
| Stab. | C9 | C9 | C9 | C9 | C9 | C9 |
| wt % | 6 | 6 | 6 | 6 | 6 | 6 |
| 60° C. | Fail | Fail | Fail | Fail | Fail | Fail |
| RT | No test | No test | No test | No test | No test | No test |
| −10° C. | No test | No test | No test | No test | No test | No test |

Example 116

Stabilizer compatibility evaluation of composition trial 765 comprising 36.9% a.e. (about 480 g a.e./L) potassium glyphosate, and the listed surfactant (Surf.) and stabilizer (Stab.) components.

| Run | A9K | B3D | C5G | D1B | E5W |
|---|---|---|---|---|---|
| Surf. | C109 | C109 | C109 | C28 | C28 |
| wt % | 9.2 | 10.6 | 12.3 | 12.3 | 10 |
| Stab. | C9 | C9 | C9 | C9 | C9 |
| wt % | 2 | 2 | 2 | 10 | 6 |
| 60° C. | Clear | Fail | Fail | Fail | Fail |
| RT | Clear | No test | No test | No test | No test |
| −10° C. | Clear | No test | No test | No test | No test |
| −10° C.* | Clear | No test | No test | No test | No test |

*@ 4 Weeks

Example 117

Stabilizer compatibility evaluation of composition trial 767 comprising 36.9% a.e. (about 480 g a.e./L) potassium glyphosate, and the listed surfactant (Surf.) and stabilizer (Stab.).

| Run | A4V | B7H | C0A | D4N | E4T | F6J | G4X | H1L | I9E | J3C |
|---|---|---|---|---|---|---|---|---|---|---|
| Surf. 1 | C27 | C27 | C27 | C27 | C27 | C27 | C17 | C17 | C17 | C17 |
| wt % | 4.9 | 4.9 | 4.9 | 4.9 | 4.9 | 4.9 | 3.7 | 4.9 | 3.7 | 4.9 |
| Surf. 2 | C30 | C30 | C30 | C30 | C30 | C30 | C42 | C42 | C42 | C42 |
| wt % | 7.4 | 4.1 | 7.4 | 4.1 | 7.4 | 7.4 | 8.6 | 7.4 | 8.6 | 7.4 |
| Stab. | C91 | C91 | C9 | C9 | C14 | C14 | C47 | C47 | C49 | C49 |
| wt % | 2.7 | 6 | 2.7 | 6 | 2.7 | 6 | 2.7 | 6 | 2.7 | 6 |
| 60° C. | Fail | Fail | Fail | Fail | Fail | Fail | Fail | Fail | Fail | Fail |
| RT | No test | No test | No test | No test | No test | No test | No test | No test | No test | No test |
| −10° C. | No test | No test | No test | No test | No test | No test | No test | No test | No test | No test |

Example 118

Stabilizer compatibility evaluation of composition trial 768 comprising 36.9% a.e. (about 480 g a.e./L) potassium glyphosate, and the listed surfactant (Surf.) and stabilizer (Stab.) components.

| Run | A7T | B3N | C5W | D0A |
|---|---|---|---|---|
| Surf. 1 | C46 | C46 | C46 | C46 |
| wt % | 4.9 | 4.9 | 4.9 | 4.9 |
| Surf. 2 | C30 | C30 | C30 | C30 |
| wt % | 7.4 | 4.1 | 7.4 | 4.1 |
| Stab. | C91 | C91 | C9 | C9 |
| wt % | 2.7 | 6 | 2.7 | 6 |
| 60° C. | Fail | Fail | Fail | Fail |
| RT | No test | No test | No test | No test |
| −10° C. | No test | No test | No test | No test |

Example 119

Stabilizer compatibility evaluation of composition trial 771 comprising 36.9% a.e. (about 480 g a.e./L) potassium glyphosate, and the listed surfactant (Surf.) and stabilizer (Stab.) components.

| Run | A7T | B3N | C5W |
|---|---|---|---|
| Surf. 1 | C109 | C109 | C109 |
| wt % | 12.3 | 10.6 | 9.2 |
| Stab. | C9 | C9 | C9 |
| wt % | 3 | 3 | 3 |
| 60° C. | Fail | Fail | Clear |
| RT | No test | No test | Clear |
| −10° C. | No test | No test | Clear |
| −10° C.* | No test | No test | Clear |

*@ 4 Weeks

Example 120

Stabilizer compatibility evaluation of composition trial 773 comprising 36.9% a.e. (about 480 g a.e./L) potassium glyphosate, and the listed surfactant (Surf.), Additive (Add.) and stabilizer (Stab.) components.

| Run | A8J | B1C | C0H | D5V | E5W |
|---|---|---|---|---|---|
| Surf. 1 | C46 | C46 | C46 | C46 | C46 |
| wt % | 3 | 3 | 3 | 3 | 3 |
| Surf. 2 | C109 | C109 | C109 | C109 | C109 |
| wt % | 7 | 7 | 7 | 7 | 7 |
| Add. | C30 | C30 | C30 | C30 | C30 |
| wt % | 7.4 | 4.1 | 7.4 | 4.1 | 7.4 |
| Stab. | C91 | C91 | C91 | C91 | C91 |
| wt % | 6.5 | 6.5 | 6.5 | 6.5 | 6.5 |
| 60° C. | Fail | Fail | Fail | Fail | Fail |
| RT | No test | No test | No test | No test | No test |
| −10° C. | No test | No test | No test | No test | No test |

Example 121

Stabilizer compatibility evaluation of composition trial 775 comprising 36.9% a.e. (about 480 g a.e./L) potassium glyphosate, and the listed surfactant (Surf.) and stabilizer (Stab.) components.

| Run | A4L | B3P | C2L | D7U | E4V | F5G | G4T |
|---|---|---|---|---|---|---|---|
| Surf. 1 | C110 | C109 | C5 | C5 | C21 | C23 | C46 |
| wt % | 12.3 | 12.3 | 4.9 | 4.9 | 4.9 | 4.9 | 4.9 |
| Surf. 2 | — | — | C109 | C110 | C109 | C109 | C110 |
| wt % | — | — | 7.4 | 7.4 | 7.4 | 7.4 | 7.4 |
| Stab. | C91 | C91 | C91 | C91 | C91 | C91 | C91 |
| wt % | 6.5 | 6.5 | 6.5 | 6.5 | 6.5 | 6.5 | 6.5 |
| 60° C. | Fail | Fail | Fail | Fail | Fail | Fail | Fail |
| RT | No test | No test | No test | No test | No test | No test | No test |
| −10° C. | No test | No test | No test | No test | No test | No test | No test |

Example 122

Stabilizer compatibility evaluation of composition trial 776 comprising 36.9% a.e. (about 480 g a.e./L) potassium glyphosate and the listed surfactant (Surf.) and stabilizer (Stab.) components.

| Run | A3X | B0G | C0J | D6Y | E3F | F2S | G9O | H1B |
|---|---|---|---|---|---|---|---|---|
| Surf. | C86 | C28 | C86 | C86 | C86 | C46 | C46 | C46 |
| wt % | 4.9 | 4.9 | 4.9 | 4.9 | 4.9 | 4.9 | 4.9 | 4.9 |
| Stab. | C30 | C30 | C9 | C38 | C14 | C9 | C38 | C9 |
| wt % | 6.3 | 6.3 | 7.4 | 7.4 | 7.4 | 7.4 | 7.4 | 7.4 |
| 60° C. | Fail | Fail | Fail | Fail | Fail | Clear | Fail | Fail |
| RT | No test | No test | No test | No test | No test | No test | No test | No test |
| −10° C. | No test | No test | No test | No test | No test | No test | No test | No test |

Example 123

Stabilizer compatibility evaluation of composition trial 777 comprising 36.9% a.e. (about 480 g a.e./L) potassium glyphosate and the listed surfactant (Surf.) and stabilizer (Stab.) components.

| Run | A9I | B2V | C4F | D2U | E7K | F1A | G5D | H9K | I0H | J4Z |
|---|---|---|---|---|---|---|---|---|---|---|
| Surf. 1 | C46 | C46 | C46 | C46 | C46 | C46 | C46 | C46 | C46 | C46 |
| wt % | 5.2 | 5.6 | 12.3 | 10.6 | 9.2 | 12.3 | 10.6 | 9.2 | 6.2 | 7.4 |
| Surf. 2 | C110 | C110 | — | — | — | — | — | — | — | — |
| wt % | 7.8 | 8.4 | — | — | — | — | — | — | — | — |
| Stab. | C92 | C92 | C9 | C9 | C9 | C9 | C9 | C9 | C9 | C9 |
| wt % | 1 | 1 | 4 | 4 | 4 | 6 | 6 | 6 | 6 | 5 |
| 60° C. | Clear | Clear | Fail | Fail | Fail | Fail | Fail | Fail | Clear | Fail |
| RT | Fail | Fail | No test | No test | No test | No test | No test | No test | No test | No test |
| −10° C. | No test | No test | No test | No test | No test | No test | No test | No test | No test | No test |

Example 124

Stabilizer compatibility evaluation of composition trial 778 comprising 36.9% a.e. (about 480 g a.e./L) potassium glyphosate, and the listed surfactant (Surf.) and stabilizer (Stab.) components.

| Run | A5T | B1S | C7B | D4L | E8J | F6T | G0M | H7R | I7B | J3S | K1A |
|---|---|---|---|---|---|---|---|---|---|---|---|
| Surf. | C46 | C27 | C28 | C86 | C18 | C18 | C18 | C20 | C17 | C16 | C23 |
| wt % | 4.9 | 4.9 | 4.9 | 4.9 | 4.9 | 4.9 | 4.9 | 4.9 | 4.9 | 4.9 | 4.9 |

-continued

| Run | A5T | B1S | C7B | D4L | E8J | F6T | G0M | H7R | I7B | J3S | K1A |
|---|---|---|---|---|---|---|---|---|---|---|
| Stab. | C9 | C9 | C9 | C9 | C9 | C9 | C9 | C9 | C9 | C9 | C9 |
| wt % | 7.4 | 7.4 | 7.4 | 7.4 | 7.4 | 7.4 | 7.4 | 7.4 | 7.4 | 7.4 | 7.4 |
| 60° C. | Fail | Fail | Fail | Fail | Fail | Fail | Fail | Fail | Fail | Fail | Fail |
| RT | No test | No test | No test | No test | No test | No test | No test | No test | No test | No test | No test |
| −10° C. | No test | No test | No test | No test | No test | No test | No test | No test | No test | No test | No test |

Example 125

Stabilizer compatibility evaluation of composition trial 779 comprising 36.9% a.e. (about 480 g a.e./L) potassium glyphosate, and the listed surfactant (Surf.) and stabilizer (Stab.) components.

| Run | A2F | B8K | C1P | D4S |
|---|---|---|---|---|
| Surf. | C46 | C46 | C46 | C46 |
| wt % | 5.6 | 6 | 6.4 | 5.2 |
| Stab. | C9 | C9 | C9 | C9 |
| wt % | 8.4 | 9 | 9.6 | 7.8 |
| 60° C. | Fail | Fail | Fail | Fail |
| RT | No test | No test | No test | No test |
| −10° C. | No test | No test | No test | No test |

Example 126

Stabilizer compatibility evaluation of composition trial 780 comprising 31% a.e. (about 370 g a.e./L) isopropylamine glyphosate, and the listed surfactant (Surf.) and stabilizer (Stab.) components.

| Run | A2W | B0F | C4V | D3J | E9I | F6N | G4C | H2X | I8H |
|---|---|---|---|---|---|---|---|---|---|
| Surf. 1 | C46 | C46 | C46 | C46 | C46 | C46 | C46 | C46 | C46 |
| wt % | 4.9 | 4.9 | 4.9 | 4.9 | 4.9 | 4.9 | 4.9 | 3.1 | 3.1 |
| Surf. 2 | C110 | C110 | C109 | C110 | C109 | C110 | C109 | C110 | C109 |
| wt % | 7.4 | 7.4 | 7.4 | 7.4 | 7.4 | 7.4 | 7.4 | 3.1 | 3.1 |
| Stab. | C92 | C92 | C92 | C91 | C91 | C9 | C9 | — | — |
| wt % | 1 | 1.5 | 1 | 1 | 1 | 1 | 1 | — | — |
| 60° C. | Fail | Fail | Fail | Fail | Fail | Fail | Fail | Fail | Fail |
| RT | No test | No test | No test | No test | No test | No test | No test | No test | No test |
| −10° C. | No test | No test | No test | No test | No test | No test | No test | No test | No test |

Example 127

Stabilizer compatibility evaluation of composition trial 781 comprising 31% a.e. (about 370 g a.e./L) isopropylamine glyphosate and the listed surfactant (Surf.) and stabilizer (Stab.).

| Run | A4C | B6Y | C9K | D5R | E2X | F8I | G3D |
|---|---|---|---|---|---|---|---|
| Surf 1. | C46 | C46 | C46 | C46 | C46 | C46 | C46 |
| wt % | 4.92 | 4.92 | 4.92 | 4.92 | 4.92 | 4.92 | 4.92 |
| Surf. 2 | C110 | C110 | C110 | C110 | C110 | C110 | C110 |
| wt % | 7.4 | 7.4 | 7.4 | 7.4 | 7.4 | 7.4 | 7.4 |
| Stab. | — | C38 | C38 | C38 | C15 | C15 | C15 |
| wt % | — | 1 | 3 | 5 | 1 | 3 | 5 |
| 60° C. | Fail | Fail | Fail | Fail | Fail | Clear | Clear |
| RT | No test | No test | No test | No test | No test | Clear | Clear |
| −10° C. | No test | No test | No test | No test | No test | Clear | Clear |
| −10° C.* | No test | No test | No test | No test | No test | Clear | Clear |

| Run | H7N | I3W | J7M | K8D | L1B | M6Y | N0F |
|---|---|---|---|---|---|---|---|
| Surf 1. | C46 | C46 | C46 | C46 | C46 | C46 | C46 |
| wt % | 4.92 | 4.92 | 4.92 | 4.92 | 4.92 | 4.92 | 4.92 |
| Surf. 2 | C110 | C110 | C110 | C110 | C110 | C110 | C110 |
| wt % | 7.4 | 7.4 | 7.4 | 7.4 | 7.4 | 7.4 | 7.4 |
| Stab. | C9 | C9 | C9 | C77 | C77 | C77 | C39 |
| wt % | 1 | 3 | 5 | 1 | 3 | 5 | 1 |
| 60° C. | Fail | Fail | Fail | Clear | Clear | Clear | Fail |
| RT | No test | No test | No test | Clear | Clear | Clear | No test |
| −10° C. | No test | No test | No test | Clear | Clear | Clear | No test |
| −10° C.* | No test | No test | No test | Clear | Fail | Fail | No test |

| Run | O4G | P3E | Q7X | R9V | S2T | T7K | U4F |
|---|---|---|---|---|---|---|---|
| Surf. 1 | C46 | C46 | C46 | C46 | C46 | C46 | C46 |
| wt % | 4.92 | 4.92 | 4.92 | 4.92 | 4.92 | 4.92 | 4.92 |
| Surf. 2 | C110 | C110 | C110 | C110 | C110 | C110 | C110 |
| wt % | 7.4 | 7.4 | 7.4 | 7.4 | 7.4 | 7.4 | 7.4 |
| Stab. | C39 | C39 | C122 | C122 | C122 | C70 | C70 |
| wt % | 3 | 5 | 1 | 3 | 5 | 1 | 3 |
| 60° C. | Fail | Fail | Fail | Fail | Fail | Fail | Fail |
| RT | No test | No test | No test | No test | No test | No test | No test |
| −10° C. | No test | No test | No test | No test | No test | No test | No test |

| Run | V8F | W0R | X3G | Y9O | Z2F | AA8P | BB4E |
|---|---|---|---|---|---|---|---|
| Surf. 1 | C46 | C46 | C46 | C46 | C46 | C46 | C46 |
| wt % | 4.92 | 4.92 | 4.92 | 4.92 | 4.92 | 4.92 | 4.92 |
| Surf. 2 | C110 | C110 | C110 | C110 | C110 | C110 | C110 |
| wt % | 7.4 | 7.4 | 7.4 | 7.4 | 7.4 | 7.4 | 7.4 |
| Stab. | C70 | C37 | C37 | C37 | C30 | C30 | C30 |
| wt % | 5 | 1 | 3 | 5 | 1 | 3 | 5 |
| 60° C. | Fail | Fail | Fail | Fail | Fail | Fail | Fail |

-continued

| | | | | | | | |
|---|---|---|---|---|---|---|---|
| RT | No test | No test | No test | No test | No test | No test | No test |
| −10° C. | No test | No test | No test | No test | No test | No test | No test |

| Run | CC9H | DD1K | EE3S | FF7U | GG7J | HH2P |
|---|---|---|---|---|---|---|
| Surf 1. | C46 | C46 | C46 | C46 | C46 | C46 |
| wt % | 4.92 | 4.92 | 4.92 | 4.92 | 4.92 | 4.92 |
| Surf. 2 | C110 | C110 | C110 | C110 | C110 | C110 |
| wt % | 7.4 | 7.4 | 7.4 | 7.4 | 7.4 | 7.4 |
| Stab. | C14 | C14 | C14 | C10 | C10 | C10 |
| wt % | 1 | 3 | 5 | 1 | 3 | 5 |
| 60° C. | Fail | Fail | Fail | Fail | Fail | Fail |
| RT | No test | No test | No test | No test | No test | No test |
| −10° C. | No test | No test | No test | No test | No test | No test |

*@ 4 weeks

Example 128

Stabilizer compatibility evaluation of composition trial 782 comprising 31% a.e. (about 370 g a.e./L) isopropylamine glyphosate, and the listed surfactant (Surf.) and stabilizer (Stab.) components.

| Run | A4F | B7A | C2V | D0W | E3P | F1K | G8S | H5K | I9T | J6B |
|---|---|---|---|---|---|---|---|---|---|---|
| Surf. 1 | C46 | C46 | C46 | C46 | C46 | C46 | C46 | C46 | C46 | C46 |
| wt % | 4.9 | 4.9 | 4.9 | 4.9 | 4.9 | 4.9 | 4.9 | 4.9 | 4.9 | 4.9 |
| Surf. 2 | C110 | C110 | C110 | C109 | C109 | C109 | C109 | C109 | C109 | C109 |
| wt % | 7.4 | 7.4 | 7.4 | 7.4 | 7.4 | 7.4 | 7.4 | 7.4 | 7.4 | 7.4 |
| Stab. | C77 | C77 | C77 | — | C77 | C77 | C77 | C9 | C9 | C9 |
| wt % | 1 | 3 | 5 | — | 1 | 3 | 5 | 1 | 3 | 5 |
| 60° C. | Clear | Fail | Fail | Fail | Clear | Clear | Fail | Fail | Fail | Fail |
| RT | Clear | No test | No test | No test | Clear | Clear | No test | No test | No test | No test |
| −10° C. | Clear | No test | No test | No test | Clear | Clear | No test | No test | No test | No test |
| −10° C.* | Fail | No test | No test | No test | Cloudy | Fail | No test | No test | No test | No test |

*@ 4 weeks

Example 129

Stabilizer compatibility evaluation of composition trial 783 comprising 36.9% a.e. (about 480 g a.e./L) potassium glyphosate, and the listed surfactant (Surf.) and stabilizer (Stab.) components.

| Run | A6Y | B0S | C8F | D9X | E4N | F0L | G3J | H2Q | I3B |
|---|---|---|---|---|---|---|---|---|---|
| Surf. | C109 | C109 | C109 | C110 | C110 | C110 | C43 | C43 | C43 |
| wt % | 9.2 | 10.6 | 12.3 | 9.2 | 10.6 | 12.3 | 9.2 | 10.6 | 12.3 |
| Stab. | C9 | C9 | C9 | C9 | C9 | C9 | C9 | C9 | C9 |
| wt % | 2 | 2 | 2 | 4 | 4 | 4 | 6 | 6 | 6 |
| 60° C. | Fail | Fail | Fail | Fail | Fail | Fail | Fail | Fail | Fail |
| RT | No test | No test | No test | No test | No test | No test | No test | No test | No test |
| −10° C. | No test | No test | No test | No test | No test | No test | No test | No test | No test |

Example 130

Stabilizer compatibility evaluation of composition trial 784 comprising 36.9% a.e. (about 480 g a.e./L) potassium glyphosate and the listed surfactant (Surf.) and stabilizer (Stab.) components.

| Run | A9K | B3C | C2H | D7U | E2S | F5F | G5R | H2O |
|---|---|---|---|---|---|---|---|---|
| Surf. 1 | C46 | C46 | C46 | C46 | C46 | C46 | C46 | C46 |
| wt % | 1.2 | 2.6 | 3.7 | 4.9 | 1.2 | 2.6 | 3.7 | 4.9 |
| Surf. 2 | C42 | C42 | C42 | C42 | C42 | C42 | C42 | C42 |
| wt % | 11.1 | 9.9 | 8.7 | 7.4 | 11.1 | 9.9 | 8.7 | 7.4 |
| Stab. | C91 | C91 | C91 | C91 | C9 | C9 | C9 | C9 |
| wt % | 5 | 5 | 5 | 5 | 5 | 5 | 5 | 5 |
| 60° C. | Clear | Clear | Clear | Clear | Fail | Fail | Fail | Fail |
| RT | Clear | Cloudy | Cloudy | Cloudy | No test | No test | No test | No test |
| −10° C. | Clear | Cloudy | Cloudy | Cloudy | No test | No test | No test | No test |
| −10° C.* | Clear | Fail | Fail | Fail | No test | No test | No test | No test |

*@ 4 Weeks

Example 131

Stabilizer compatibility evaluation of composition trial 785 comprising 36.9% a.e. (about 480 g a.e./L) potassium glyphosate, and the listed surfactant (Surf.) and stabilizer (Stab.) components.

| Run | A9L | B5V | C1U | D5B | E7Y | F5T | G7J | H2S | I8M | J3W | K0C |
|---|---|---|---|---|---|---|---|---|---|---|---|
| Surf. 1 | C46 | C46 | C46 | C46 | C46 | C46 | C46 | C46 | C46 | C46 | C46 |
| wt % | 4 | 4 | 4.9 | 4.9 | 4.9 | 4.9 | 4 | 4 | 4 | 4 | 4 |
| Surf. 2 | C109 | C109 | C109 | C109 | C109 | C109 | C109 | C109 | C109 | C109 | C109 |
| wt % | 6 | 6 | 7.4 | 7.4 | 7.4 | 7.4 | 6 | 6 | 6 | 6 | 6 |
| Stab. 1 | C91 | C91 | C91 | C91 | C91 | C91 | C91 | C91 | C91 | C91 | C91 |
| wt % | 2 | 1 | 6 | 6 | 6 | 6 | 6 | 6 | 6 | 6 | 2 |
| Stab. 2 | C9 | C9 | — | C77 | C77 | C77 | — | C77 | C77 | C77 | C77 |
| wt % | 4 | 4 | — | 1 | 3 | 5 | — | 1 | 3 | 5 | 1 |
| 60° C. | Fail | Fail | Fail | Fail | Fail | Fail | Fail | Clear | Fail | Fail | Fail |
| RT | No test | No test | No test | No test | No test | No test | Fail | Clear | No test | No test | No test |
| −10° C. | No test | No test | No test | No test | No test | No test | Fail | Clear | No test | No test | No test |
| −10° C.* | | | | | | | No test | Fail | No test | No test | No test |

*@ 4 weeks

Example 132

Stabilizer compatibility evaluation of composition trial 786 comprising 31% a.e. (about 370 g a.e./L) isopropylamine glyphosate and the listed surfactant (Surf.) and stabilizer (Stab.).

| Run | A5G | B2X | C6J | D7Q | E3H | F6U | G7W | H1M | I8L | J3S | K0J | L6P | M2V | N5G | O3U | P2B | Q6W |
|---|---|---|---|---|---|---|---|---|---|---|---|---|---|---|---|---|---|
| Surf 1. | C46 | C46 | C46 | C46 | C46 | C46 | C46 | C46 | C46 | C46 | C46 | C46 | C46 | C46 | C46 | C46 | C46 |
| wt % | 5.6 | 5.6 | 4.3 | 5.6 | 4 | 4.4 | 4.8 | 4.6 | 4 | 4.1 | 4.5 | 4.8 | 5.1 | 5.1 | 5.6 | 4.7 | 5.4 |
| Surf. 2 | C110 | C110 | C110 | C110 | C110 | C110 | C110 | C110 | C110 | C110 | C110 | C110 | C110 | C110 | C110 | C110 | C110 |
| wt % | 8.4 | 8.4 | 6.5 | 8.4 | 6 | 6.5 | 7.3 | 7 | 6 | 6.1 | 6.8 | 7.2 | 7.7 | 7.7 | 8.4 | 7 | 8.1 |
| Stab. | C77 | — | C77 | C77 | C77 | C77 | — | C77 | C77 | — | C77 | C77 | C77 | C77 | C77 | C77 | C77 |
| wt % | 0.7 | — | 1.4 | 2 | 0.8 | 0.4 | — | 0.8 | 2 | — | 2 | 2 | 0.4 | 1.4 | 1.1 | 0.9 | 1 |
| 60° C. | Fail | Fail | Clear | Clear | Clear | Fail | Fail | Fail | Clear | Fail | Clear | Clear | Fail | Clear | Fail | Fail | Clear |
| RT | Fail | Fail | Clear | Clear | Clear | No test | No test | No test | Clear | No test | Clear | Clear | No test | Clear | No test | No test | Clear |
| −10° C. | Fail | Fail | Clear | Clear | Clear | No test | No test | No test | Clear | No test | Clear | Clear | No test | Clear | No test | No test | Cloudy |
| −10° C.* | No test | No test | Fail | Fail | Cloudy | No test | No test | | | | | | | | | | |

*@ 4 weeks

Example 133

Stabilizer compatibility evaluation of composition trial 787 comprising 31% a.e. (about 370 g a.e./L) isopropylamine glyphosate, and the listed surfactant (Surf.) and stabilizer (Stab.) components.

| Run | A6B | B9P | C1Z | D4M | E8Y | F3L | G5Q | H9K | I3R | J7S | K6A | L0B | M2C |
|---|---|---|---|---|---|---|---|---|---|---|---|---|---|
| Surf 1 | C46 | C46 | C46 | C46 | C46 | C46 | C46 | C46 | C46 | C46 | C46 | C46 | C46 |
| wt % | 5.2 | 5.6 | 6 | 6.4 | 6.8 | 7.2 | 7.6 | 8 | 8.4 | 8.8 | 9.2 | 9.6 | 4.9 |
| Surf. 2 | C109 | C109 | C109 | C109 | C109 | C109 | C109 | C109 | C109 | C109 | C109 | C109 | C110 |
| wt % | 7.8 | 8.4 | 9 | 9.6 | 10.2 | 10.8 | 11.4 | 12 | 12.6 | 13.2 | 13.8 | 14.4 | 7.4 |
| Stab. | — | — | — | — | — | — | — | — | — | — | — | — | C77 |
| wt % | — | — | — | — | — | — | — | — | — | — | — | — | 1 |
| 60° C. | Fail | Fail | Fail | Fail | Fail | Fail | Fail | Fail | Fail | Fail | Fail | Fail | Clear |
| RT | No test | No test | No test | No test | No test | No test | No test | No test | No test | No test | No test | No test | Clear |
| −10° C. | No test | No test | No test | No test | No test | No test | No test | No test | No test | No test | No test | No test | Clear |
| −10° C.* | | | | | | | | No test | No test | No test | No test | No test | Cloudy |

*@ 4 weeks

Example 134

Stabilizer compatibility evaluation of composition trial 788 comprising 31% a.e. (about 370 g a.e./L) isopropylamine glyphosate, and the listed surfactant (Surf.) and stabilizer (Stab.) components.

| Run | A3R | B2K | C9P | D5H | E5R | F1V | G9J | H6M | I3U | J2X | K0W | L8B |
|---|---|---|---|---|---|---|---|---|---|---|---|---|
| Surf 1 | C46 | C46 | C46 | C46 | C46 | C46 | C46 | C46 | C46 | C46 | C46 | C46 |
| wt % | 5.2 | 5.6 | 6 | 6.4 | 6.8 | 7.2 | 7.6 | 8 | 8.4 | 8.8 | 9.2 | 9.6 |
| Surf. 2 | C110 | C110 | C110 | C110 | C110 | C110 | C110 | C110 | C110 | C110 | C110 | C110 |
| wt % | 7.8 | 8.4 | 9 | 9.6 | 10.2 | 10.8 | 11.4 | 12 | 12.6 | 13.2 | 13.8 | 14.4 |
| Stab. | C77 | C77 | C77 | C77 | C77 | C77 | C77 | C77 | C77 | C77 | C77 | C77 |
| wt % | 1.5 | 1.5 | 1.5 | 1.5 | 1.5 | 1.5 | 1.5 | 1.5 | 1.5 | 1.5 | 1.5 | 1.5 |
| 60° C. | Clear | Clear | Clear | Fail | Fail | Fail | Fail | Fail | Fail | Fail | Fail | Fail |
| RT | Clear | Clear | Clear | No test | No test | No test | No test | No test | No test | No test | No test | No test |
| −10° C. | Clear | Clear | Clear | No test | No test | No test | No test | No test | No test | No test | No test | No test |
| −10° C.* | Fail | Cloudy | Fail | No test | No test | No test | No test | | | | | |

*@ 4 weeks

Example 135

Stabilizer compatibility evaluation of composition trial 789 comprising 36.9% a.e. (about 480 g a.e./L) potassium glyphosate, and the listed surfactant (Surf.) and stabilizer (Stab.) components.

| Run | A3R | B2K | C9P | D5H | E5R | F1V | G9J | H6M | I3U | J2X | K0W | L8B |
|---|---|---|---|---|---|---|---|---|---|---|---|---|
| Surf 1 | C46 | C46 | C27 | C46 | C46 | C46 | C46 | C46 | C27 | C46 | C46 | C27 |
| wt % | 4.9 | 4.9 | 4.9 | 4.9 | 4.9 | 4.9 | 4.9 | 4.9 | 4.9 | 4.9 | 4.9 | 4.9 |
| Surf. 2 | C110 | C109 | C43 | C109 | — | — | C110 | C109 | C43 | C110 | C109 | C43 |
| wt % | 7.4 | 7.4 | 7.4 | 7.4 | — | — | 7.4 | 7.4 | 7.4 | 7.4 | 7.4 | 7.4 |
| Stab. 1 | C91 | C91 | C91 | C91 | C77 | C77 | C74 | C74 | C74 | C92 | C92 | C92 |
| wt % | 6 | 5 | 6 | 5 | 1 | 1 | 4 | 4 | 6 | 4 | 4 | 5 |
| Stab. 2 | C77 | C77 | C77 | C77 | C9 | C91 | C77 | C77 | C77 | C77 | C77 | C77 |
| wt % | 1 | 1 | 1 | 1 | 7.4 | 7.4 | 1 | 1 | 1 | 1 | 1 | 1 |
| 60° C. | Fail | Fail | Fail | Fail | Clear | Clear | Fail | Fail | Fail | Fail | Fail | Fail |
| RT | No test | No test | No test | No test | Clear | Clear | No test | No test | No test | No test | No test | No test |
| −10° C. | No test | No test | No test | No test | Clear | Clear | No test | No test | No test | No test | No test | No test |
| −10° C. | No test | No test | No test | No test | Fail | Fail | No test | | | | | |

*@ 4 weeks

Example 136

Stabilizer compatibility evaluation of composition trial 790 comprising 36.9% A.e. (about 480 g a.e./L) potassium glyphosate, and the listed surfactant (Surf.) and stabilizer (Stab.) components.

| Run | A5T | B3O | C2X | D0H | E5B | F7T | G1B | H9K | I3G | J4N |
|---|---|---|---|---|---|---|---|---|---|---|
| Surf. 1 | C46 | C46 | C46 | C46 | C46 | C46 | C46 | C46 | C46 | C46 |
| wt % | 4.9 | 4.9 | 4.9 | 4.9 | 4.9 | 4.9 | 4.9 | 4.9 | 4.9 | 4.9 |
| Surf. 2 | C109 | C109 | C109 | C109 | C109 | C109 | C109 | C109 | C109 | C109 |
| wt % | 7.4 | 7.4 | 7.4 | 7.4 | 7.4 | 7.4 | 7.4 | 7.4 | 7.4 | 7.4 |
| Stab. 1 | — | C9 | C91 | C91 | C9 | C91 | C91 | C91 | C91 | C91 |
| wt % | — | 3 | 4 | 3 | 6 | 1 | 2 | 3 | 6 | 1 |
| Stab. 2 | — | — | — | C9 | — | C9 | C9 | — | — | C9 |
| wt % | — | — | — | 4 | — | 5 | 1 | — | — | 1 |
| 60° C. | Fail | Fail | Fail | Fail | Fail | Fail | Fail | Fail | Fail | Fail |
| RT | No test | No test | No test | No test | No test | No test | No test | No test | No test | No test |
| −10° C. | No test | No test | No test | No test | No test | No test | No test | No test | No test | No test |

Example 137

Stabilizer compatibility evaluation of composition trial 791 comprising 36.9% a.e. (about 480 g a.e./L) potassium glyphosate, and the listed surfactant (Surf.) and stabilizer (Stab.) components.

| Run | A0F | B6H | C4B | D5W | E1Z | F9V | G8J | H3V | I2K | J2F | K0M |
|---|---|---|---|---|---|---|---|---|---|---|---|
| Surf. | C27 | C27 | C27 | C27 | C27 | C27 | C27 | C27 | C27 | C27 | C27 |
| wt % | 4.9 | 2.5 | 4 | 2 | 4 | 2 | 2.5 | 4.9 | 2.5 | 4 | 2 |
| Stab. 1 | C9 | C9 | C9 | C9 | C9 | C9 | C9 | C9 | C9 | C9 | C9 |
| wt % | 7.4 | 9.8 | 6 | 8 | 6 | 8 | 9.8 | 7.4 | 9.8 | 6 | 8 |
| Stab. 2 | C77 | C77 | C77 | C77 | — | — | — | C15 | C15 | C15 | C15 |
| wt % | 1 | 1 | 1 | 1 | — | — | — | 1 | 1 | 1 | 1 |
| 60° C. | Fail | Fail | Fail | Fail | Fail | Fail | Fail | Fail | Fail | Fail | Fail |
| RT | No test | No test | No test | No test | No test | No test | No test | No test | No test | No test | No test |
| −10° C. | No test | No test | No test | No test | No test | No test | No test | No test | No test | No test | No test |

Example 138

Stabilizer compatibility evaluation of composition trial 792 comprising 31% a.e. (about 370 g a.e./L) isopropylamine glyphosate and the listed surfactant (Surf.) and stabilizer (Stab.) components.

| Run | A0P | B4R | C7B | D8J | E1S | F8K | G0P | H3X |
|---|---|---|---|---|---|---|---|---|
| Surf. 1 | C46 | C46 | C46 | C46 | C27 | C27 | C27 | C27 |
| wt % | 4 | 4.6 | 4.8 | 5.6 | 4.9 | 4.9 | 4 | 4 |
| Surf. 2 | C110 | C110 | C110 | C110 | C9 | C9 | C9 | C9 |
| wt % | 6 | 7 | 7.1 | 8.3 | 7.4 | 7.4 | 6 | 6 |
| Stab. | C77 | C77 | C77 | C77 | — | C77 | — | C77 |
| wt % | 1.4 | 1.7 | 1.5 | 1.8 | — | 1 | — | 1 |
| 60° C. | Clear | Clear | Clear | Fail | Fail | Fail | Fail | Clear |
| RT | Clear | Clear | Clear | No test | No test | No test | No test | Clear |
| −10° C. | Clear | Clear | Clear | No test | No test | No test | No test | Clear |
| −10° C.* | Cloudy | Cloudy | Cloudy | No test | No test | No test | No test | Clear |

*@ 4 weeks

Example 139

Stabilizer compatibility evaluation of composition trial 793 comprising 36.9% a.e. (about 480 g a.e./L) potassium glyphosate, and the listed surfactant (Surf.) and stabilizer (Stab.) components.

| Run | A5T | B3O | C2X | D0H | E5B | F7T | G1B | H9K | I3G |
|---|---|---|---|---|---|---|---|---|---|
| Surf 1 | C27 | C27 | C46 | C46 | C46 | C46 | C46 | C46 | C46 |
| wt % | 4.9 | 4 | 1.6 | 1.6 | 1.6 | 4.9 | 4 | 4.9 | 4 |
| Surf. 2 | — | — | C110 | C110 | C110 | C109 | C109 | C109 | C109 |
| wt % | — | — | 2.4 | 2.4 | 2.4 | 7.4 | 7.4 | 7.4 | 7.4 |
| Stab. 1 | — | C38 | C38 | C9 | C9 | C91 | C91 | C9 | C9 |
| wt % | — | 7.4 | 6 | 7.4 | 6 | 7.4 | 6 | 7.4 | 6 |
| Stab. 2 | — | — | — | — | C77 | — | — | — | — |
| wt % | — | — | — | — | 1 | — | — | — | — |
| 60° C. | Fail | Clear | Clear | Clear | Clear | Clear | Clear | Fail | Fail |
| RT | No test | Clear | Clear | Clear | Clear | Clear | Clear | No test | No test |
| −10° C. | No test | Fail | Clear | Clear | Clear | Clear | Clear | No test | No test |
| −10° C.* | No test | No test | Clear | Clear | Clear | | | | |

*@4 Weeks

Example 140

Stabilizer compatibility evaluation of composition trial 795 comprising 36.9% a.e. (about 480 g a.e./L) potassium glyphosate and the listed surfactant (Surf.) and stabilizer (Stab.) components.

| Run | A0P | B4R | C7B | D8J | E1S | F8K | G0F | H3X |
|---|---|---|---|---|---|---|---|---|
| Surf. 1 | C27 | C27 | C27 | C27 | C27 | C46 | C46 | C46 |
| wt % | 4.9 | 4 | 4 | 4 | 4.9 | 4.9 | 4.9 | 6.2 |
| Surf. 2 | C110 | C110 | C110 | C110 | C110 | C110 | C110 | — |
| wt % | 7.4 | 6 | 6 | 6 | 7.4 | 7.4 | 7.4 | — |
| Stab. 1 | — | — | C91 | C9 | C91 | C77 | C91 | C77 |
| wt % | — | — | 6 | 6 | 6 | 1 | 4 | 1 |
| Stab. 2 | — | — | — | — | C77 | — | C77 | — |
| wt % | — | — | — | — | 1 | — | 1 | — |
| 60° C. | Fail | Fail | Fail | Fail | Fail | Fail | Fail | Fail |
| RT | No test | No test | No test | No test | No test | No test | No test | No test |
| −10° C. | No test | No test | No test | No test | No test | No test | No test | No test |

Example 141

Stabilizer compatibility evaluation of composition trial 798 comprising 36.9% a.e. (about 480 g a.e./L) potassium glyphosate, and the listed surfactant (Surf.) and stabilizer (Stab.) components.

| Run | A5T | B3O | C2X | D0H | E5B |
|---|---|---|---|---|---|
| Surf. 1 | C46 | C46 | C46 | C27 | C27 |
| wt % | 6.3 | 7.4 | 9.8 | 3.7 | 3.7 |
| Stab. 1 | C91 | C91 | C91 | C9 | C9 |
| wt % | 6.3 | 4.9 | 2.5 | 8.6 | 8.6 |
| Stab. 2 | — | — | — | — | C77 |
| wt % | — | — | — | — | 1 |
| 60° C. | Fail | Fail | Fail | Fail | Fail |
| RT | No test | No test | No test | No test | No test |
| −10° C. | No test | No test | No test | No test | No test |

Example 142

Stabilizer compatibility evaluation of composition trial 097 comprising 38% a.e. glyphosate IPA, and the listed surfactant (Surf.) and stabilizer (Stab.) components.

"Stable" is defined as one phase.

| Run | A4R | B9K | C4F | D2Z |
|---|---|---|---|---|
| Surf. 1 | C11 | C11 | C132 | C132 |
| wt % | 4 | 4 | 2 | 2 |
| Surf. 2 | C43 | C43 | C133 | C133 |
| wt % | 6 | 7 | 2 | 2 |
| Surf. 3 | — | — | C43 | C43 |
| wt % | — | — | 6 | 7 |
| Stab. 1 | C125 | C125 | C125 | C125 |
| wt % | 1 | 1 | 1 | 1 |
| 50° C. | Stable | Stable | Fail | Fail |
| RT | Stable | Stable | Fail | Fail |

Example 143

Stabilizer compatibility evaluation of composition trial 099 comprising 36.5% a.e. potassium glyphosate, and the listed surfactant (Surf.) and stabilizer (Stab.) components.

"Stable" is defined as one phase.

| Run | A3X | B4F | C7G | D9S | E7L | F0P | G6B | H8M |
|---|---|---|---|---|---|---|---|---|
| Surf. 1 | C11 | C11 | C133 | C133 | C134 | C134 | C135 | C135 |
| wt % | 4 | 4 | 4 | 4 | 4 | 4 | 4 | 4 |
| Surf. 2 | C47 | C47 | C47 | C47 | C47 | C47 | C47 | C47 |
| wt % | 7 | 9 | 7 | 9 | 7 | 9 | 7 | 9 |
| Stab. 1 | C14 | C14 | C14 | C14 | C14 | C14 | C14 | C14 |
| wt % | 1 | 1 | 1 | 1 | 1 | 1 | 1 | 1 |
| 50° C. | Stable | Stable | Fail | Fail | Fail | Fail | Fail | Fail |
| RT | Stable | Stable | Fail | Fail | Fail | Fail | Fail | Fail |

Example 144

Stabilizer compatibility evaluation of composition trial 100 comprising 38% a.e. glyphosate IPA, and the listed surfactant (Surf.) and stabilizer (Stab.) components.

"Stable" is defined as one phase.

| Run | A0L | B6V | C8N | D4X | E3S | F2H |
|---|---|---|---|---|---|---|
| Surf. 1 | C11 | C11 | C11 | C133 | C133 | C133 |
| wt % | 4 | 4 | 4 | 4 | 4 | 4 |
| Surf. 2 | C43 | C43 | C43 | C43 | C43 | C43 |
| wt % | 6 | 6 | 7 | 6 | 6 | 7 |
| Stab. 1 | C125 | — | C125 | C125 | — | C125 |
| wt % | 1 | — | 1 | 1 | — | 1 |
| 50° C. | Stable | Fail | Stable | Fail | Fail | Fail |
| RT* | Stable | Fail | Stable | Fail | Fail | Fail |
| 0° C.* | Stable | Fail | Stable | Fail | Fail | Fail |

*@ 1 week

Example 145

Stabilizer compatibility evaluation of composition trial 706 comprising 36.5% a.e. potassium glyphosate, and the listed surfactant (Surf.) and stabilizer (Stab.) components.

"Stable" is defined as one phase.

| Run | A0L | B6V | C8N | D4X | E3S | F2H |
|---|---|---|---|---|---|---|
| Surf. 1 | C11 | C11 | C11 | C132 | C132 | C132 |
| wt % | 4 | 4 | 4 | 4 | 4 | 4 |
| Surf. 2 | C43 | C43 | C43 | C43 | C43 | C43 |
| wt % | 7 | 7 | 9 | 7 | 7 | 9 |
| Stab. 1 | C125 | — | C125 | C125 | — | C125 |
| wt % | 1 | — | 1 | 1 | — | 1 |
| 50° C. | Stable | Fail | Stable | Fail | Fail | Fail |
| RT* | Stable | Fail | Stable | Fail | Fail | Fail |
| 0° C.* | Stable | Fail | Stable | Fail | Fail | Fail |

*@ 1 week

Example 146

The efficacy effect of stabilizers on glyphosate IPA salts with cationic and nonioic surfactants was evaluated. Aqueous compositions were prepared with as indicated in Example 146 Table a. The glyphosate concentrations for each composition was about 448 g a.e./liter. All components were added and then shaken to a uniform formulation. Each formulation was a stable, clear and dark yellow solution.

EXAMPLE 146 TABLE a

| Comp. | Comp. 1 | % w/v | Comp. 2 | % w/v | Comp. 3 | % w/v | Comp. 4 | % w/v |
|---|---|---|---|---|---|---|---|---|
| 706A3M | C11 | 4 | C43 | 7 | C125 | 1 | — | — |
| 706B8U | C11 | 4 | C136 | 7 | C125 | 1 | — | — |
| 706C9K | C11 | 4 | C137 | 7 | C125 | 1 | — | — |
| 706D1S | C11 | 4 | C43 | 7 | C125 | 1 | C138 | 0.5 |

EXAMPLE 146 TABLE a-continued

| Comp. | Comp. 1 | % w/v | Comp. 2 | % w/v | Comp. 3 | % w/v | Comp. 4 | % w/v |
|---|---|---|---|---|---|---|---|---|
| 706E8J | C11 | 4 | C43 | 7 | C125 | 1 | C139 | 1 |
| 706F9V | C11 | 4 | C43 | 7 | C125 | 1 | C140 | 1 |

The compositions of Example 146 Table a and comparative compositions of glyphosate IPA were applied to Velvetleaf (*Abutilon theophrasti*, ABUTH) plants. Results, averaged for all replicates of each treatment, are shown in Example 146 Table a.

EXAMPLE 146 TABLE a

ABUTH % inhibition

| Composition | 75 g a.e./ha | 150 g a.e./ha | 225 g a.e./ha | 300 g a.e./ha |
|---|---|---|---|---|
| 706A3M | 55.8 | 80.2 | 91.8 | 96.2 |
| 706B8U | 60 | 78.2 | 93.7 | 96.5 |
| 706C9K | 57.5 | 81.3 | 93.2 | 95.8 |
| 706D1S | 52.5 | 85.2 | 95.3 | 98.7 |
| 706E8J | 65.8 | 80.5 | 94.3 | 98.5 |
| 706F9V | 60 | 82.2 | 94.2 | 97 |
| Composition 570I | 20 | 58.3 | 72.2 | 79.3 |
| Roundup Ultra | 57.5 | 76.3 | 92 | 95.5 |
| Composition IPA | 63.3 | 81.3 | 95.5 | 97.7 |

The efficacy of formulations 706D1S, 706E8J and 706F9V was similar to the efficacy of the glyphosate standards.

Example 147

The efficacy effect of stabilizers on potassium glyphosate salts with cationic and nonioic surfactants was evaluated. Aqueous compositions were prepared with as indicated in Example 147 Table a. The glyphosate concentrations for each composition is indicated in g a.e./liter. All components were added and then shaken to a uniform formulation. Each formulation was a stable, clear and dark yellow solution.

EXAMPLE 147 TABLE a

| Comp. | [Gly] | Comp. 1 | % w/v | Comp. 2 | % w/v | Comp. 3 | % w/v |
|---|---|---|---|---|---|---|---|
| 750A3C | 475 | C11 | 4 | C47 | 9 | C14 | 1 |
| 750B8W | 475 | C11 | 5 | C47 | 9 | C14 | 1 |
| 750C3D | 465 | C11 | 6 | C47 | 11 | C14 | 2.5 |

The compositions of Example 147 Table a and comparative compositions of glyphosate IPA were applied to Velvetleaf (*Abutilon theophrasti*, ABUTH) plants. Results, averaged for all replicates of each treatment, are shown in Example 147 Table b.

EXAMPLE 147 TABLE b

ABUTH % inhibition

| Composition | 100 g a.e./ha | 200 g a.e./ha | 300 g a.e./ha | 400 g a.e./ha |
|---|---|---|---|---|
| 750A2X | 38.2 | 69.2 | 79.4 | 92.4 |
| 750B9O | 38.7 | 66.4 | 80.5 | 88.1 |
| 750C0W | 57.3 | 75.1 | 85.8 | 91.3 |
| Composition IPA | 53 | 83.7 | 92.4 | 90.2 |
| Roundup Ultra | 49.3 | 72.7 | 89.1 | 90.8 |
| Roundup UltraMax | 60.3 | 78.8 | 87.9 | 90.8 |

The efficacy of formulation 750C0W was similar to the efficacy of the glyphosate standards.

Example 148

The efficacy effect of stabilizers on potassium glyphosate salts with cationic and nonioic surfactants was evaluated. Aqueous compositions were prepared with as indicated in Example 148 Table a. The glyphosate concentrations for each composition is indicated in g a.e./liter. All components were added and then shaken to a uniform formulation. Each formulation was a stable, clear and yellow solution.

EXAMPLE 148 TABLE a

| Comp. | [Gly] | Comp. 1 | % w/v | Comp. 2 | % w/v | Comp. 3 | % w/v |
|---|---|---|---|---|---|---|---|
| 774A3X | 478 | C11 | 4 | C47 | 9 | C14 | 1 |
| 774B7J | 478 | C11 | 4 | C47 | 9 | C14 | 1.3 |
| 774C0P | 475 | C11 | 4 | C47 | 9 | C14 | 1.5 |
| 774D3Q | 478 | C11 | 4 | C47 | 9 | C14/C138 | 1/2 |
| 774E9K | 481 | C11 | 4 | C141 | 9 | C125 | 2.5 |
| 774F7N | 481 | C11 | 4 | C141 | 9 | C14 | 2.5 |

The compositions of Example 148 Table a and comparative compositions of glyphosate IPA were applied to Velvetleaf (*Abutilon theophrasti*, ABUTH) plants. Results, averaged for all replicates of each treatment, are shown in Example 148 Table b. Application rates are given in g a.e./ha.

EXAMPLE 148 TABLE b

| Composition | ABUTH % inhibition | | | | |
|---|---|---|---|---|---|
| | 75 g/ha | 150 g/ha | 225 g/ha | 300 g/ha | 375 g/ha |
| 774A3X | 24.2 | 61.7 | 78.3 | 85.8 | 95 |
| 69774B7J | 22.5 | 70.8 | 84.2 | 90.8 | 96.3 |
| 774C0P | 55.5 | 69.7 | 80 | 90.2 | 95.2 |
| 774D3Q | 40 | 70 | 84.2 | 92.2 | 93.3 |
| 774E9K | 29.2 | 70.8 | 88 | 93.3 | 95.3 |
| 774F7N | 25.8 | 70 | 84.2 | 88.2 | 95.8 |
| Composition 570I | 1.7 | 25 | 54.2 | 66.7 | 78.8 |
| Roundup Ultra | 30.8 | 76 | 87 | 96.8 | 97 |

The efficacy of formulation 774C0P, 774D3Q and 774E9K was similar to the efficacy of the Roundup Ultra standard.

Example 149

The efficacy effect of stabilizers on glyphosate IPA salts with cationic and nonioic surfactants was evaluated. The glyphosate salt and concentration in g a.e./liter for each composition, and the remaining components are as indicated in Example 149 Table a.

EXAMPLE 149 TABLE a

| Comp. | Salt | [Gly] | Comp. 1 | % w/v | Comp. 2 | % w/v | Comp. 3 | % w/v |
|---|---|---|---|---|---|---|---|---|
| 033A7Y | IPA | 360 | C27 | 6.4 | C43 | 9.6 | C10* | 1 |
| 033B3S | K | 480 | C46 | 4.9 | C110 | 7.4 | C72 | 6.5 |
| 033C9P | IPA | 360 | C142 | 2.2 | C110 | 5.9 | — | — |
| 033D5V | K | 473 | C11 | 4 | C121 | 9 | C14 | 1 |
| 033E5G | IPA | 360 | C46 | 4.9 | C110 | 7.4 | C72 | 6.5 |
| 033F8L | K | 480 | C21 | 4.9 | C109 | 7.4 | C74 | 6.5 |
| 033G7N | K | 480 | C27 | 3.7 | C3 | 8.3 | C72 | 6.5 |

*033A7Y additionally contains 1.5% THF-OH (C114) and 1% Isopar L (C77)

The compositions of Example 149 Table a and comparative compositions of glyphosate IPA were applied to morningglory (IPOSS) plants. Results, averaged for all replicates of each treatment, are shown in Example 149 Table b.

EXAMPLE 149 TABLE b

| Composition | IPOSS % inhibition 14 days after treatment | | | |
|---|---|---|---|---|
| | 200 g a.e./ha | 400 g a.e./ha | 600 g a.e./ha | 800 g a.e./ha |
| 033A7Y | 54.2 | 80.8 | 84.2 | 84.2 |
| 033B3S | 35 | 65 | 75 | 80 |
| 033C9P | 43.3 | 63.3 | 77.5 | 79.2 |
| 033D5V | 35 | 71.7 | 77.5 | 79.2 |
| 033E5G | 59.2 | 80 | 81.7 | 81.7 |
| 033F8L | 2.5 | 71.7 | 72.5 | 80 |
| 033G7N | 10 | 58.3 | 70 | 78.3 |
| Roundup UltraMax | 41.7 | 70.8 | 76.7 | 80 |

The efficacy of formulations 033A7Y, 033C9P, 033D5V and 033E5G, containing short chain amine stabilizers, was similar to or exceeded the efficacy of the Roundup UltraMax standard.

Example 150

The efficacy effect of stabilizers on glyphosate IPA salts with cationic and nonioic surfactants was evaluated. The glyphosate salt and concentration in g a.e./liter for each composition, and the remaining components are as indicated in Example 150 Table a.

EXAMPLE 150 TABLE a

| Comp. | Salt | [Gly] | Comp. 1 | % w/v | Comp. 2 | % w/v | Comp. 3 | % w/v |
|---|---|---|---|---|---|---|---|---|
| 043A3C | IPA | 360 | C27 | 6.4 | C43 | 9.6 | C10* | 1 |
| 043B9M | K | 480 | C5 | 4.9 | C110 | 7.4 | C91 | 6.5 |
| 043C3D | K | 480 | C5 | 4.9 | C109 | 7.4 | C91 | 6.5 |
| 043D1L | K | 480 | C46 | 3.7 | C107 | 5.6 | C15** | 2 |
| 043E5G | K | 480 | C46 | 3.7 | C108 | 5.6 | C15** | 2 |
| 043F8K | K | 480 | C46 | 3.7 | C109 | 5.6 | C15** | 2 |
| 043G1Q | K | 480 | C46 | 3.7 | C110 | 5.6 | C15** | 2 |

*043A3C additionally contains 1.5% THF-OH(C114)
**043D1L, 043E5G, 043F8K and 043G1Q eachadditionally contain 1.5% Octylamine (C91)

The compositions of Example 150 Table a and comparative compositions of glyphosate IPA were applied to Velvetleaf (ABUTH) and Japanese millet (ECHCF) plants. Results, averaged for all replicates of each treatment, are shown in Example 150 Tables b and c.

EXAMPLE 150 TABLE b

ABUTH % inhibition 17 days after treatment

| Composition | 100 g a.e./ha | 200 g a.e./ha | 300 g a.e./ha | 400 g a.e./ha |
|---|---|---|---|---|
| 043A3C | 75 | 89.2 | 95.5 | 98.5 |
| 043B9M | 49.2 | 81.7 | 90 | 95.8 |
| 043C3D | 59.2 | 80.8 | 89.2 | 94 |
| 043D1L | 27.5 | 76.7 | 80 | 88.3 |
| 043E5G | 66.7 | 76.7 | 88.3 | 93.3 |
| 043F8K | 68.3 | 81.7 | 87.5 | 90.8 |
| 043G1Q | 76.7 | 78.3 | 88.3 | 93 |
| Roundup UltraMax | 26.7 | 81.7 | 87.5 | 92.5 |
| Comp. 725 K | 14.2 | 41.7 | 65 | 79.2 |

EXAMPLE 150 TABLE c

ECHCF % inhibition 17 days after treatment

| Composition | 100 g a.e./ha | 200 g a.e./ha | 300 g a.e./ha | 400 g a.e./ha |
|---|---|---|---|---|
| 043A3C | 65 | 78.3 | 80 | 85 |
| 043B9M | 57.5 | 73.3 | 80.8 | 86.7 |
| 043C3D | 57.5 | 72.5 | 80 | 88.5 |
| 043D1L | 55.8 | 70.8 | 75.8 | 77.5 |
| 043E5G | 52.5 | 69.2 | 75.8 | 85 |
| 043F8K | 53.3 | 70.8 | 72.5 | 80 |
| 043G1Q | 59.2 | 72.5 | 73.3 | 87.3 |
| Roundup UltraMax | 55 | 70.8 | 79.2 | 88.8 |
| Comp. 725 K | 33.3 | 48.3 | 56.7 | 60 |

The efficacy of formulations 043E5G, 043F8K and 043G1Q containing short chain amine stabilizers, exceeded the efficacy of the Roundup UltraMax standard on velvetleaf.

Example 151

The efficacy effect of stabilizers on glyphosate IPA salts with cationic and nonioic surfactants was evaluated. The glyphosate salt and concentration in g a.e./liter for each composition, and the remaining components are as indicated in Example 151 Table a.

The compositions of Example 151 Table a and comparative compositions of glyphosate IPA were applied to Velvetleaf (ABUTH) and Japanese millet (ECHCF) plants. Results, averaged for all replicates of each treatment, are shown in Example 151 Tables b and c.

EXAMPLE 151 TABLE b

ABUTH % inhibition 17 days after treatment

| Composition | 100 g a.e./ha | 200 g a.e./ha | 300 g a.e./ha | 400 g a.e./ha |
|---|---|---|---|---|
| 044A3X | 71.7 | 85.8 | 90.8 | 95.5 |
| 044B8J | 61.7 | 84.2 | 92.5 | 93.3 |
| 044C5G | 65 | 82.5 | 89.2 | 91.7 |
| 044D7U | 35 | 74.2 | 86.7 | 90 |
| 044E2K | 46.7 | 78.3 | 86.7 | 90 |
| 044F1Z | 60 | 75.8 | 87.5 | 90 |
| 044G0P | 45.8 | 77.5 | 85.8 | 90 |
| Roundup UltraMax | 3.3 | 79.2 | 88.3 | 90 |
| Comp. 725 K | 0 | 40 | 77.5 | 79.2 |

EXAMPLE 151 TABLE c

ECHCF % inhibition 17 days after treatment

| Composition | 100 g a.e./ha | 200 g a.e./ha | 300 g a.e./ha | 400 g a.e./ha |
|---|---|---|---|---|
| 044A3X | 60 | 72 | 83 | 91 |
| 044B8J | 53 | 63 | 71 | 76 |
| 044C5G | 54 | 73 | 77 | 86 |
| 044D7U | 48 | 65 | 71 | 78 |
| 044E2K | 44 | 65 | 68 | 84 |
| 044F1Z | 48 | 66 | 68 | 74 |
| 044G0P | 42 | 63 | 78 | 81 |
| Roundup UltraMax | 33 | 67 | 75 | 83 |
| Comp. 725 K | 3 | 38 | 56 | 58 |

The efficacy of all formulations equaled or exceeded the standards for velvetleaf. 044A3X, 044C5G and 043G0P containing short chain amine stabilizers, exceeded the efficacy of the Roundup UltraMax standard on barnyard grass.

Example 152

Stabilizer compatibility evaluation of a mixed active composition comprising about 35.7 wt % a.e. of the potas EXAMPLE 151 TABLE a

| Comp. | Salt | [Gly] | Comp. 1 | % w/v | Comp. 2 | % w/v | Comp. 3 | % w/v |
|---|---|---|---|---|---|---|---|---|
| 044A3X | IPA | 360 | C27 | 6.4 | C43 | 9.6 | C10* | 1 |
| 044B8J | K | 480 | C5 | 4.9 | C110 | 7.4 | C91 | 6.5 |
| 044C5G | K | 480 | C5 | 4.9 | C109 | 7.4 | C91 | 6.5 |
| 044D7U | K | 480 | C86 | 3.7 | C107 | 5.6 | C15** | 2 |
| 044E2K | K | 480 | C86 | 3.7 | C108 | 5.6 | C15** | 2 |
| 044F1Z | K | 480 | C86 | 3.7 | C109 | 5.6 | C15** | 2 |
| 044G0P | K | 480 | C86 | 3.7 | C110 | 5.6 | C15** | 2 |

*043A3X additionally contains 1.5% THF-OH (C114)

**043D7U, 043E2K, 043F1Z and 043G0P each additionally contain 1.5% Octylamine (C91)

sium salt of glyphosate and about 3.1 wt % a.i. of 2,4-D (Run 018A3D contained about 41.9 wt % a.e. glyphosate IPA and about 3.3% a.i. 2,4-D), and the listed surfactant (Surf.) and stabilizer (Stab.) components.

| Run | Surf. | wt % | Stab. | wt % | Cloudpoint ° C. |
|---|---|---|---|---|---|
| 014A4T | C124 | 9.2 | C91 | 2.8 | 84 |
| 014B8J | C129 | 9.2 | C91 | 2.8 | 85 |
| 014C5V | C108 | 9.2 | C91 | 2.8 | >90 |
| 014D0K | C123 | 9.2 | C91 | 2.8 | 79 |
| 015E3C | C109 | 9.2 | C91 | 2.8 | 60 |
| 015F7H | C130 | 9.2 | C91 | 2.8 | 76 |
| 024G7L | C131 | 9.2 | C91 | 2.8 | 62 |
| 024H3E | C124 | 9.2 | C125 | 4.0 | 69 |
| 024I2X | C129 | 9.2 | C125 | 4.3 | 71 |
| 018A3D | C131 | 9.8 | — | — | 83 |

Example 152: Pitted morningglory (IPOLA) % Control 5 Days after Treatment for potassium glyphosate+2,4-D formulations, and standard Composition 304I

| Run | 50 g a.e./ha | 100 g a.e./ha | 200 g a.e./ha | 300 g a.e./ha |
|---|---|---|---|---|
| 014A4T | 61 | 70 | 88 | 90 |
| 014B8J | 64 | 75 | 83 | 86 |
| 014C5V | 63 | 77 | 81 | 86 |
| 014D0K | 60 | 84 | 87 | 86 |
| 015E3C | 68 | 72 | 82 | 84 |
| 015F7H | 63 | 73 | 85 | 85 |
| 024G7L | 61 | 75 | 82 | 86 |
| 024H3E | 64 | 68 | 77 | 83 |
| 024I2X | 54 | 74 | 83 | 83 |
| 018A3D | 63 | 75 | 87 | 83 |
| 78510 | 61 | 75 | 86 | 88 |

All formulations tested gave results that were statistically the same.

Example 152: Cockleburr (XANST) % Control 7 Days after Treatment for potassium glyphosate+2,4-D formulations, and standard Composition 304I

| Run | 50 g a.e./ha | 100 g a.e./ha | 200 g a.e./ha | 300 g a.e./ha |
|---|---|---|---|---|
| 014A4T | 21 | 37 | 65 | 78 |
| 014B8J | 20 | 43 | 66 | 70 |
| 014C5V | 21 | 41 | 60 | 78 |
| 014D0K | 20 | 40 | 61 | 68 |
| 015E3C | 21 | 48 | 62 | 69 |
| 015F7H | 18 | 34 | 55 | 74 |
| 024G7L | 18 | 38 | 63 | 64 |
| 024H3E | 15 | 46 | 55 | 62 |
| 024I2X | 15 | 38 | 66 | 90 |

-continued

| Run | 50 g a.e./ha | 100 g a.e./ha | 200 g a.e./ha | 300 g a.e./ha |
|---|---|---|---|---|
| 018A3D | 20 | 34 | 61 | 77 |
| 78510 | 21 | 40 | 50 | 68 |

Performance varied with application rate. At 100 g/ha formulations 015E3C and 024H3E were surperior; at 200 g/ha formulations 014A4T and 014B8J gave the highest efficacy; and at 300 g/ha formulation 024I2X gave the highest performance.

Example 153

Stabilizer compatibility evaluation of a mixed active composition comprising about the potassium salt of glyphosate (reported in wt % a.e.) and 2,4-D (reported in wt % a.i.), and the listed surfactant (Surf.) and stabilizer (Stab.) components.

| Run | wt % gly | wt % 2,4-D | Surf. | wt % | Stab. | wt % | Cloudpoint ° C. |
|---|---|---|---|---|---|---|---|
| 034A3C | 35.7 | 2.9 | 0124 | 9.3 | C128 | 2.7 | 58 |
| 034B5F | 34.9 | 2.9 | 0129 | 9.2 | C128 | 2.7 | 60 |
| 034C7U | 32.0 | 2.8 | 0130 | 9.7 | C128 | 2.6 | 59 |
| 028A5V | 34.5 | 3.0 | 0123 | 8.7 | C47 | 5.8 | 61 |
| 028B7J | 34.7 | 3.3 | 0129 | 10.1 | C47 | 6.1 | 58 |

Example 153: XANST % Control 7 Days after Treatment for potassium glyphosate+2,4-D formulations, and standard Composition 304I.

| Run | 50 g a.e./ha | 100 g a.e./ha | 200 g a.e./ha | 300 g a.e./ha |
|---|---|---|---|---|
| 034A3C | 24 | 34 | 50 | 50 |
| 034B5F | 29 | 34 | 49 | 45 |
| 034C7U | 27 | 40 | 47 | 55 |
| 028A5V | 30 | 35 | 45 | 45 |
| 028B7J | 30 | 35 | 50 | 52 |
| 78510 | 32 | 39 | 41 | 45 |

All formulations gave statistically equal efficacy at all application rates.

Example 154

Stabilizer compatibility evaluation of composition trials 762 and 542 comprising 30.5% a.e. glyphosate IPA and the listed components. Stability was evaluated after 3 days at 50° C. and at RT. Table 154a give the formulation and Table 154b give the stability results.

TABLE 154a

| Run | Comp 1 | wt % | Comp 2 | wt % | Comp 3 | wt % | Comp 4 | wt % |
|---|---|---|---|---|---|---|---|---|
| 762A3S | C143 | 5 | C43 | 4 | C146 | 4 | C147 | 2 |
| 762B9I | C144 | 5 | C145 | 5 | C146 | 4 | C147 | 2 |
| 542A7B | C28 | 54 | C43 | 4.6 | C146 | 2 | C147 | 3 |

TABLE 154b

| Run | 50° C. | RT |
|---|---|---|
| 762A3S | Stable | Stable |
| 762B9I | Stable | Stable |
| 542A7B | Stable | Stable |

The present invention is not limited to the above embodiments and can be variously modified. The above description of the preferred embodiment is intended only to acquaint others skilled in the art with the invention, its principles, and its practical application so that others skilled in the art may adapt and apply the invention in its numerous forms, as may be best suited to the requirements of a particular use.

With reference to the use of the word(s) "comprise" or "comprises" or "comprising" in this entire specification (including the claims below), Applicants note that unless the context requires otherwise, those words are used on the basis and clear understanding that they are to be interpreted inclusively, rather than exclusively, and that Applicants intend each of those words to be so interpreted in construing this entire specification.

What is claimed is:

1. An aqueous pesticidal concentrate microemulsion composition comprising:
   a pesticidal component consisting of a water-soluble pesticide component comprising glyphosate or a salt or ester thereof dissolved in an aqueous medium, the water-soluble pesticide being present in a concentration that is biologically effective when the composition is diluted in a suitable volume of water and applied to the foliage of a susceptible plant;
   a substantially water-immiscible organic solvent; and
   a surfactant system comprising a surfactant component and a stabilizer, said surfactant component comprising one or more alkoxylated amine cationic surfactants present in a concentration sufficient to provide acceptable temperature stability of the microemulsion such that the microemulsion has a cloud point of at least about 50° C. and a crystallization point not greater than about −10° C., said stabilizer comprising one or more compounds selected from the group consisting of dimethylcocoamine, hexylamine, dimethylhexylamine, octylamine, decylamine, dimethyloctylamine, dodecyltrimethylamide, $C_{4-8}$ trialkylamines and quaternary ammonium salts thereof present in an amount sufficient to enhance the compatibility of said surfactant component with the pesticide.

2. The composition of claim 1 wherein the glyphosate is predominantly in the form of the potassium, monoammonium, diammonium, sodium, monoethanolamine, n-propylamine, ethylamine, ethylenediamine, hexamethylenediamine or trimethylsulfonium salt thereof.

3. The composition of claim 2 wherein the glyphosate is predominantly in the form of the potassium salt thereof.

4. The composition of claim 3 wherein said glyphosate, predominantly in the form of the potassium salt thereof is in solution in said aqueous phase in an amount of about 310 to about 600 grains of acid equivalent per liter of the composition.

5. The composition of claim 4 wherein said glyphosate, predominantly in the form of the potassium salt thereof, is in solution in said aqueous phase in an amount of about 360 to about 600 grams of acid equivalent per liter of the composition.

6. The composition of claim 5 wherein said glyphosate, predominantly in the form of the potassium salt thereof, is in solution in said aqueous phase in an amount of about 400 to about 600 grams of acid equivalent per liter of the composition.

7. The composition of claim 6 wherein said glyphosate, predominantly in the form of the potassium salt thereof, is in solution in said aqueous phase in an amount of about 450 to about 600 grams of acid equivalent per liter of the composition.

8. The composition of claim 7 wherein said glyphosate, predominantly in the form of the potassium salt thereof, is in solution in said aqueous phase in an amount of about 480 to about 600 grams of acid equivalent per liter of the composition.

9. The composition of claim 8 wherein said glyphosate, predominantly in the form of the potassium salt thereof, is in solution in said aqueous phase in an amount of about 500 to about 600 grams of acid equivalent per liter of the composition.

10. The composition of claim 8 wherein said glyphosate, predominantly in the form of the potassium salt thereof, is in solution in said aqueous phase in an amount of about 480 to about 580 grams of acid equivalent per liter of the composition.

11. The composition of claim 8 wherein said glyphosate, predominantly in the form of the potassium salt thereof, is in solution in said aqueous phase in an amount of about 540 to about 600 grams of acid equivalent per liter of the composition.

12. The composition of claim 1 wherein said stabilizer comprises octylamine.

13. A liquid herbicidal concentrate emulsion composition having a continuous aqueous phase and a discontinuous oil phase, the composition comprising:
   a pesticidal component consisting of glyphosate predominantly in the form of the potassium, monoammonium, diammonium, sodium, monoethanolamine, n-propylamine, ethylamine, ethylenediamine, hexamethylenediamine or trimethylsulfonium salt thereof, in solution in said aqueous phase in a concentration that is biologically effective when the composition is diluted in a suitable volume of water to form an enhanced application mixture and applied to foliage of a susceptible plant;
an oil phase comprising a substantially water-immiscible organic solvent; and
a surfactant system comprising a surfactant component and a stabilizer in solution or stable suspension, emulsion, or dispersion in said aqueous phase, said surfactant component comprising one or more alkoxylated amine cationic surfactants present in a concentration sufficient to provide acceptable temperature stability of the concentrate emulsion composition such that the concentrate emulsion composition has a cloud point of at least about 50° C. and a crystallization point not greater than about −10° C., said stabilizer comprising one or more compounds selected from the group consisting of dimethylcocoamine, hexylamine, dimethylhexylamine, octylamine, decylamine, dimethyloctylamine, dodecyltrimethylamide, $C_{4-8}$ trialkylamines and quaternary ammonium salts thereof present in an amount sufficient to enhance the compatibility of said surfactant component with the glyphosate.

14. The composition of claim 13 wherein said stabilizer is present in an amount which provides an optically transparent composition.

15. The composition of claim 13 wherein the crystallization point is not greater than about −20° C.

16. The composition of claim 13 wherein the cloud point is at least about 60° C.

17. The composition of claim 13 wherein the glyphosate is predominantly in the form of the potassium, monoammonium, diammonium, sodium, monoethanolamine, n-propylamine, ethylamine, ethylenediamine, or hexamethylenediamine salt thereof.

18. The composition of claim 13 wherein said glyphosate is in solution in said aqueous phase in an amount of about 400 to about 600 grams of acid equivalent per liter of the composition.

19. The composition of claim 13 wherein said surfactant component comprises at least one cationic surfactant.

20. The composition of claim 13 wherein said surfactant component comprises at least one nonionic surfactant.

21. The composition of claim 13 wherein said stabilizer comprises octylamine.

22. An aqueous pesticidal concentrate microemulsion composition comprising:
a pesticidal component consisting of a water-soluble pesticide component comprising glyphosate or a salt or ester thereof dissolved in an aqueous medium, the water-soluble pesticide being present in a concentration tat is biologically effective when the composition is diluted in a suitable volume of water and applied to the foliage of a susceptible plant;
a substantially water-immiscible organic solvent; and
a surfactant system comprising a surfactant component and a stabilizer, said surfactant component comprising at least one alkoxylated amine cationic surfactant and at least one nonionic surfactant, the surfactant component being present in a concentration sufficient to provide acceptable temperature stability of the microemulsion such that the microemulsion has a cloud point of at least about 50° C. and a crystallization point not greater than about −10° C., said stabilizer comprising and one or more amine compounds or quaternary ammonium salts thereof, each of which comprises an alkyl or aryl substituent having from about 4 to about 16 carbon atoms and not more than ten ethylene oxide linkages within the compound, wherein said stabilizer is present in an amount sufficient to enhance the compatibility of said surfactant component with the pesticide and the weight ratio of said at least one cationic surfactant to said stabilizer is between about 1.5:1 and about 6:1.

23. The composition of claim 22 wherein said stabilizer comprises one or more amine or quaternary ammonium salt compounds having the formula:

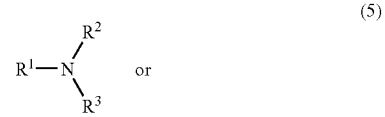

(5)

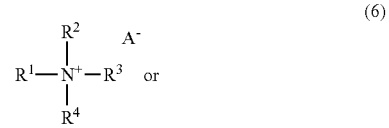

(6)

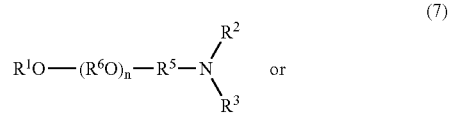

(7)

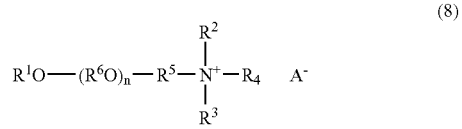

(8)

wherein $R^1$ is linear or branched alkyl or aryl having from about 4 to about 16 carbon atoms, $R^2$ is hydrogen, methyl, ethyl, or —$(CH_2CH_2O)_xH$, $R^3$ is hydrogen, methyl, ethyl, or —$(CH_2CH_2O)_yH$, the sum of x and y is not more than about 5, $R^4$ is hydrogen or methyl, $R^6$ in each of the n ($R^6O$) groups is independently $C_2$–$C_4$ alkylene, $R^5$ is hydrocarbylene or substituted hydrocarbylene having from 2 to about 6 carbon atoms, and A- is an agriculturally acceptable anion.

24. The composition of claim 23 wherein said stabilizer comprises octylamine.

25. The composition of claim 22 wherein the glyphosate is predominantly in the form of the potassium, monoammonium, diammonium, sodium, monoethanolamine, n-propylamine, ethylamine, ethylenediamine, hexamethylenediamine or trimethylsulfonium salt thereof.

26. The composition of claim 25 wherein the glyphosate is predominantly in the form of the potassium salt thereof.

27. The composition of claim 22 wherein said glyphosate is in solution in said aqueous phase in an amount of about 310 to about 600 grams of acid equivalent per liter of the composition.

28. The composition of claim 27 wherein said glyphosate is in solution in said aqueous phase in an amount of about 360 to about 600 grams of acid equivalent per liter of the composition.

29. The composition of claim 28 wherein said glyphosate is in solution in said aqueous phase in an amount of about 400 to about 600 grams of acid equivalent per liter of the composition.

30. The composition of claim 22 wherein said surfactant component further comprises at least one cationic surfactant comprising:

(a) an aminated alkoxylated alcohol having the formula:

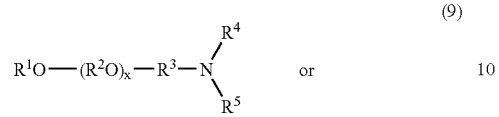

(9)

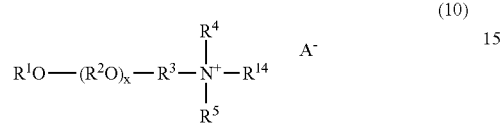

(10)

wherein $R^1$ is hydrogen or hydrocarbyl or substituted hydrocarbyl having from 1 to about 30 carbon atoms, $R^4$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-C(=S)NR^{12}R^{13}$ or together with $R^5$ and the nitrogen atom to which they are attached, form a cyclic or heterocyclic ring, $R^5$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-C(=S)NR^{12}R^{13}$ or together with $R^4$ and the nitrogen atom to which they are attached, form a cyclic or heterocyclic ring, $R^7$ is hydrogen or a liner or branched alkyl group having 1 to about 4 carbon atoms, $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, or $-C(=S)NR^{12}R^{13}$, $R^2$ in each of the x ($R^2O$) and y ($R^2O$) groups is independently $C_2$–$C_4$ alkylene, $R^3$ and $R^6$ are each independently hydrocarbylene or substituted hydrocarbylene having from 1 to about 6 carbon atoms, n is 0 or 1, x and y are independently an average number from 1 to about 60, and A- is an agriculturally acceptable anion; or (b) a hydroxylated amide having the formula:

(11)

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and is hydroxyalkyl, polyhydroxyalkyl, or poly(hydroxyalkyl)alkyl; or (c) a diamine having the formula:

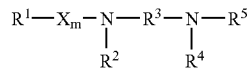

(13)

wherein $R^1$ $R^2$ and $R^5$ are independently hydrogen or hydrocarbyl or substituted hydrocarbyl having from 1 to about 30 carbon atoms or $-R^8(OR^9)_nOR^{10}$, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, and X is $-C(O)-$ or $-SO_2-$; or (d) a mono- or di-ammonium salt having the formula:

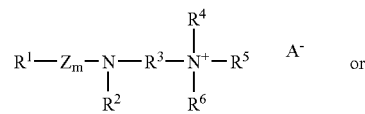

(14)

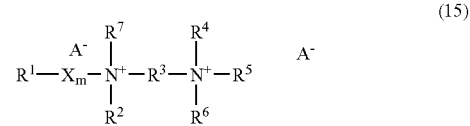

(15)

wherein $R^1$, $R^2$, $R^4$, $R^5$ and $R^7$ are independently hydrogen or hydrocarbyl or substituted hydrocarbyl having from 1 to about 30 carbon atoms or $-R^8(OR^9)_nOR^{10}$, $R^6$ is hydrocarbyl or substituted hydrocarbyl having from 1 to about 30 carbon atoms, $R^3$ is hydrocarbylene or substituted hydrocarbylene having from 2 to about 30 carbon atoms, $R^8$ and $R^9$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is $-C(O)-$ or $-SO_2-$, Z is $-C(O)-$, and A- is an agriculturally acceptable anion; or (e) a poly(hydroxyalkyl)amine having the formula:

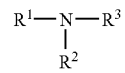

(16)

wherein $R^1$ is hydrocarbyl or substituted hydrocarbyl having from about 4 to about 30 carbon atoms or $-R^4OR^5$, $R^2$ is hydrogen or hydrocarbyl or substituted hydrocarbyl having from 1 to about 30 carbon atoms, $R^3$ is hydroxyalkyl, polyhydroxyalkyl, or poly(hydroxyalkyl)alkyl, $R^4$ is hydrocarbylene or substituted hydrocarbylene having from 2 to about 18 carbon atoms, and $R^5$ is hydrogen or hydrocarbyl or substituted hydrocarbyl having from 1 to about 30 carbon atoms; or (f) an alkoxylated poly(hydroxyalkyl)amine having the formula:

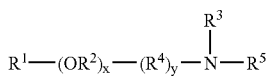
(19)

wherein $R^1$ and $R^3$ are independently hydrogen, hydrocarbyl or substituted hydrocarbyl having from 1 to about 30 carbon atoms, $R^2$ in each of the x $(R^2O)$ groups is independently $C_2$–$C_4$ alkylene, $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl, x is an average number from 0 to about 30, and y is 0 or 1; or (g) a di-poly(hydroxyalkyl)amine having the formula:

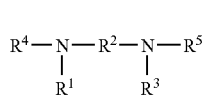
(22)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and $R^4$ and $R^5$ are independently hydroxyalkyl, polyhydroxyalkyl, or poly(hydroxyalkyl)alkyl; or (h) a quaternary poly(hydroxyalkyl)amine salts having the formula:

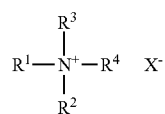
(24)

wherein $R^1$ is hydrocarbyl or substituted hydrocarbyl having from about 4 to about 30 carbon atoms or $-X_m-(R^6O)_yR^5$, $R^2$ and $R^3$ are independently hydrogen or hydrocarbyl or substituted hydrocarbyl having from 1 to about 30 carbon atoms, $R^4$ is hydroxyalkyl, polyhydroxyalkyl, or poly(hydroxyalkyl)alkyl, $X^-$ is an agriculturally acceptable anion, $R^6$ in each of the $y(R^6O)$ groups is independently $C_2$–$C_4$ alkylene, $R^5$ is hydrogen or a linear or branched alkyl group having 1 to about 4 carbon atoms, X is hydrocarbylene or substituted hydrocarbylene having from 2 to about 18 carbon atoms, m is 0 or 1, and y is an average number from 0 to about 30; or (i) a triamine having the formula:

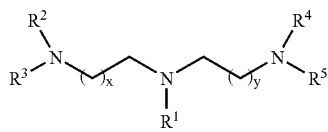
(27)

wherein $R^1$ is hydrocarbyl or substituted hydrocarbyl having from 1 to about 30 carbon atoms, $R^2$, $R^3$, $R^4$ and $R^5$ are independently hydrogen, hydrocarbyl or substituted hydrocarbyl having from 1 to about 30 carbon atoms, or $-(R^8)_s(R^7O)_nR^6$, $R^6$ is hydrogen or a linear or branched alkyl group having from 1 to about 4 carbon atoms, $R^7$ in each of the n $(R^7O)$ groups is independently $C_2$–$C_4$ alkylene, $R^8$ is hydrocarbylene or substituted hydrocarbylene having from 1 to about 6 carbon atoms, n is an average number from 1 to about 10, s is 0 or 1, and x and y are independently an integer from 1 to about 4; or (j) a diamine having the formula:

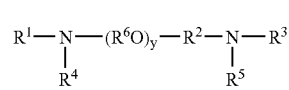
(28)

wherein $R^1$, $R^3$, $R^4$ and $R^5$ are independently hydrogen, hydrocarbyl or substituted hydrocarbyl having from 1 to about 30 carbon atoms, or $-(R^6O)_xR^7$, $R^2$ is hydrocarbylene or substituted hydrocarbylene having from 2 to about 30 carbon atoms, $-C(=NR^{11})NR^{12}R^{13}-$, $-C(=O)NR^{12}R^{13}-$, $-C(=S)NR^{12}R^{13}-$, $-C(=NR^{12})-$, $-C(S)-$, or $-C(O)-$, $R^6$ in each of the $x(R^6O)$ and $y(R^6O)$ groups is independently $C_2$–$C_4$ alkylene, $R^7$ is hydrogen, or a linear or branched alkyl group having from 1 to about 30 carbon atoms, $R^{11}$, $R^{12}$ and $R^{13}$ are hydrogen, hydrocarbyl or substituted hydrocarbyl having from 1 to about 30 carbon atoms, x is an average number from 1 to about 50, and y is an average number from 0 to about 60; or (k) a mono- or di-quaternary ammonium salt having the formula:

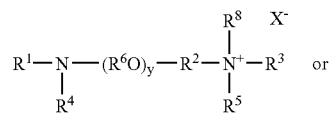
(30)

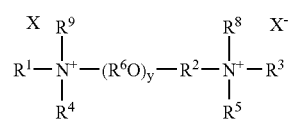
(29)

wherein $R^1$, $R^3$, $R^4$, $R^5$, $R^8$ and $R^9$ are independently hydrogen, polyhydroxyalkyl, hydrocarbyl or substituted hydrocarbyl having from 1 to about 30 carbon atoms, or $-(R^6O)_xR^7$, $R^2$ is hydrocarbylene or substituted hydrocarbylene having from 2 to about 30 carbon atoms, $R^6$ in each of the x $(R^6O)$ and y $(R^6O)$ groups is independently $C_2$–$C_4$ alkylene, $R^7$ is hydrogen, or a linear or branched alkyl group having from 1 to about 4 carbon atoms, x is an average number from 1 to about 30, y is an average number from about 3 to about 60, and $X^-$ is an agriculturally acceptable anion; or (l) a secondary or tertiary amine having the formula:

(31)

wherein $R^1$ and $R^2$ are hydrocarbyl having from 1 to about 30 carbon atoms, and $R^3$ is hydrogen or hydrocarbyl having from 1 to about 30 carbon atoms; or (m) a monoalkylated amine having the formula:

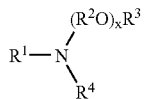

(32)

wherein $R^1$ and $R^4$ are independently hydrocarbyl or substituted hydrocarbyl groups having from 1 to about 30 carbon atoms or —$R^5SR^6$, $R^2$ in each of the x $(R^2O)$ groups is independently $C_2$–$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60; or (n) a dialkoxylated quaternary ammonium salt having the formula:

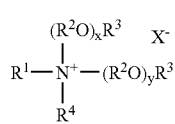

(33)

wherein $R^1$ is hydrocarbyl or substituted hydrocarbyl having from 1 to about 30 carbon atoms, $R^2$ in each of the x $(R^2O)$ and y $(R^2O)$ groups is independently $C_2$–$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X- is an agriculturally acceptable anion; or (o) a monoalkoxylated quaternary ammonium salt having the formula:

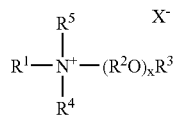

(34)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x $(R^2O)$ groups is independently $C_2$–$C_4$ alkylene, $R^3$ is hydrogen, or a linear or branched alkyl group having from 1 to about 30 carbon atoms, x is an average number from 1 to about 60, and X- is an agriculturally acceptable anion; or (p) a quaternary ammonium salt having the formula:

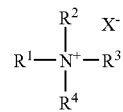

(35)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X- is an agriculturally acceptable anion; or (q) an etheramine having the formula:

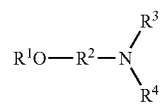

(36)

wherein $R^1$ is hydrocarbyl or substituted hydrocarbyl having from 1 to about 30 carbon atoms, $R^2$ is hydrocarbyl or substituted hydrocarbylene having from 2 to about 30 carbon atoms, $R^3$ and $R^4$ are independently hydrogen, hydrocarbyl or substituted hydrocarbyl having from 1 to about 30 carbon atoms, or —$(R^5O)_xR^6$, $R^5$ in each of the $x(R^5O)$ groups is independently $C_2$–$C_4$ alkylene, $R^6$ is hydrogen, or a linear or branched alkyl group having from 1 to about 4 carbon atoms, and x is an average number from 1 to about 50; or (r) a diamine having the formula:

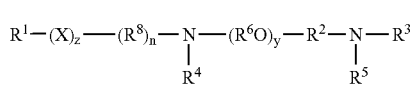

(37)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$, $R^2$ and $R^8$ are independently hydrocarbylene or substituted hydrocarbylene having from 2 to about 30 carbon atoms, $R^6$ in each of the x $(R^6O)$ and y $(R^6O)$ groups is independently $C_2$–$C_4$ alkylene, $R^7$ is hydrogen, or a linear or branched alkyl group having from 1 to about 30 carbon atoms, x is an average number from 1 to about 30, X is —O—, —N($R^6$)—, —C(O)—, —C(O)O—, —OC(O)—, —N($R^9$)C(O)—, —C(O)N($R^9$)—, —S—, —SO—, or —SO$_2$—, y is 0 or an average number from 1 to about 30, n and z are independently 0 or 1, and $R^9$ is hydrogen or hydrocarbyl or substituted hydrocarbyl; or (s) an amine oxide having the formula:

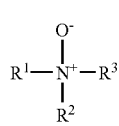
(38)

wherein $R^1$, $R^2$ and $R^3$ are independently hydrogen, hydrocarbyl or substituted hydrocarbyl having from 1 to about 30 carbon atoms, $-(R^4O)_xR^5$, or $-R^6(OR^4)_xOR^5$, $R^4$ in each of the x ($R^4O$) groups is independently $C_2$–$C_4$ alkylene, $R^5$ is hydrogen, or a hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8; or (t) an alkoxylated amine oxide having the formula:

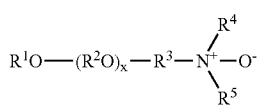
(39)

wherein $R^1$ is hydrogen or hydrocarbyl or substituted hydrocarbyl having from 1 to about 30 carbon atoms, $R^3$ is a hydrocarbylene or substituted hydrocarbylene having from 2 to about 6 carbon atoms, $R^4$ and $R^5$ are each independently hydrogen, hydrocarbyl or substituted hydrocarbyl having from 1 to about 30 carbon atoms, or $-(R^6)_n-(R^2O)_yR^7$, $R^2$ in each of the x ($R^2O$) and y ($R^2O$) groups is independently $C_2$–$C_4$ alkylene, $R^6$ is hydrocarbylene or substituted hydrocarbylene containing from 1 to about 6 carbon atoms, $R^7$ is hydrogen or a linear or branched alkyl group having 1 to about 4 carbon atoms, n is 0 or 1, and x and y are independently an average number from 1 to about 60; or (u) a dialkoxylated amine having the formula:

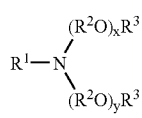
(40)

wherein $R^1$ is hydrogen or hydrocarbyl or substituted hydrocarbyl having from 1 to about 30 carbon atoms, $-R^4SR^5$, or $-(R^2O)_zR^3$, $R^2$ in each of the x ($R^2O$), y ($R^2O$) and z ($R^2O$) groups is independently $C_2$–$C_4$ alkylene, $R^3$ is hydrogen, or a linear or branched alkyl group having from 1 to about 22 carbon atoms, $R^4$ is a linear or branched alkyl group having from about 6 to about 30 carbon atoms, $R^5$ is a linear or branched alkyl group having from about 4 to about 15 carbon atoms, and x, y and z are independently an average number from 1 to about 40, provided, however, that when $R^1$ is alkyl, either the sum of x and y is greater than 20 or $R^3$ is other than hydrogen; or (v) an aminated alkoxylated alcohol having the formula:

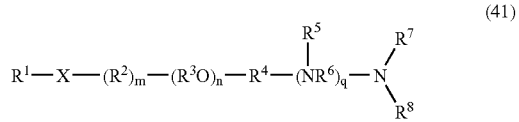
(41)

wherein $R^1$, $R^7$, $R^8$, and $R^9$ are each independently hydrogen, hydrocarbyl or substituted hydrocarbyl having from 1 to about 30 carbon atoms, or $-(R^{11})_s(R^3O)_vR^{10}$, X is $-O-$, $-OC(O)-$, $-C(O)O-$, $-N(R^{12})C(O)-$, $-C(O)N(R^{12})-$, $-S-$, $-SO-$, $-SO_2-$ or $-N(R^9)-$, $R^3$ in each of the n ($R^3O$) groups and the v ($R^3O$) groups is independently $C_2$–$C_4$ alkylene, $R^{10}$ is hydrogen, or a linear or branched alkyl group having from 1 to about 30 carbon atoms, n is an average number from 1 to about 60, v is an average number from 1 to about 50, $R^2$ and $R^{11}$ are each independently hydrocarbylene or substituted hydrocarbylene having from 1 to about 6 carbon atoms, $R^4$ is hydrocarbylene or substituted hydrocarbylene having from 2 to about 6 carbon atoms, $R^{12}$ is hydrogen or hydrocarbyl or substituted hydrocarbyl having from 1 to about 30 carbon atoms, m and s are each independently 0 or 1, $R^6$ is hydrocarbylene or substituted hydrocarbylene having from 2 to about 30 carbon atoms, $-C(=NR^{12})-$, $-C(S)-$, or $-C(O)-$, q is an integer from 0 to 5, and $R^5$ is hydrogen or hydrocarbyl or substituted hydrocarbyl having from 1 to about 30 carbon atoms; or (w) a quaternary ammonium, sulfonium or sulfoxonium salt having the formula:

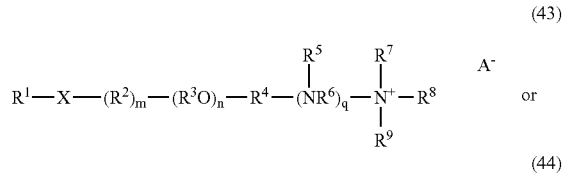
(43)

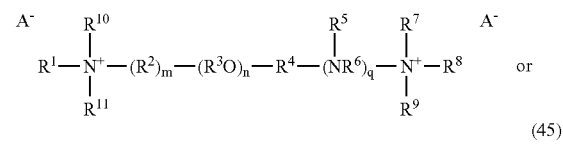
(44)

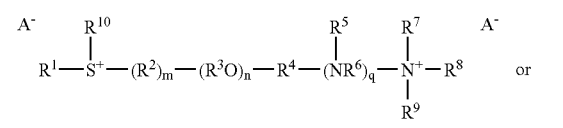
(45)

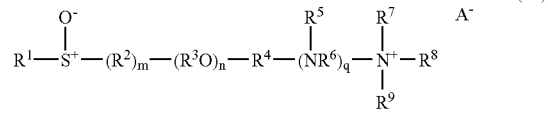
(46)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or $-(R^{13})_s(R^3O)_vR^{12}$, X is $-O-$, $-OC(O)-$, $-N(R^{14})C(O)-$, $-C(O)N(R^{14})-$, $-C(O)O-$, or $-S-$, $R^3$ in each of the n ($R^{13}O$) groups and v ($R^3O$) groups is independently $C_2$–$C_4$ alkylene, $R^{12}$ is hydrogen, or a linear or branched alkyl group having from 1 to about 30 carbon atoms, n is an average number from 1 to about 60, v is an average number from 1 to about 50, $R^2$ and $R^{13}$ are each independently hydrocarbylene or substituted hydrocarbylene having from 1 to about 6 carbon atoms, m and s are each independently 0 or 1, $R^4$ is hydrocarbylene or substituted hydrocarbylene having from 2 to about 6 carbon atoms, $R^6$ is hydrocarbylene or substituted hydrocarbylene having from 2 to about 30 carbon atoms, —C(=NR$^{12}$)—, —C(S)—, or —C(O)—, $R^{14}$ is hydrogen or hydrocarbyl or substituted hydrocarbyl having from 1 to about 30 carbon atoms, q is an integer from 0 to 5, $R^5$ is hydrogen or hydrocarbyl or substituted hydrocarbyl having from 1 to about 30 carbon atoms, and each A$^-$ is an agriculturally acceptable anion; or (x) a diamine or diammonium salt having the formula:

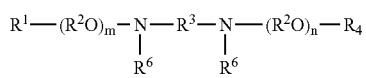
(47)

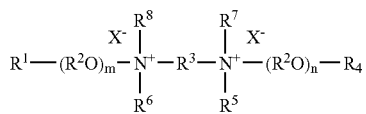
(48)

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m($R^2$O) and n($R^2$O) groups and $R^9$ are independently $C_2$–$C_4$ alkylene, $R^3$ is hydrocarbylene or substituted hydrocarbylene having from about 2 to about 6 carbon atoms or —(R$^2$O)$_p$R$_9$—, m and n are individually an average number from 0 to about 50, and p is an average number from 0 to about 60; or (y) a compound of the formula:

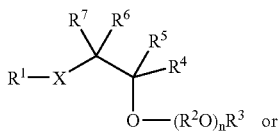
(52)

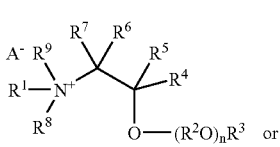
(53)

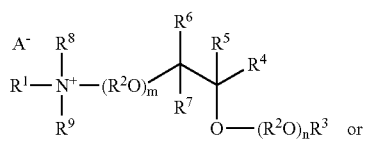
(54)

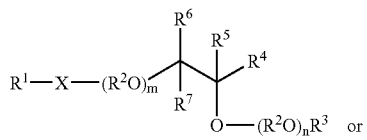
(56)

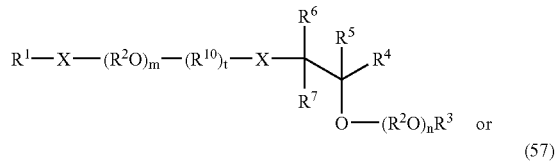
(55)

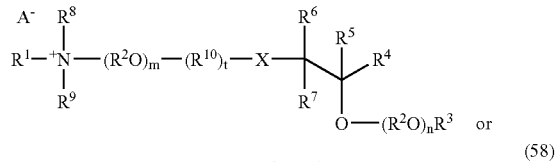
(57)

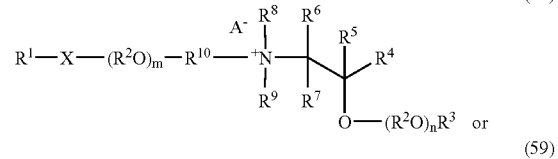
(58)

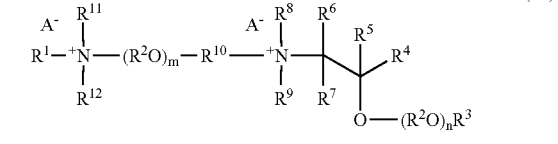
(59)

wherein $R^1$, $R^9$, and $R^{12}$ are independently hydrocarbyl or substituted hydrocarbyl having from 1 to about 30 carbon atoms, or —(R$^2$O)$_p$R$^{13}$, $R^2$ in each of the m (R$^2$O), n(R$^2$O), p (R$^2$O) and q (R$^2$O) groups is independently $C_2$–$C_4$ alkylene, $R^3$, $R^8$, $R^{11}$, $R^{13}$ and $R^{15}$ are independently hydrogen, or a hydrocarbyl or substituted hydrocarbyl having from 1 to about 30 carbon atoms, $R^4$ is —(CH$_2$)$_y$OR$^{13}$ or —(CH$_2$)$_y$O(R$^2$O)$_q$R$^3$, $R^5$, $R^6$ and $R^7$ are independently hydrogen, hydrocarbyl or substituted hydrocarbyl having from 1 to about 30 carbon atoms, or $R^4$, $R^{10}$ is hydrocarbylene or substituted hydrocarbylene having from 2 to about 30 carbon atoms, $R^{14}$ is hydrogen, hydrocarbyl or substituted hydrocarbyl having from 1 to about 30 carbon atoms, or —(CH$_2$)$_z$O(R$^2$O)$_p$R$^3$, m, n, p and q are independently an average number from 1 to about 50, X is independently —O—, —N(R$^{11}$)—, —C(O)—, —C(O)O—, —OC(O)—, —N(R$^{15}$)C(O)—, —C(O)N(R$^{15}$)—, —S—, —SO—, or —SO$_2$—, t is 0 or 1, A- is an agriculturally acceptable anion, and y and z are independently an integer from 0 to about 30.

31. The composition of claim 22 wherein said nonionic surfactant comprises:

(a) an alkoxylated alcohol having the formula:

(49)

wherein $R^1$ is hydrocarbyl or substituted hydrocarbyl having from 1 to about 30 carbon atoms, $R^2$ in each of the x (R$^2$O) groups is independently $C_2$–$C_4$ alkylene, $R^3$ is hydrogen, or a linear or branched alkyl group having from 1 to about 4 carbon atoms, and x is an average number from 1 to about 60; or (b) a dialkoxylated alcohol having the formula:

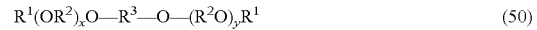
(50)

wherein $R^1$ is independently hydrogen, or a linear or branched alkyl group having from 1 to about 4 carbon atoms, $R^2$ in each of the x (R$^2$O) and the y (R$^2$O) groups is independently $C_2$–$C_4$ alkylene, $R^3$ is hydrocarbylene or substituted hydrocarbylene having from 2 to about 30 carbon atoms, and x and y are independently an average number from 1 to about 60; or (c) an alkoxylated dialkylphenol having the formula:

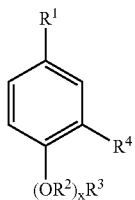

(51)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x $(R^2O)$ groups is independently $C_2$–$C_4$ alkylene, $R^3$ is hydrogen, or a linear or branched alkyl group having from 1 to about 4 carbon atoms, and x is an average number from 1 to about 60; or (d) a glycoside having the formula:

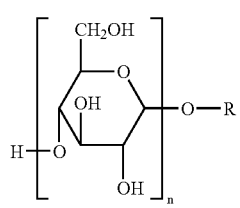

(61)

wherein n is the degree of polymerization, or number of glycose groups, and R is a branched or straight chain alkyl group preferably having from 4 to 18 carbon atoms, or a mixture of alkyl groups having an average value within the given range.

32. A liquid herbicidal concentrate emulsion composition having a continuous aqueous phase and a discontinuous oil phase, the composition comprising:

a pesticidal component consisting of a water-soluble pesticide component comprising glyphosate or a salt or ester thereof di ssolved in said aqueous phase, the water-soluble herbicide being present in a concentration that is biologically effective when the composition is diluted in a suitable volume of water and applied to the foliage of a susceptible plant;

an oil phase comprising a substantially water-immiscible organic solvent; and a surfactant system comprising a surfactant component and a stabilizer, said surfactant component comprising at least one alkoxylated amine cationic surfactant and present in a concentration sufficient to provide acceptable temperature stability of the emulsion such tat the emulsion has a cloud point of at least about 50° C. and a crystallization point not greater than about 0° C., said stabilizer comprising one or more amine compounds or quaternary ammonium salts thereof, each of which comprises an alkyl or aryl substituent having from about 4 to about 16 carbon atoms and not more than ten ethylene oxide linkages within the compound, wherein said stabilizer is present in an amount sufficient to enhance the compatibility of said surfactant component wit the herbicide and the weight ratio of said at least one cationic surfactant to said stabilizer is between about 1.5:1 and about 6:1.

33. The composition of claim 32 wherein the glyphosate is predominantly in the form of the potassium, monoammonium, diammonium, sodium, monoethanolamine, n-propylamine, ethylamine, ethylenediamine, hexamethylenediamine or trimethylsulfonium salt thereof.

34. The composition of claim 33 wherein the glyphosate is predominantly in the form of the potassium salt thereof.

35. The composition of claim 34 wherein said glyphosate, predominantly in the form of the potassium salt thereof, is in solution in said aqueous phase in an amount of about 400 to about 600 grams of acid equivalent per liter of the composition.

36. The composition of claim 32 wherein said glyphosate is in solution in said aqueous phase in an amount of about 310 to about 600 grams of acid equivalent per liter of the composition.

37. The composition of claim 36 wherein said glyphosate is in solution in said aqueous phase in an amount of about 360 to about 600 grams of acid equivalent per liter of the composition.

38. The composition of claim 32 wherein said surfactant component further comprises at least one cationic surfactant comprising:

(a) an aminated alkoxylated alcohol having the formula:

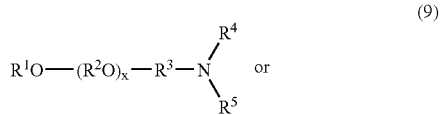

(9)

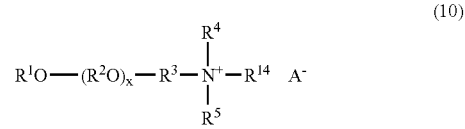

(10)

wherein $R^1$ is hydrogen or hydrocarbyl or substituted hydrocarbyl having from 1 to about 30 carbon atoms, $R^4$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-C(=S)NR^{12}R^{13}$ or together with $R^5$ and the nitrogen atom to which they are attached, form a cyclic or heterocyclic ring, $R^5$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, $-C(=S)NR^{12}R^{13}$ or together with $R^4$ and the nitrogen atom to which they are attached, form a cyclic or heterocyclic ring, $R^7$ is hydrogen or a linear or branched alkyl group having 1 to about 4 carbon atoms, $R^{11}$, $R^{12}$ and $R^{13}$ are hydrogen, hydrocarbyl or substituted hydrocarbyl, $R^{14}$ is hydrogen, hydrocarbyl or substituted hydrocarbyl having from 1 to about 30 carbon atoms, hydroxy substituted hydrocarbyl, $-(R^6)_n-(R^2O)_yR^7$, $-C(=NR^{11})NR^{12}R^{13}$, $-C(=O)NR^{12}R^{13}$, or $-C(=S)NR^{12}R^{13}$, $R^2$ in each of the x $(R^2O)$ and y $(R^2O)$ groups is independently $C_2$–$C_4$ alkylene, $R^3$ and $R^6$ are each independently hydrocarbylene or substituted hydrocarbylene having from 1 to about 6 carbon atoms, n is 0 or 1, x and y are independently an average number from 1 to about 60, and A- is an agriculturally acceptable anion; or (b) a hydroxylated amide having the formula:

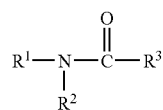
(11)

wherein $R^1$ is hydrocarbyl or substituted hydrocarbyl having from about 4 to about 30 carbon atoms, $R^2$ is hydrogen or hydrocarbyl or substituted hydrocarbyl having from 1 to about 30 carbon atoms, and $R^3$ is hydroxyalkyl, polyhydroxyalkyl, or poly(hydroxyalkyl)alkyl; or (c) a diamine having the formula:

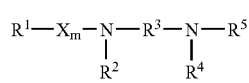
(13)

wherein $R^1$, $R^2$ and $R^5$ are independently hydrogen or hydrocarbyl or substituted hydrocarbyl having from 1 to about 30 carbon atoms or —$R^8(OR^9)_nOR^{10}$, $R^3$ is hydrocarbylene or substituted hydrocarbylene having from 2 to about 18 carbon atoms, $R^8$ and $R^9$ are individually hydrocarbylene or substituted hydrocarbylene having from 2 to about 4 carbon atoms, $R^4$ and $R^{10}$ are independently hydrogen or hydrocarbyl or substituted hydrocarbyl having from 1 to about 30 carbon atoms, m is 0 or 1, n is an average number from 0 to about 40, and X is —C(O)— or —SO$_2$—; or (d) a mono- or di-ammonium salt having the formula:

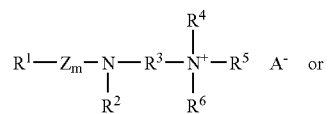
(14)

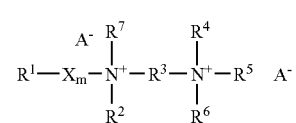
(15)

wherein $R^1$, $R^2$, $R^4$, $R^5$ and $R^7$ are independently hydrogen or hydrocarbyl or substituted hydrocarbyl having from 1 to about 30 carbon atoms or —$R^8(OR^9)_nOR^{10}$, $R^6$ is hydrocarbyl or substituted hydrocarbyl having from 1 to about 30 carbon atoms, $R^3$ is hydrocarbylene or substituted hydrocarbylene having from 2 to about 30 carbon atoms, $R^8$ and $R^9$ are individually hydrocarbylene or substituted hydrocarbylene having from 2 to about 4 carbon atoms, $R^{10}$ is hydrogen or hydrocarbyl or substituted hydrocarbyl having from 1 to about 30 carbon atoms, m is 0 or 1, n is an average number from 0 to about 40, X is —C(O)— or —SO$_2$—, Z is —C(O)—, and A$^-$ is an agriculturally acceptable anion; or (e) a poly(hydroxyalkyl)amine having the formula:

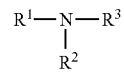
(16)

wherein $R^1$ is hydrocarbyl or substituted hydrocarbyl having from about 4 to about 30 carbon atoms or —$R^4OR^5$, $R^2$ is hydrogen or hydrocarbyl or substituted hydrocarbyl having from 1 to about 30 carbon atoms, $R^3$ is hydroxyalkyl, polyhydroxyalkyl, or poly(hydroxyalkyl)alkyl, $R^4$ is hydrocarbylene or substituted hydrocarbylene having from 2 to about 18 carbon atoms, and $R^5$ is hydrogen or hydrocarbyl or substituted hydrocarbyl having from 1 to about 30 carbon atoms; or (f) an alkoxylated poly(hydroxyalkyl)amine having the formula:

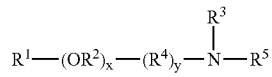
(19)

wherein $R^1$ and $R^3$ are independently hydrogen, hydrocarbyl or substituted hydrocarbyl having from 1 to about 30 carbon atoms, $R^2$ in each of the x (R$^2$O) groups is independently C$_2$–C$_4$ alkylene, $R^4$ is hydrocarbylene or substituted hydrocarbylene having from 1 to about 30 carbon atoms, $R^5$ is hydroxyalkyl, polyhydroxyalkyl, or poly(hydroxyalkyl)alkyl; x is an average number from 0 to about 30, and y is 0 or 1; or (g) a di-poly(hydroxyalkyl)amine having the formula:

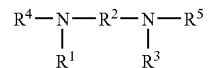
(22)

wherein $R^1$ and $R^3$ are independently hydrogen or hydrocarbyl or substituted hydrocarbyl having from 1 to about 22 carbon atoms, $R^2$ is hydrocarbylene or substituted hydrocarbylene having from 2 to about 18 carbon atoms, and $R^4$ and $R^5$ are independently hydroxyalkyl, polyhydroxyalkyl, or poly(hydroxyalkyl)alkyl; or (h) a quaternary poly(hydroxyalkyl)amine salt having the formula:

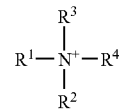
(24)

wherein $R^1$ is hydrocarbyl or substituted hydrocarbyl having from about 4 to about 30 carbon atoms or —$X_m$—(R$^6$O)$_y$R$^5$, $R^2$ and $R^3$ are independently hydrogen or hydrocarbyl or substituted hydrocarbyl having from 1 to about 30 carbon atoms, $R^4$ is hydroxyalkyl, polyhydroxyalkyl, or poly(hydroxyalkyl)alkyl, X- is an agriculturally acceptable anion; $R^6$ in each of the y($R^6$O) groups is independently $C_2$–$C_4$ alkylene, $R^5$ is hydrogen or a linear or branched alkyl group having 1 to about 4 carbon atoms, X is hydrocarbylene or substituted hydrocarbylene having from 2 to about 18 carbon atoms, m is 0 or 1, and y is an average number from 0 to about 30; or (i) a triamine having the formula:

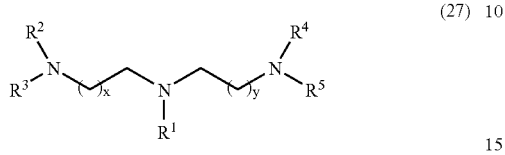
(27)

wherein $R^1$ is hydrocarbyl or substituted hydrocarbyl having from 1 to about 30 carbon atoms, $R^2$, $R^3$, $R^4$ and $R^5$ are independently hydrogen, hydrocarbyl or substituted hydrocarbyl having from 1 to about 30 carbon atoms, or —($R^8$)$_s$($R^7$O)$_n$$R^6$, $R^6$ is hydrogen or a linear or branched alkyl group having from 1 to about 4 carbon atoms, $R^7$ in each of the n ($R^7$O) groups is independently $C_2$–$C_4$ alkylene, $R^8$ is hydrocarbylene or substituted hydrocarbylene having from 1 to about 6 carbon atoms, n is an average number from 1 to about 10, s is 0 or 1, and x and y are independently an integer from 1 to about 4; or (j) a diamine having the formula:

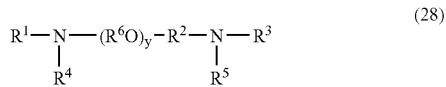
(28)

wherein $R^1$, $R^3$, $R^4$ and $R^5$ are independently hydrogen, hydrocarbyl or substituted hydrocarbyl having from 1 to about 30 carbon atoms, or —($R^6$O)$_x$$R^7$, $R^2$ is hydrocarbylene or substituted hydrocarbylene having from 2 to about 30 carbon atoms, —C(=N$R^{11}$)N$R^{12}$$R^{13}$—, —C(=O)N$R^{12}$$R^{13}$—, —C(=S)N$R^{12}$$R^{13}$—, —C(=N$R^{12}$)—, —C(S)—, or —C(O)—, $R^6$ in each of the x ($R^6$O) and y ($R^6$O) groups is independently $C_2$–$C_4$ alkylene, $R^7$ is hydrogen, or a linear or branched alkyl group having from 1 to about 30 carbon atoms, $R^{11}$, $R^{12}$ and $R^{13}$ are hydrogen, hydrocarbyl or substituted hydrocarbyl having from 1 to about 30 carbon atoms, x is an average number from 1 to about 50, and y is an average number from 0 to about 60; or (k) a mono- or di-quaternary ammonium salt having the formula:

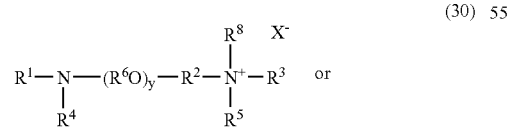
(30)

or

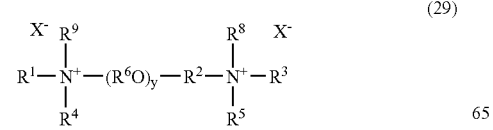
(29)

wherein $R^1$, $R^3$, $R^4$, $R^5$, $R^8$ and $R^9$ are independently hydrogen, polyhydroxyalkyl, hydrocarbyl or substituted hydrocarbyl having from 1 to about 30 carbon atoms, or —($R^6$O)$_x$$R^7$, $R^2$ is hydrocarbylene or substituted hydrocarbylene having from 2 to about 30 carbon atoms, $R^6$ in each of the x ($R^6$O) and y ($R^6$O) groups is independently $C_2$–$C_4$ alkylene, $R^7$ is hydrogen, or a linear or branched alkyl group having from 1 to about 4 carbon atoms, x is an average number from 1 to about 30, y is an average number from about 3 to about 60, and X⁻ is an agriculturally acceptable anion; or (l) a secondary or tertiary amine having the formula:

(31)

wherein $R^1$ and $R^2$ are hydrocarbyl having from 1 to about 30 carbon atoms, and $R^3$ is hydrogen or hydrocarbyl having from 1 to about 30 carbon atoms; or (m) a monoalkylated amine having the formula:

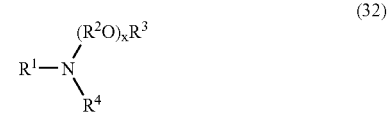
(32)

wherein $R^1$ and $R^4$ are independently hydrocarbyl or substituted hydrocarbyl groups having from 1 to about 30 carbon atoms or —$R^5$S$R^6$, $R^2$ in each of the x ($R^2$O) groups is independently $C_2$–$C_4$ alkylene, $R^3$ is hydrogen, or a linear or branched alkyl group having from 1 to about 4 carbon atoms, $R^5$ is a linear or branched alkyl group having from about 6 to about 30 carbon atoms, $R^6$ is a hydrocarbyl or substituted hydrocarbyl group having from 4 to about 15 carbon atoms and x is an average number from 1 to about 60; or (n) a dialkoxylated quaternary ammonium salt having the formula:

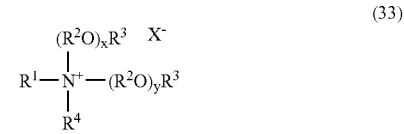
(33)

wherein $R^1$ is hydrocarbyl or substituted hydrocarbyl having from 1 to about 30 carbon atoms, $R^2$ in each of the x ($R^2$O) and y ($R^2$O) groups is independently $C_2$–$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and X- is an agriculturally acceptable anion; or (o) a monoalkoxylated quaternary ammonium salt having the formula:

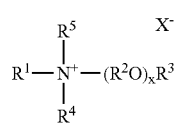
(34)

wherein $R^1$ and $R^5$ are independently hydrogen or hydrocarbyl or substituted hydrocarbyl having from 1 to about 30 carbon atoms, $R^4$ is hydrocarbyl or substituted hydrocarbyl having from 1 to about 30 carbon atoms, $R^2$ in each of the x ($R^2O$) groups is independently $C_2$–$C_4$ alkylene, $R^3$ is hydrogen, or a linear or branched alkyl group having from 1 to about 30 carbon atoms, x is an average number from 1 to about 60, and X- is an agriculturally acceptable anion; or (p) a quaternary ammonium salt having the formula:

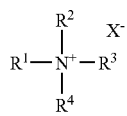
(35)

wherein $R^1$, $R^3$ and $R^4$ are independently hydrogen or hydrocarbyl or substituted hydrocarbyl having from 1 to about 30 carbon atoms, $R^2$ is hydrocarbyl or substituted hydrocarbyl having from 1 to about 30 carbon atoms, and X- is an agriculturally acceptable anion; or (q) an etheramine having the formula:

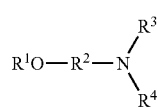
(36)

wherein $R^1$ is hydrocarbyl or substituted hydrocarbyl having from 1 to about 30 carbon atoms, $R^2$ is hydrocarbylene or substituted hydrocarbylene having from 2 to about 30 carbon atoms, $R^3$ and $R^4$ are independently hydrogen, hydrocarbyl or substituted hydrocarbyl having from 1 to about 30 carbon atoms, or —$(R^5O)_xR^6$, $R^5$ in each of the x($R^5$—O) groups is independently $C_2$–$C_4$ alkylene, $R^6$ is hydrogen, or a linear or branched alkyl group having from 1 to about 4 carbon atoms, and x is an average number from 1 to about 50; or (r) a diamine having the formula:

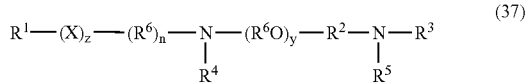
(37)

wherein $R^1$, $R^3$, $R^4$ and $R^5$ are independently hydrogen, hydrocarbyl or substituted hydrocarbyl having from 1 to about 30 carbon atoms, or —$(R^6O)_xR^7$, $R^2$ and $R^8$ are independently hydrocarbylene or substituted hydrocarbylene having from 2 to about 30 carbon atoms, $R^6$ in each of the x ($R^6O$) and y ($R^6O$) groups is independently $C_2$–$C_4$ alkylene, $R^7$ is hydrogen, or a linear or branched alkyl group having from 1 to about 30 carbon atoms, x is an average number from 1 to about 30, X is —O—, —N($R^6$)—, —C(O)—, —C(O)O—, —OC(O)—, —N($R^9$)C(O)—, —C(O)N($R^9$)—, —S—, —SO—, or —$SO_2$—, y is 0 or an average number from 1 to about 30, n and z are independently 0 or 1, and $R^9$ is hydrogen or hydrocarbyl or substituted hydrocarbyl; or (s) an amine oxide having the formula:

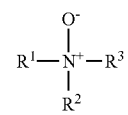
(38)

wherein $R^1$, $R^2$ and $R^3$ are independently hydrogen, hydrocarbyl or substituted hydrocarbyl having from 1 to about 30 carbon atoms, —$(R^4O)_xR^5$, or —$R^6(OR^4)_xOR^5$, $R^4$ in each of the x ($R^4O$) groups is independently $C_2$–$C_4$ alkylene, $R^5$ is hydrogen, or a hydrocarbyl or substituted hydrocarbyl having from 1 to about 30 carbon atoms, $R^6$ is a hydrocarbylene or substituted hydrocarbylene having from 1 to about 6 carbon atoms, x is an average number from 1 to about 50, and the total number of carbon atoms in $R^1$, $R^2$ and $R^3$ is at least 8; or (t) an alkoxylated amine oxide having the formula:

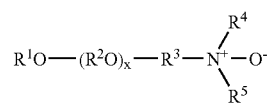
(39)

wherein $R^1$ is hydrogen or hydrocarbyl or substituted hydrocarbyl having from 1to about 30 carbon atoms, $R^3$ is a hydrocarbylene or substituted hydrocarbylene having from 2 to about 6 carbon atoms, $R^4$ and $R^5$ are each independently hydrogen, hydrocarbyl or substituted hydrocarbyl having from 1 to about 30 carbon atoms, or —$(R^6)_n$—$(R^2O)_yR^7$, $R^2$ in each of the x ($R^2O$) and y ($R^2O$) groups is independently $C_2$–$C_4$ alkylene, $R^6$ is hydrocarbylene or substituted hydrocarbylene containing from 1to about 6 carbon atoms, $R^7$ is hydrogen or a linear or branched alkyl group having 1 to about 4 carbon atoms, n is 0 or 1, and x and y are independently an average number from 1 to about 60; or (u) a dialkoxylated amine having the formula:

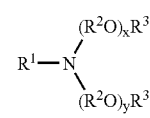
(40)

wherein $R^1$ is hydrogen or hydrocarbyl or substituted hydrocarbyl having from 1 to about 30 carbon atoms, —$R^4SR^5$, or —$(R^2O)_zR^3$, $R^2$ in each of the x ($R^2O$), y ($R^2O$) and z ($R^2O$) groups is independently $C_2$–$C_4$ alkylene, $R^3$ is hydrogen, or a linear or branched alkyl group having from 1 to about 22 carbon atoms, $R^4$ is a linear or branched alkyl group having from about 6 to about 30 carbon atoms, $R^5$ is a linear or branched alkyl group having from about 4 to about 15 carbon atoms, and x, y and z are independently an average number from 1 to about 40, provided, however, that when $R^1$ is alkyl, either the sum of x and y is greater than 20 or $R^3$ is other than hydrogen; or (v) an aminated alkoxylated alcohol having the formula:

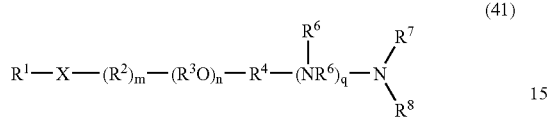
(41)

wherein $R^1$, $R^7$, $R^8$, and $R^9$ are each independently hydrogen, hydrocarbyl or substituted hydrocarbyl having from 1 to about 30 carbon atoms, or $—(R^{11})_s(R^3O)_v R^{10}$, X is —O—, —OC(O)—, —C(O)O—, —N($R^{12}$)C(O)—, —C(O)N($R^{12}$)—, —S—, —SO—, —SO$_2$— or —N($R^9$)—, $R^3$ in each of the n ($R^3$O) groups and the v ($R^3$O) groups is independently $C_2$–$C_4$ alkylene, $R^{10}$ is hydrogen, or a linear or branched alkyl group having from 1 to about 30 carbon atoms, n is an average number from 1 to about 60, v is an average number from 1 to about 50, $R^2$ and $R^{11}$ are each independently hydrocarbylene or substituted hydrocarbylene having from 1 to about 6 carbon atoms, $R^4$ is hydrocarbylene or substituted hydrocarbylene having from 2 to about 6 carbon atoms, $R^{12}$ is hydrogen or hydrocarbyl or substituted hydrocarbyl having from 1 to about 30 carbon atoms, m and s are each independently 0 or 1, $R^6$ is hydrocarbylene or substituted hydrocarbylene having from 2 to about 30 carbon atoms, —C(=$NR^{12}$)—, —C(S)—, or —C(O)—, q is an integer from 0 to 5, and $R^5$ is hydrogen or hydrocarbyl or substituted hydrocarbyl having from 1 to about 30 carbon atoms; or (w) a quaternary ammonium, sulfonium or sulfoxonium salt having the formula:

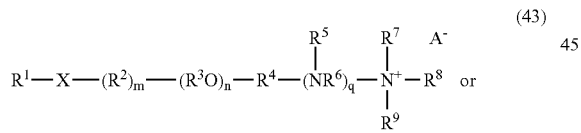
(43)

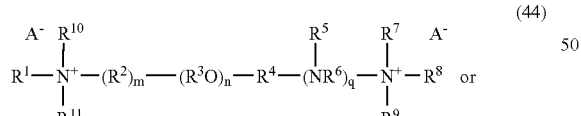
(44)

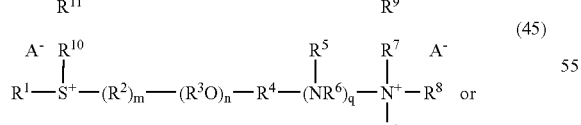
(45)

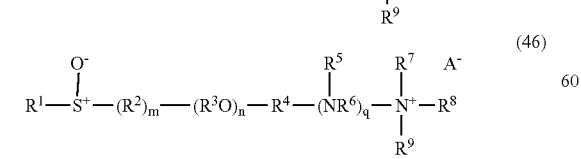
(46)

wherein $R^1$, $R^7$, $R^8$, $R^9$, $R^{10}$ and $R^{11}$ are independently hydrogen, hydrocarbyl or substituted hydrocarbyl having from 1 to about 30 carbon atoms, or $—(R^{13})_s(R^3O)_v R^{12}$, X is —O—, —OC(O)—, —N($R^{14}$)C(O)—, —C(O)N($R^{14}$)—, —C(O)O—, or —S—, $R^3$ in each of the n ($R^3$O) groups and v ($R^3$O) groups is independently $C_2$–$C_4$ alkylene, $R^{12}$ is hydrogen, or a linear or branched alkyl group having from 1 to about 30 carbon atoms, n is an average number from 1 to about 60, v is an average number from 1 to about 50, $R^2$ and $R^{13}$ are each independently hydrocarbylene or substituted hydrocarbylene having from 1 to about 6 carbon atoms, m and s are each independently 0 or 1, $R^4$ is hydrocarbylene or substituted hydrocarbylene having from 2 to about 6 carbon atoms, $R^6$ is hydrocarbylene or substituted hydrocarbylene having from 2 to about 30 carbon atoms, —C(=$NR^{12}$)—, —C(S)—, or —C(O)—, $R^{14}$ is hydrogen or hydrocarbyl or substituted hydrocarbyl having from 1 to about 30 carbon atoms, q is an integer from 0 to 5, $R^5$ is hydrogen or hydrocarbyl or substituted hydrocarbyl having from 1 to about 30 carbon atoms, and each $A^-$ is an agriculturally acceptable anion; or (x) a diamine or diammonium salt having the formula:

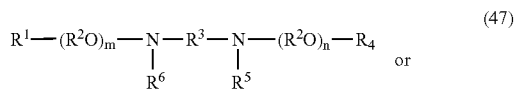
(47)

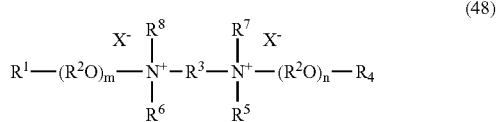
(48)

wherein $R^1$, $R^4$, $R^5$, $R^6$, $R^7$ and $R^8$ are independently hydrogen or hydrocarbyl or substituted hydrocarbyl having from 1 to about 30 carbon atoms, $R^2$ in each of the m($R^2$O) and n($R^2$O) groups and $R^9$ are independently $C_2$–$C_4$ alkylene, $R^3$ is hydrocarbylene or substituted hydrocarbylene having from about 2 to about 6 carbon atoms or $—(R^2O)_p R_9—$, m and n are individually an average number from 0 to about 50, and p is an average number from 0 to about 60; or (y) a compound of the formula:

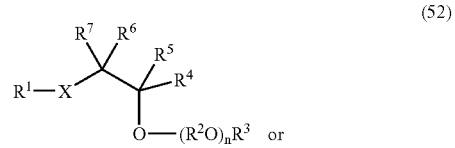
(52)

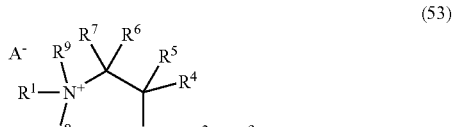
(53)

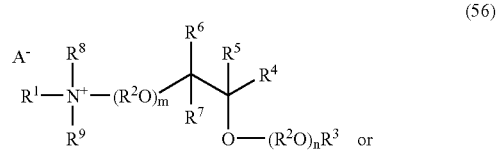
(56)

-continued

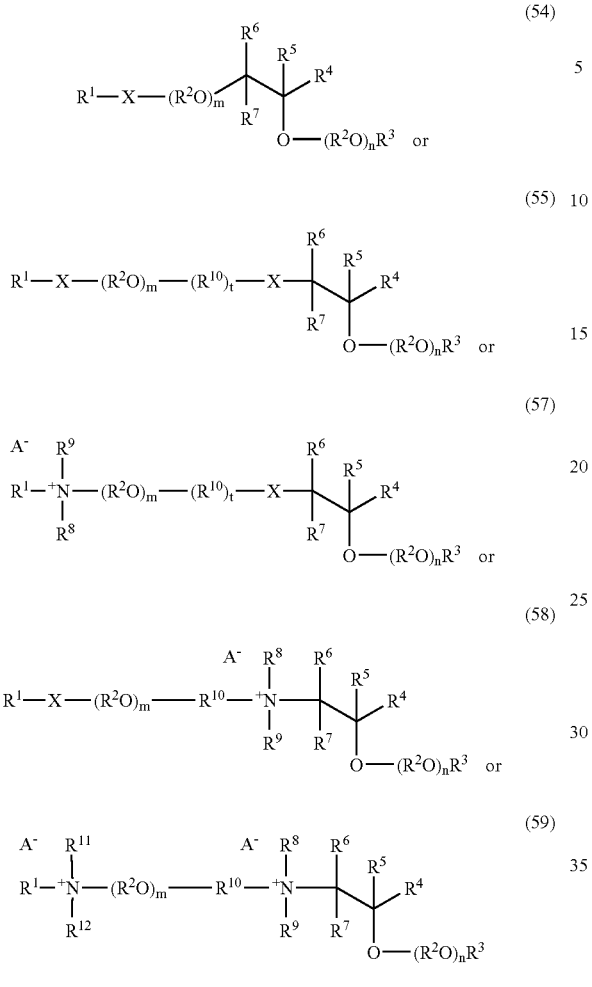

wherein $R^1$, $R^9$, and $R^{12}$ are independently hydrocarbyl or substituted hydrocarbyl having from 1 to about 30 carbon atoms, or $-(R^2O)_pR^{13}$, $R^2$ in each of the m $(R^2O)$, $n(R^2O)$, p $(R^2O)$ and q $(R^2O)$ groups is independently $C_2-C_4$ alkylene, $R^3$, $R^8$, $R^{11}$, $R^{13\ and\ R15}$ are independently hydrogen, or a hydrocarbyl or substituted hydrocarbyl having from 1 to about 30 carbon atoms, $R^4$ is $-(CH_2)_yOR^{13}$ or $-(CH_2)_yO(R^2O)_qR^3$, $R^5$, $R^6$ and $R^7$ are independently hydrogen, hydrocarbyl or substituted hydrocarbyl having from 1 to about 30 carbon atoms, or $R^4$, $R^{10}$ is hydrocarbylene or substituted hydrocarbylene having from 2 to about 30 carbon atoms, $R^{14}$ is hydrogen, hydrocarbyl or substituted hydrocarbyl having from 1 to about 30 carbon atoms, or $-(CH_2)_zO(R^2O)_pR^3$, m, n, p and q are independently an average number from 1 to about 50, X is independently $-O-$, $-N(R^{14})-$, $-C(O)-$, $-C(O)O-$, $-OC(O)-$, $-N(R^{15})C(O)-$, $-C(O)N(R^{15})-$, $-S-$, $-SO-$, or $-SO_2-$, t is 0 or 1, A- is an agriculturally acceptable anion, and y and z are independently an integer from 0 to about 30.

39. The composition of claim 32 wherein said surfactant component further comprises at least one nonionic surfactant comprising:

(a) an alkoxylated alcohol having the formula:

(49)

wherein $R^1$ is hydrocarbyl or substituted hydrocarbyl having from 1 to about 30 carbon atoms, $R^2$ in each of the x $(R^2O)$ groups is independently $C_2-C_4$ alkylene, $R^3$ is hydrogen, or a linear or branched alkyl group having from 1 to about 4 carbon atoms, and x is an average number from 1 to about 60; or (b) a dialkoxylated alcohol having the formula:

(50)

wherein $R^1$ is independently hydrogen, or a linear or branched alkyl group having from 1 to about 4 carbon atoms, $R^2$ in each of the x $(R^2O)$ and the y $(R^2O)$ groups is independently $C_2-C_4$ alkylene, $R^3$ is hydrocarbylene or substituted hydrocarbylene having from 2 to about 30 carbon atoms, and x and y are independently an average number from 1 to about 60; or (c) an alkoxylated dialkylphenol having the formula:

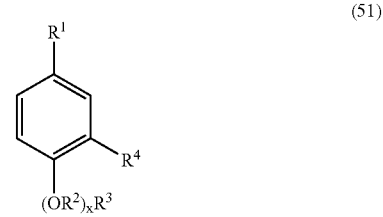

(51)

wherein $R^1$ and $R^4$ are independently hydrogen, or a linear or branched alkyl group having from 1 to about 30 carbon atoms and at least one of $R^1$ and $R^4$ is an alkyl group, $R^2$ in each of the x $(R^2O)$ groups is independently $C_2-C_4$ alkylene, $R^3$ is hydrogen, or a linear or branched alkyl group having from 1 to about 4 carbon atoms, and x is an average number from 1 to about 60; or (d) a glycoside having the formula:

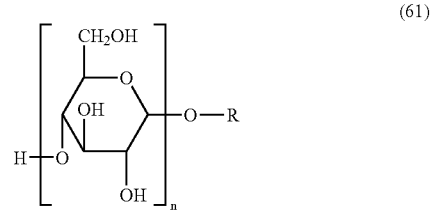

(61)

wherein n is the degree of polymerization, or number of glycose groups, and R is a branched or straight chain alkyl group preferably having from 4 to 18 carbon atoms, or a mixture of alkyl groups having an average value within the given range.

40. The composition of claim 32 wherein said stabilizer comprises octylamine.

* * * * *

UNITED STATES PATENT AND TRADEMARK OFFICE
CERTIFICATE OF CORRECTION

| | |
|---|---|
| PATENT NO. | : 7,135,437 B2 |
| APPLICATION NO. | : 09/988352 |
| DATED | : November 14, 2006 |
| INVENTOR(S) | : Pallas et al. |

It is certified that error appears in the above-identified patent and that said Letters Patent is hereby corrected as shown below:

Column 3, Line 60:
"$(R^1)(R^2)(R^3)N^+\text{-}CH_2CH_2O\text{-}(CH_2CH(CH_3)O)_n$ HCl".

should read

-- $(R^1)(R^2)(R^3)N^+\text{-}CH_2CH_2O\text{-}(CH_2CH(CH_3)O)_nH$ Cl⁻ --.

Column 14, Line 42: "octyamine" should read -- octylamine --.

Column 22, Line 55:

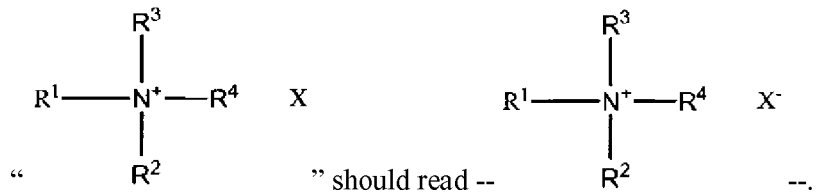

Column 36, Line 10: "$R^4$ and $R^1$" should read -- $R^4$ and $R^5$ --.

Column 36, Line 19: "$C_{15\text{-}16}$" should read -- $C_{16\text{-}18}$ --.

Column 37, Line 2: "A" should read -- A⁻ --.

Column 37, Line 32: "$R^5$, R, $R^7$" should read -- $R^5$, $R^6$, $R^7$ --.

Column 37, Line 41: "cocoa mine" should read -- cocoamine --.

Column 37, Line 65: "CC42" should read -- CC-42 --.

Signed and Sealed this
Seventeenth Day of July, 2012

David J. Kappos
*Director of the United States Patent and Trademark Office*

CERTIFICATE OF CORRECTION (continued)
U.S. Pat. No. 7,135,437 B2

Column 38, Line 34: "R" should read -- $R^2$ --.

Column 40, Line 12: "$C_{11}$, linear" should read -- $C_{11}$ linear --.

Column 40, Line 13: "TERGITO™" should read -- TERGITOL™ --.

Column 41, Formula 59A:

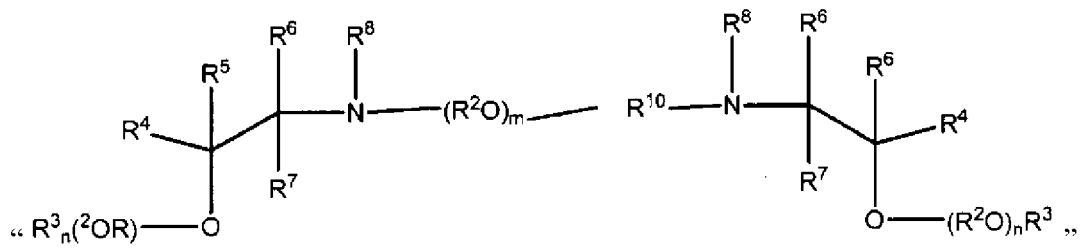

should read

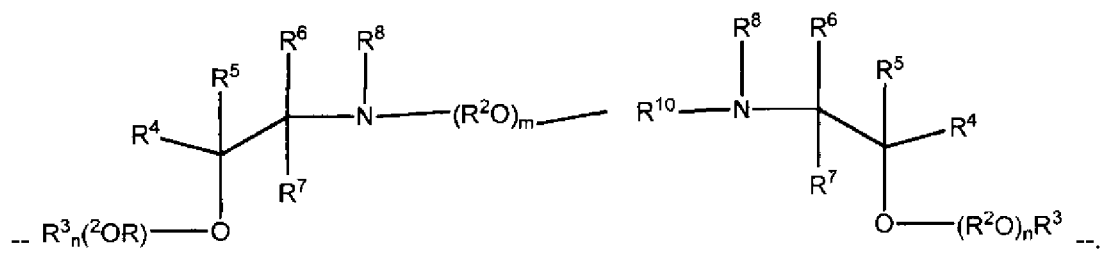

Column 41, Line 36: "$(CH_2)_zO(R^2O)_xR^3$" should read -- $(CH_2)_zO(R^2O)_pR^3$ --.

Column 43, Line 2: "$C_{1-28}$" should read -- $C_{1-18}$ --.

Column 44, Line 46: "butyl or t-butyl" should read -- -butyl or t-butyl --.

Column 46, Line 48: "*Poitulaca*" should read -- *Portulaca* --.

Column 46, Line 61: "(*Sinapis aevensis*)" should read -- (*Sinapis arvensis*) --.

Column 54, Line 51: "(about 490 9 a.e./L) should read -- (about 490 g a.e./L) --.

Column 127, Claim 22, Line 51: "tat" should read -- that --.

Column 129, Claim 30, Line 65: "and is" should read -- and $R^3$ is --.

Column 131, Claim 30, Line 33: "salts" should read -- salt --.

Column 139, Claim 32, Line 48: "di ssolved" should read -- dissolved --.

Column 139, Claim 32, Line 59: "tat" should read -- that --.

CERTIFICATE OF CORRECTION (continued)
U.S. Pat. No. 7,135,437 B2

Column 140, Claim 32, Line 2: "wit" should read -- with --.

Column 141, Claim 38, Line 2: "I to 60" should read -- 1 to 60 --.

Column 142, Claim 38, Formula 24:

" 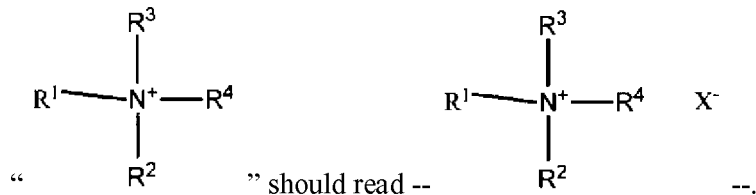 " should read -- --.

Column 145, Claim 38, Formula 37:

" 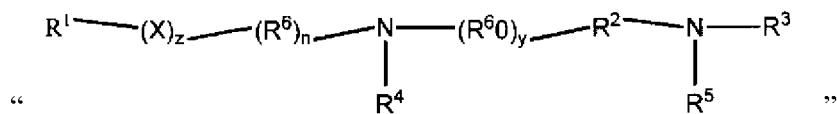 "

should read

-- 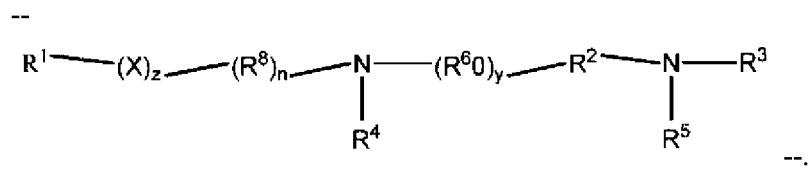 --.

Column 149, Claim 38, Line 45: "$R^{13}$ $^{and}$ $^{R15}$" should read -- $R^{13}$ and $R^{15}$ --.